US010249831B2

(12) United States Patent
Stoessel et al.

(10) Patent No.: US 10,249,831 B2
(45) Date of Patent: Apr. 2, 2019

(54) ELECTRONIC DEVICE CONTAINING CYCLIC LACTAMS

(71) Applicant: Merck Patent GmbH, Darmstadt (DE)

(72) Inventors: Philipp Stoessel, Frankfurt am Main (DE); Amir Hossain Parham, Frankfurt am Main (DE); Christof Pflumm, Darmstadt (DE); Anja Jatsch, Frankfurt am Main (DE); Thomas Eberle, Landau (DE); Jonas Valentin Kroeber, Frankfurt am Main (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 15/549,556

(22) PCT Filed: Jan. 11, 2016

(86) PCT No.: PCT/EP2016/000034
§ 371 (c)(1),
(2) Date: Aug. 8, 2017

(87) PCT Pub. No.: WO2016/128103
PCT Pub. Date: Aug. 18, 2016

(65) Prior Publication Data

US 2018/0040832 A1 Feb. 8, 2018

(30) Foreign Application Priority Data

Feb. 9, 2015 (EP) .................................... 15000375

(51) Int. Cl.

| | |
|---|---|
| ***H01L 51/54*** | (2006.01) |
| ***C09K 11/06*** | (2006.01) |
| ***H01L 51/00*** | (2006.01) |
| ***H01L 51/50*** | (2006.01) |
| ***C07D 239/96*** | (2006.01) |
| ***C07D 403/10*** | (2006.01) |
| ***C07D 403/14*** | (2006.01) |
| ***C07D 405/14*** | (2006.01) |
| ***C07D 409/10*** | (2006.01) |
| ***C07D 413/10*** | (2006.01) |
| ***C07D 487/04*** | (2006.01) |
| ***C07D 493/04*** | (2006.01) |
| ***C07D 495/04*** | (2006.01) |
| ***C09K 11/02*** | (2006.01) |

(52) U.S. Cl.
CPC ........ *H01L 51/0072* (2013.01); *C07D 239/96* (2013.01); *C07D 403/10* (2013.01); *C07D 403/14* (2013.01); *C07D 405/14* (2013.01); *C07D 409/10* (2013.01); *C07D 413/10* (2013.01); *C07D 487/04* (2013.01); *C07D 493/04* (2013.01); *C07D 495/04* (2013.01); *C09K 11/025* (2013.01); *H01L 51/006* (2013.01); *H01L 51/0053* (2013.01); *H01L 51/0061* (2013.01); *H01L 51/0067* (2013.01); *H01L 51/0068* (2013.01); *H01L 51/0073* (2013.01); *H01L 51/5016* (2013.01); *H01L 51/0052* (2013.01); *H01L 51/0085* (2013.01); *H01L 51/0087* (2013.01); *H01L 51/5092* (2013.01); *H01L 2251/5384* (2013.01); *Y02E 10/549* (2013.01)

(58) Field of Classification Search
CPC .. C07D 239/96; C07D 403/00; C07D 403/10; C07D 403/14; C07D 405/00; C07D 405/10; C07D 405/14; C07D 409/00; C07D 409/10; C07D 409/14; C07D 413/00; C07D 413/10; C07D 413/14; C07D 493/00; C07D 493/04; C07D 495/00; C07D 495/04; C09K 11/025; C09K 11/06; C09K 2211/00; C09K 2211/10; C09K 2211/1018; C09K 2211/1022; C09K 2211/1029; C09K 2211/1044; H01L 51/0032; H01L 51/005; H01L 51/0062; H01L 51/0067; H01L 51/0072; H01L 51/006; H01L 51/0061; H01L 51/0052; H01L 51/50; H01L 51/5012; H01L 51/5016
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | | |
|---|---|---|---|---|
| 8,835,626 | B2 | 9/2014 | Parham et al. | |
| 9,139,582 | B2 | 9/2015 | Parham et al. | |
| 2002/0076823 | A1* | 6/2002 | Natrajan ............. | C07D 219/04 436/172 |

(Continued)

FOREIGN PATENT DOCUMENTS

| | | | |
|---|---|---|---|
| WO | WO-2011116865 | A1 | 9/2011 |
| WO | WO-2011137951 | A1 | 11/2011 |

(Continued)

OTHER PUBLICATIONS

International Search Report for PCT/EP2016/000034 dated Apr. 25, 2016.

(Continued)

*Primary Examiner* — Andrew K Bohaty
(74) *Attorney, Agent, or Firm* — Drinker Biddle & Reath LLP

(57) ABSTRACT

The present invention relates to electronic devices containing special cyclic lactams, more particularly organic electroluminescent devices, and to special cyclic lactams for use in electronic devices, more particularly in organic electroluminescent devices.

16 Claims, No Drawings

(56) References Cited

U.S. PATENT DOCUMENTS

2015/0270495 A1 9/2015 Stoessel et al.

FOREIGN PATENT DOCUMENTS

WO WO-2013071217 A1 5/2013
WO WO-2014056567 A1 4/2014

OTHER PUBLICATIONS

Kuethe, J., et al., "Synthesis of Disubstituted Imidazo[4,5-b]pyridin-2-ones", Journal of Organic Chemistry, vol. 69, No. 22, (2004), pp. 7752-7754.

Majumder, A., et al., "Air-stable palladium(0) phosphine sulfide catalysts for Ullmann-type C—N and C—O coupling reactions" Journal of Organometallic Chemistry, vol. 781, (2015), pp. 23-34.

Written Opinion of the International Searching Authority for PCT/EP2016/000034 dated Apr. 25, 2016.

* cited by examiner

ELECTRONIC DEVICE CONTAINING CYCLIC LACTAMS

CROSS-REFERENCE TO RELATED APPLICATIONS

This application is a national stage application (under 35 U.S.C. § 371) of PCT/EP2016/000034, filed Jan. 11, 2016, which claims benefit of European Application No. 15000375.4, filed Feb. 9, 2015, both of which are incorporated herein by reference in their entirety.

The present invention relates to electronic devices comprising specific cyclic lactams, especially organic electroluminescent devices, and to specific cyclic lactams for use in electronic devices, especially in organic electroluminescent devices.

The structure of organic electroluminescent devices (OLEDs) in which organic semiconductors are used as functional materials is described, for example, in U.S. Pat. Nos. 4,539,507, 5,151,629, EP 0676461 and WO98/27136. Emitting materials used here are increasingly organometallic complexes which exhibit phosphorescence rather than fluorescence. For quantum-mechanical reasons, up to four times the quantum efficiency and power efficiency is possible using organometallic compounds as phosphorescent emitters. In general terms, there is still a need for improvement in OLEDs, especially also in OLEDs which exhibit triplet emission (phosphorescence), for example with regard to efficiency, operating voltage and lifetime. This is especially also true of OLEDs which emit in the shorter-wave range, for example in the green.

The properties of phosphorescent OLEDs are not just determined by the triplet emitters used. More particularly, the other materials used, such as matrix materials, hole blocker materials, electron transport materials etc., are also of particular significance here. Improvements to these materials can thus also lead to distinct improvements in the OLED properties. For fluorescent OLEDs too, there is still a need for improvement in these materials.

According to the prior art, lactams, for example according to WO 2011/116865, WO2011/137951 or WO2014/056567, are among the matrix materials used for phosphorescent emitters in organic electroluminescent devices. It is generally the case that further improvements are desirable here, especially in relation to the efficiency, lifetime and thermal stability of the materials.

It is an object of the present invention to provide electronic devices comprising compounds suitable for use as matrix material or as electron transport or hole blocker material. More particularly, it is an object of the present invention to provide green-, yellow- and red-phosphorescing and possibly also blue-phosphorescing OLEDs, or to provide specific matrix materials that are suitable for green- and red-phosphorescing and possibly also blue-phosphorescing OLEDs.

It has been found that, surprisingly, this object is achieved by the compounds of the formula (1) described in detail below, and these lead to improvements in the organic electroluminescent device, especially with regard to lifetime, efficiency and/or operating voltage. This is especially true of red- and green-phosphorescing electroluminescent devices, particularly when the compounds of the formula (1) or the compounds of the invention are used as matrix material. The materials additionally feature high thermal stability. The present invention therefore provides electronic devices, especially organic electroluminescent devices, comprising such compounds.

The present invention provides an electronic device comprising at least one compound of the formula (1)

Formula (1)

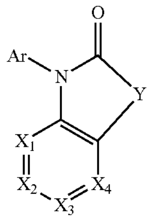

or at least two compounds of the formula (1) that are connected via at least one common aromatic or heteroaromatic ring system Ar or at least two compounds of the formula (1) that have a common structural unit

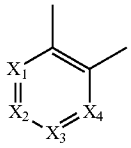

where the symbols used are as follows:

$X_1$, $X_2$, $X_3$, $X_4$ are each independently CR or N;

Y at each instance is

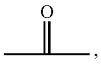, 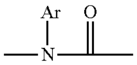 or 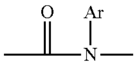;

Ar is the same or different at each instance and is an aromatic or heteroaromatic ring system which has 5-60 aromatic ring atoms and may be substituted by one or more $R^1$ radicals;

$Ar^1$ is the same or different at each instance and is an aromatic or heteroaromatic ring system which has 5-30 aromatic ring atoms and may be substituted by one or more $R^1$ radicals; at the same time, two $Ar^1$ radicals bonded to the same nitrogen atom or phosphorus atom may also be bridged to one another by a single bond or a bridge selected from $N(R^1)$, $C(R^1)_2$ and O;

R is the same or different at each instance and is selected from the group consisting of H, D, F, Cl, Br, I, CN, CHO, $NO_2$, $Si(R^2)_3$, $B(OR^2)_2$, $N(Ar^1)_2$, $N(R^1)_2$, $C(=O)Ar^1$, $C(=O)R^1$, $P(=O)(Ar^1)_2$, $S(=O)Ar^1$, $S(=O)(Ar^1)_2$, $CR^2=CR^2Ar^1$, $C\equiv CAr^1$, $OSO_2R^1$;

a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the hydrocarbyl groups mentioned may each be substituted by one or more $R^1$ radicals and where one or more nonadjacent $CH_2$ groups may be replaced by $R^1C=CR^1$, $-C\equiv C-$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$;

an aromatic or heteroaromatic ring system which has 5 to 60 aromatic ring atoms and may be substituted in each case by one or more $R^1$ radicals, an aryloxy or heteroaryloxy group which has 5 to 60 aromatic ring atoms and may be substituted by one or more $R^1$ radicals, an aralkyl or heteroaralkyl group which has 5 to 60 aromatic ring atoms and may be substituted by one or more $R^1$ radicals, or a combination of these systems, where two or more adjacent R substituents may form a monocyclic or polycyclic, aliphatic, aromatic or heteroaromatic ring system which may be substituted by one or more $R^1$ radicals or where the R substituent of $X_1$ and/or the R substituent of $X_4$ together with the adjacent N—Ar in each case may form a monocyclic or polycyclic, aliphatic, aromatic or heteroaromatic ring system which may be substituted by one or more $R^1$ radicals;

$R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, where two or more adjacent $R^1$ substituents together may form a mono- or polycyclic, aliphatic, aromatic or heteroaromatic ring system and $R^2$ is in each case independently selected from the group consisting of H, D and an aliphatic, aromatic and/or heteroaromatic hydrocarbyl radical having 1 to 20 carbon atoms, where two or more $R^2$ radicals together may also form a ring system.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O—ICs), organic field-effect transistors (O-FETs), organic thin-film transistors (O-TFTs), organic light-emitting transistors (O-LETs), organic solar cells (O—SCs), organic dye-sensitized solar cells (O-DSSCs), solar cells comprising perovskite, organic optical detectors, organic photoreceptors, organic field-quench devices (O-FQDs), light-emitting electrochemical cells (LECs), organic laser diodes (O-lasers) and organic plasmon-emitting devices (D. M. Koller et at, *Nature Photonics* 2008, 1-4), preferably organic electroluminescent devices (OLEDs) and more preferably phosphorescent OLEDs.

The invention accordingly further provides the electronic device comprising compounds of the formula (1) as described with preference above and hereinafter, selected from organic electroluminescent devices, organic integrated circuits, organic field-effect transistors, organic thin-film transistors, organic light-emitting transistors, organic solar cells, organic dye-sensitized solar cells, solar cells comprising perovskite, organic optical detectors, organic photoreceptors, organic field-quench devices, light-emitting electrochemical cells, organic laser diodes and organic plasmon-emitting devices.

The electronic device, preferably the organic electroluminescent device, comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction, see, for example, WO2005/011013). In addition, white emission can preferably be produced by using a blue emission layer and an emission layer that emits in the red and green, where these two emission layers may be separated from one another by a charge generation layer.

The compound of formula (1) as described above or preferably as described hereinafter can be used in different layers of the electronic device of the invention, according to the exact structure. Preference is given to an organic electroluminescent device comprising at least one compound of formula (1) or the preferred embodiments recited hereinafter or the compounds of the formulae (2), (2a), (3), (3a) to (3j), (4), (4a), (5) and (5a), (6) to (11), (6*) to (11*), (12) to (33), (34) to (41) and (42) to (57) described hereinafter as matrix material for fluorescent or phosphorescent emitters, especially for phosphorescent emitters, and/or in a hole blocker layer and/or in an electron transport layer and/or in an electron-blocking or exciton-blocking layer and/or in a hole transport layer, according to the exact substitution.

The invention further provides the electronic device, characterized in that the compound of the formula (1) or the preferred embodiments of the formula (1) recited hereinafter or the compounds of the formulae (2), (2a), (3), (3a) to (3j), (4), (4a), (5) and (5a), (6) to (11), (6*) to (11*), (12) to (33), (34) to (41) and (42) to (57) described hereinafter is/are used as matrix material for a fluorescent or phosphorescent emitter and/or in a hole blocker layer and/or in an electron transport layer and/or in an electron-blocking or exciton-blocking layer and/or in a hole transport layer, according to the exact substitution.

The invention further provides the electronic device, characterized in that the compound of the formula (1) or the preferred embodiments of the formula (1) recited hereinafter or the compounds of the formulae (2), (2a), (3), (3a) to (3j), (4), (4a), (5) and (5a), (6) to (11), (6*) to (11*), (12) to (33), (34) to (41) and (42) to (57) described hereinafter is/are used as matrix material for a fluorescent or phosphorescent emitter and/or in a hole blocker layer and/or in an electron transport layer.

The organic electroluminescent devices and light-emitting electrochemical cells of the invention can be used for various applications, for example for single-color or multi-color displays, for lighting applications or for medical and/or cosmetic applications, for example in phototherapy.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. phenyl, or a simple heteroaromatic cycle, for example pyridinyl, pyrimidinyl, thiophenyl, etc., or a fused (annelated) aryl or heteroaryl group, for example naphthyl, anthracenyl, phenanthrenyl, quinolinyl or isoquinolinyl. Aromatic systems joined to one another by a single bond, for example biphenyl, by contrast, are not referred to as an aryl or heteroaryl group but as an aromatic ring system.

An aromatic ring system in the context of this invention contains 5-60 carbon atoms in the ring system. A heteroaromatic ring system in the context of this invention contains 3-60 carbon atoms and at least one heteroatom in the ring system, with the proviso that the sum total of carbon atoms and heteroatoms is at least 4. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be connected by a nonaromatic unit, for example a boron, silicon, carbon, nitrogen or oxygen atom. For example, systems derived from fluorene, 9,9'-spirobifluorene, 9,9-diarylfluorene, triarylamine, diaryl ether or stilbene shall also be regarded as aromatic ring systems in the context of this invention, and likewise systems in which two or more aryl groups are connected, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals.

An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, CI, Br, I, CN or $NO_2$, preferably F, CI or CN, further preferably F or CN, especially preferably CN.

An aromatic or heteroaromatic ring system which has 5-60 aromatic ring atoms and may also be substituted in each case by the abovementioned $R^1$ radicals and which may be joined to the aromatic or heteroaromatic system via any desired positions is especially understood to mean groups derived from benzene, naphthalene, anthracene, phenanthrene, pyrene, benzanthracene, chrysene, perylene, fluoranthene, naphthacene, pentacene, benzopyrene, biphenyl, biphenylene, terphenyl, triphenylene, fluorene, spirobifluorene, dihydrophenanthrene, di hydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

A preferred aromatic or heteroaromatic ring system having 5 to 24 aromatic ring atoms is derived from benzene, naphthalene, anthracene, phenanthrene, biphenyl, terphenyl, quaterphenyl, fluorene, spirobifluorene, pyridine, pyrimidine, thiophene, furan, pyrrole, triazine, carbazole, benzofuran, benzothiophene, dibenzofuran, dibenzothiophene, quinoline, isoquinoline, phenanthridine, phenanthroline, azacarbazole, imidazole, benzimidazole, indenocarbazole, indolocarbazole, triphenylamine or combinations of two or three of these groups.

$R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, CI, Br, I, CN or a straight-chain or branched alkyl group having 1 to 10 carbon atoms or a straight-chain or branched alkenyl group having 2 to 10 carbon atoms, where two or more adjacent $R^1$ substituents together may form a mono- or polycyclic, aliphatic, aromatic or heteroaromatic ring system.

$R^1$ is preferably H, D, F, CN or a straight-chain or branched alkyl group having 1 to 12 carbon atoms.

$R^1$ is more preferably H, F, CN, a straight-chain or branched alkyl group having 1 to 4 carbon atoms.

$R^2$ is in each case independently selected from the group consisting of H, D and an aliphatic, aromatic and/or heteroaromatic hydrocarbyl radical having 1 to 20 carbon atoms, where two or more $R^2$ radicals together may also form a ring system.

$R^2$ is preferably H, D or an alkyl group having 1 to 12 carbon atoms. $R^2$ is more preferably H.

A preferred embodiment of the electronic device of the invention includes compounds of the formula (1) in which Y is

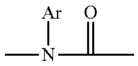

and Ar in each case independently has a definition given above.

The invention accordingly further provides the electronic device of the invention as described above or described as preferred, where Y in formula (1) is

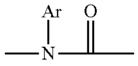

and Ar in each case independently has a definition given above.

A preferred embodiment of the electronic device of the invention includes compounds of the formula (1) in which Y is

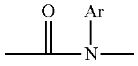

and Ar in each case independently has a definition given above.

The invention accordingly further provides the electronic device of the invention as described above or described as preferred, where Y in formula (1) is

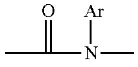

and Ar in each case independently has a definition given above.

A preferred embodiment of the electronic device of the invention includes compounds of the formula (1) in which Y is

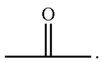.

The invention accordingly further provides the electronic device of the invention as described above or described as preferred, where Y in formula (1) is

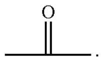.

A preferred embodiment of the electronic device of the invention includes compounds of the formula (1) in which at least one variable from the group of $X_1$, $X_2$, $X_3$ and $X_4$ is N and the rest of the variables are CR, and R in each case independently has one of the definitions given in formula (1).

The invention accordingly further provides the electronic device of the invention as described above or described as preferred, where, in formula (1), at least one variable from the group of $X_1$, $X_2$, $X_3$ and $X_4$ is N and the rest of the variables are CR, and R in each case independently has one of the definitions given in formula (1).

A preferred embodiment of the electronic device of the invention includes compounds of the formula (1) in which the variables $X_1$, $X_2$, $X_3$ and $X_4$ are CR, and R in each case independently has one of the definitions given in formula (1).

The invention accordingly further provides the electronic device of the invention as described above or described as preferred, where, in formula (1), the variables $X_1$, $X_2$, $X_3$ and $X_4$ are CR, and R in each case independently has one of the definitions given in formula (1).

Compounds of the formula (1) as described above or described as preferred can be prepared by synthesis methods known to those skilled in the art in the field of organic synthesis.

The present invention likewise further provides a process for preparing a compound of formula (1), as described above or described as preferred, by a coupling reaction at the N-H group of compounds of the formula A Formula A

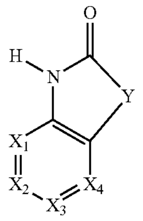

where $X_1$, $X_2$, $X_3$ and $X_4$ have a definition given in formula (1) or the preferred embodiments of the compounds of the formula (1) hereinafter, and Y at each instance is

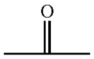 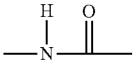 or 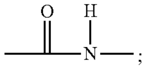;

with compounds of the formula B

Ar-L Formula B where Ar has a definition given in formula (1) and L corresponds to a leaving group suitable for the coupling reaction.

The process for preparation is especially applicable to the preparation of compounds of the formulae (42), (47) to (51), (56) and (57), where the definitions of $X_1$, $X_2$, $X_3$ and $X_4$ and of Y and Ar are matched to these compounds.

There are very many known coupling reactions. A suitable example is the Ullmann reaction. If this reaction type is chosen, L is preferably I or Br. In general terms, an Ullmann reaction describes a copper-catalyzed coupling of a nucleophile with an aryl halide.

A suitable example is the Hartwig-Buchwald reaction. If this reaction type is chosen, L is preferably Br. In general terms, a Hartwig-Buchwald reaction describes a palladium-catalyzed coupling of a nucleophile with an aryl halide.

Further process variants for preparation of compounds of the formula (1) are described hereinafter in the preferred embodiments.

Compounds of the formula (1) in which Y is

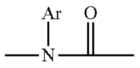

can be described synonymously by the formula (2)

(2)

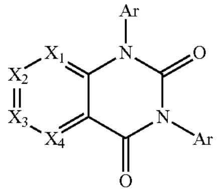

where $X_1$, $X_2$, $X_3$, $X_4$, Ar, R, $R^1$ and $R^2$ each independently have a definition given above or a definition given with preference.

In this embodiment of the electronic device of the invention including at least one compound of the formula (2) or at least two compounds of the formula (2) that are connected by at least one common aromatic or heteroaromatic ring system Ar or at least two compounds of the formula (2) that have a common structural unit

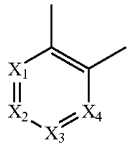

as described above, it is preferable when $X_1$, $X_2$, $X_3$ and $X_4$ are CR or are part of the second compound of the formula (2) where Ar, R, $R^1$ and $R^2$ each independently have a definition given above or have a preferred definition given hereinafter.

A preferred embodiment of said compounds of the formula (2) present in the electronic device of the invention corresponds to the formula (2a). The formula (2a) accordingly describes compounds of the formula (2) where $X_1$, $X_2$, $X_3$ and $X_4$ are CR, and where the R substituent of $X_1$ together with the adjacent N—Ar in each case forms a monocyclic or polycyclic, aliphatic, aromatic or heteroaromatic ring system which may be substituted by one or more $R^1$ radicals (2a)

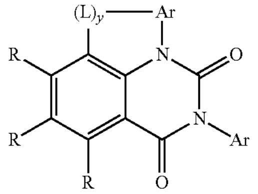

where y is 0 or 1,

L is C(═O) or —O— and where Ar, R, $R^1$ and $R^2$ each independently have a definition given above or a preferred definition given hereinafter.

Preferred embodiments of said compounds of the formula (2) in the device of the invention are the compounds of the formulae (3), (4) and (5)

(3)

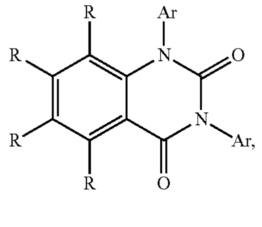

(4)

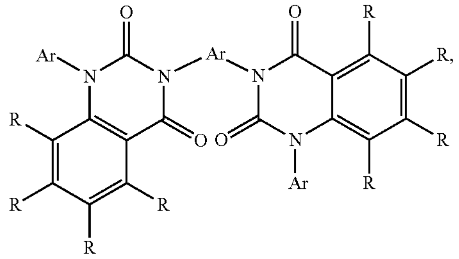

(5)

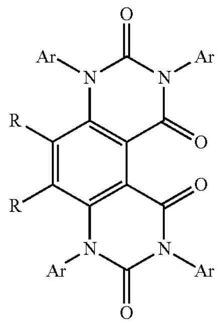

where Ar, R, $R^1$ and $R^2$ each independently have a definition given above or a preferred definition given hereinafter.

In compounds of the formula (3), R is in each case independently H or an aromatic or heteroaromatic ring system which has 5 to 60 aromatic ring atoms and may be substituted in each case by one or more $R^1$ radicals, where two or more adjacent R substituents may form a monocyclic or polycyclic, aliphatic, aromatic or heteroaromatic ring system which may be substituted by one or more $R^1$ radicals or where one of the R substituents together with the adjacent N—Ar forms a monocyclic or polycyclic, aliphatic, aromatic or heteroaromatic ring system which may be substituted by one or more $R^1$ radicals. Preferred compounds of the formula (3) of this kind may be described by the formulae (3a) to (3j).

The formula (3a) accordingly describes compounds of the formula (3) in which all R substituents are H (3a)

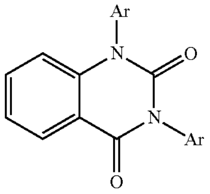

where Ar, $R^1$ and $R^2$ each independently have a definition given above or a preferred definition given hereinafter.

The formulae (3b), (3c), (3d), (3e) and (3f) accordingly describe compounds of the formula (3) in which two or three R substituents are H and two R substituents or one R substituent are/is an aromatic or heteroaromatic ring system which has 5 to 60 aromatic ring atoms and may be substituted by one or more $R^1$ radicals (3b)

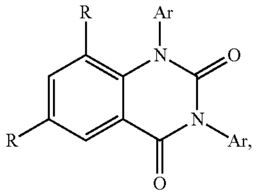

(3c)

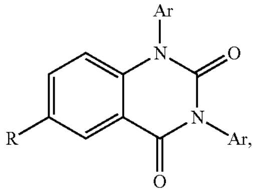

(3d)

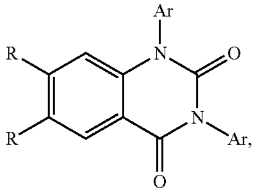

(3e)

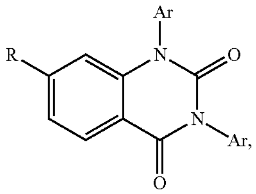

(3f)

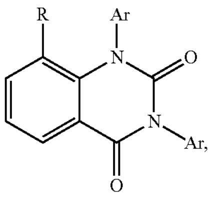

where Ar, R, $R^1$ and $R^2$ each independently have a definition given above or a preferred definition given hereinafter.

The formulae (3g), (3h), (3i) and (3j) accordingly describe compounds of the formula (3) where two or more adjacent R substituents form a monocyclid or polycyclic, aliphatic, aromatic or heteroaromatic ring system which is indicated by the symbol "(A" and the rest of the R substituents are H (3g)

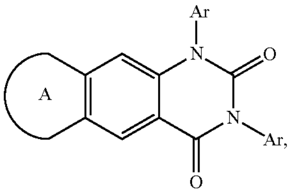

(3h)

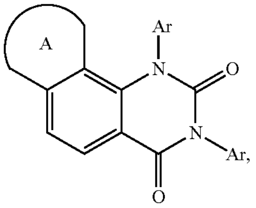

(3i)

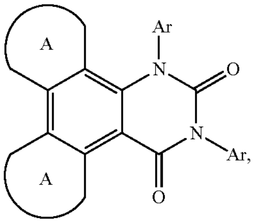

(3j)

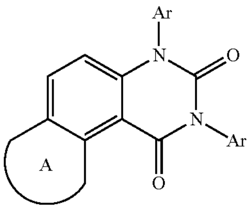

where Ar, $R^1$ and $R^2$ each independently have a definition given above or a preferred definition given hereinafter.

In compounds of the formula (4), R is preferably H, corresponding to the formula (4a)

(4a)

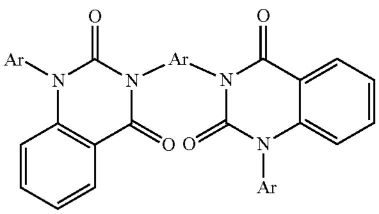

where Ar, $R^1$ and $R^2$ each independently have a definition given above or a preferred definition given hereinafter.

In compounds of the formula (5), R is preferably H, corresponding to the formula (5a)

(5a)

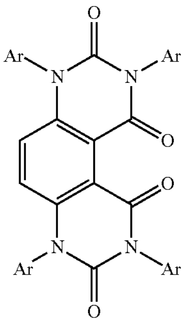

where Ar, $R^1$ and $R^2$ each independently have a definition given above or a preferred definition given hereinafter.

In the compounds of the formulae (2), (2a), (3), (3a) to (3j), (4), (4a), (5) and (5a), Ar is in each case independently preferably an aromatic or heteroaromatic ring system which has 5 to 24 aromatic ring atoms and may be substituted by one or more $R^1$ radicals. More preferably, Ar in this embodiment of the invention is substituted by a preferred $R^1$ radical as described above. More preferably, in this embodiment, Ar is unsubstituted. In the compounds of the formulae (2), (2a), (3), (3a) to (3j), (4), (4a), (5) and (5a), Ar is in each case independently more preferably phenyl, naphthyl, anthracenyl, phenanthrenyl or one of the radicals of the formulae (Ar-1) to (Ar-145)

Formula (Ar-1)

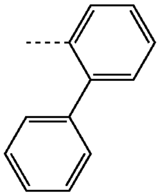

Formula (Ar-2)

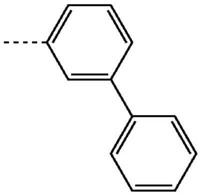

Formula (Ar-3)

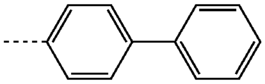

Formula (Ar-4)

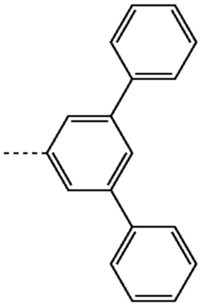

-continued

Formula (Ar-5)

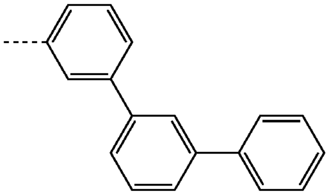

Formula (Ar-6)

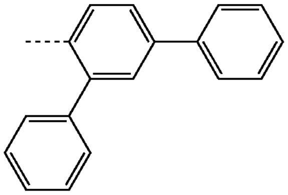

Formula (Ar-7)

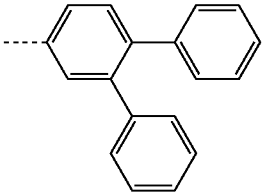

Formula (Ar-8)

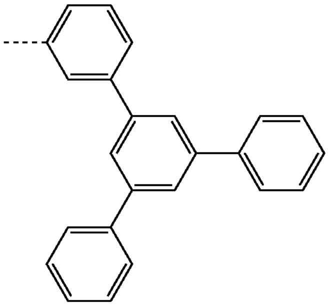

Formula (Ar-9)

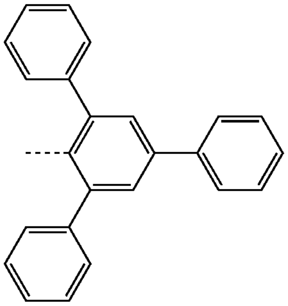

Formula (Ar-10)

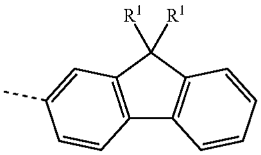

Formula (Ar-11)

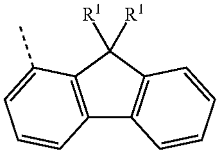

-continued
Formula (Ar-12)
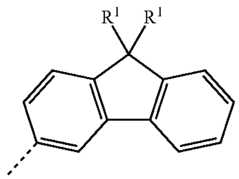
Formula (Ar-13)
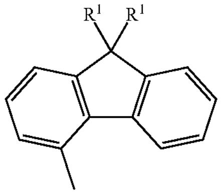
Formula (Ar-14)
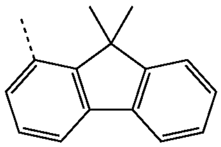
Formula (Ar-15)
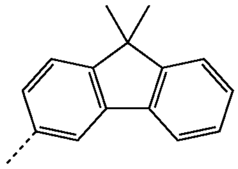
Formula (Ar-16)
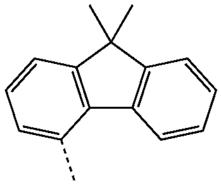
Formula (Ar-17)
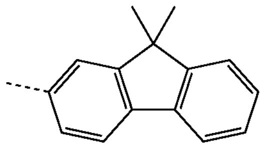
Formula (Ar-18)
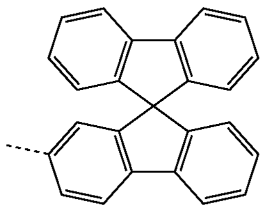
Formula (Ar-19)
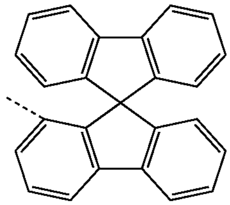
-continued
Formula (Ar-20)
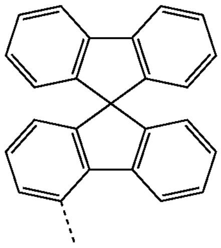
Formula (Ar-21)
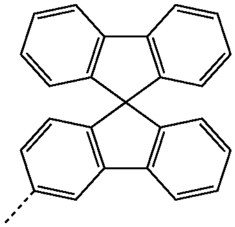
Formula (Ar-22)
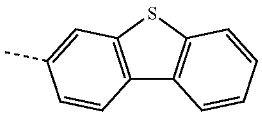
Formula (Ar-23)
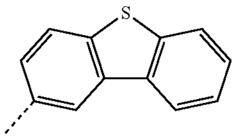
Formula (Ar-24)
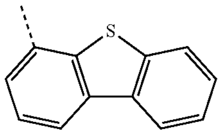
Formula (Ar-25)
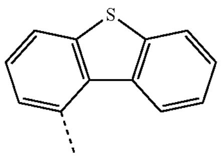
Formula (Ar-26)
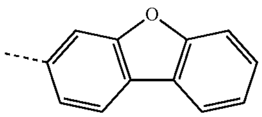
Formula (Ar-27)
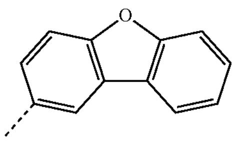
Formula (Ar-28)
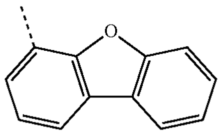

-continued
Formula (Ar-29)
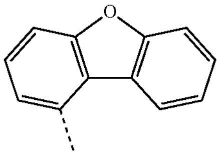
Formula (Ar-30)
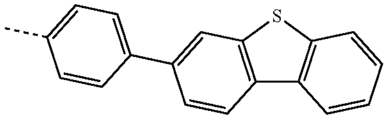
Formula (Ar-31)
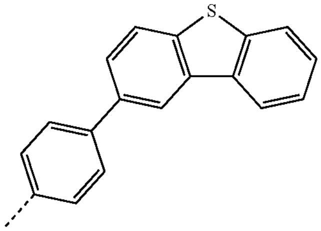
Formula (Ar-32)
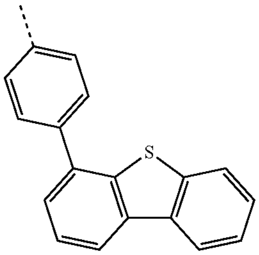
Formula (Ar-33)
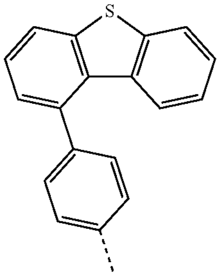
Formula (Ar-34)
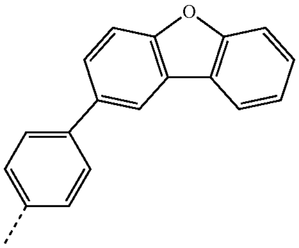
Formula (Ar-35)
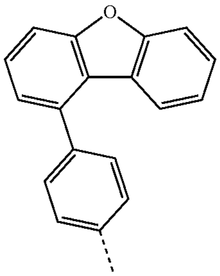
-continued
Formula (Ar-36)
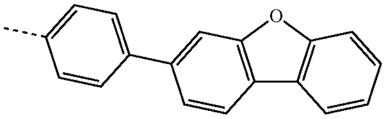
Formula (Ar-37)
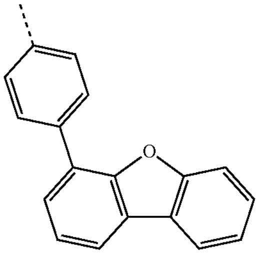
Formula (Ar-38)
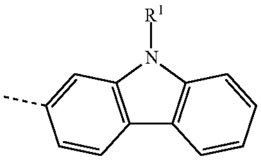
Formula (Ar-39)
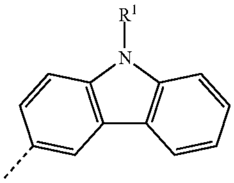
Formula (Ar-40)
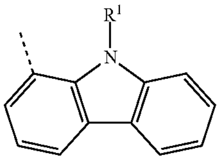
Formula (Ar-41)
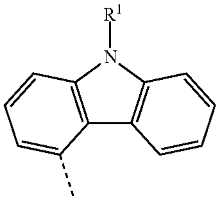
Formula (Ar-42)
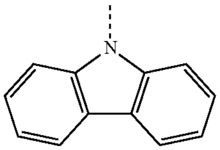
Formula (Ar-43)
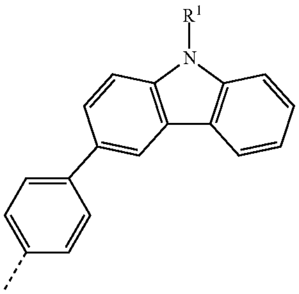

-continued
Formula (Ar-44)
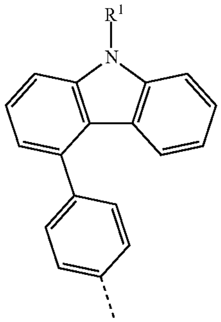
Formula (Ar-45)
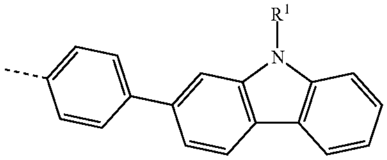
Formula (Ar-46)
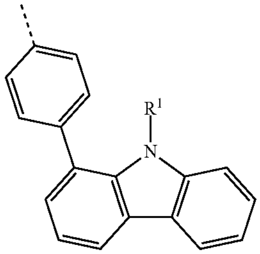
Formula (Ar-47)
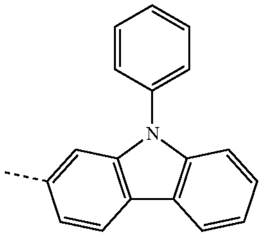
Formula (Ar-48)
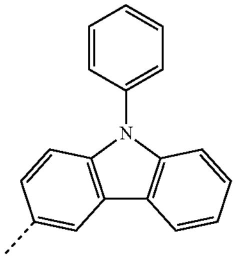
Formula (Ar-49)
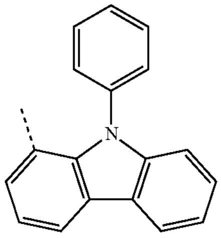
-continued
Formula (Ar-50)
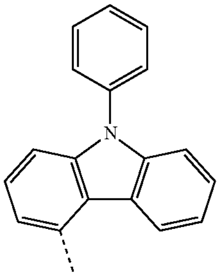
Formula (Ar-51)
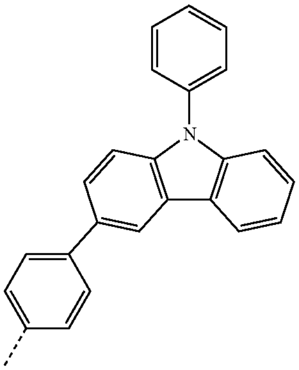
Formula (Ar-52)
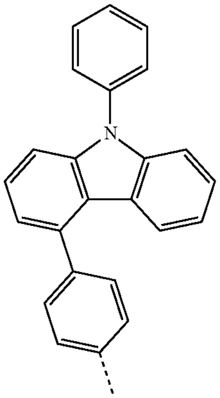
Formula (Ar-53)
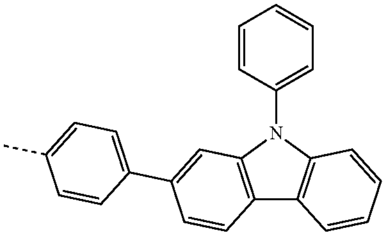
Formula (Ar-54)
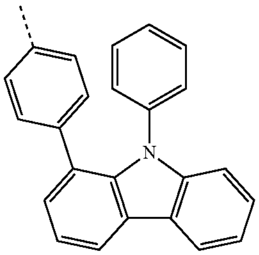

-continued
Formula (Ar-55)
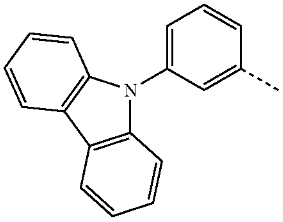
Formula (Ar-56)
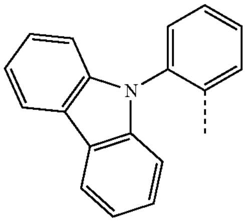
Formula (Ar-57)
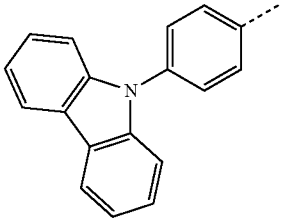
Formula (Ar-58)
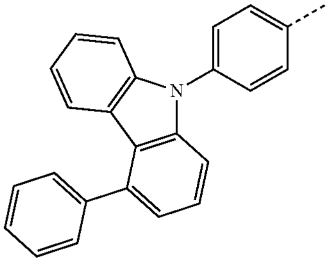
Formula (Ar-59)
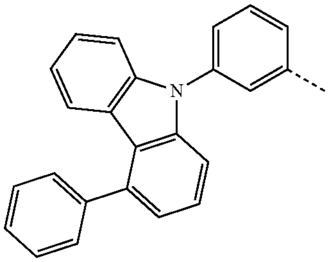
Formula (Ar-60)
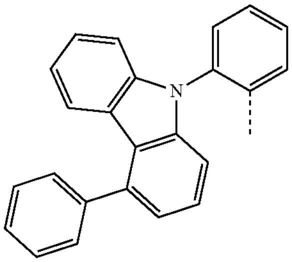
-continued
Formula (Ar-61)
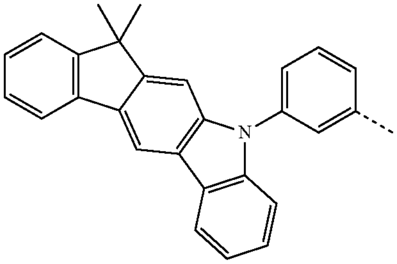
Formula (Ar-62)
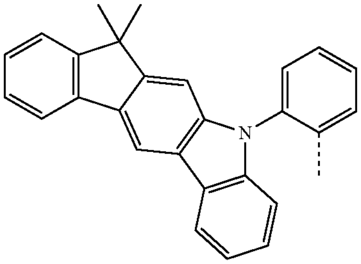
Formula (Ar-63)
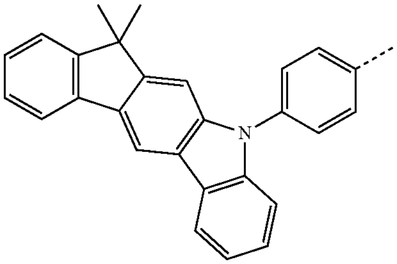
Formula (Ar-64)
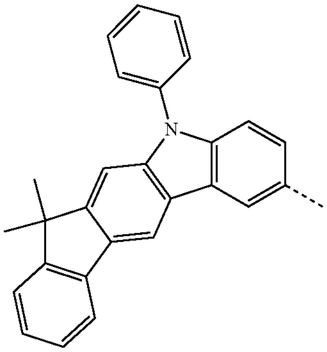
Formula (Ar-65)
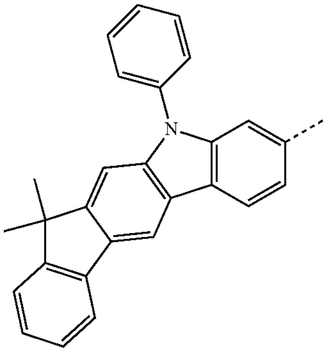

-continued
Formula (Ar-66)
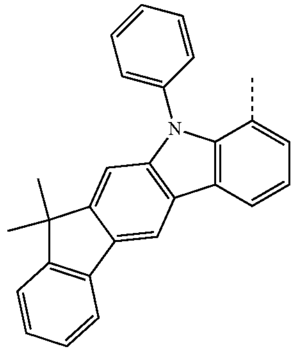
Formula (Ar-67)
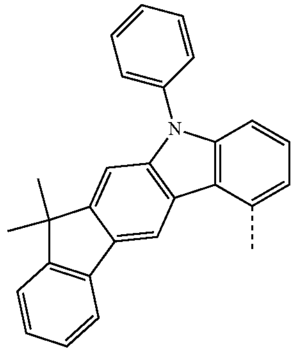
Formula (Ar-68)
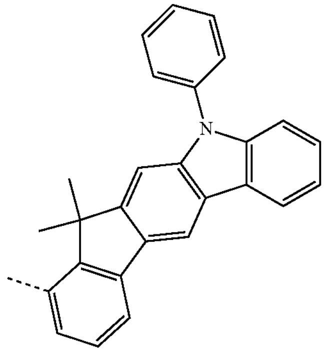
Formula (Ar-69)
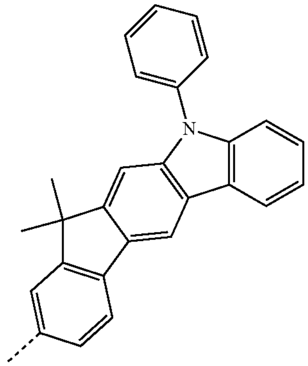
-continued
Formula (Ar-70)
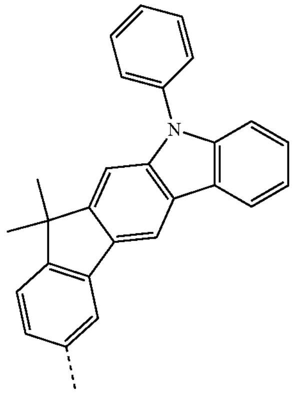
Formula (Ar-71)
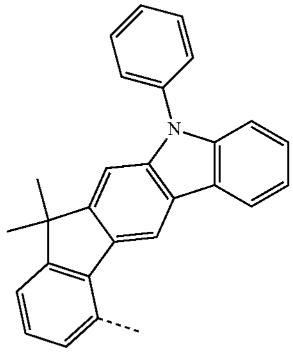
Formula (Ar-72)
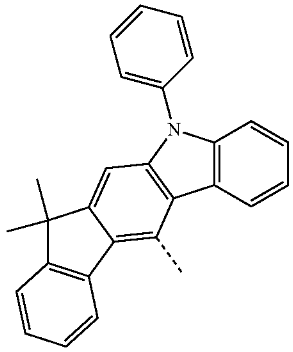
Formula (Ar-73)
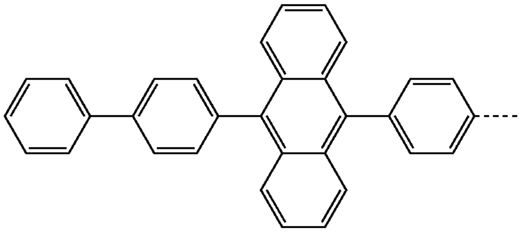
Formula (Ar-74)
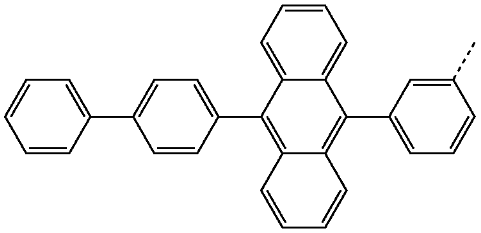

Formula (Ar-75)
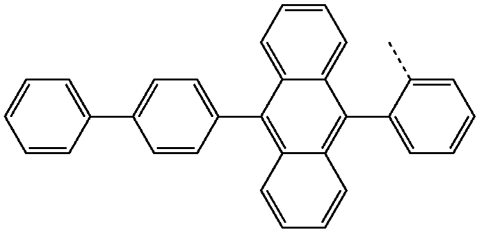
Formula (Ar-76)
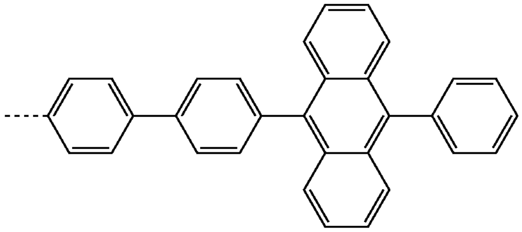
Formula (Ar-77)
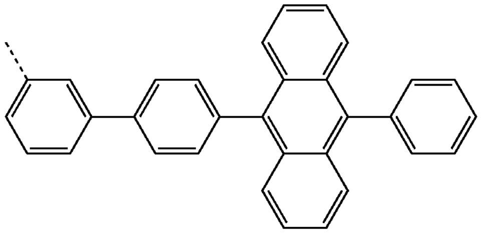
Formula (Ar-78)'
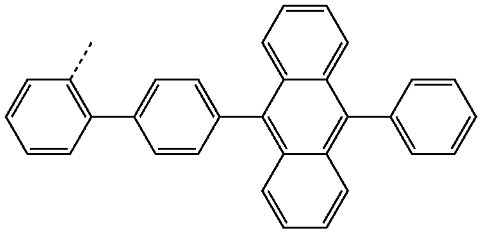
Formula (Ar-79)
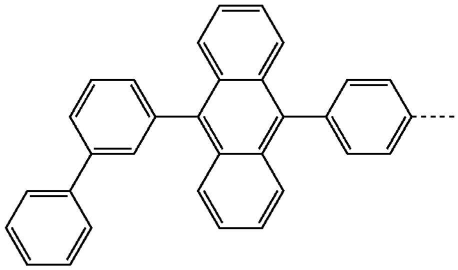
Formula (Ar-80)
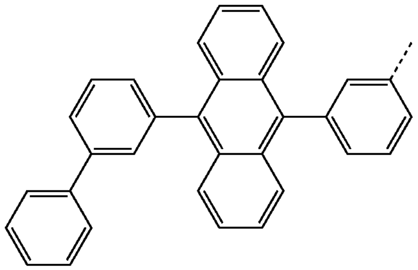
Formula (Ar-81)
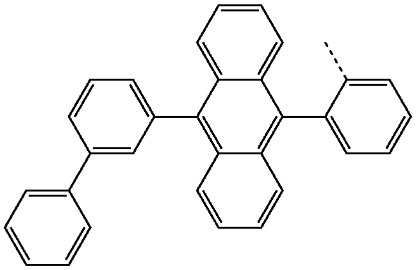
Formula (Ar-82)
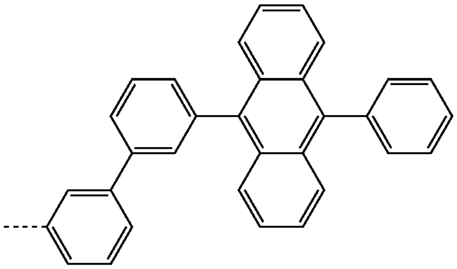
Formula (Ar-83)
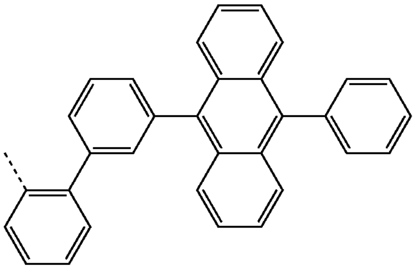
Formula (Ar-84)
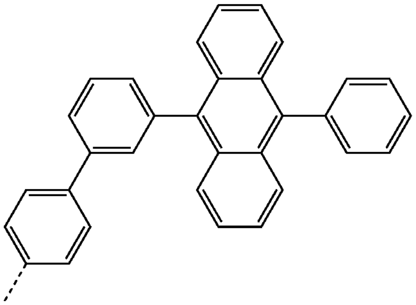
Formula (Ar-85)
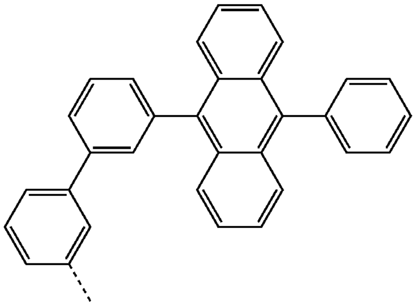

-continued
Formula (Ar-86)
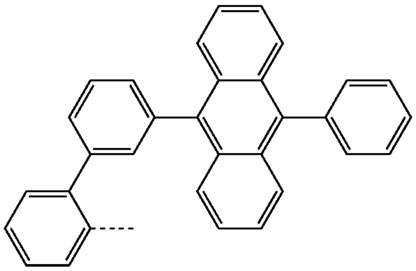
Formula (Ar-87)
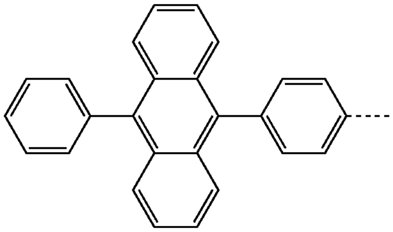
Formula (Ar-88)
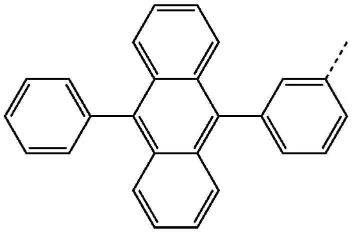
Formula (Ar-89)
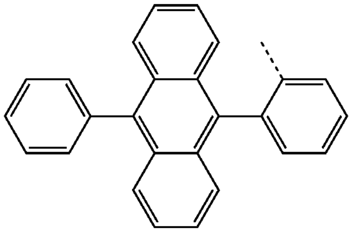
Formula (Ar-90)
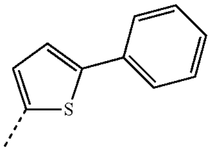
Formula (Ar-91)
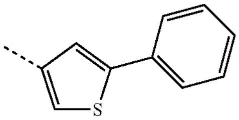
Formula (Ar-92)
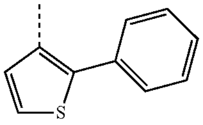
Formula (Ar-93)
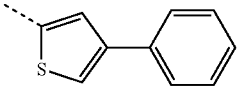
-continued
Formula (Ar-94)
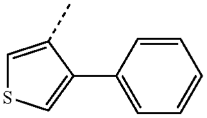
Formula (Ar-95)
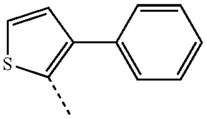
Formula (Ar-96)
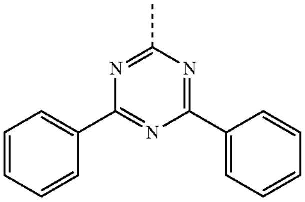
Formula (Ar-97)
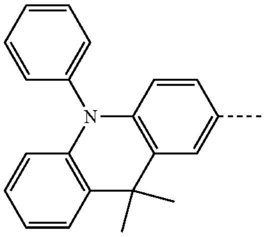
Formula (Ar-98)
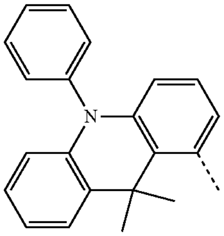
Formula (Ar-99)
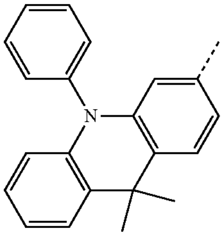
Formula (Ar-100)
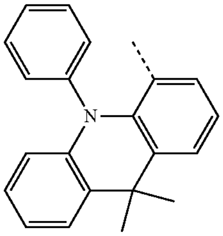

-continued
Formula (Ar-101)
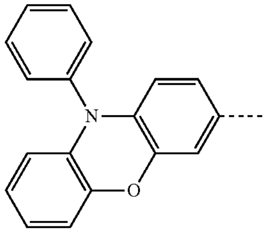
Formula (Ar-102)
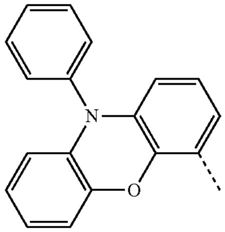
Formula (Ar-103)
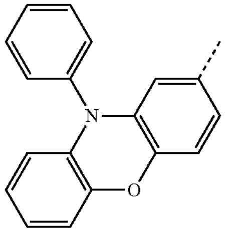
Formula (Ar-104)
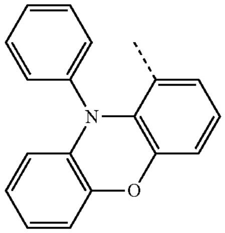
Formula (Ar-105)
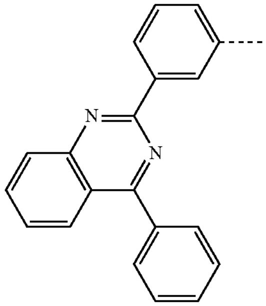
Formula (Ar-106)
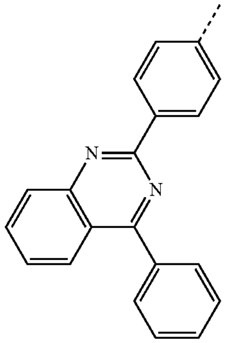
-continued
Formula (Ar-107)
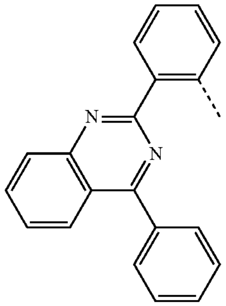
Fomula (Ar-108)
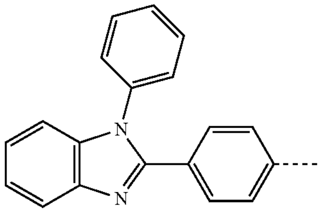
Formula (Ar-109)
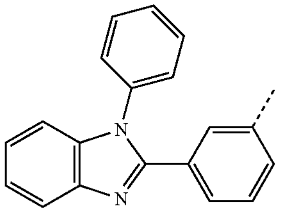
Formula (Ar-110)
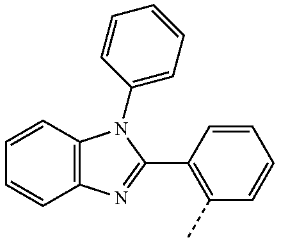
Formula (Ar-111)
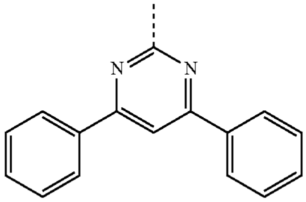
Formula (Ar-112)
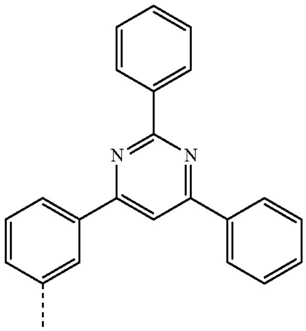

-continued
Formula (Ar-113)
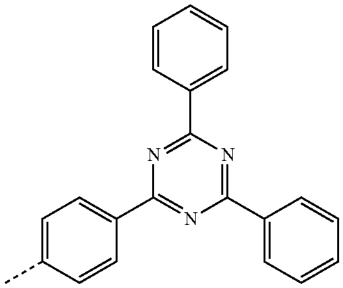
Formula (Ar-114)
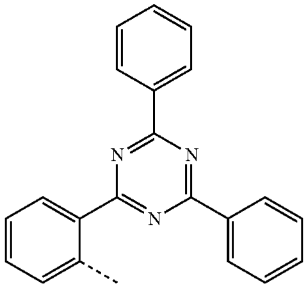
Formula (Ar-115)
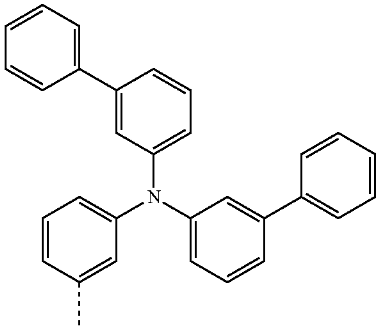
Formula (Ar-116)
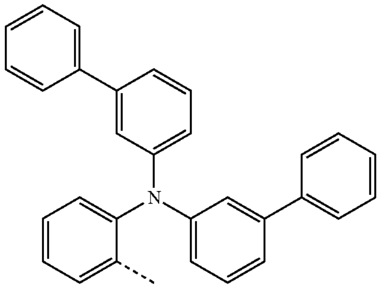
Formula (Ar-117)
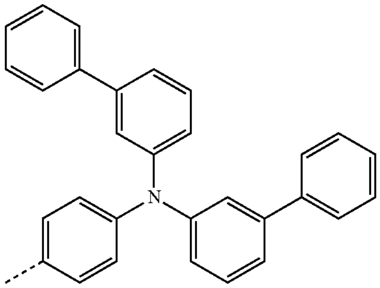
-continued
Formula (Ar-118)
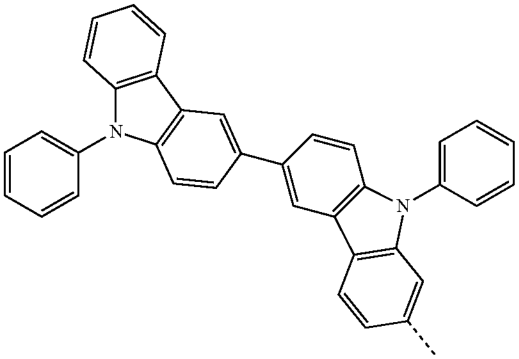
Formula (Ar-119)
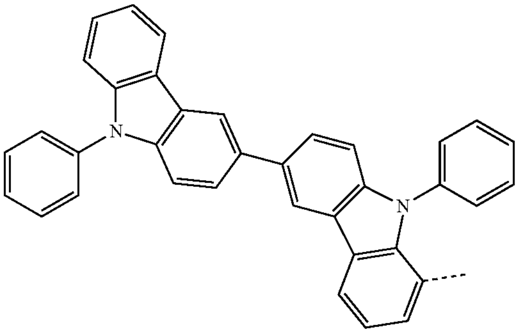
Formula (Ar-120)
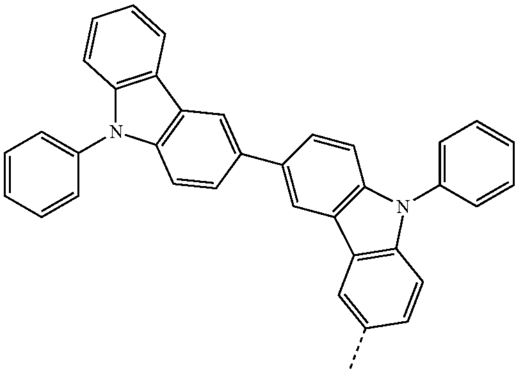
Formula (Ar-121)
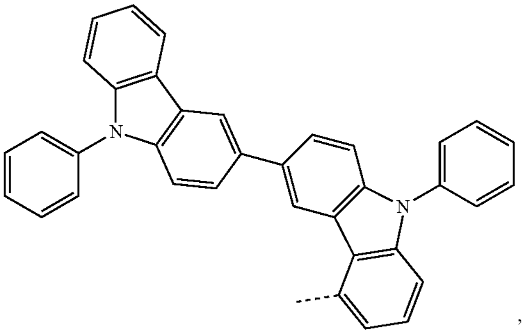
, -continued
Formula (Ar-122)
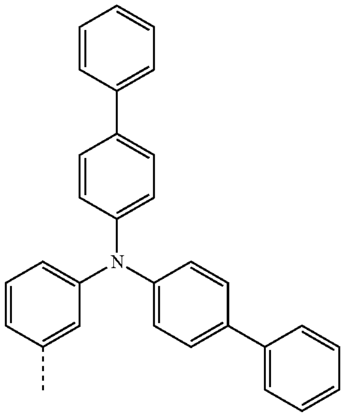
,
Formula (Ar-123)
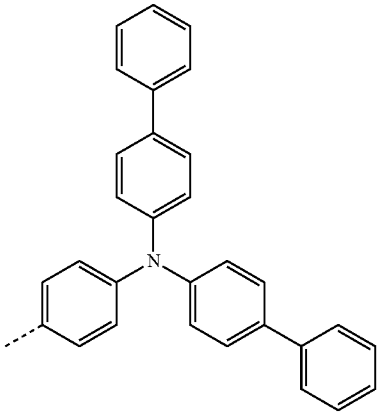
,
Formula (Ar-124)
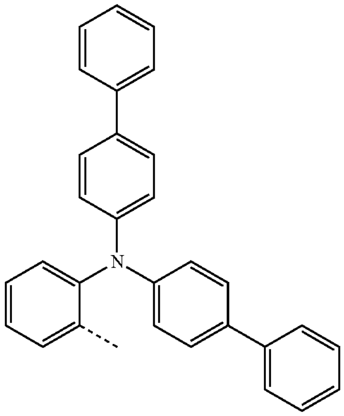
,
Formula (Ar-125)
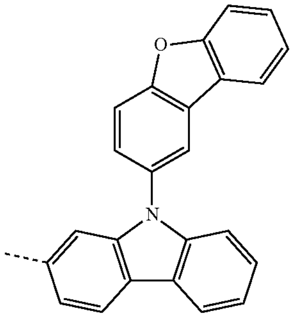
,
-continued
Formula (Ar-126)
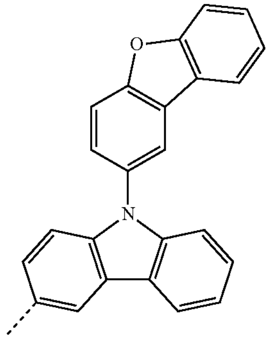
,
Formula (Ar-127)
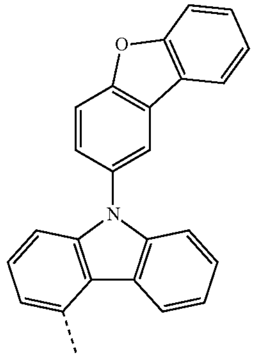
,
Formula (Ar-128)
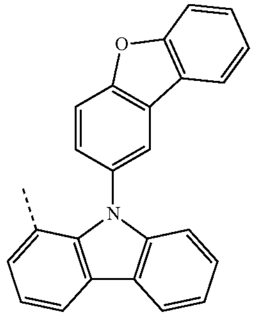
,
Formula (Ar-129)
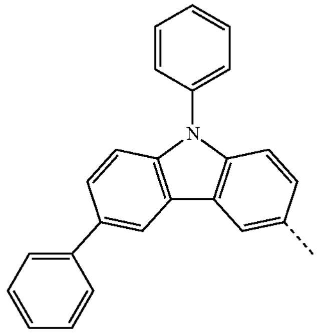
, Formula (Ar-130)
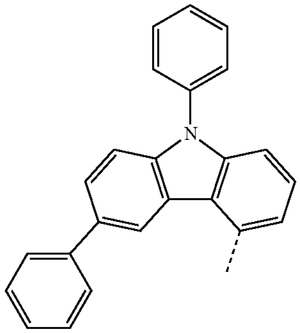
,
Formula (Ar-131)
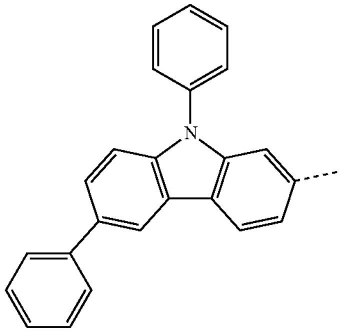
,
Formula (Ar-132)
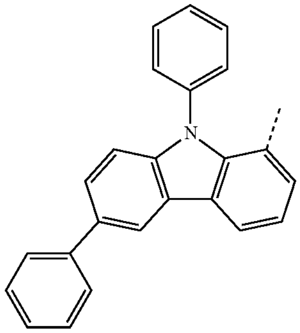
,
Formula (Ar-133)
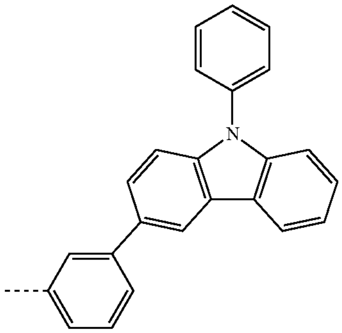
,
Formula (Ar-134)
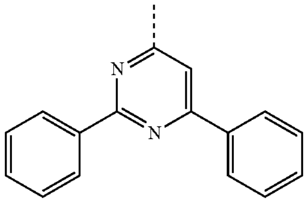
,
Formula (Ar-135)
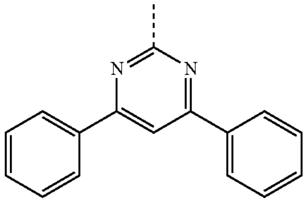
Formula (Ar-136)
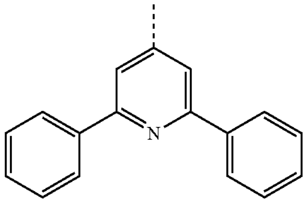
Formula (Ar-137)
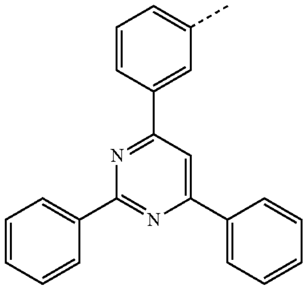
Formula (Ar-138)
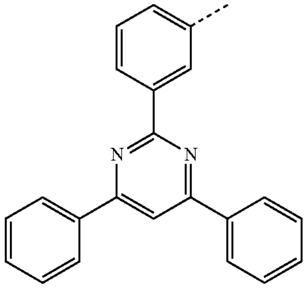
Formula (Ar-139)
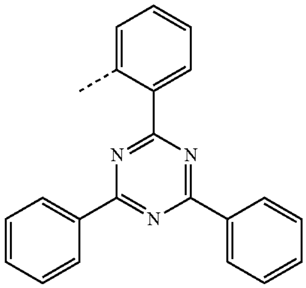
Formula (Ar-140)
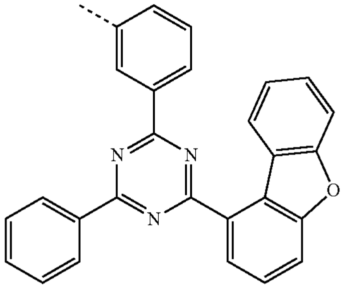

-continued

Formula (Ar-141)

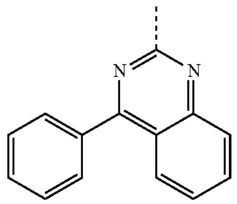

Formula (Ar-144)

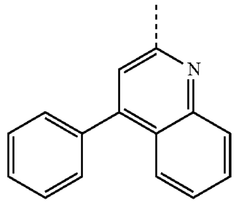

Formula (Ar-145)

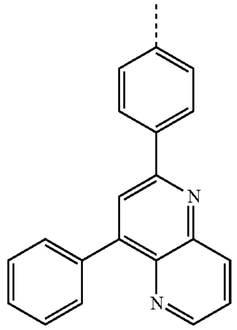

Formula (Ar-146)

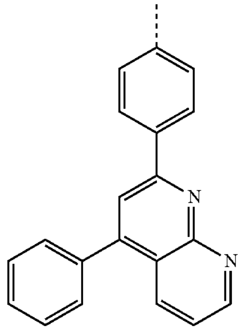

Formula (Ar-145)

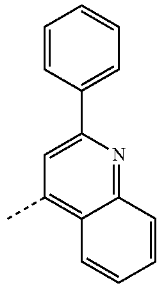

where the dotted bond denotes the bond to the base skeleton and the specified groups for Ar may each be substituted by one or more $R^1$ radicals, but are preferably unsubstituted.

In compounds of the formula (4) or (4a), as described above, the connecting aromatic or heteroaromatic ring system Ar is most preferably a radical of the formula (Ar-10), (Ar-17), (Ar-22), (Ar-23), (Ar-29), (Ar-39) or (Ar-43), where the dotted bond denotes a linkage to one base skeleton and the second linkage site to the second base skeleton may be at any site. In a preferred embodiment of the compounds of the formula (4) or (4a), the two linkage sites of the connecting aromatic or heteroaromatic ring system Ar are preferably chosen in a symmetric manner, for example shown by the formulae (Ar-146) to (Ar-152)

Formula (Ar-146)

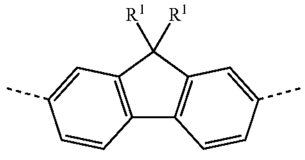

Formula (Ar-147)

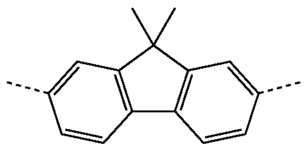

Formula (Ar-148)

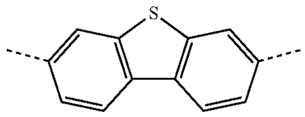

Formula (Ar-149)

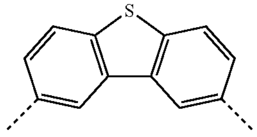

Formula (Ar-150)

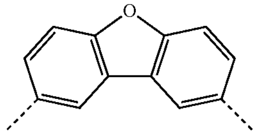

Formula (Ar-151)

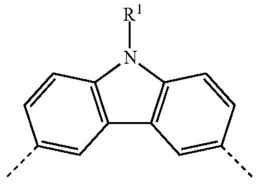

Formula (Ar-152)

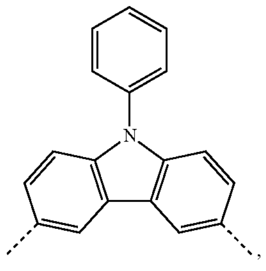

or the two linkage sites of the connecting aromatic or heteroaromatic ring system Ar are preferably selected from the partial formulae (Ar-153) or (Ar-154)

Formula (Ar-153)

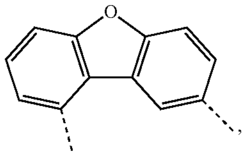

Formula (Ar-154)

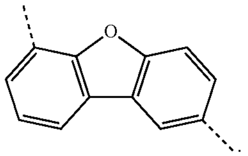

Preferred compounds of the formula (2a) are compounds of the formulae (6) bis (11)

(6)

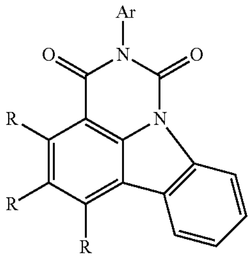

(7)

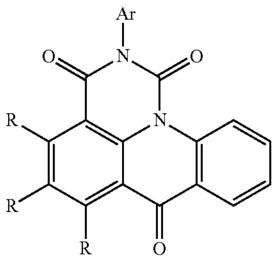

(8)

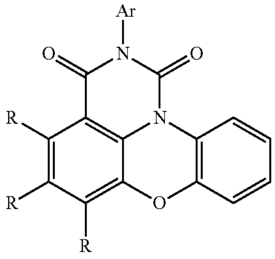

(9)

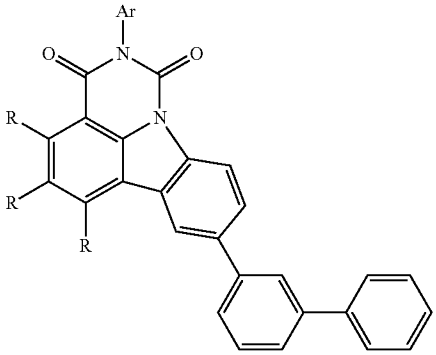

-continued (10)

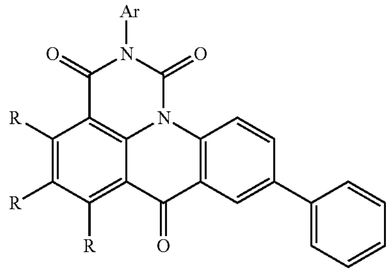

(11)

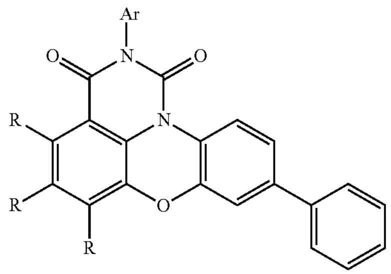

where Ar, R, $R^1$ and $R^2$ each independently have a definition given above or a preferred definition given above or hereinafter. In compounds of the formulae (6) to (11), 2 R substituents are preferably H and one R substituent corresponds to an $R^3$ substituent, where $R^3$ is selected from the group consisting of D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, CI, Br, I, CN, or a straight-chain branched alkyl group having 1 to 10 carbon atoms or a straight-chain or branched alkenyl group having 2 to 10 carbon atoms.

Preferred compounds are illustrated by the formulae (6*) to (11*)

(6*)

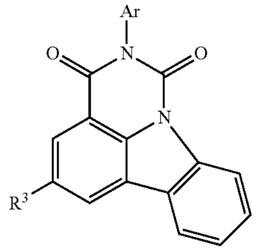

(7*)

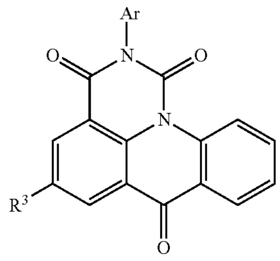

-continued
(8*)
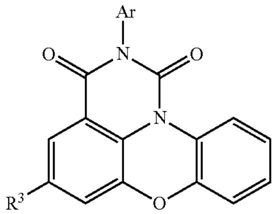
(9*)
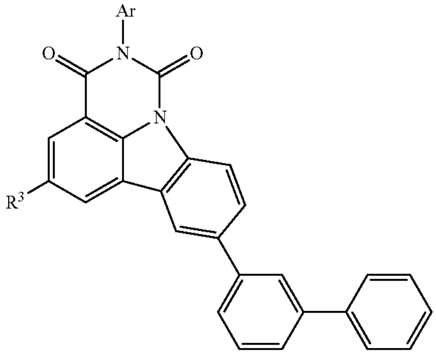
(10*)
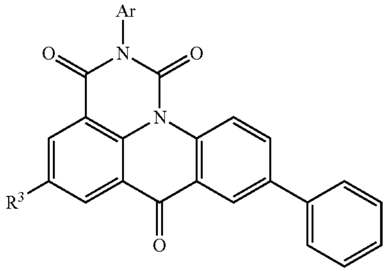
(11*)
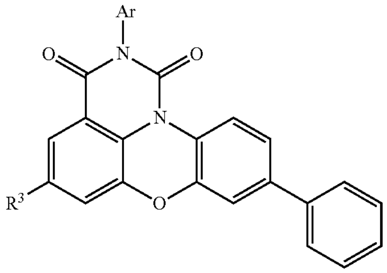
where Ar, R, $R^1$, $R^2$ and $R^3$ each independently have a definition given above or a preferred definition given above or hereinafter.
Preferred compounds of the formulae (3g), (3h), (3i) and (3j) are compounds of the formulae (12) to (33) which may be substituted by one or more $R^1$ radicals
(12)
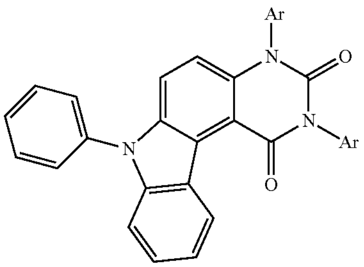
-continued
(13)
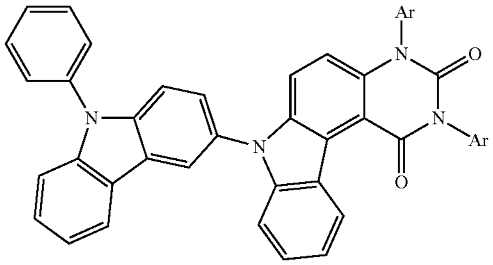
(14)
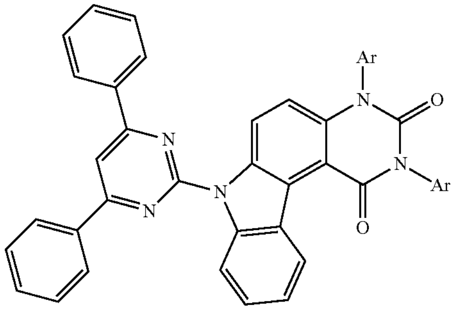
(15)
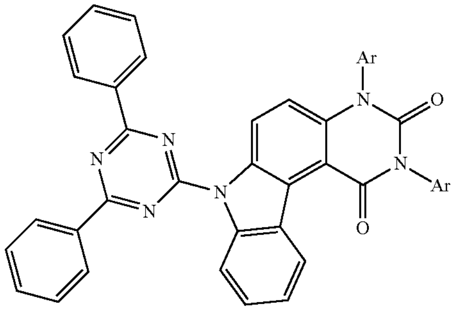
(16)
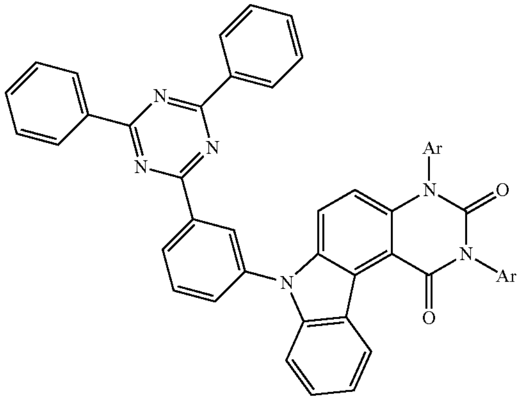
(17)
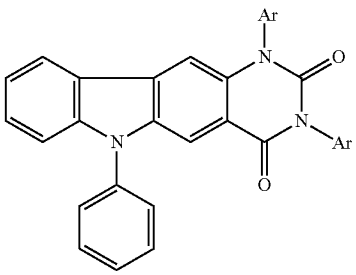

-continued
(18)
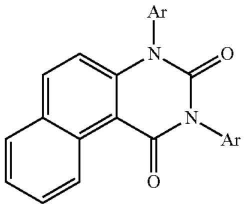
(19)
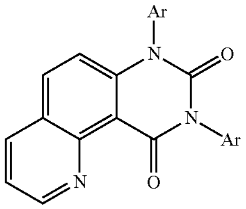
(20)
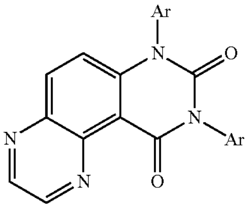
(21)
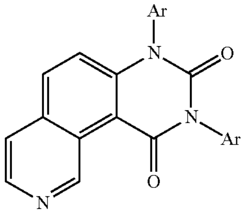
(22)
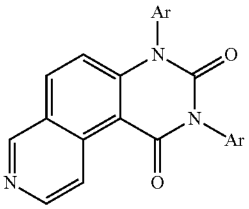
(23)
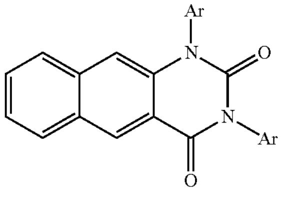
(24)
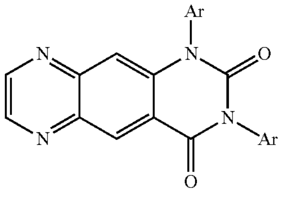
-continued
(25)
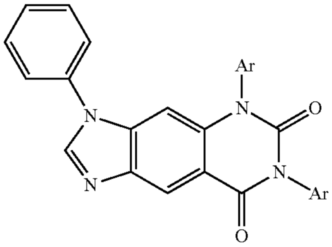
(26)
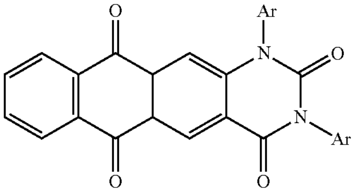
(27)
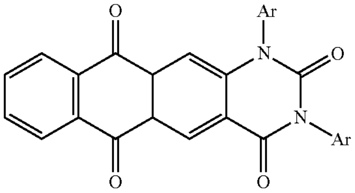
(28)
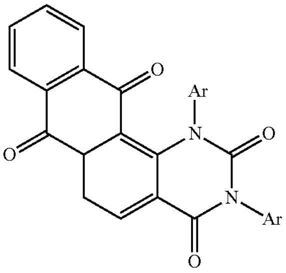
(29)
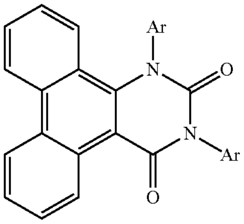
(30)
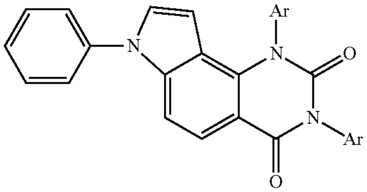
(31)
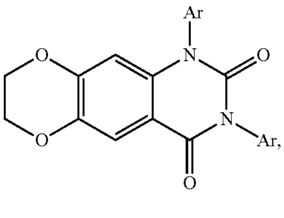
, -continued (32)

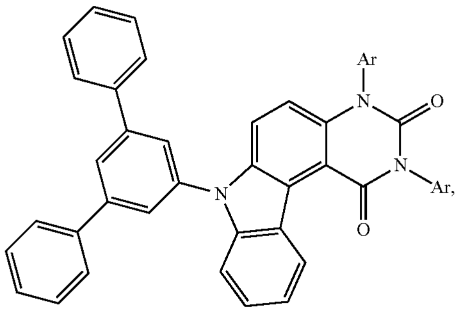

(33)

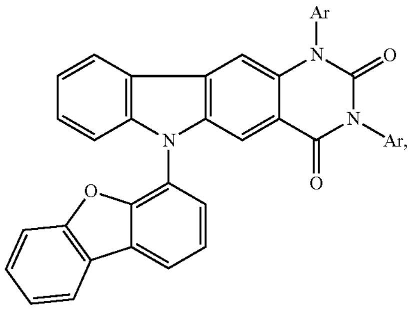

where Ar, $R^1$ and $R^2$ each independently have a definition given above or a preferred definition given above or hereinafter. In the compounds of the formulae (12) to (33), $R^1$ is most preferably H.

In compounds of the formula (2) as described above or described as preferred compounds of the formulae (2a), (3), (3a) to (3j), (4), (4a), (5) and (5a), (6) to (33) or (6*) to (11*), R or $R^3$ is in each case independently preferably H or an aromatic or heteroaromatic ring system having 5 to 24 ring atoms, as described above. R is in each case independently more preferably

H, phenyl,

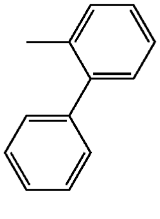

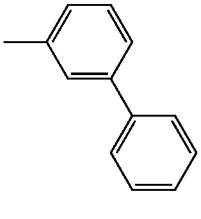

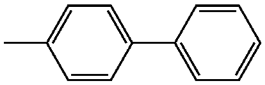,

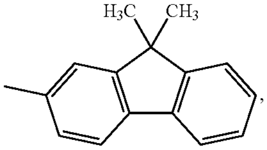,

-continued

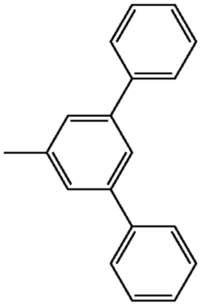,

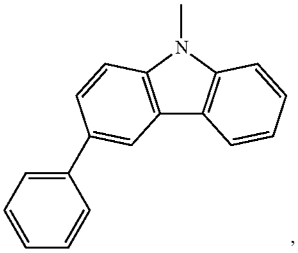,

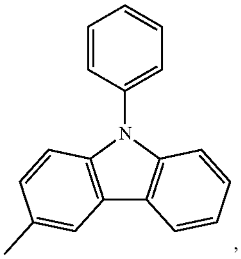,

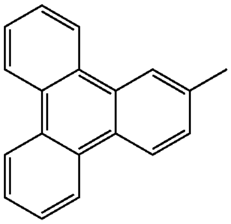,

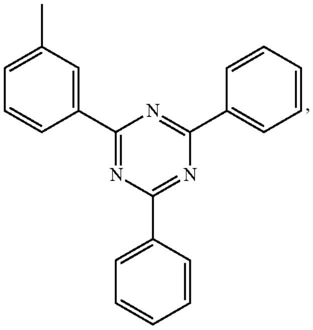,

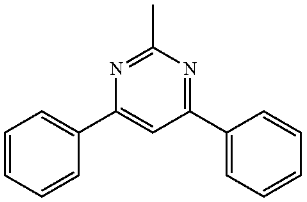,

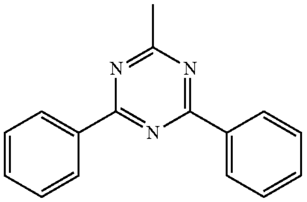,

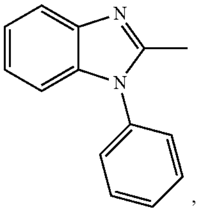,

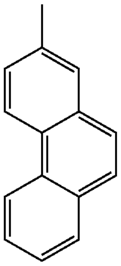,

-continued
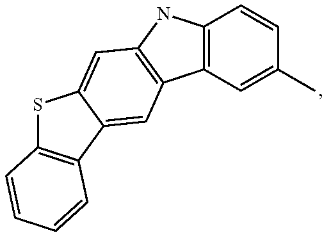
,
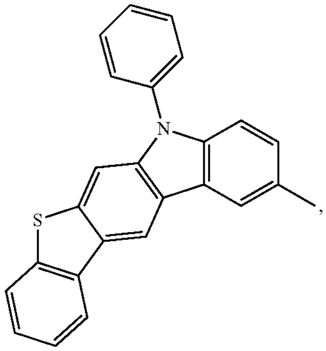
,
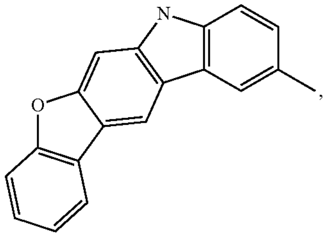
,
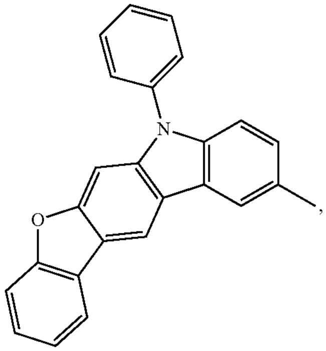
,
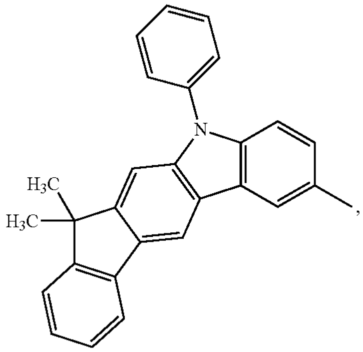
,
-continued
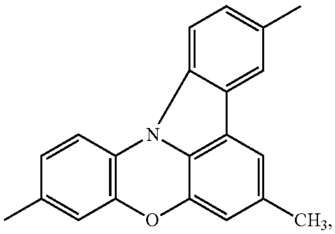
,
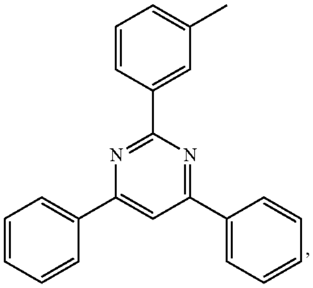
,
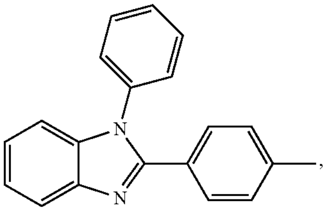
,
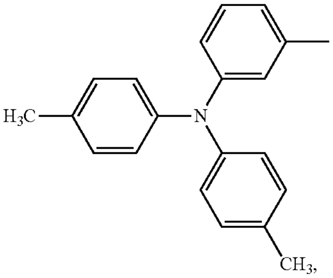
,
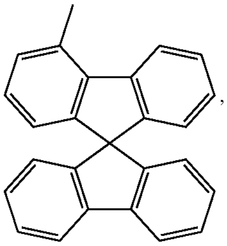
,
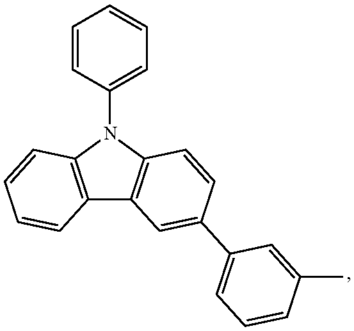
, -continued
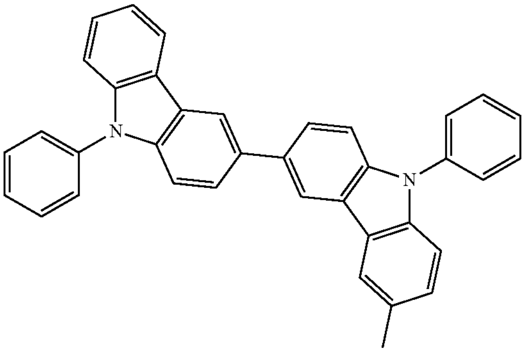
,
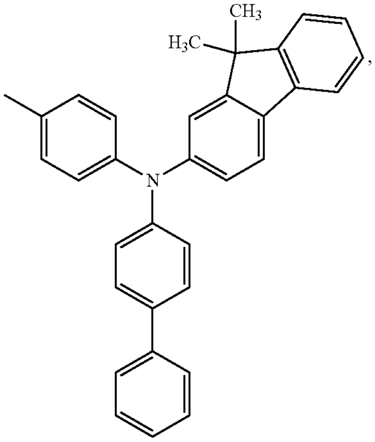
,
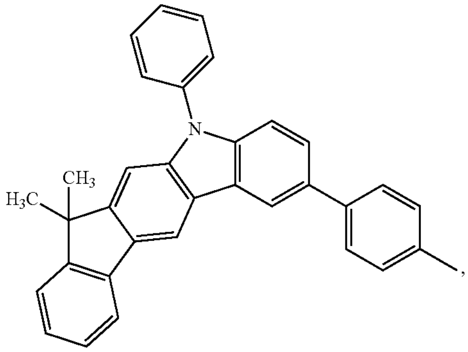
,
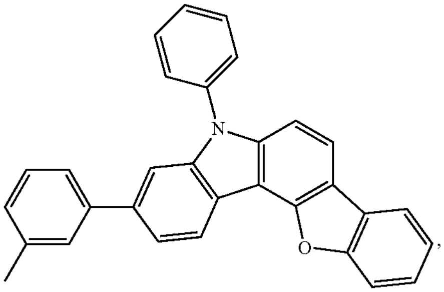
,
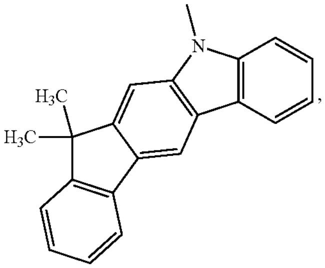
,
-continued
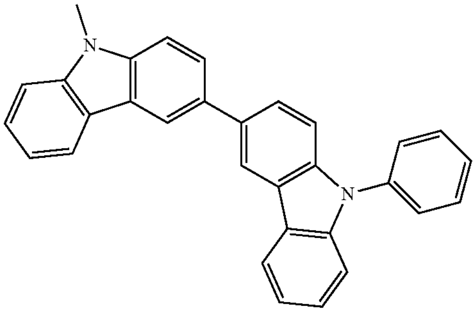
,
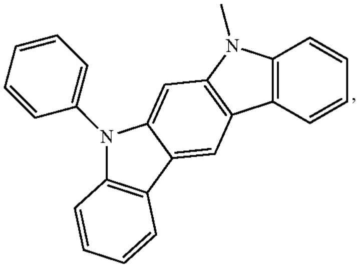
,
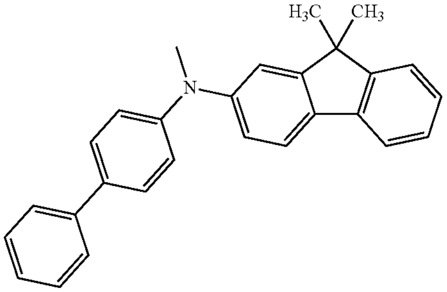
,
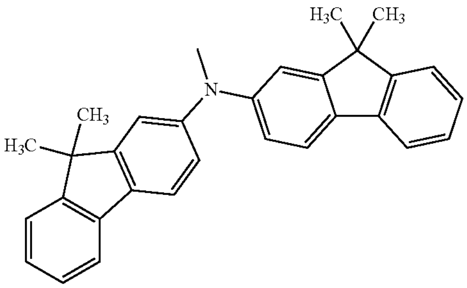
,
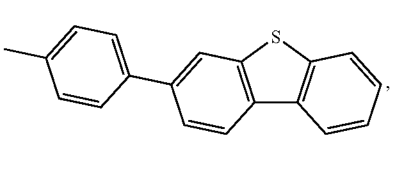
,
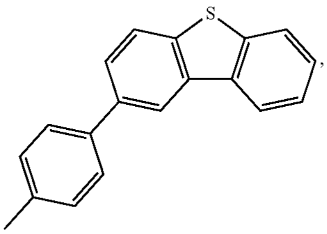
, -continued
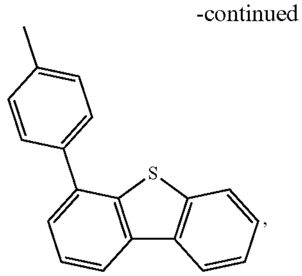
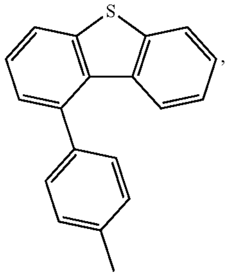
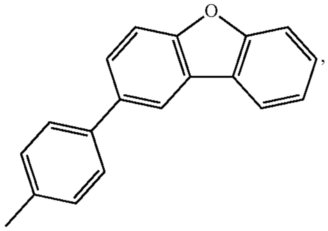
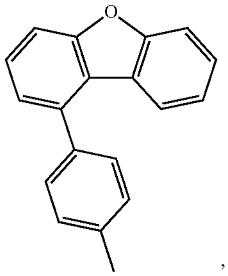
,
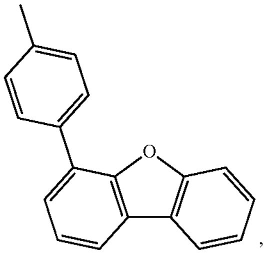
,
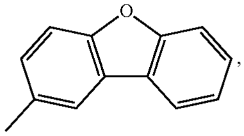
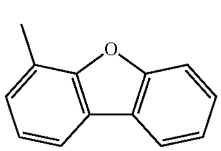
or
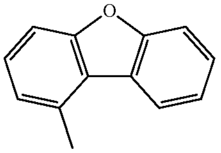
.
R is in each case independently most preferably H or phenyl.
$R^3$ is in each case independently more preferably phenyl,
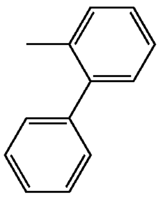
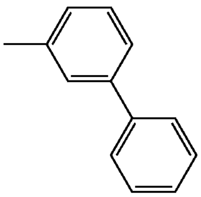
-continued
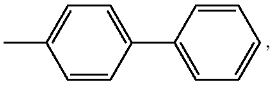
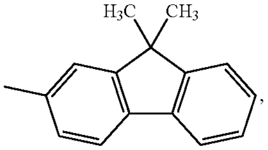
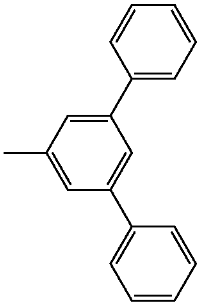
,
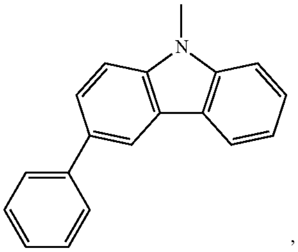
,
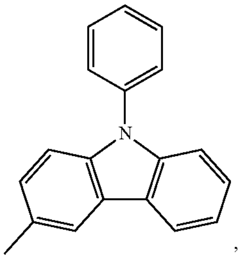
,
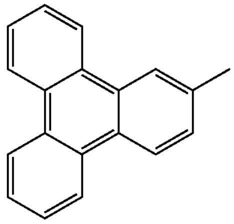
,
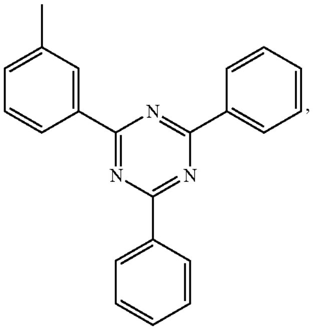
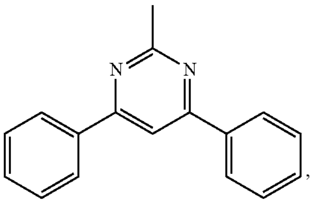
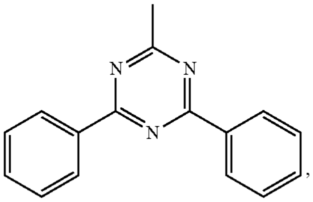

-continued
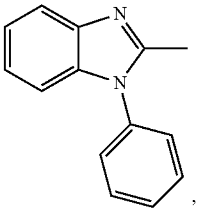,
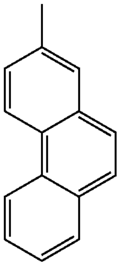,
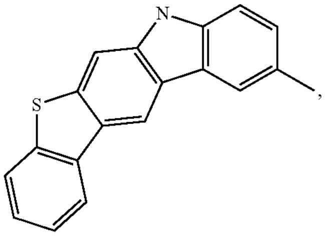,
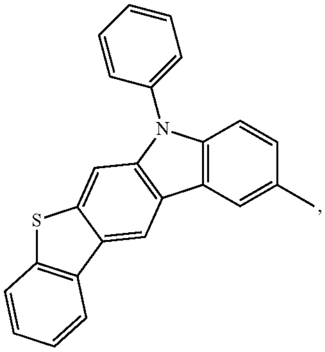,
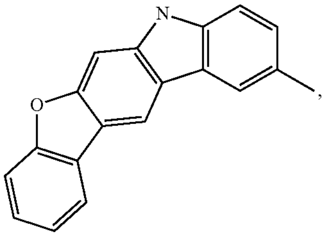,
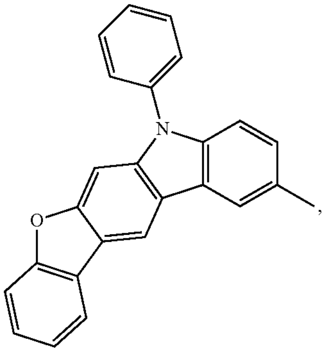,
-continued
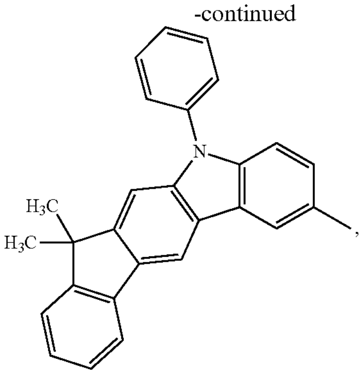,
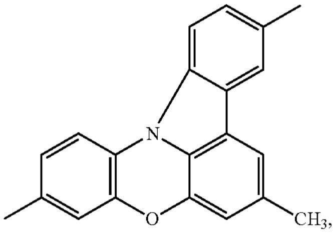,
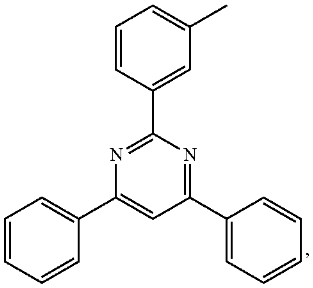,
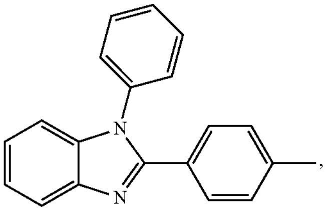,
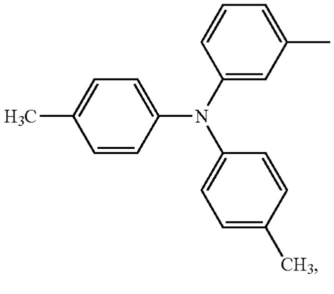,
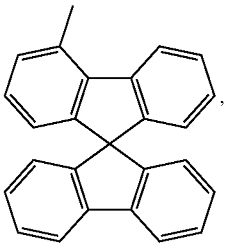, -continued
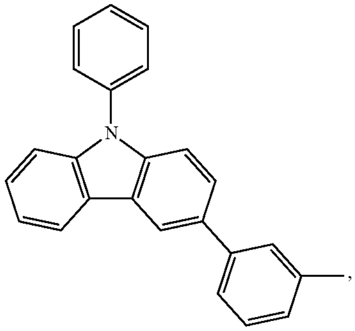
,
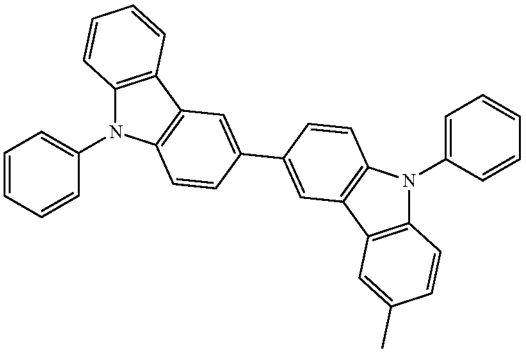
,
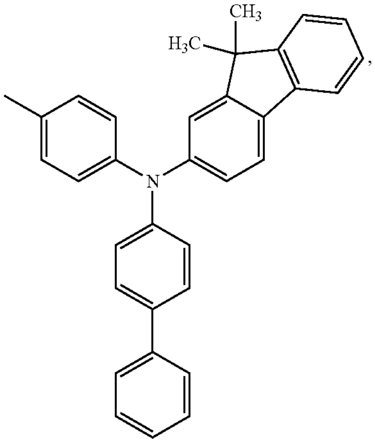
,
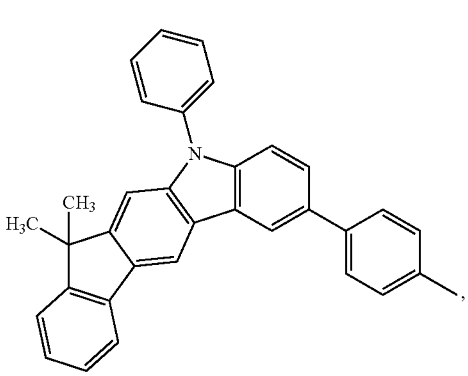
,
-continued
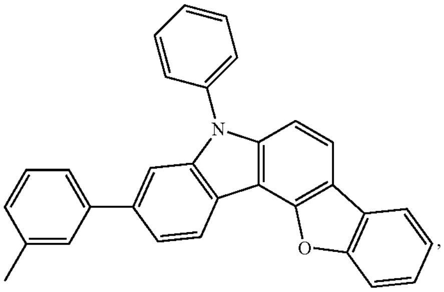
,
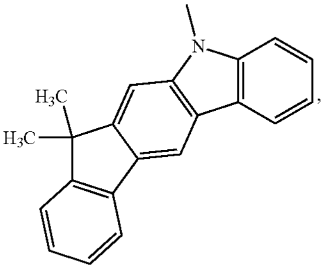
,
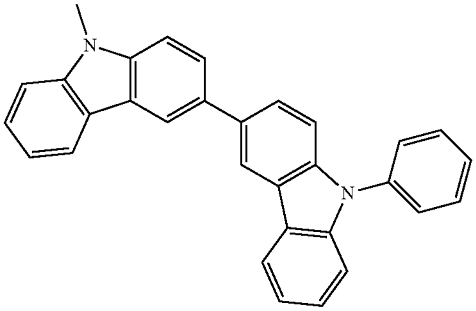
,
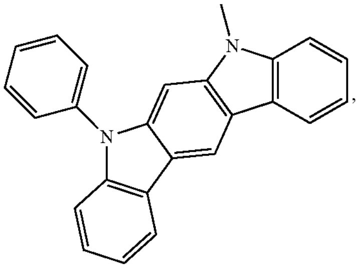
,
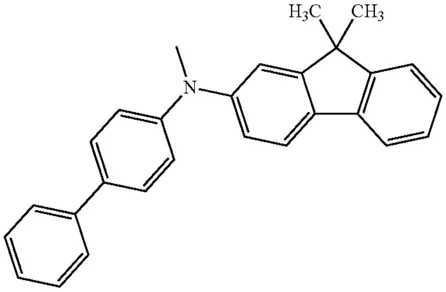
,
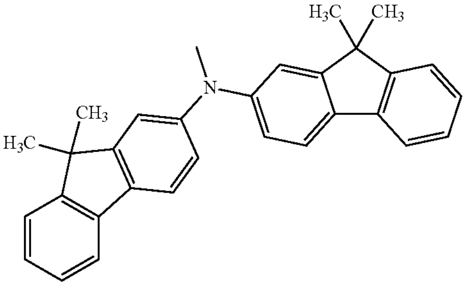
, -continued

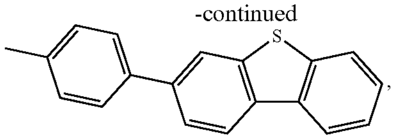,

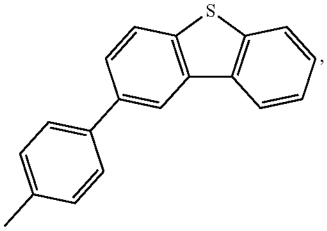,

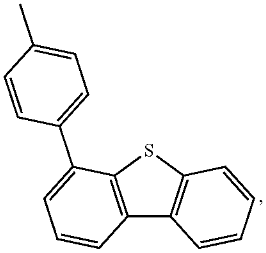,

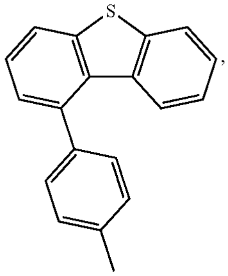,

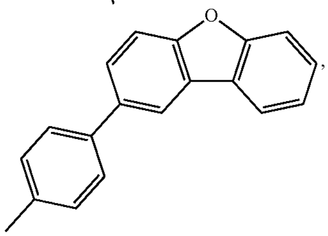,

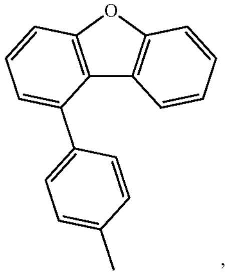,

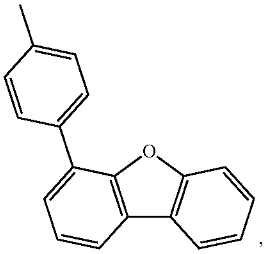,

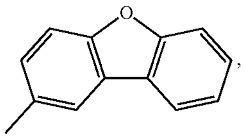,

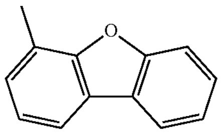 or 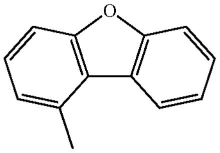.

In compounds of the formula (2) as described above or described as preferred compounds of the formulae (2a), (3), (3a) to (3k), (4), (4a), (5) and (5a), (6) to (33), (6*) to (11*), Ar is in each case independently preferably a ring system corresponding to the formulae (Ar-1) to (Ar-145).

The compounds of the formula (2) to be used in accordance with the invention, as described above or described as preferred, can be prepared by synthesis steps known in principle to those skilled in the art, as described hereinafter.

Aryl-substituted compounds of the formula (2) as described above or described as preferred can be prepared according to scheme 1:

Scheme 1

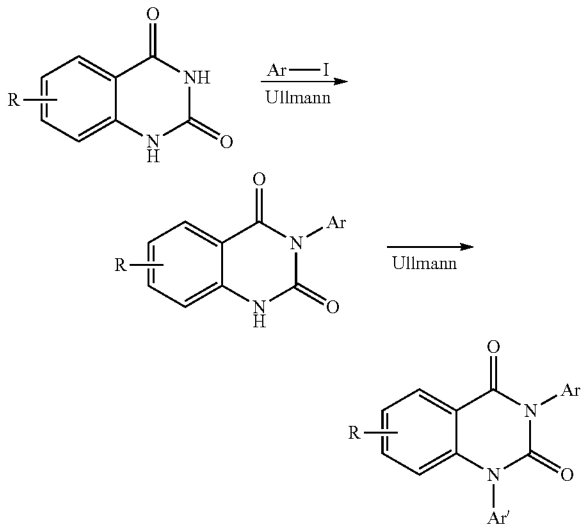

In scheme 1, the 2,4(1H,3H)-quinazoline base skeleton is converted in an Ullmann reaction to a symmetric or unsymmetric compound of the formula (2) as described above. The reaction conditions and starting materials for the Ullmann reaction are known to those skilled in the art.

Scheme 2 shows a further alternative for preparation of the aryl-substituted compounds of the formula (2) as described above, wherein optionally R-substituted quinoxaline is reduced and the amine formed is correspondingly arylated by a Buchwald reaction and subsequently oxidized with an oxidizing agent, for example potassium permanganate.

Scheme 2

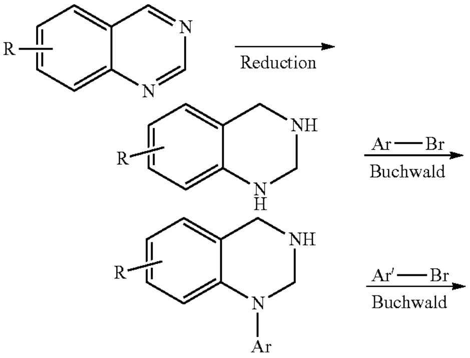

-continued

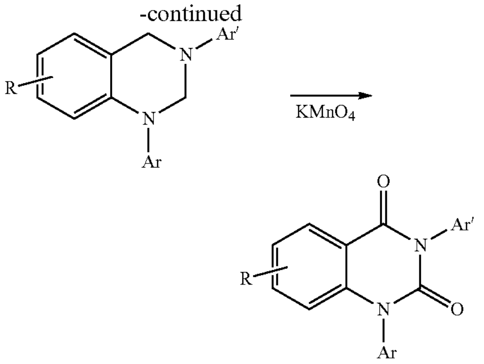

In scheme 2, R and Ar are as defined above. The label Ar' means merely that Ar is independent in each case. The reaction conditions for a reduction and the Buchwald arylation are known to those skilled in the art. The reduction can be effected, for example, by reaction with sodium tetrahydridoborate.

Scheme 3 shows an alternative preparation of the compounds of the formula (2) as described above, wherein the starting material used is an optionally R-substituted 2-amino-5-bromobenzoic acid.

Scheme 3

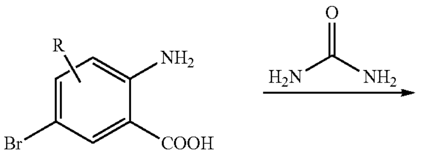

-continued

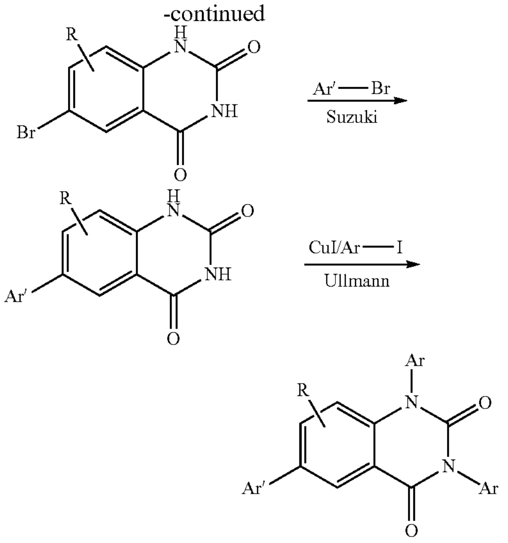

Scheme 4 shows an alternative preparation of the compounds of the formula (2) as described above, wherein the starting material used is an optionally R-substituted 2-amino-5-bromobenzoic acid.

In scheme 3 and scheme 4, the labels R and Ar are as defined above. The label Ar' means merely that Ar is independent in each case.

The reaction conditions for a Suzuki reaction, an Ullmann reaction or a Buchwald reaction are known to those skilled in the art.

Scheme 4

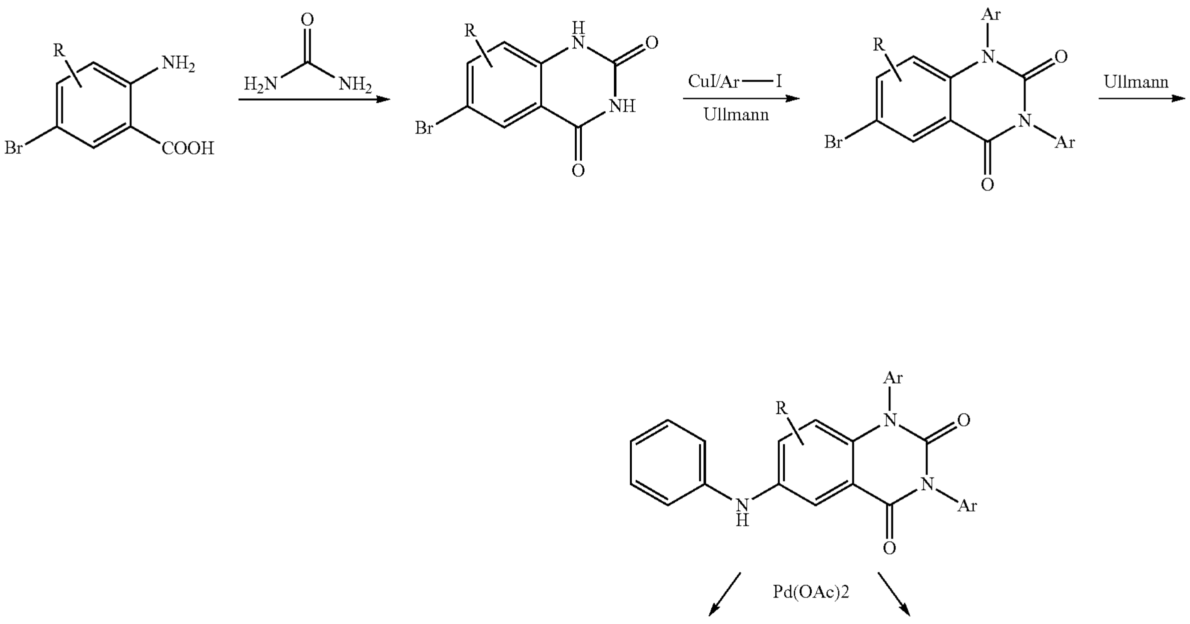

-continued

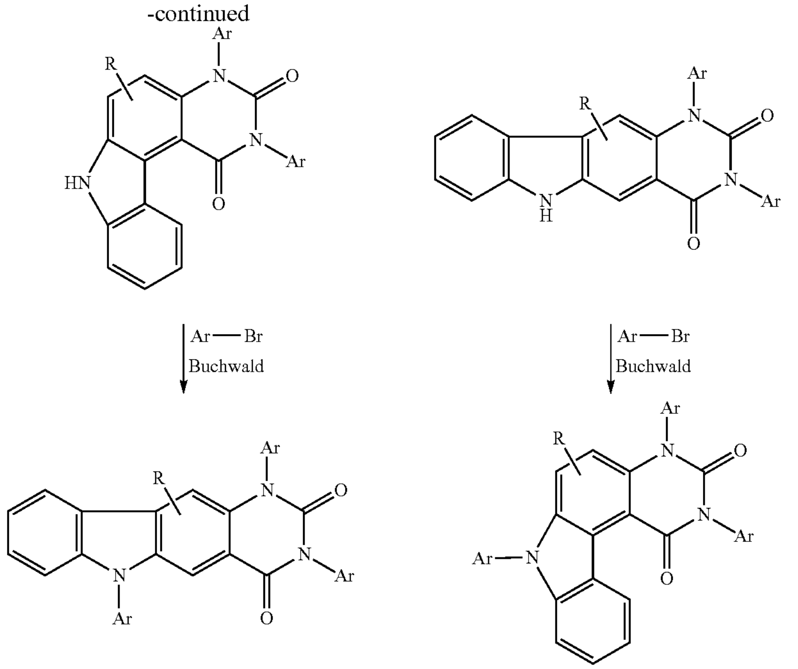

Suitable reaction conditions are also described in the implementation section.

Compounds of the formula (1) in which Y is

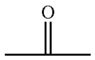

can be described synonymously by the formula (34)

(34)

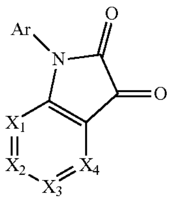

where $X_1$, $X_2$, $X_3$, $X_4$, Ar, R, $R^1$ and $R^2$ each independently have a definition given in formula (1).

In a preferred embodiment of compounds of the formula (34), $X_1$, $X_2$, $X_3$ and $X_4$ are CR. More preferably, in this embodiment, three R substituents are H and one substituent preferably corresponds to phenyl,

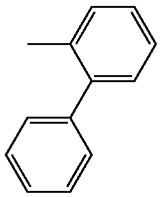

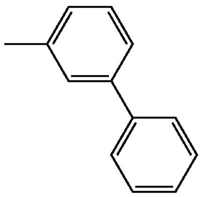

-continued

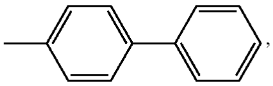
,

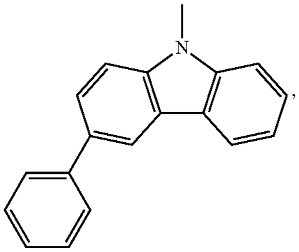
,

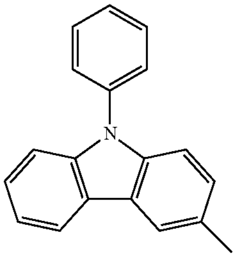
or

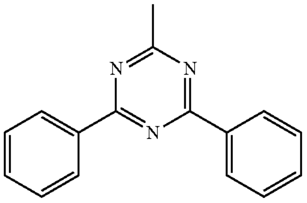
, or two adjacent R substituents are connected to one another so as to form a monocyclic or polycyclic, aliphatic, aromatic or heteroaromatic ring system.

Most preferably, in this embodiment, three R substituents are H and one substituent preferably corresponds to phenyl,

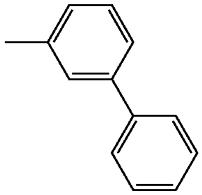

or

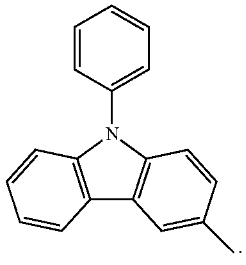

Embodiments of the compound of the formula (34) in which two adjacent R substituents are connected to one another so as to form a monocyclic or polycyclic, aliphatic, aromatic or heteroaromatic ring system are preferably described by the compounds of the formulae (35) to (38)

(35)

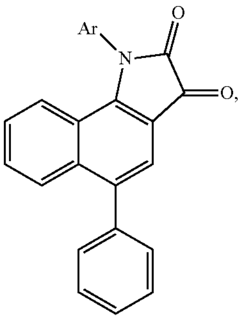

(36)

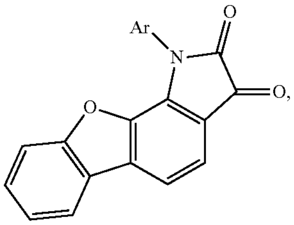

(37)

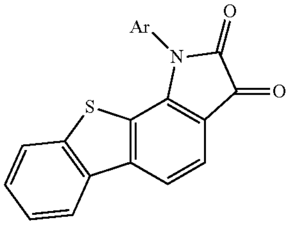

or (38)

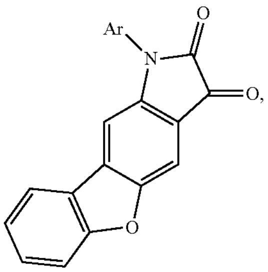

where Ar has a definition given above or a preferred definition given hereinafter.

A preferred embodiment of the electronic device includes compounds of the formula (39) in which two compounds of the formula (1) in which Y is

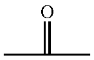

are connected to one another via an aromatic or heteroaromatic ring system (39)

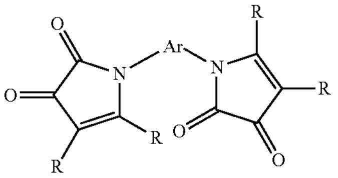

where Ar, R, $R^1$ and $R^2$ each independently have a definition given above or a preferred definition given hereinafter. The connecting aromatic or heteroaromatic ring system Ar is preferably phenylene or corresponds to one of the formulae (Ar-146) to (Ar-152).

Preferably, in compounds of the formula (39), the R substituents are H or phenyl or they are connected to one another so as to form a monocyclic or polycyclic, aliphatic, aromatic or heteroaromatic ring system.

Preferred compounds of the formula (39) correspond to the formulae (40) and (41)

(40)

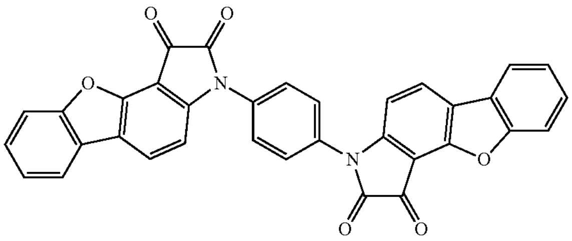

(41)

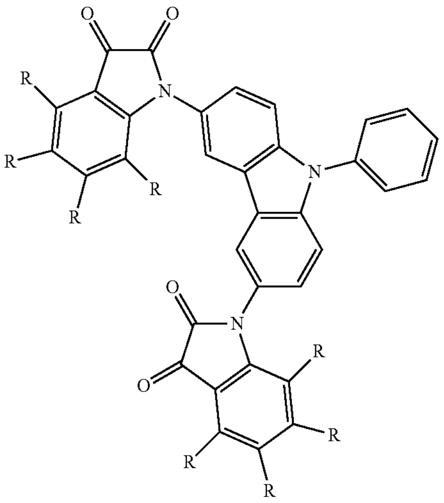

where R in each case independently has a definition given above or a preferred definition given hereinafter. In the compounds of the formula (41), most preferably, 3 R substituents are H and 1 R substituent is phenyl.

In one embodiment of compounds of the formulae (34) to (41) as described above or described as preferred with regard to the R substituents, Ar is preferably phenyl, naphthyl, anthracenyl, phenanthrenyl or one of the radicals of the formulae (Ar-1) to (Ar-145)

In one embodiment of compounds of the formulae (34) to (41) as described above or described as preferred with regard to the R substituents, Ar is more preferably one of the radicals of the formula (Ar-2), (Ar-4), (Ar-18), (Ar-27), (Ar-48), (Ar-113), (Ar-126) or (Ar-129).

Compounds of the formula (34) can be prepared proceeding from diarylamines by reaction with oxalyl chloride, for example. Scheme 5 describes reactions of this kind, where Ar and R have a definition or preferred definition given above:

Scheme 5

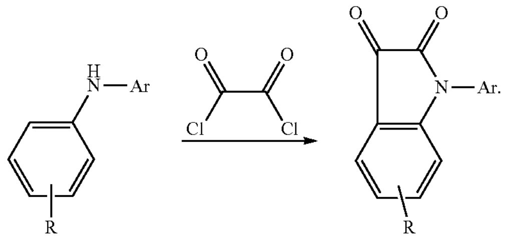

Alternatively, compounds of the formula (34) can be prepared by reacting a commercially available 1H-indole-2,3-dione with an aryl halide under Ullmann reaction conditions or with an arylboronic acid according to the literature Organic Letters, 2004, 6, 18, 3079-82. It is optionally also possible to prepare 1H-indole-2,3-dione from an aniline derivative. Scheme 6 summarizes this alternative synthesis, where Ar and R have a definition or preferred definition given above:

Scheme 6

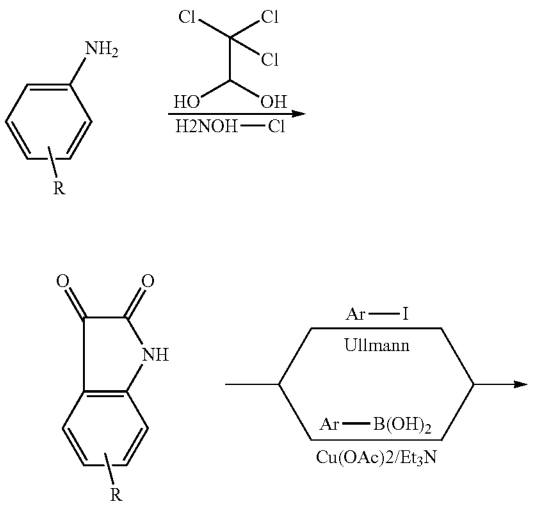

-continued

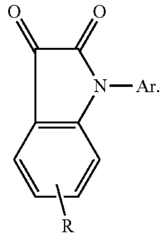

Compounds of the formula (1) in which Y is

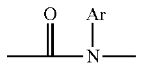

can be described synonymously by the formula (42)

(42)

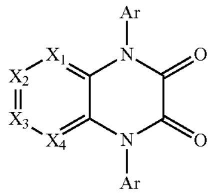

where $X_1$, $X_2$, $X_3$, $X_4$, Ar, R, $R^1$ and $R^2$ each independently have a definition given in formula (1).

A preferred embodiment of the electronic device of the invention includes compounds of the formula (42) in which the variables $X_1$, $X_2$, $X_3$ and $X_4$ are CR, and R and Ar each independently have one of the definitions given in formula (1).

The invention accordingly further provides the electronic device of the invention as described above or described as preferred, where, in formula (42), the variables $X_1$, $X_2$, $X_3$ and $X_4$ are CR, and R and Ar each independently have one of the definitions given in formula (1).

A preferred embodiment of the electronic device of the invention includes compounds of the formula (42) as described above or described as preferred, where $X_1$, $X_2$, $X_3$ and $X_4$ are each independently CR and R is in each case independently H or an aromatic or heteroaromatic ring system which has 5 to 60 aromatic ring atoms and may be substituted by one or more $R^1$ radicals in each case, or where two or more adjacent R substituents may form a monocyclic or polycyclic, aliphatic, aromatic or heteroaromatic ring system which may be substituted by one or more $R^1$ radicals, or where the R substituent in $X_1$ and/or the R substituent in $X_4$ together with the adjacent N—Ar in each case form(s) a monocyclic or polycyclic, aliphatic, aromatic or heteroaromatic ring system which may be substituted by one or more $R^1$ radicals.

$R^1$ is preferably H, D, F, CN or a straight-chain or branched alkyl group having 1 to 12 carbon atoms.

$R^1$ is more preferably H, F, CN, a straight-chain or branched alkyl group having 1 to 4 carbon atoms.

The formula (43) accordingly describes compounds of the formula (42) in which the $X_1$ to $X_4$ substituents are CR, (43)

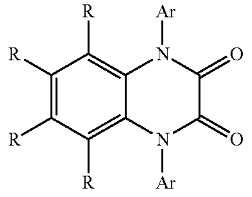

where Ar, $R^1$ and $R^2$ each independently have a definition given above or a preferred definition given hereinafter and R is H or an aromatic or heteroaromatic ring system which has 5 to 60 aromatic ring atoms and may be substituted in each case by one or more $R^1$ radicals.

In this embodiment of the electronic device comprising at least one compound of the formula (43), R is more preferably in each case independently H, phenyl,

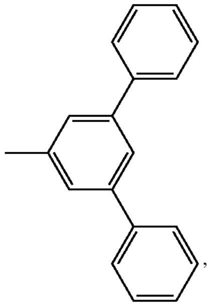

,

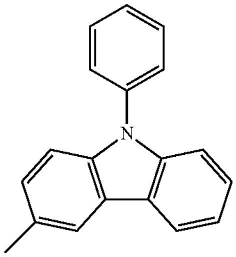

,

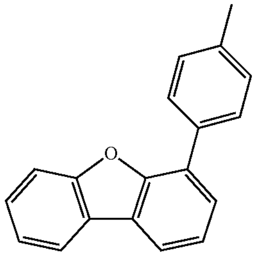

or

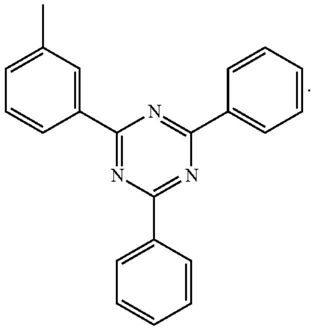

.

The formulae (44), (45) and (46) accordingly describe compounds of the formula (42) where $X_1$, $X_2$, $X_3$ and $X_4$ are each independently CR and two or more adjacent R substituents form a monocyclic or polycyclic, aliphatic, aromatic or heteroaromatic ring system which is indicated by the symbol "(A" and the rest of the R substituents are H (44)

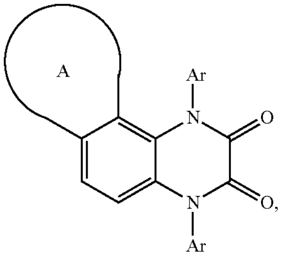

(45)

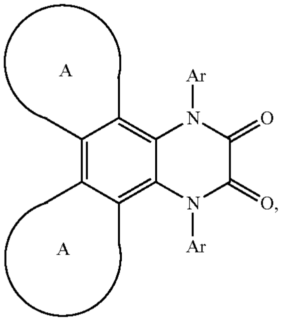

(46)

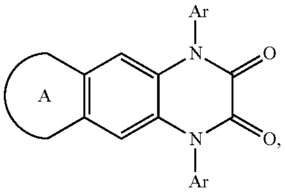

where Ar, $R^1$ and $R^2$ each independently have a definition given above or a preferred definition given hereinafter.

Preferred compounds of the formulae (44) to (46) correspond to the compounds of the formulae (47) to (51)

(47)

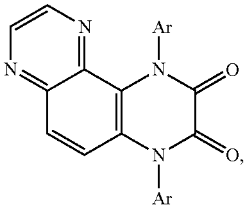

(48)

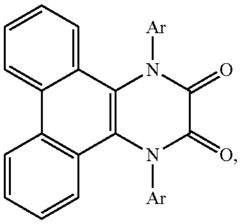

-continued (49)

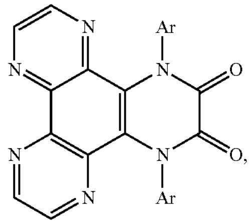

(50)

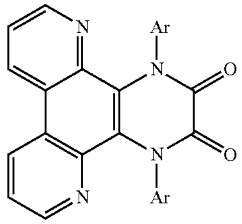

or (51)

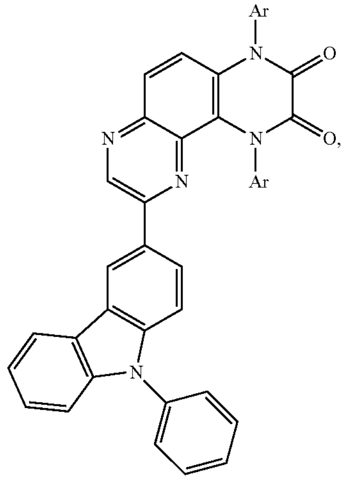

where Ar, $R^1$ and $R^2$ each independently have a definition given above or a preferred definition given hereinafter.

A preferred embodiment of the electronic device of the invention includes compounds of the formula (42) where $X_1$, $X_2$, $X_3$ and $X_4$ are each independently CR, where the R substituent in $X_1$ and/or the R substituent in $X_4$ together with the adjacent N—Ar in each case form a monocyclic or polycyclic, aliphatic, aromatic or heteroaromatic ring system which may be substituted by one or more $R^1$ radicals, and Ar, R, $R^1$ and $R^2$ each independently have a definition given above or a preferred definition given hereinafter.

The invention likewise provides the compounds of the formula (42)

(42)

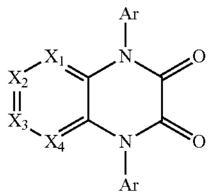

where $X_1$, $X_2$, $X_3$ and $X_4$ are each independently CR, where the R substituent in $X_1$ and/or the R substituent in $X_4$ together with the adjacent N—Ar in each case form a monocyclic or polycyclic, aliphatic, aromatic or heteroaromatic ring system which may be substituted by one or more $R^1$ radicals, and Ar, R, $R^1$ and $R^2$ each independently have a definition given above or a preferred definition given hereinafter.

The formula (52) accordingly describes compounds of the formula (42) where $X_1$, $X_2$, $X_3$ and $X_4$ are each independently CR, and the R substituent of $X_1$ and/or the R substituent of $X_4$ together with the adjacent N—Ar in each case form a monocyclic or polycyclic, aliphatic, aromatic or heteroaromatic ring system which may be substituted by one or more $R^1$ radicals, (52)

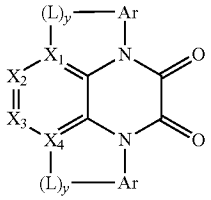

where y is in each case independently 0 or 1,

L is in each case independently $—C(R^1)_2—$ and Ar, R, $R^1$ and $R^2$ each independently have a definition given above or a preferred definition given hereinafter.

Preferred compounds of the formula (52) are described by the formulae (53) to (55)

(53)

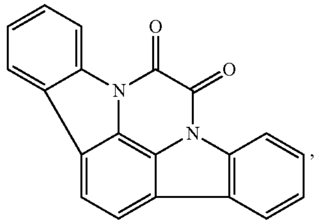

, (54)

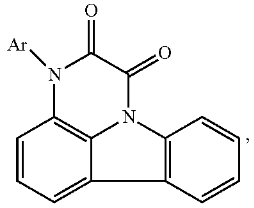

, (55)

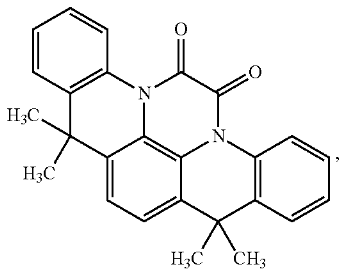

, which may be substituted by one or more $R^1$ radicals, and Ar, $R^1$ and $R^2$ each independently have a definition given above.

In the compounds of the formulae (42) to (55), Ar is in each case independently preferably an aromatic or heteroaromatic ring system which has 5 to 24 aromatic ring atoms and may be substituted by one or more $R^1$ radicals. More preferably, Ar in this embodiment of the invention is substituted by a preferred $R^1$ radical as described above. More preferably, in this embodiment, Ar is unsubstituted.

In the compounds of the formulae (42) to (55), Ar is in each case independently more preferably
phenyl, naphthyl, anthracenyl, phenanthrenyl or one of the radicals of the formulae (Ar-1) to (Ar-145).

The invention further provides the novel compounds of the formula (56)

(56)

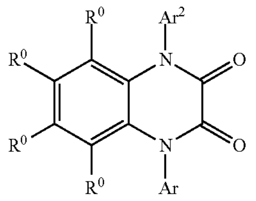

where

Ar is an aromatic or heteroaromatic ring system which has 5-60 aromatic ring atoms and may be substituted by one or more nonaromatic $R^1$ radicals, $Ar^2$ is an aromatic ring system which has 13 to 40 carbon atoms or a heteroaromatic ring system which has 4 to 40 carbon atoms and may be substituted by one or more nonaromatic $R^1$ radicals, $R^0$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic ring system which has 5 to 30 aromatic ring atoms and in which one or more hydrogen atoms may be replaced by D, F, CI, Br, I, CN, or a straight-chain or branched alkyl group having 1 to 10 carbon atoms or a straight-chain or branched alkenyl group having 2 to 10 carbon atoms, and where $R^1$ and R each independently have a definition given in formula (1).

The compounds of the formula (56) are specific compounds of the formula (42) as described above.

In preferred compounds of the formula (56), $R^0$ is H or phenyl.

In particularly preferred compounds of the formula (56), $R^0$ is H or phenyl and Ar is in each case independently phenyl, naphthyl, anthracenyl, phenanthrenyl or one of the radicals of the formulae (Ar-1) to (Ar-133).

In particularly preferred embodiments of the formula (56), $R^0$ is H or phenyl and $Ar^2$ is in each case independently one of the radicals of the formulae (Ar-1) to (Ar-133).

In very particularly preferred compounds of the formula (56), $R^0$ is H or phenyl and $Ar^2$ is in each case independently one of the radicals of the formulae (Ar-1) to (Ar-145) and Ar is in each case independently phenyl, naphthyl, anthracenyl, phenanthrenyl or one of the radicals of the formulae (Ar-1) to (Ar-145).

A preferred embodiment of the electronic device of the invention includes compounds of the formula (42) in which at least one variable from the group of $X_1$, $X_2$, $X_3$ and $X_4$ is N and the rest of the variables are CR or N, and R and Ar each independently have one of the definitions given in formula (1).

The invention accordingly further provides the electronic device of the invention as described above or described as preferred, where, in formula (42), at least one variable from the group of $X_1$, $X_2$, $X_3$ and $X_4$ is N and the rest of the variables are CR, and R and Ar each independently have one of the definitions given in formula (1).

Preferred compounds of the formula (42) in which at least one variable from the group of $X_1$, $X_2$, $X_3$ and $X_4$ is N and the rest of the variables are CR or N, and R and Ar each independently have one of the definitions given in formula (1) conform to the formula (57)

(57)

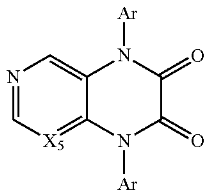

where $X_5$ is CR or N and Ar has a definition given in formula (1).

The invention likewise further provides the compounds of the formula (57)

(57)

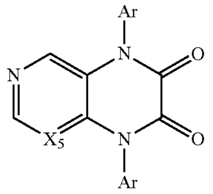

where $X_5$ is CR or N and Ar and R have a definition given in formula (1).

The compounds of the formula (57) are specific compounds of the formula (42) as described above.

In preferred compounds of the formula (57), Ar is in each case independently phenyl, naphthyl, anthracenyl, phenanthrenyl or one of the radicals of the formulae (Ar-1) to (Ar-133) which may optionally be mono- or polysubstituted by $R^1$, and R and $R^1$ have a definition given or a definition given with preference in formula (1).

In particularly preferred compounds of the formula (57), Ar is in each case independently phenyl, naphthyl, anthracenyl, phenanthrenyl or one of the radicals of the formulae (Ar-1) to (Ar-133) which may optionally be mono- or polysubstituted by $R^1$, and R is H.

The compounds of the formula (42) to be used in accordance with the invention or the inventive compounds of the formula (42), as described above or described as preferred, can be prepared by synthesis steps known in principle to those skilled in the art, as described hereinafter. Some of the suitable starting materials as shown in the schemes which follow are commercially available, or they can be prepared by known synthesis methods.

1,4-Dihydro-1,4-diaryl-2,3-quinoxalinedione derivatives of the formula (42) are synthesized, for example, by reacting an ortho-dibromo-substituted aromatic with a primary amine or an ortho-diamino-substituted aromatic with an aryl bromide in a Hartwig-Buchwald coupling and then using ethyl oxalate to conduct a reaction as described in scheme 7 where R and Ar have a definition as described above or described as preferred:

Scheme 7

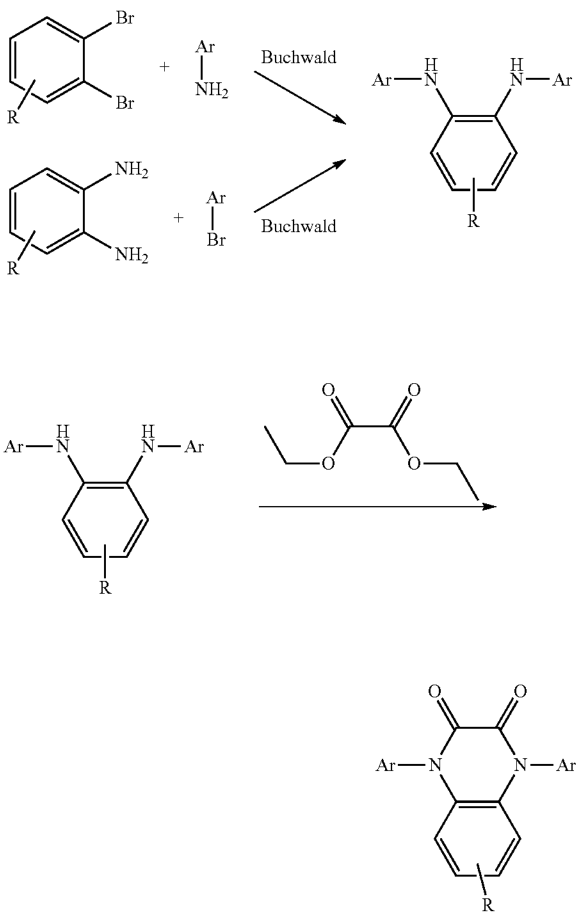

Alternatively, the synthesis can take place according to scheme 8 where R and Ar have a definition or preferred definition given above. The label Ar' means that Ar each independently has a definition as given above.

Scheme 8

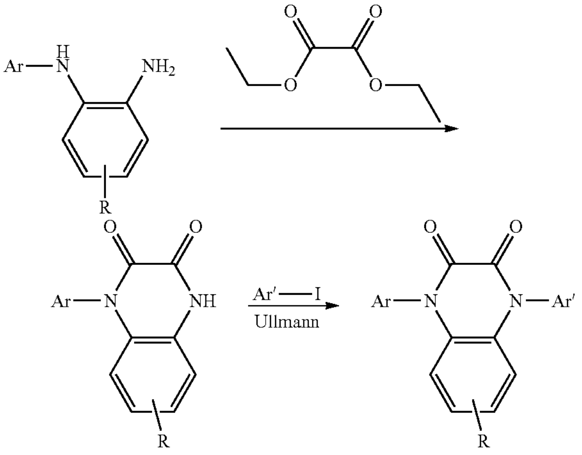

The reaction conditions for an Ullmann reaction are known to those skilled in the art and are likewise described in the implementation section, Alternatively, the synthesis can take place according to scheme 9 where R and Ar have a definition or preferred definition given above. The label Ar' means that Ar each independently has a definition as given above.

Scheme 9

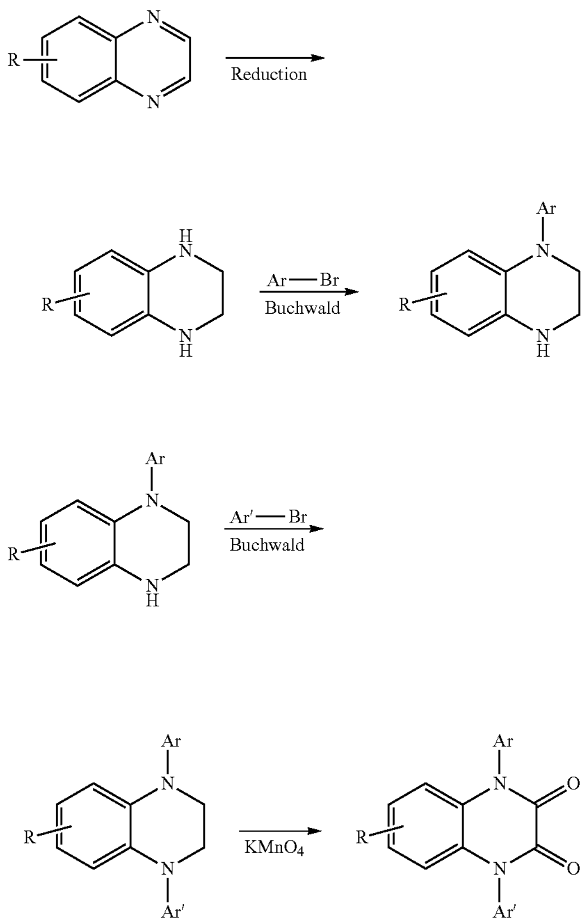

Scheme 9 describes reduction of optionally R-substituted quinoxaline and corresponding arylation of the amine formed by a Buchwald reaction, followed by oxidation with an oxidizing agent, for example potassium permanganate. The reaction conditions for a Buchwald reaction are known to those skilled in the art. The reducing agent used may be sodium tetrahydridoborate.

There follows an enumeration of preferred compounds of the formula (1) present in the electronic device of the invention. The individual compounds can likewise be assigned to a compound which has been specified as preferred and is of the formulae (2), (2a), (3), (3a) to (3j), (4), (4a), (5) and (5a), (6) to (11), (6*) to (11*), (12) to (33), (34) to (41) and (42) to (57). The individual compounds are usable with very particular preference in the electronic device.

Preferred compounds of the formula (1) as described above or described as preferred are:

[Compound 1]
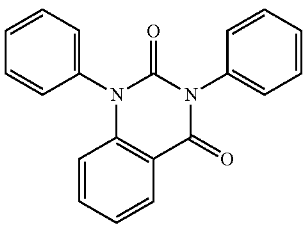
[Compound 2]
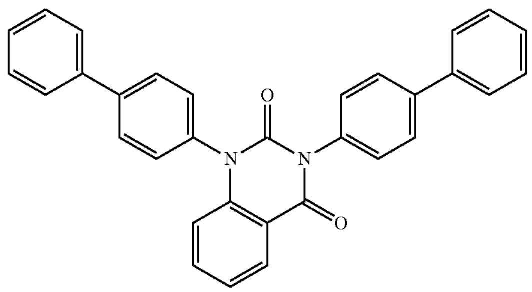
[Compound 3]
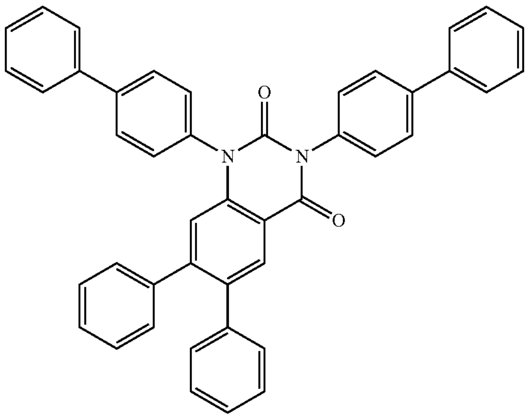
[Compound 4]
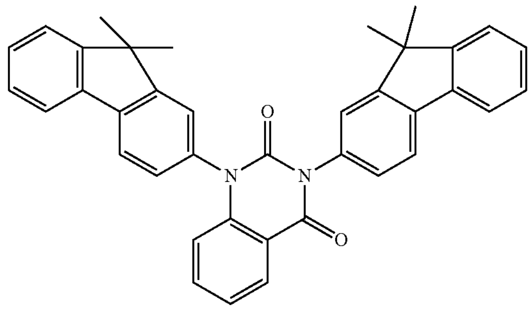
[Compound 5]
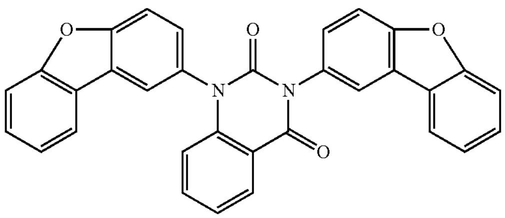
[Compound 6]
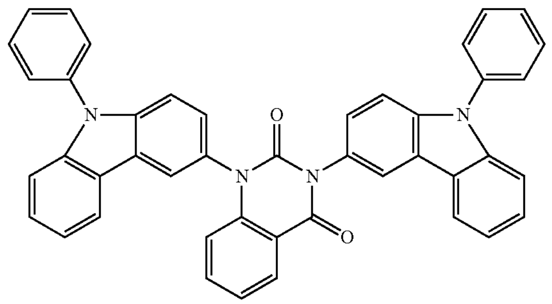
[Compound 7]
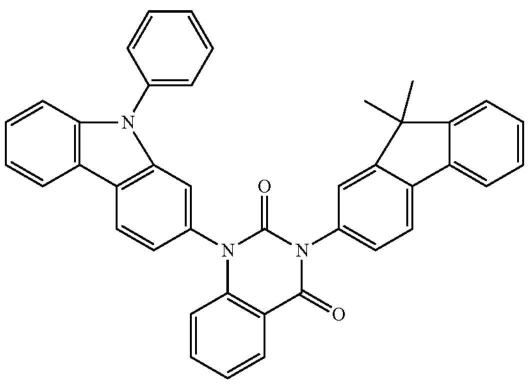
[Compound 8]
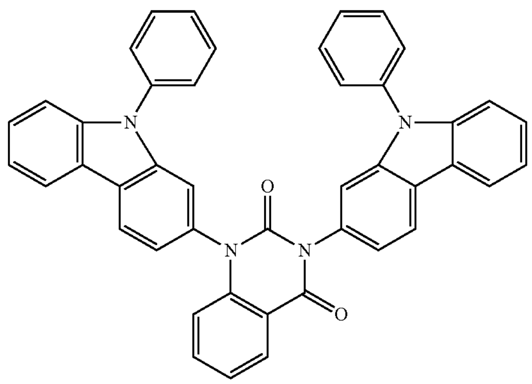

-continued
[Compound 9]
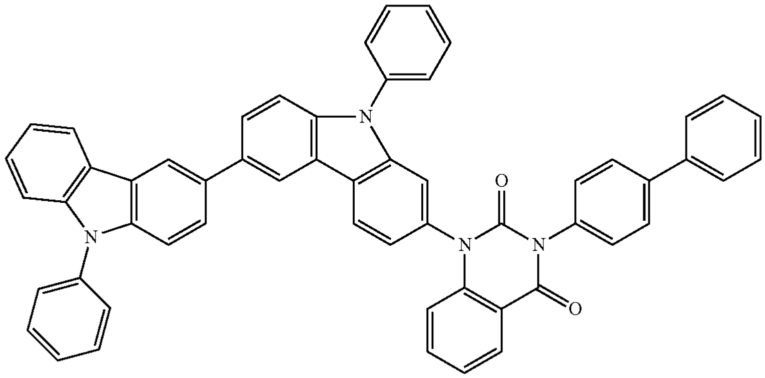
[Compound 10]
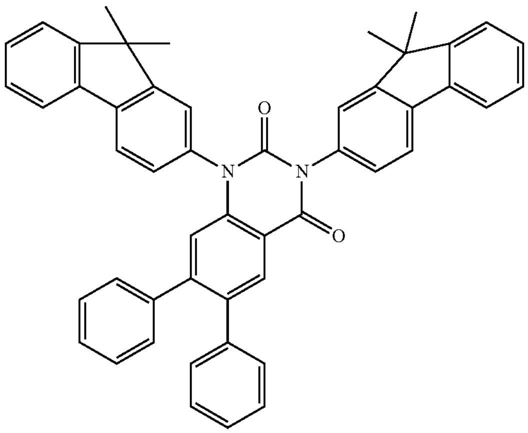
[Compound 11]
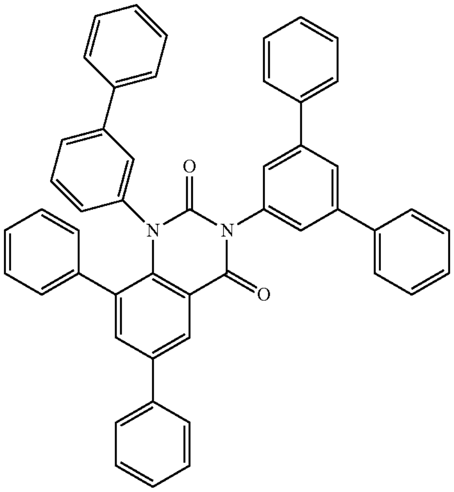
[Compound 12]
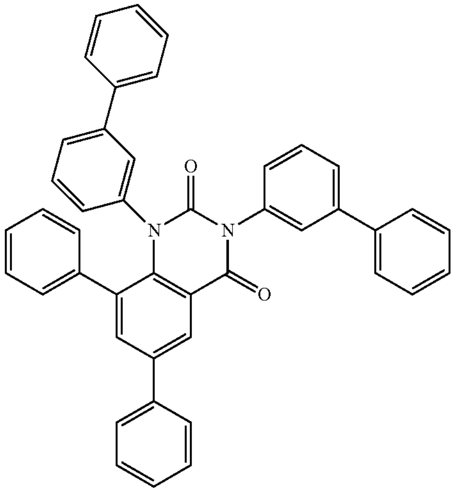
[Compound 13]
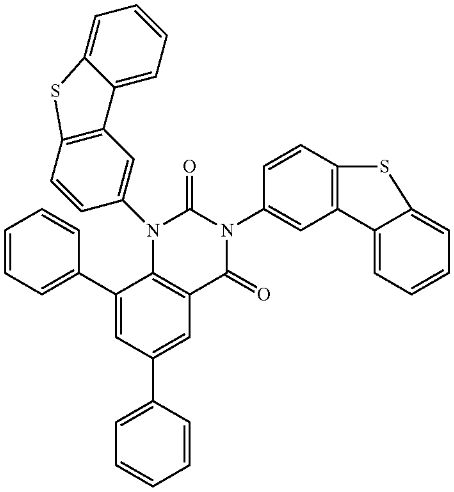

-continued
[Compound 14]
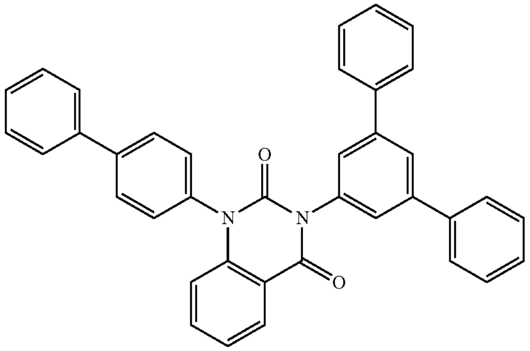
[Compound 15]
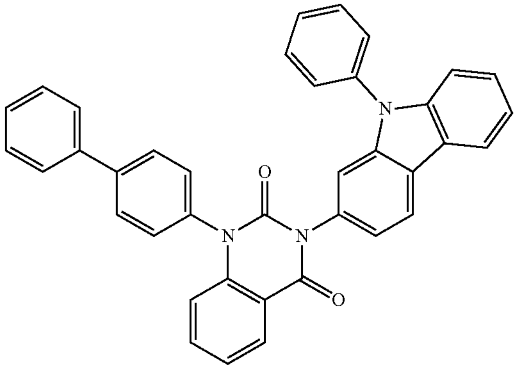
[Compound 16]
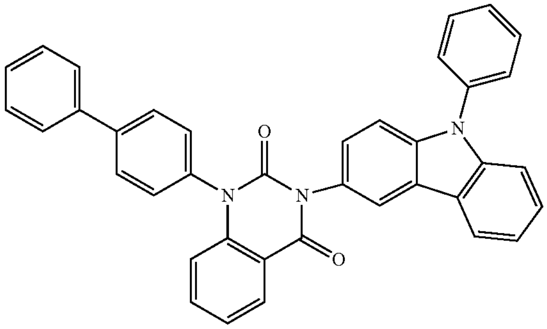
[Compound 17]
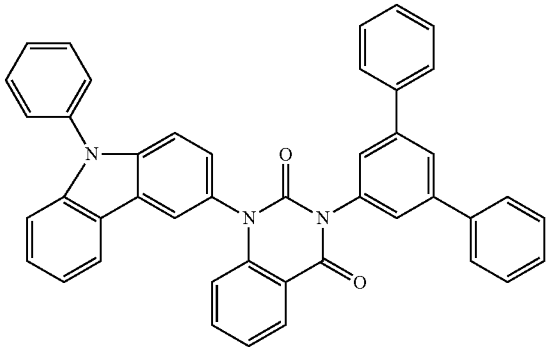
[Compound 18]
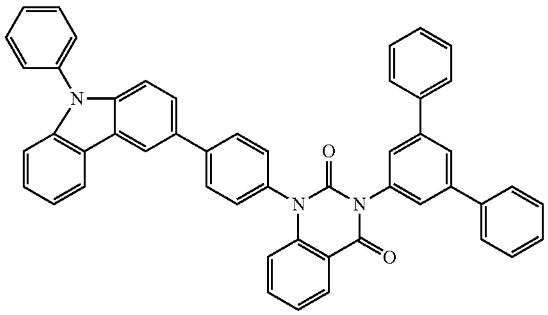
[Compound 19]
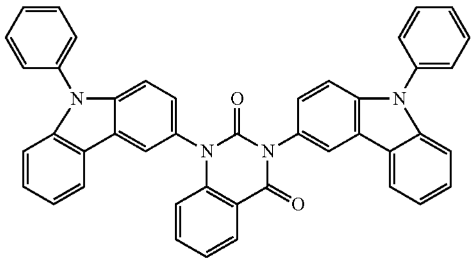
[Compound 20]
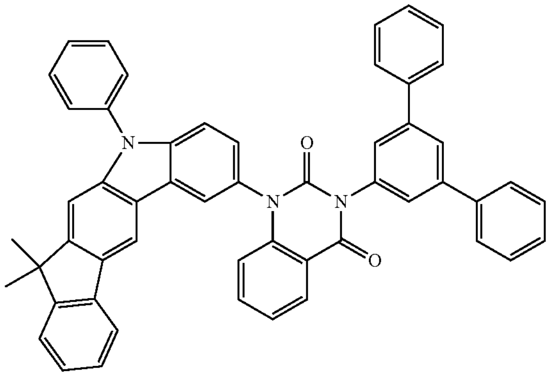
[Compound 21]
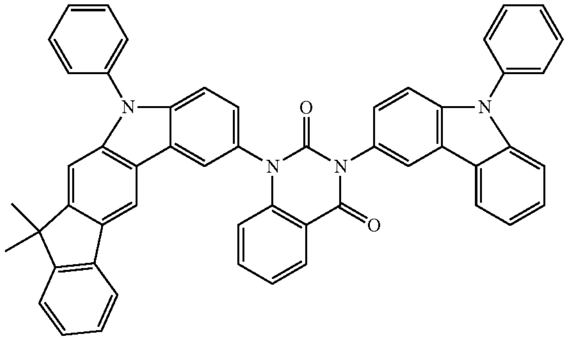

-continued
[Compound 22]
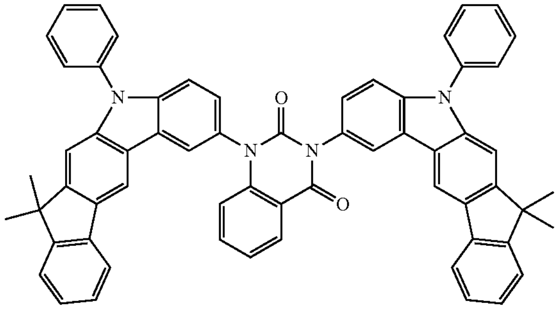
[Compound 23]
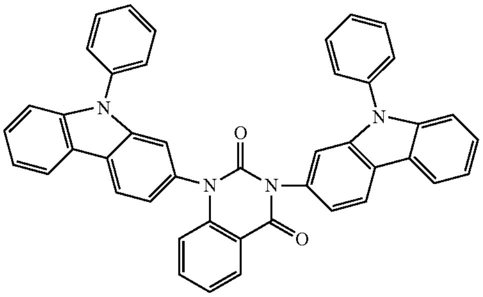
[Compound 24]
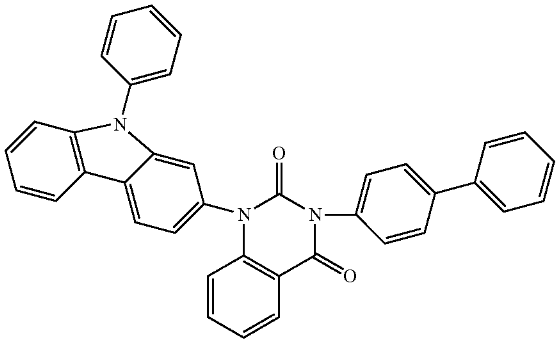
[Compound 25]
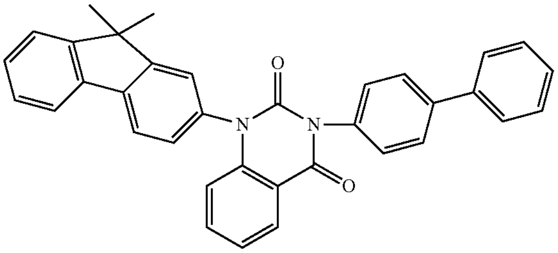
[Compound 26]
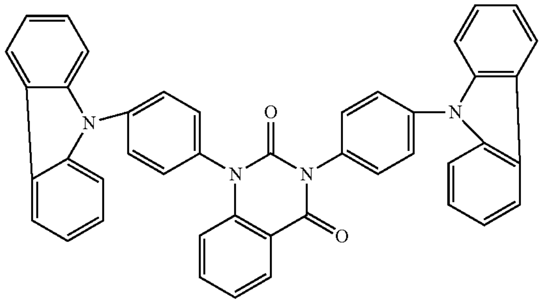
[Compound 27]
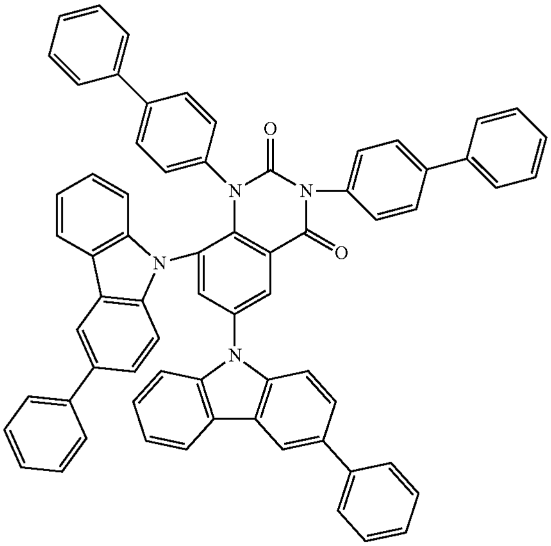

-continued
[Compound 28]
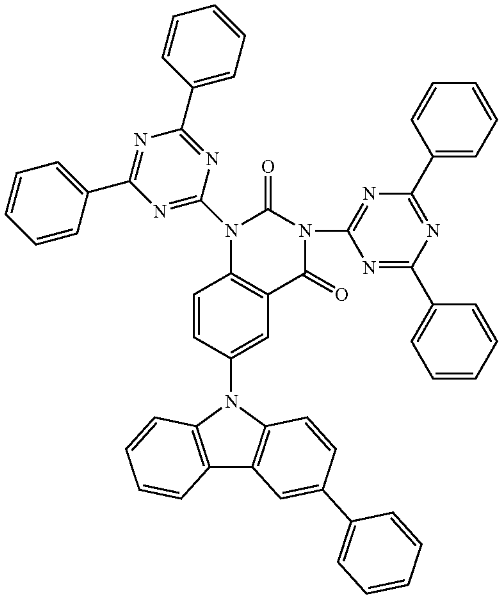
[Compound 29]
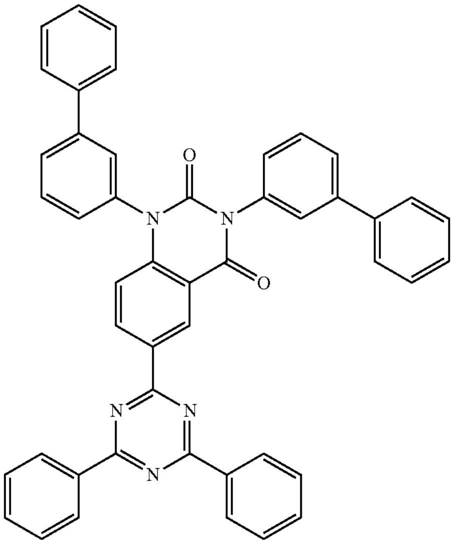
[Compound 30]
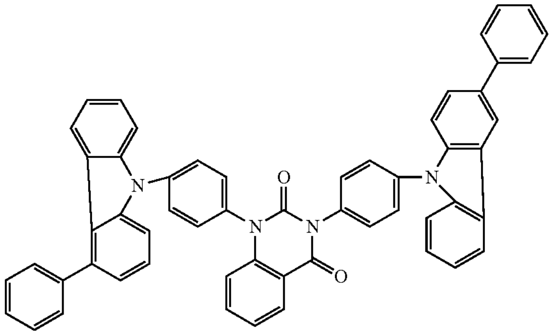
[Compound 31]
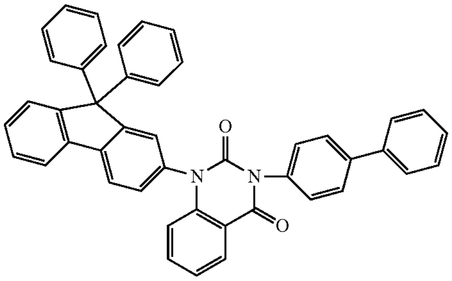
[Compound 32]
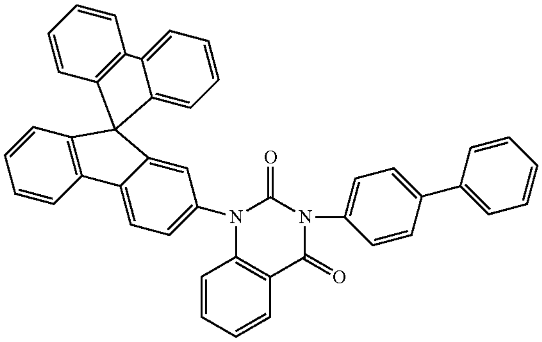
[Compound 33]
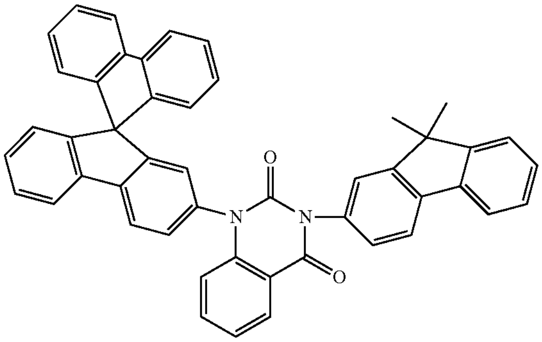

-continued
[Compound 34]
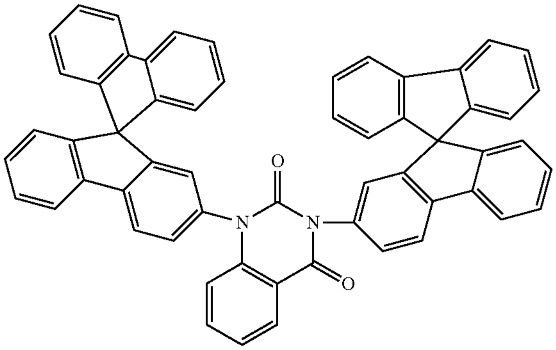
[Compound 35]
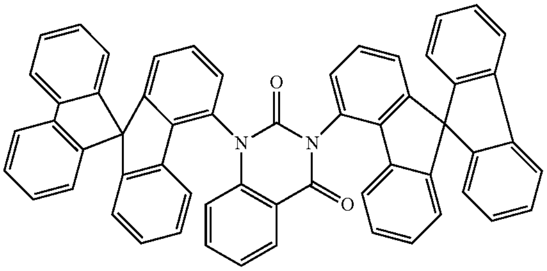
[Compound 36]
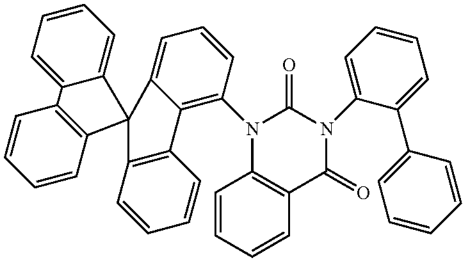
[Compound 37]
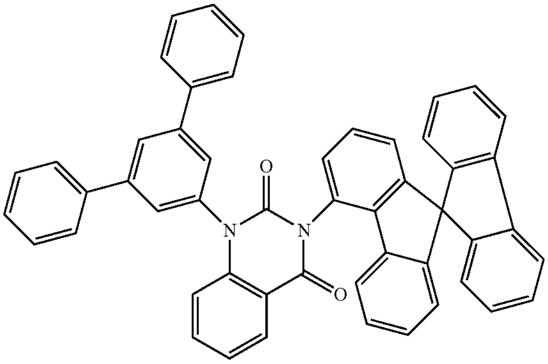
[Compound 38]
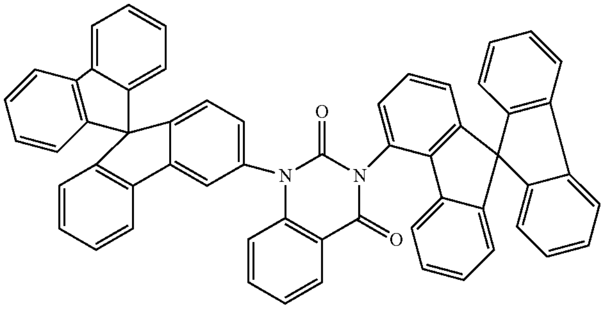
[Compound 39]
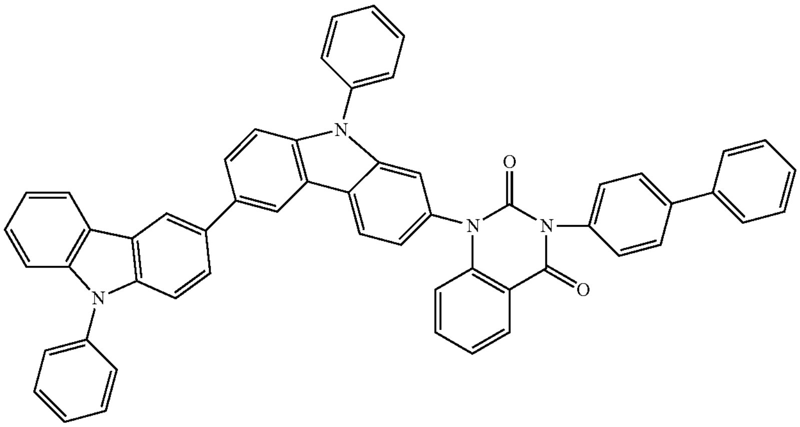

-continued
[Compound 40]
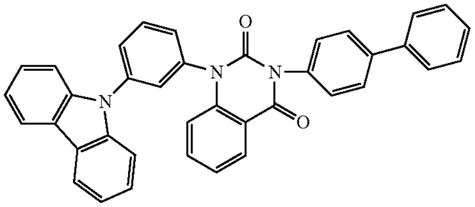
[Compound 41]
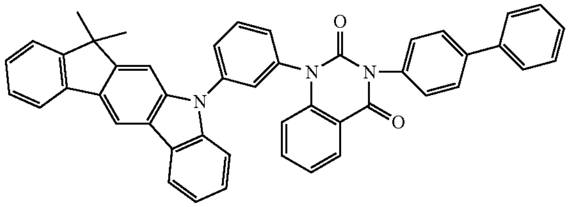
[Compound 42]
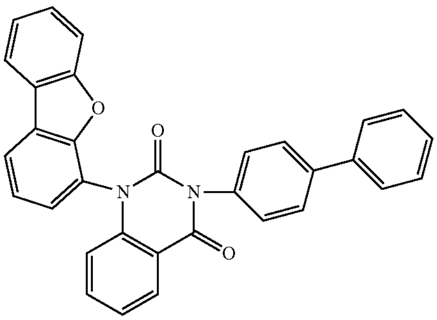
[Compound 43]
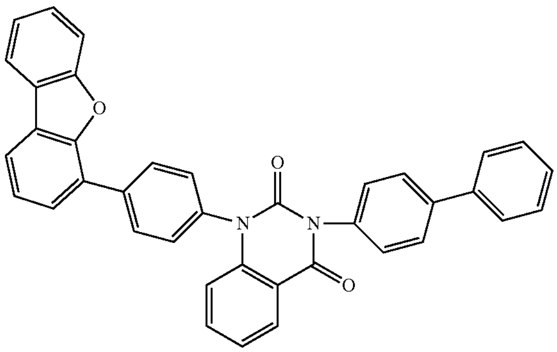
[Compound 44]
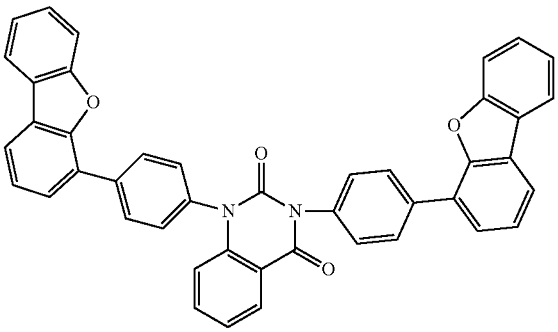
[Compound 45]
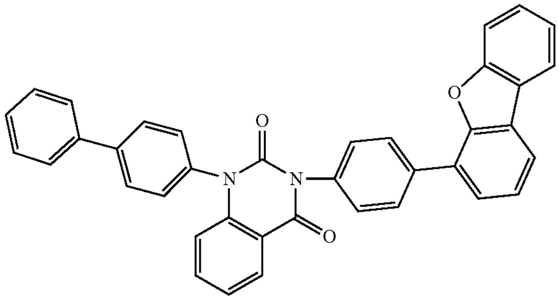
[Compound 46]
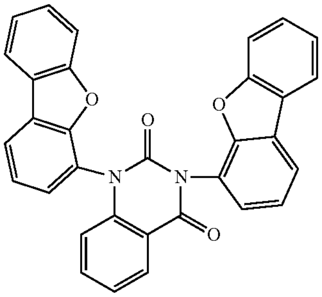
[Compound 47]
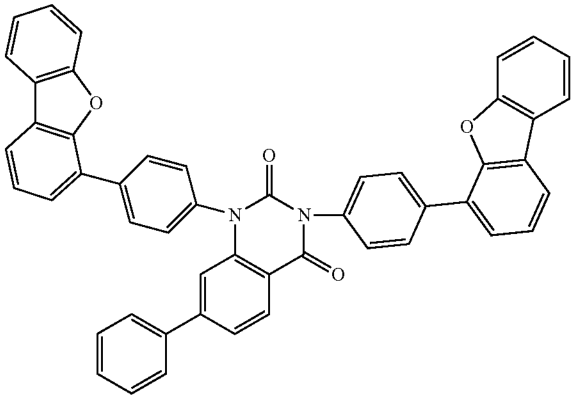

-continued
[Compound 48]
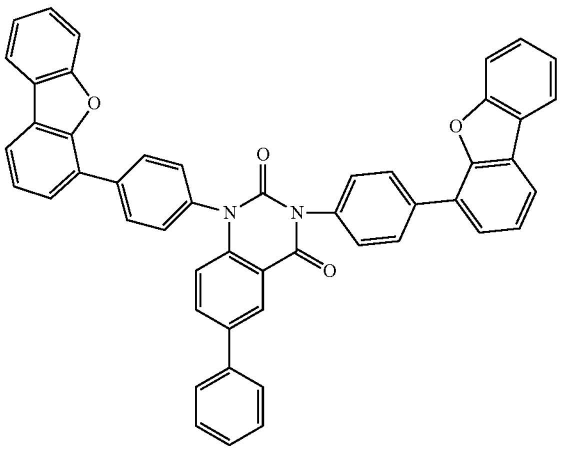
[Compound 49]
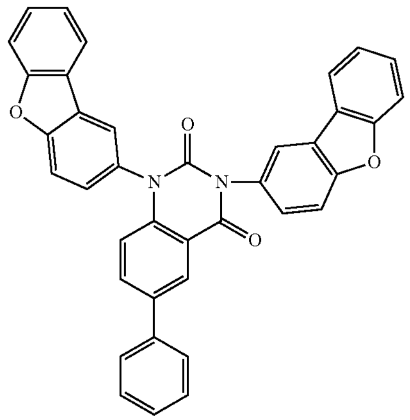
[Compound 50]
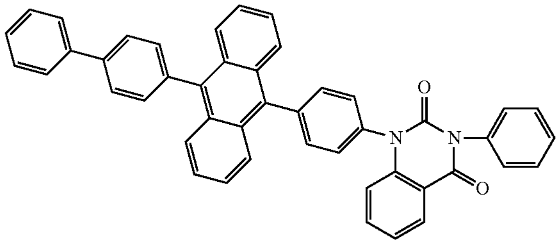
[Compound 51]
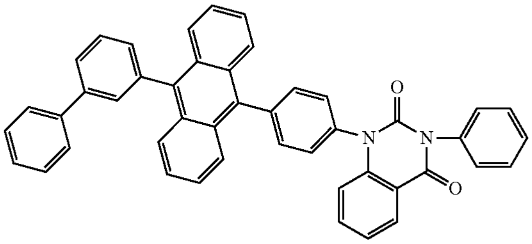
[Compound 52]
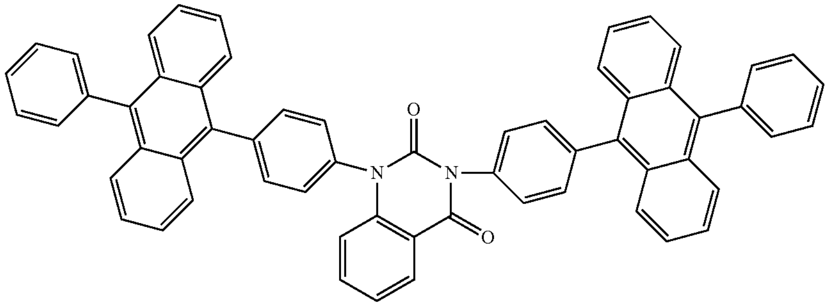
[Compound 53]
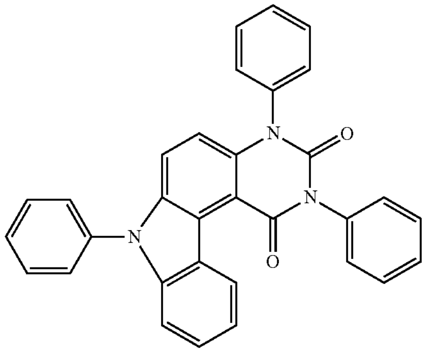
[Compound 54]
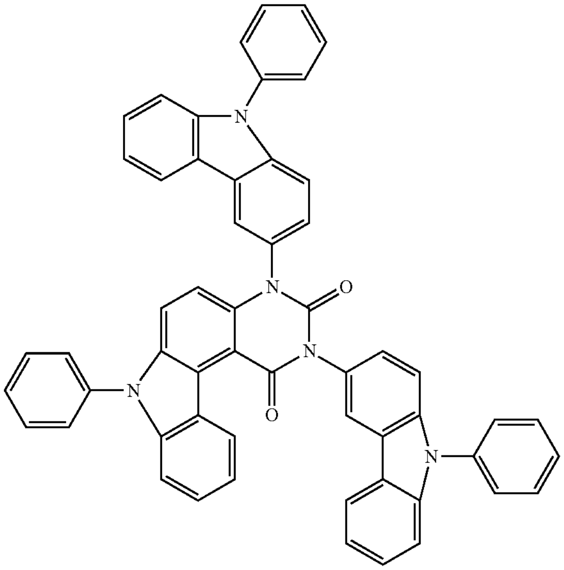

-continued
[Compound 55]
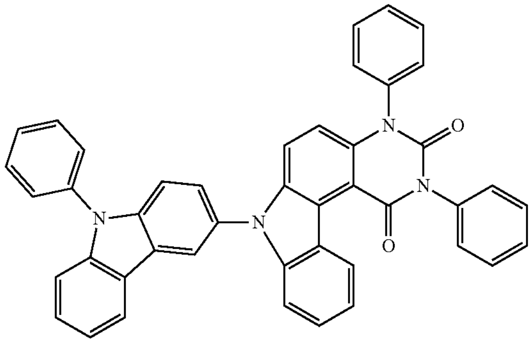
[Compound 56]
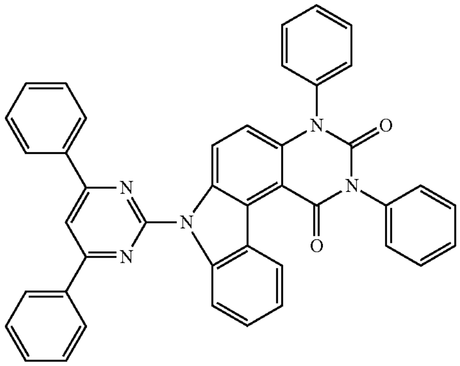
[Compound 57]
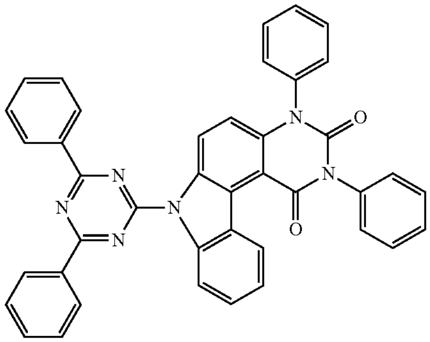
[Compound 58]
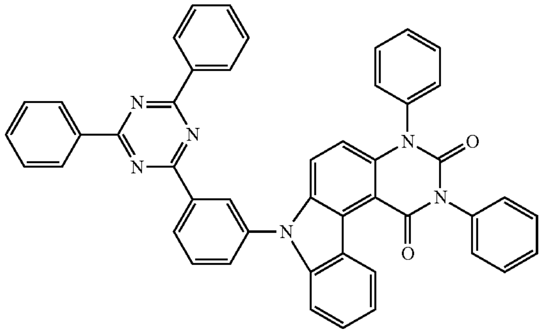
[Compound 59]
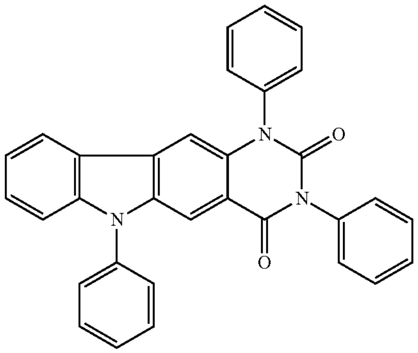
[Compound 60]
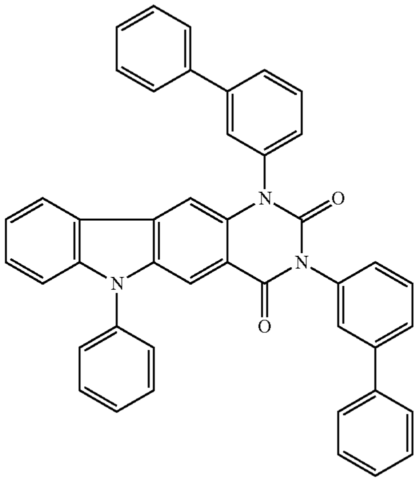

-continued
[Compound 61]
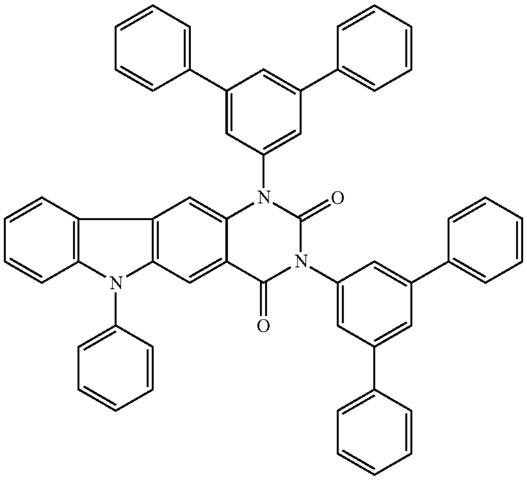
[Compound 62]
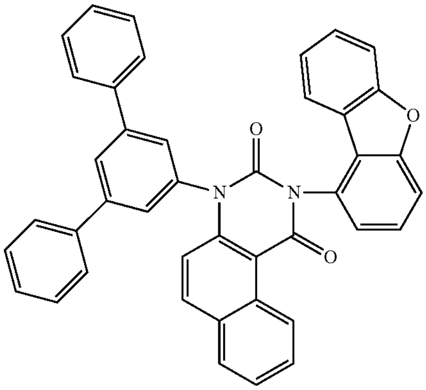
[Compound 63]
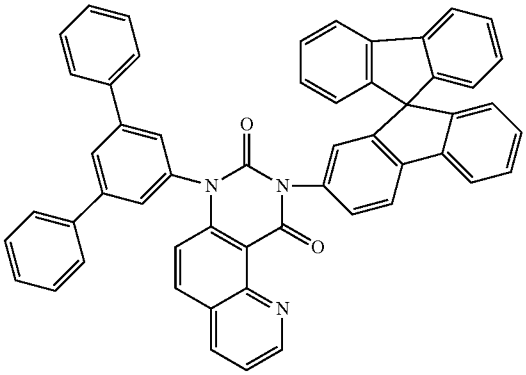
[Compound 64]
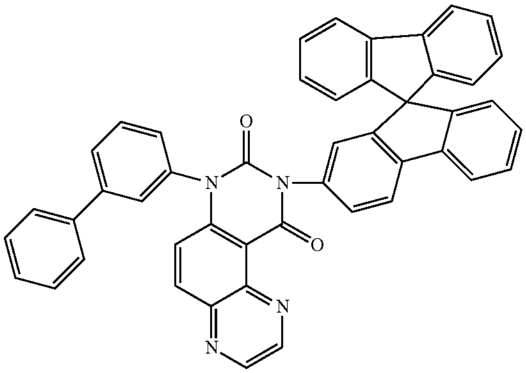
[Compound 65]
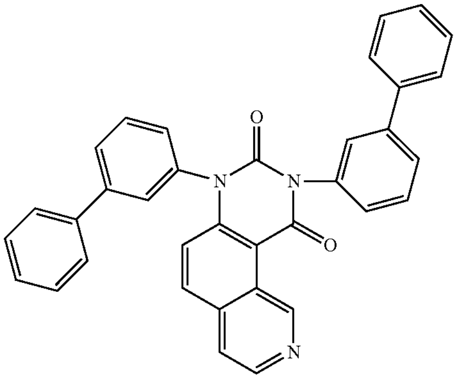
[Compound 66]
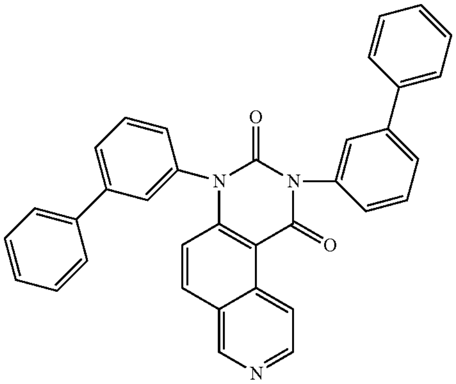

-continued
[Compound 67]
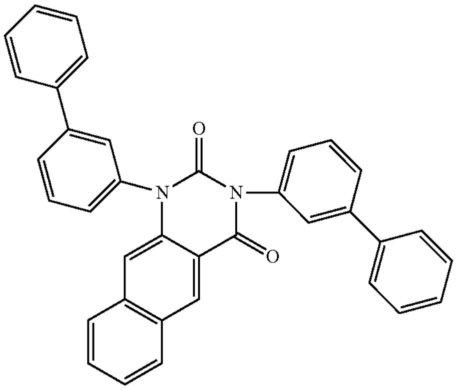
[Compound 68]
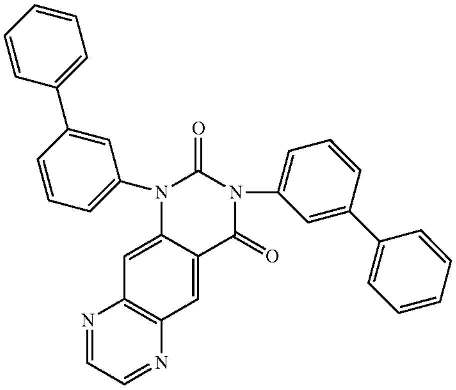
[Compound 69]
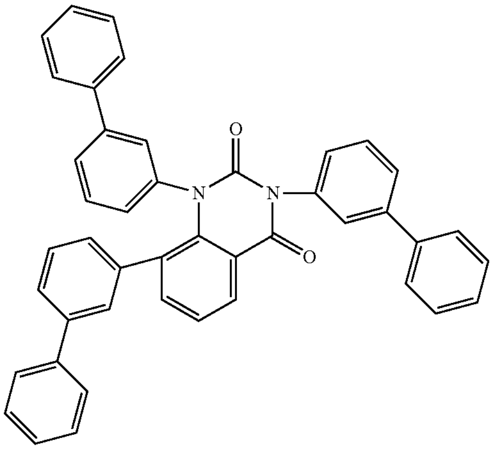
[Compound 70]
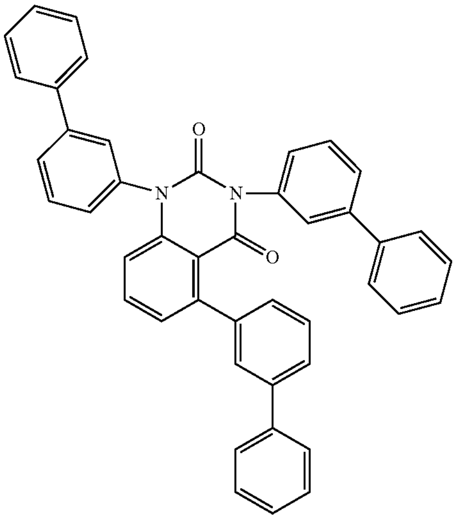
[Compound 71]
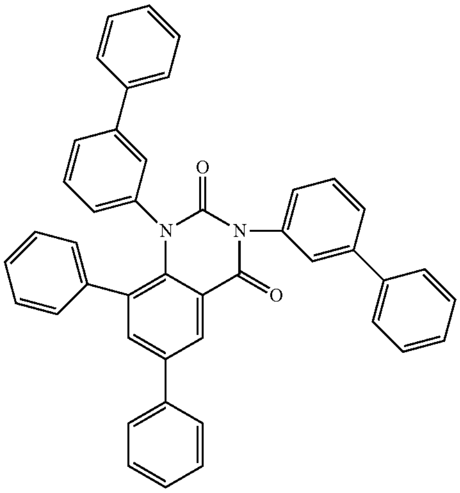
[Compound 72]
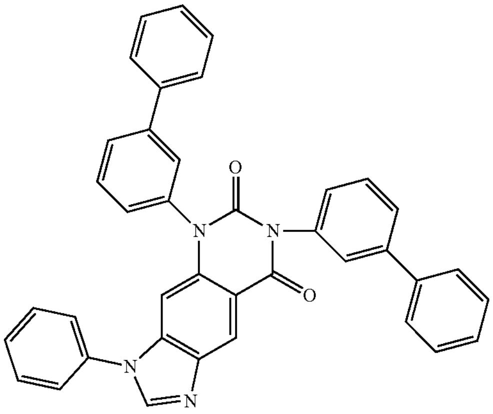

-continued
[Compound 73]
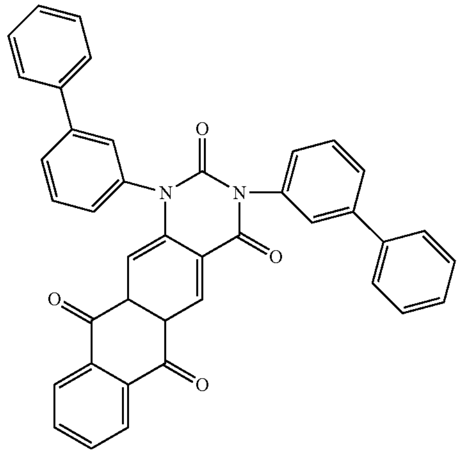
[Compound 74]
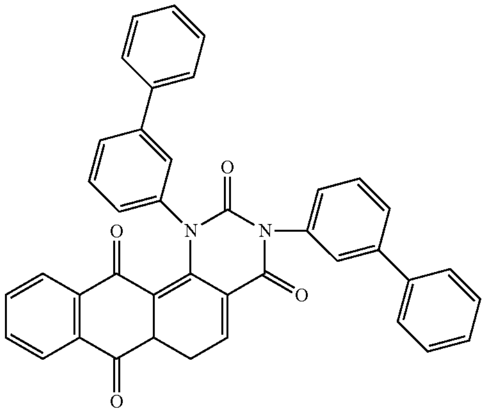
[Compound 75]
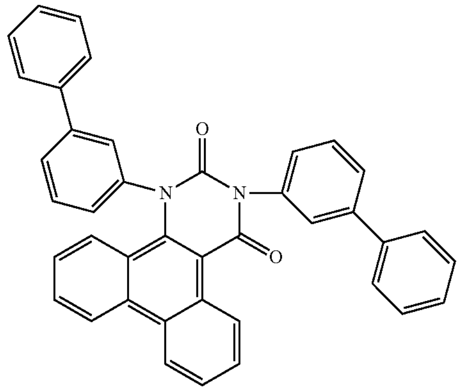
[Compound 76]
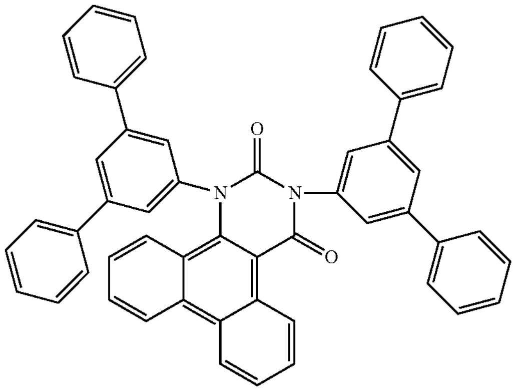
[Compound 77]
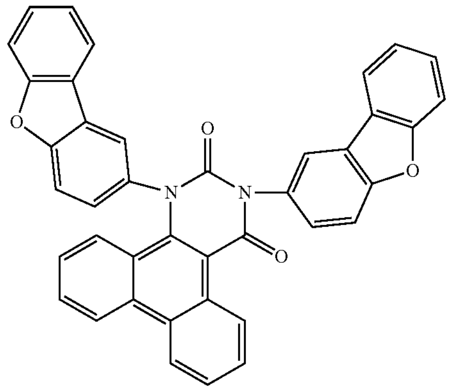
[Compound 78]
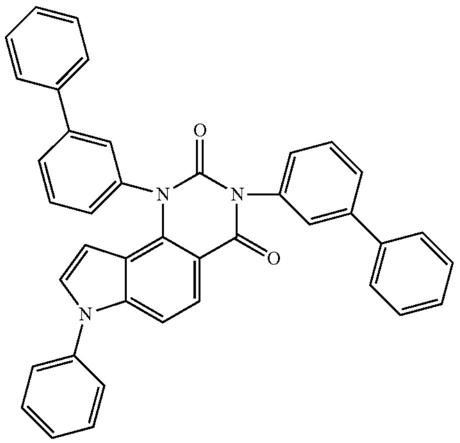

-continued
[Compound 79]
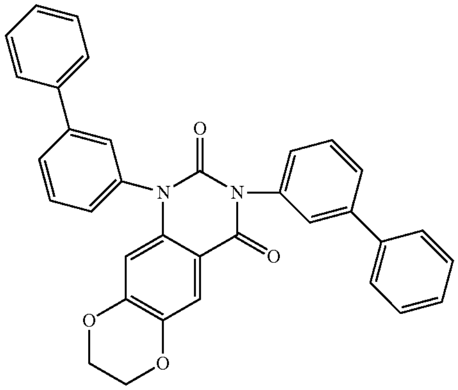
[Compound 80]
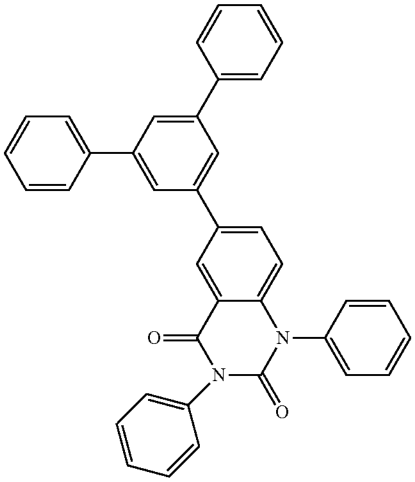
[Compound 81]
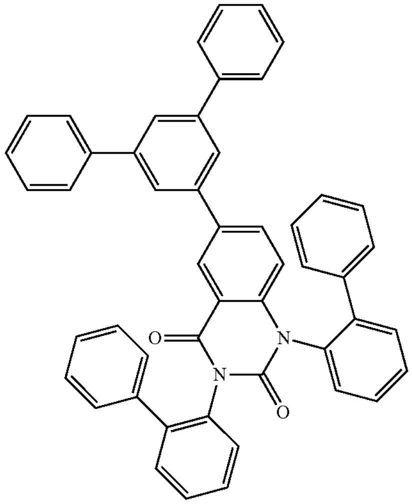
[Compound 82]
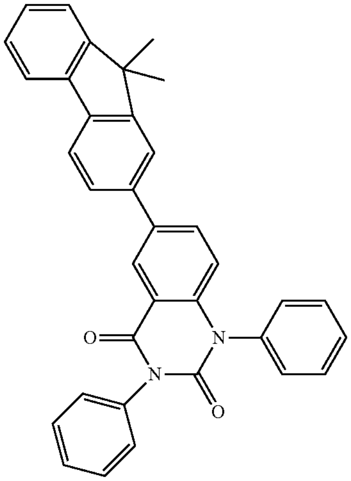
[Compound 83]
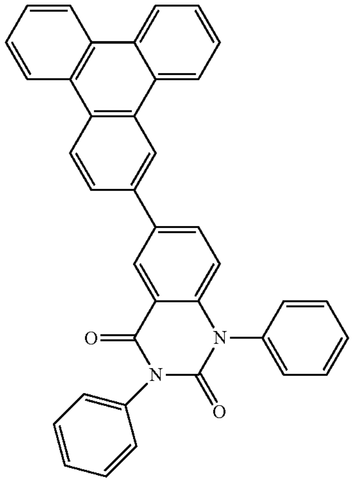
[Compound 84]
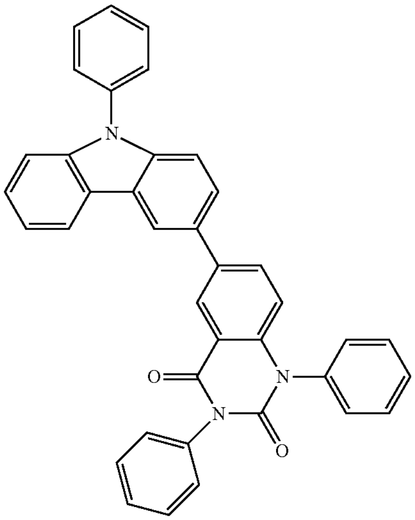

-continued
[Compound 85]
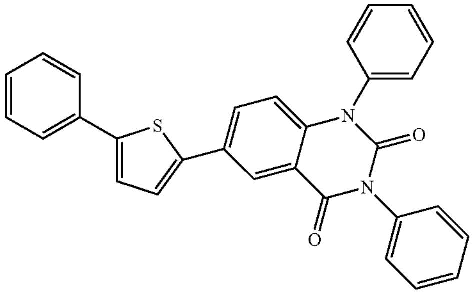
[Compound 86]
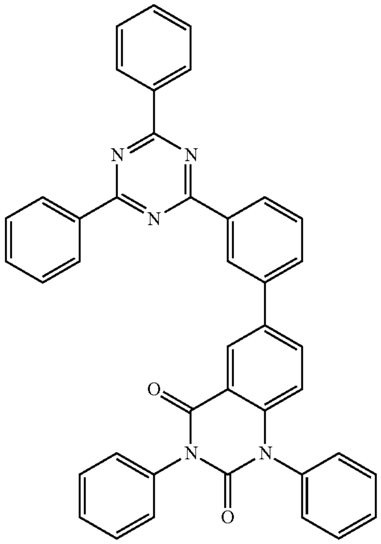
[Compound 87]
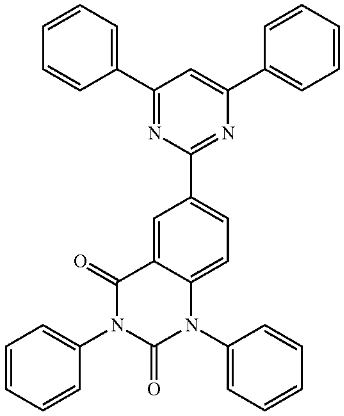
[Compound 88]
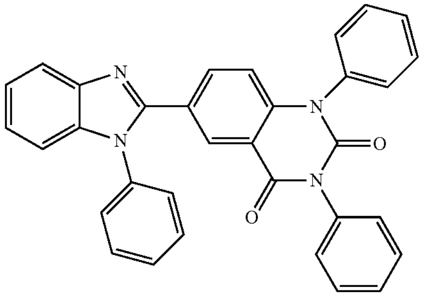
[Compound 89]
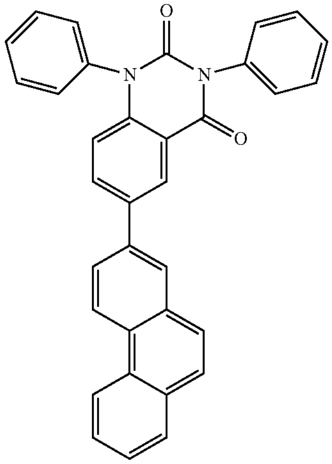
[Compound 90]
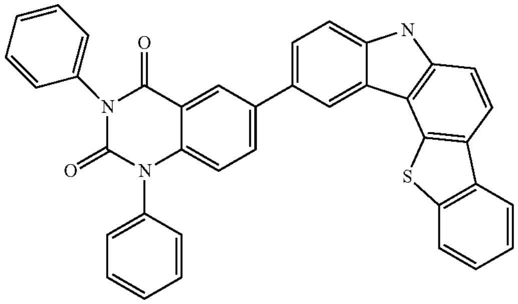

-continued
[Compound 91]
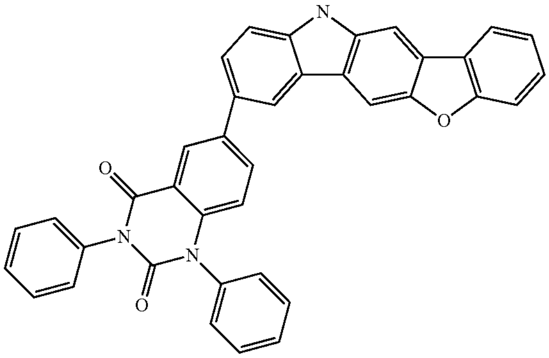
[Compound 92]
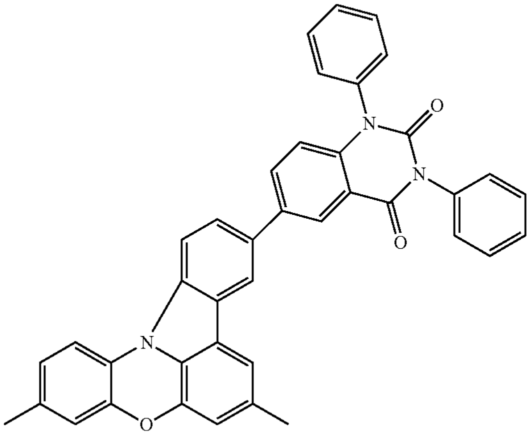
[Compound 93]
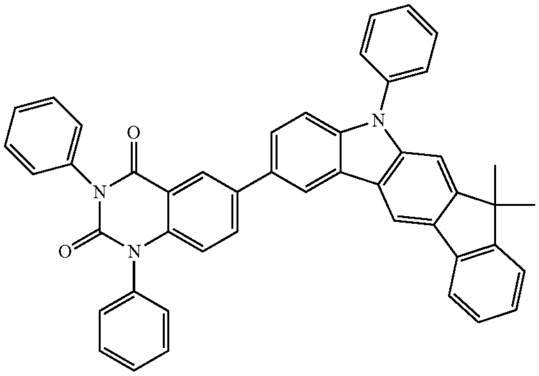
[Compound 94]
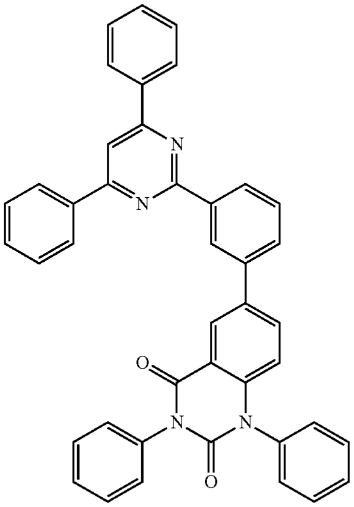
[Compound 95]
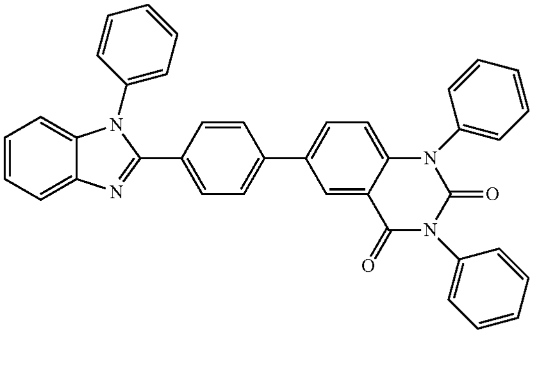
[Compound 96]
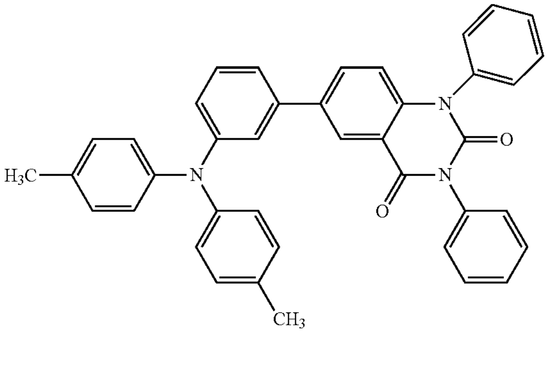

-continued
[Compound 97]
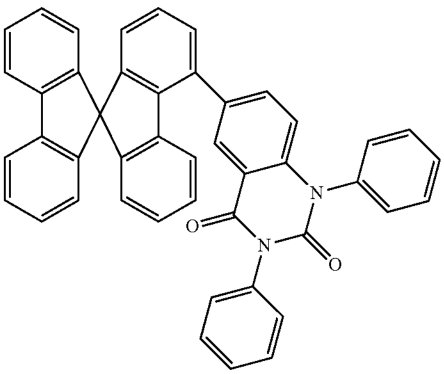
[Compound 98]
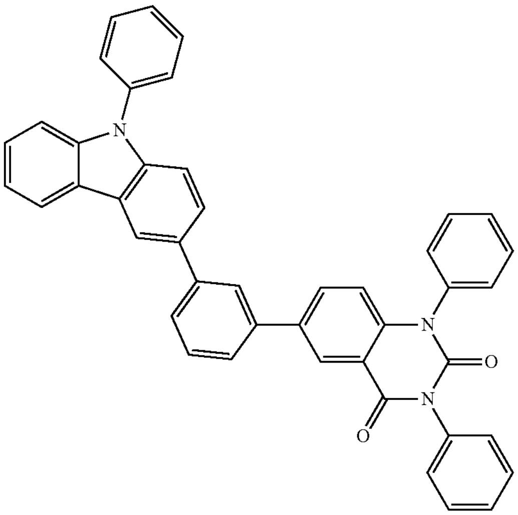
[Compound 99]
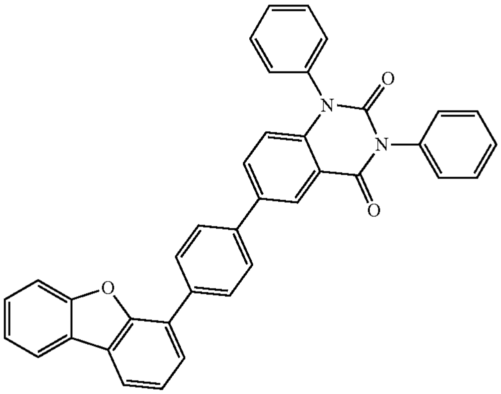
[Compound 100]
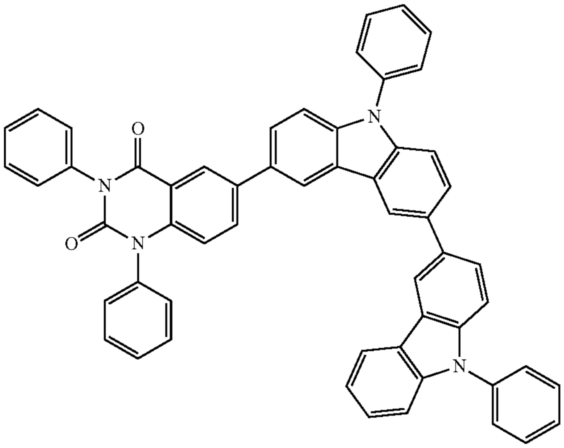
[Compound 101]
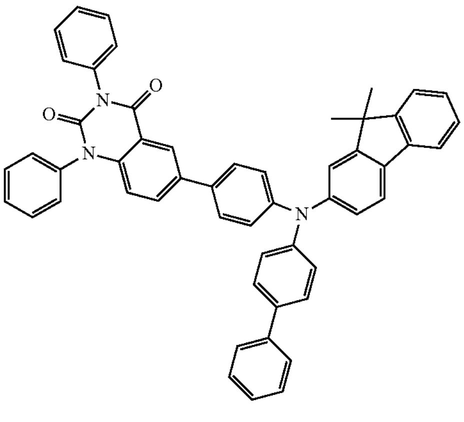
[Compound 102]
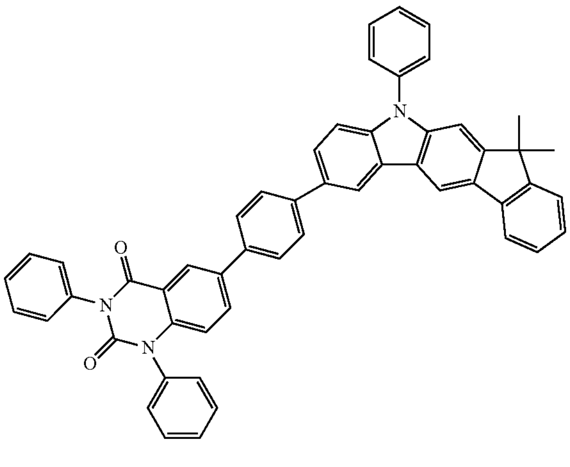

-continued
[Compound 103]
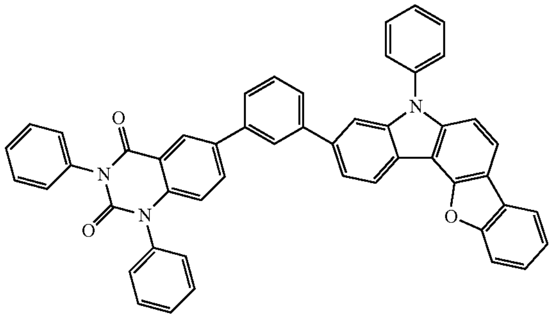
[Compound 104]
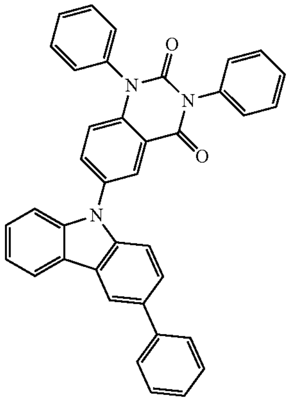
[Compound 105]
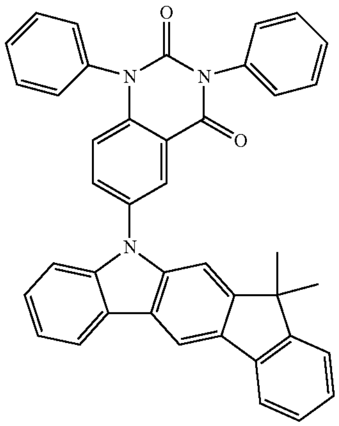
[Compound 106]
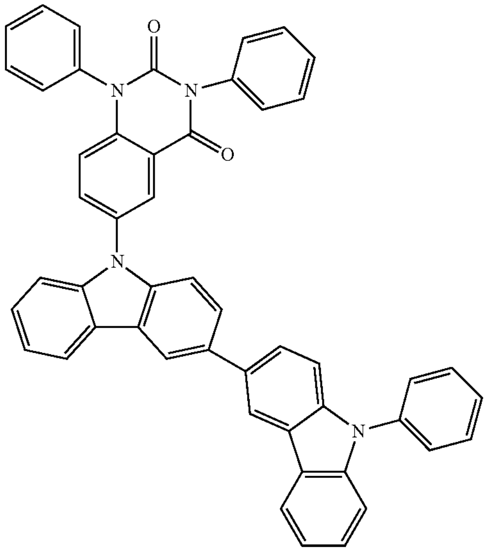
[Compound 107]
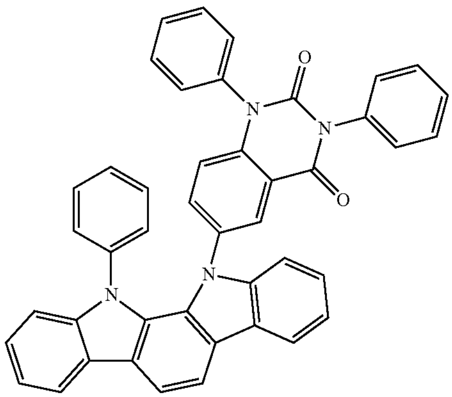
[Compound 108]
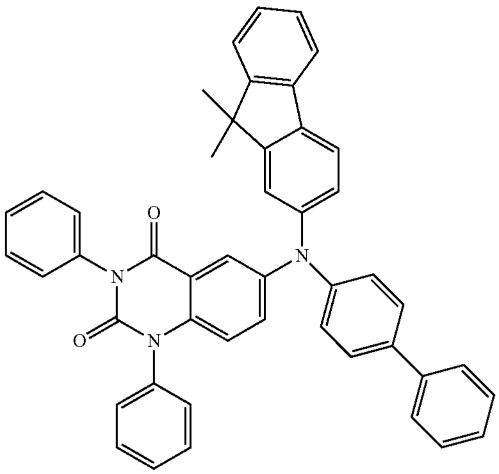

-continued
[Compound 109]
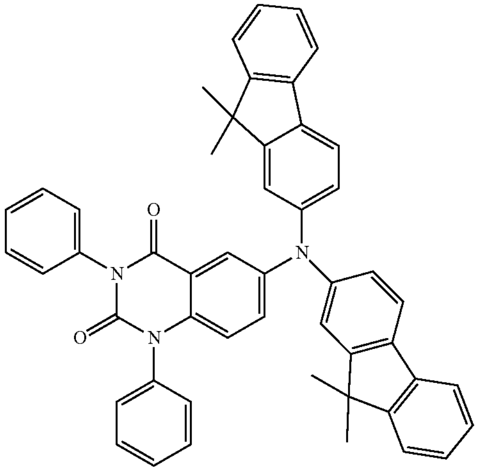
[Compound 110]
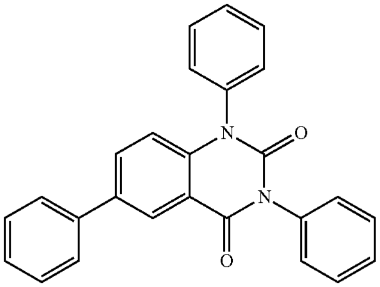
[Compound 111]
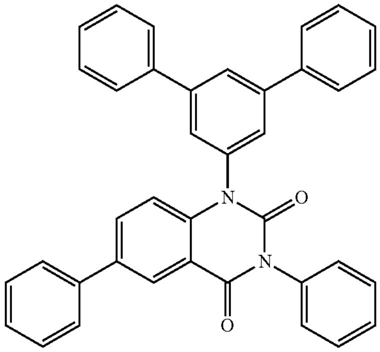
[Compound 112]
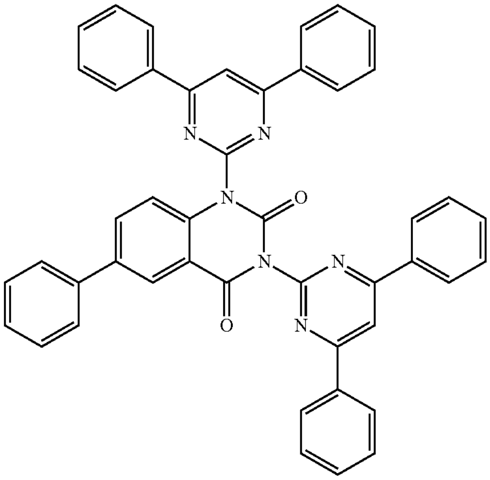
[Compound 113]
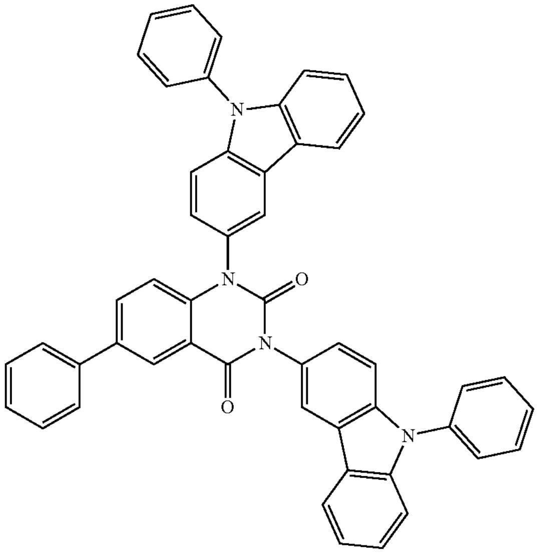
[Compound 114]
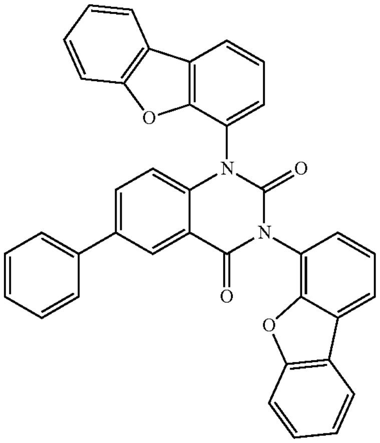

-continued
[Compound 115]
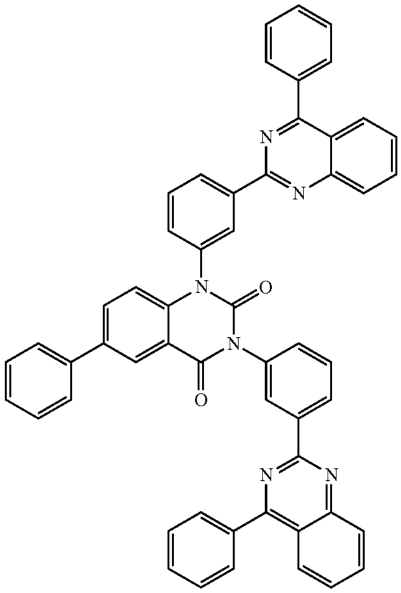
[Compound 116]
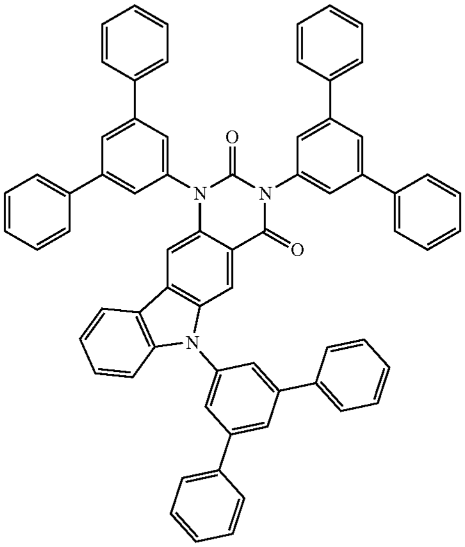
[Compound 117]
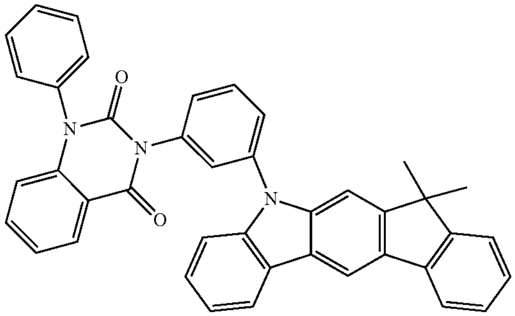
[Compound 118]
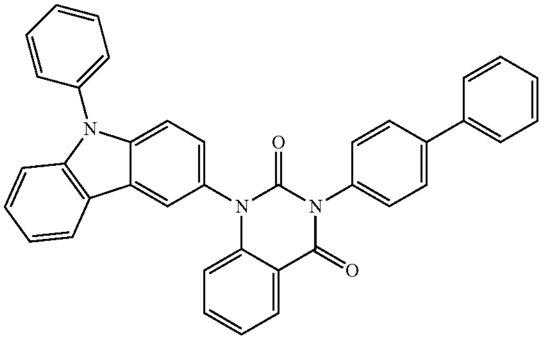
[Compound 119]
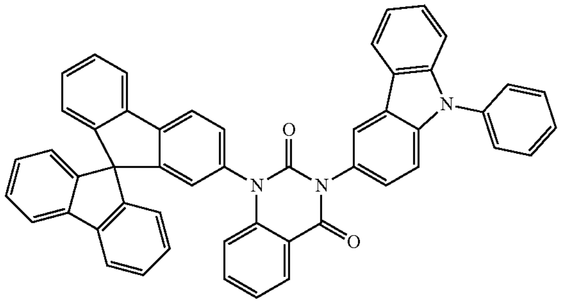
[Compound 120]
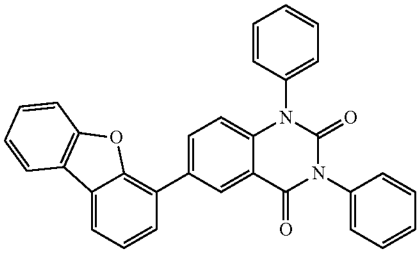

-continued
[Compound 121]
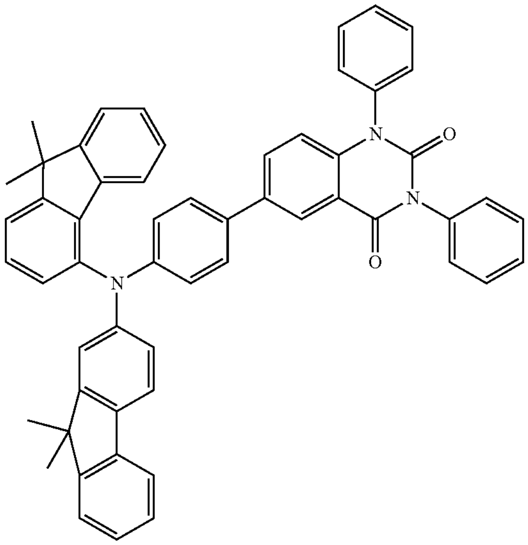
[Compound 122]
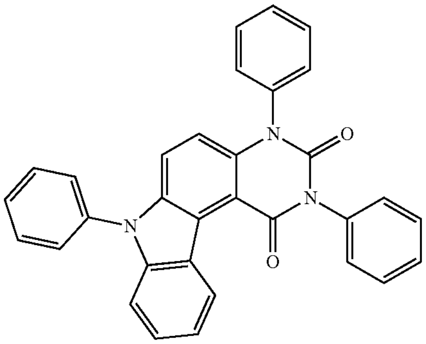
[Compound 123]
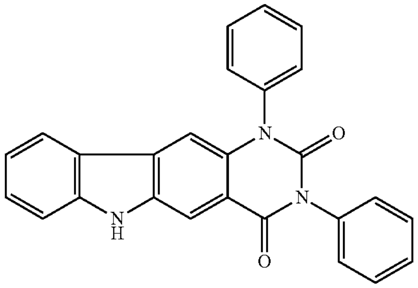
[Compound 124]
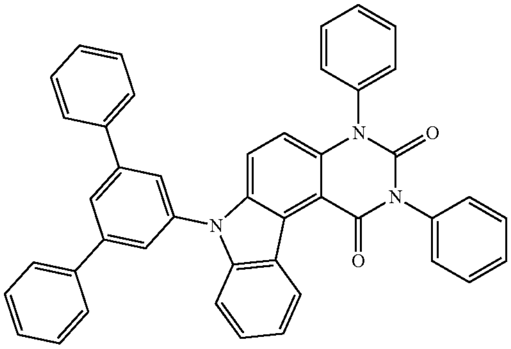
[Compound 125]
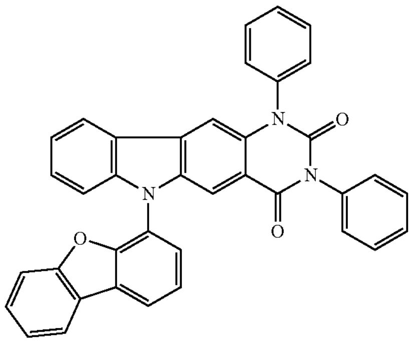
[Compound 126]
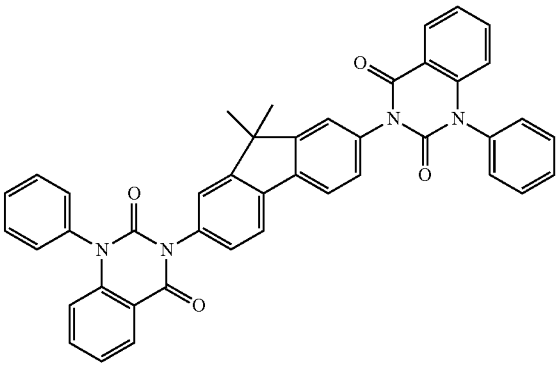

-continued
[Compound 127]
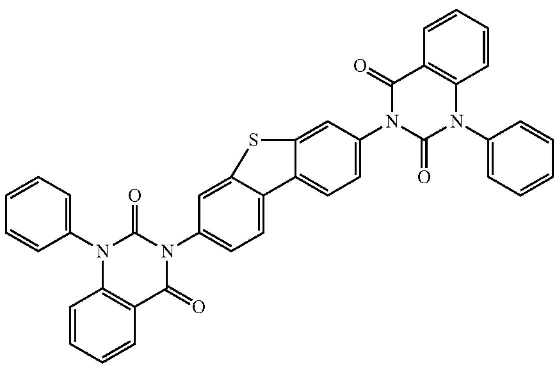
[Compound 128]
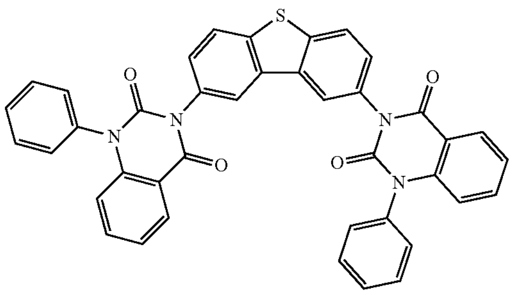
[Compound 129]
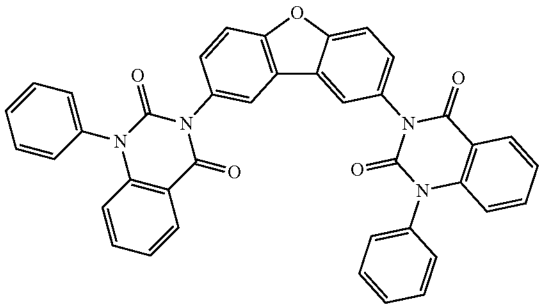
[Compound 130]
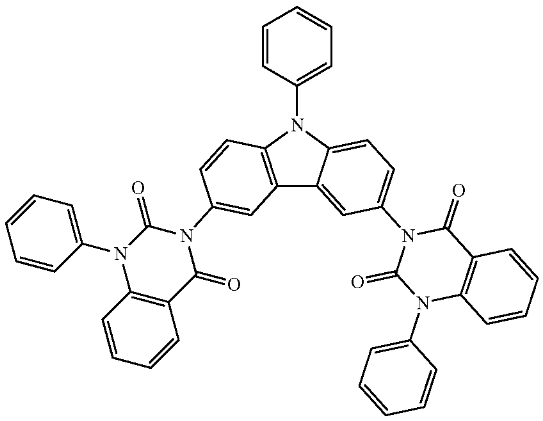
[Compound 131]
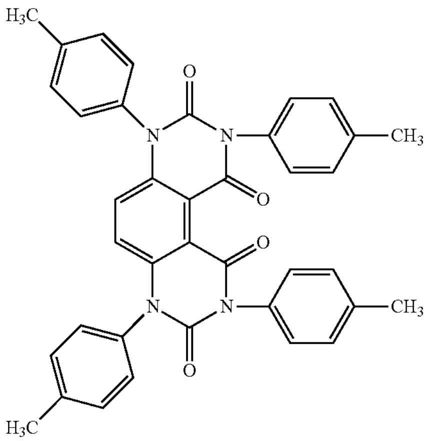
[Compound 132]
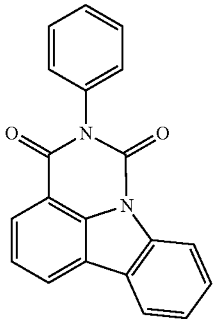
[Compound 133]
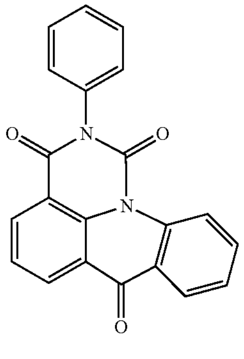
[Compound 134]
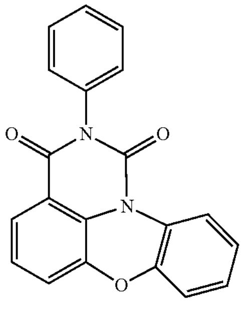

-continued
[Compound 135]
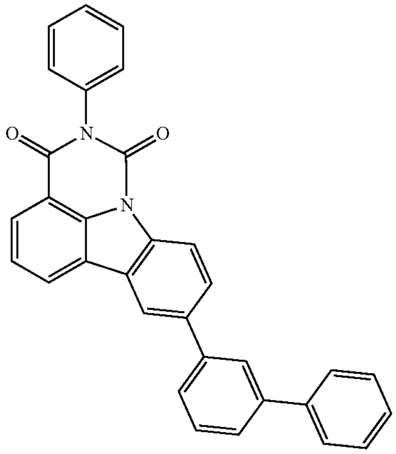
[Compound 136]
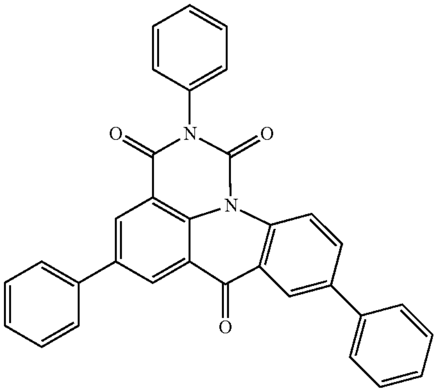
[Compound 137]
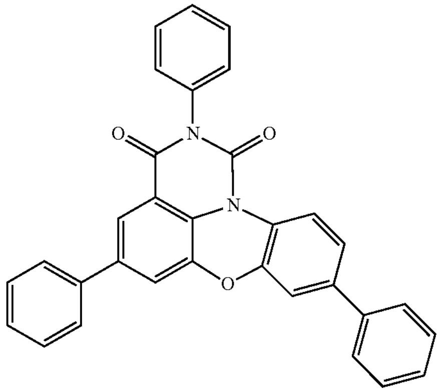
[Compound 138]
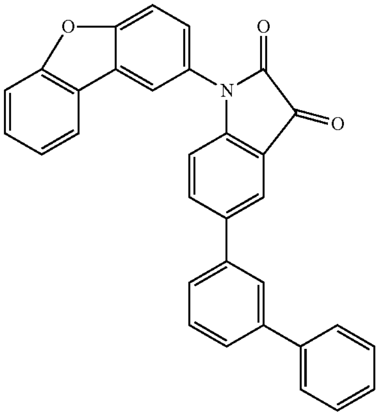
[Compound 139]
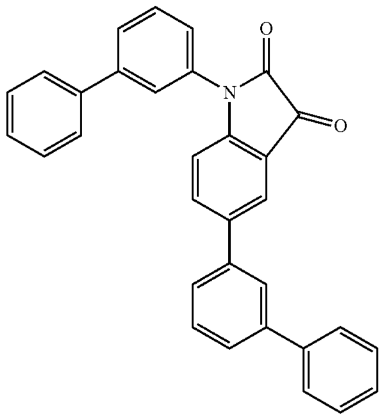
[Compound 140]
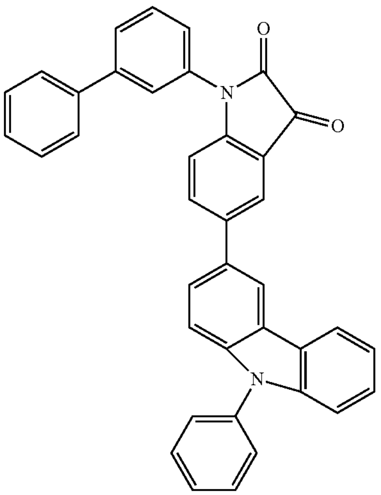

-continued
[Compound 141]
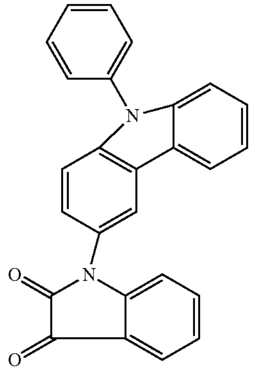
[Compound 142]
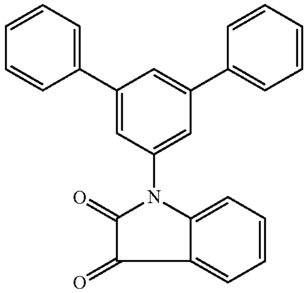
[Compound 143]
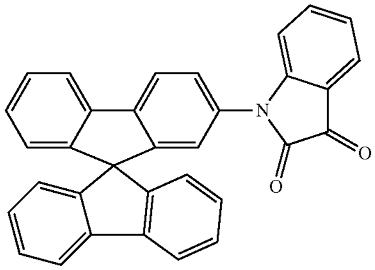
[Compound 144]
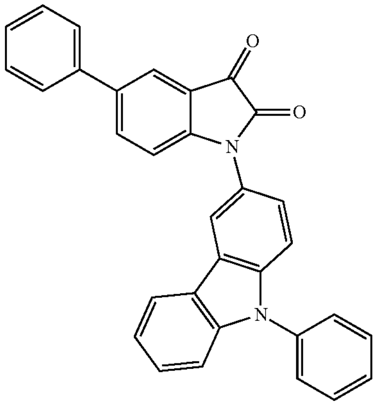
[Compound 145]
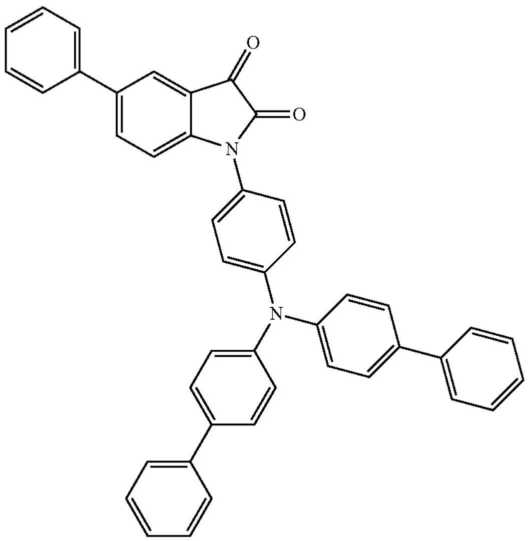
[Compound 146]
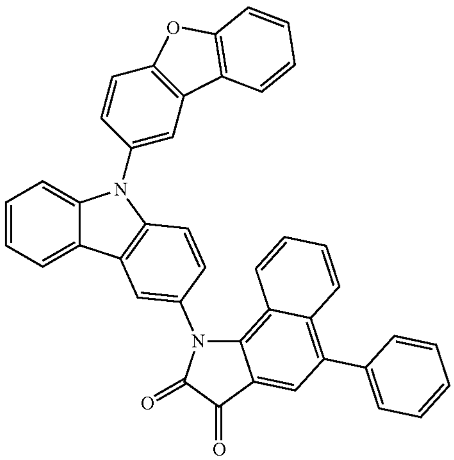

-continued
[Compound 147]
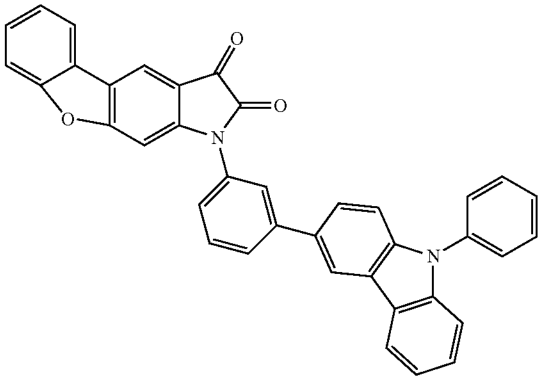
[Compound 148]
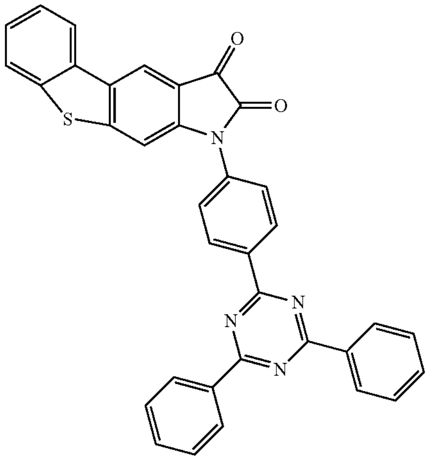
[Compound 149]
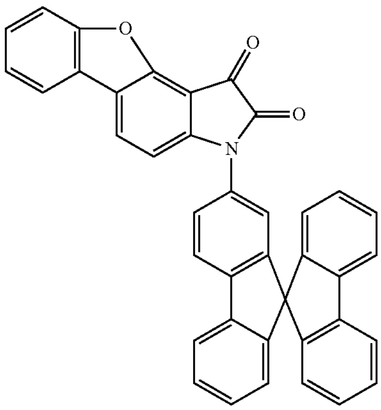
[Compound 150]
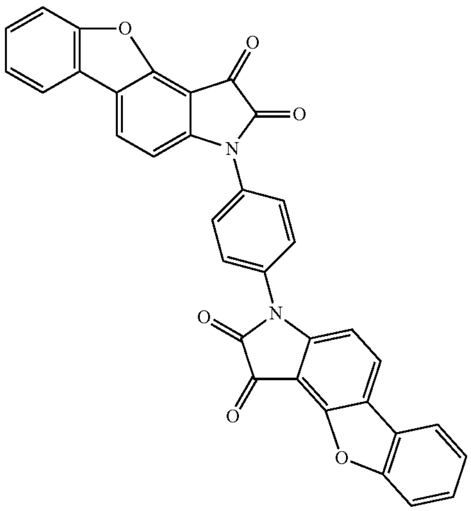
[Compound 151]
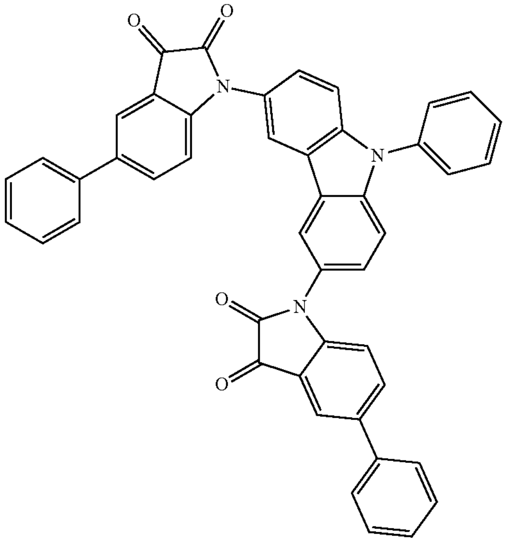
[Compound 152]
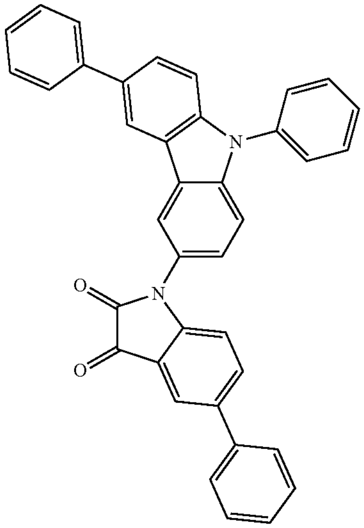

-continued
[Compound 153]
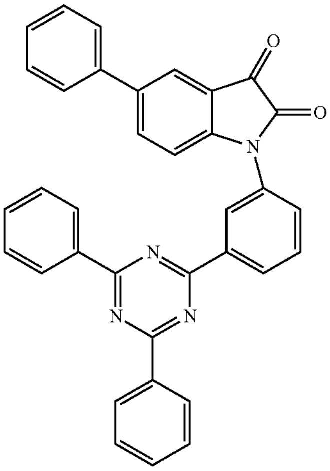
[Compound 154]
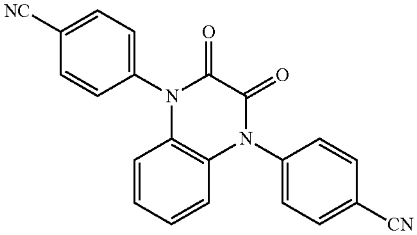
[Compound 155]
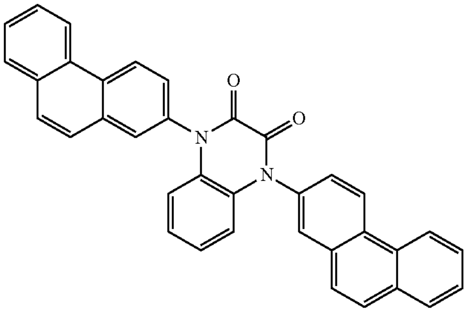
[Compound 166]
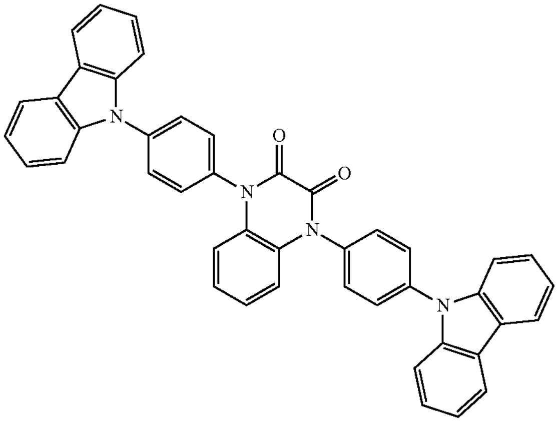
[Compound 167]
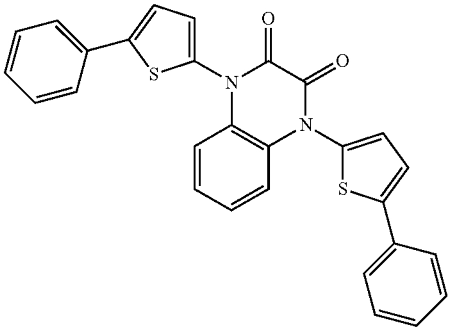
[Compound 168]
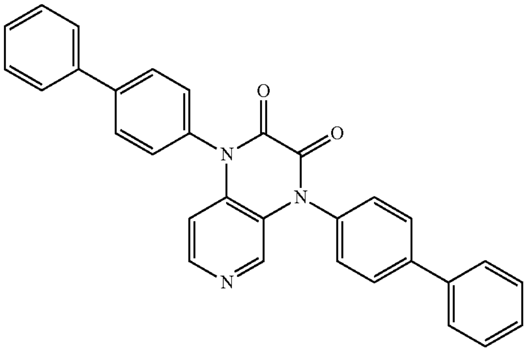

-continued
[Compound 169]
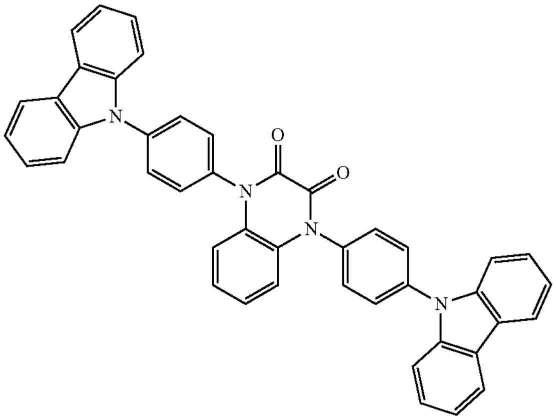
[Compound 170]
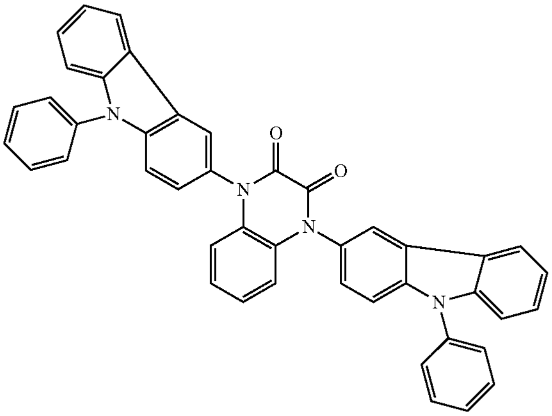
[Compound 171]
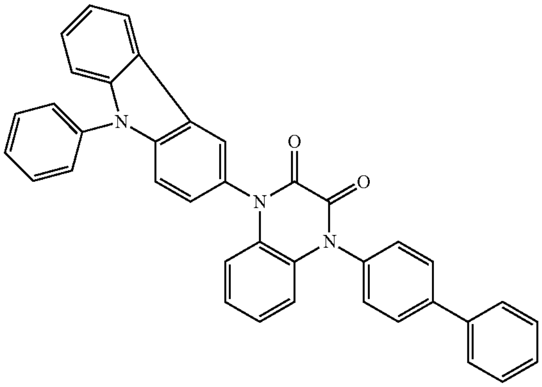
[Compound 172]
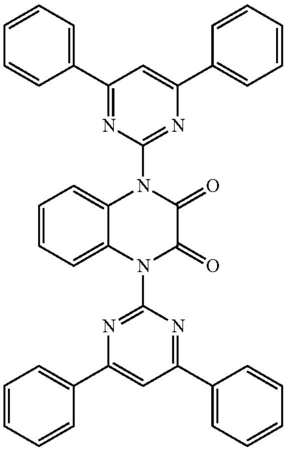
[Compound 173]
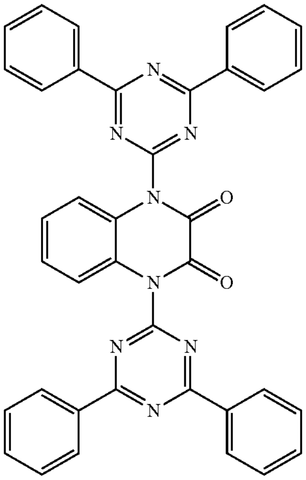
[Compound 174]
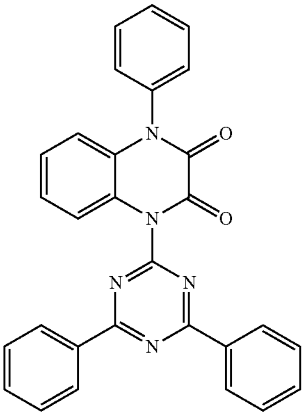

-continued
[Compound 175]
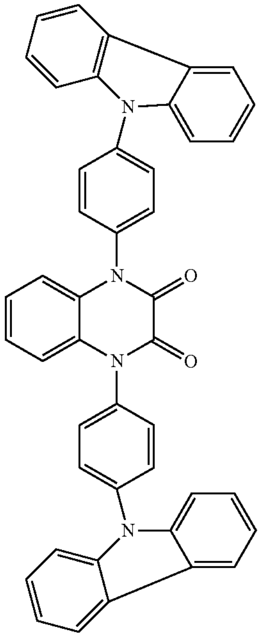
[Compound 176]
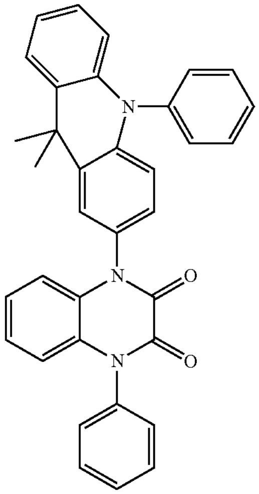
[Compound 177]
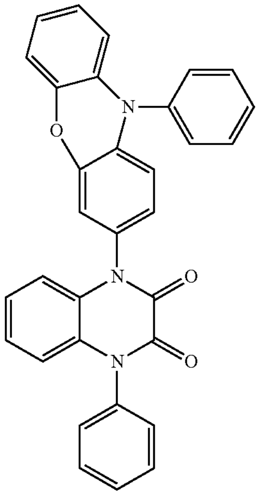
[Compound 178]
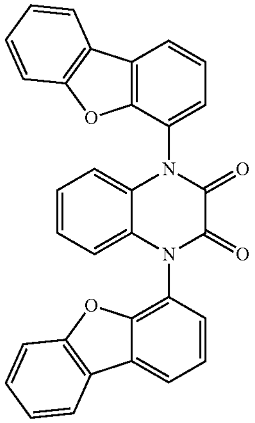

-continued
[Compound 179]
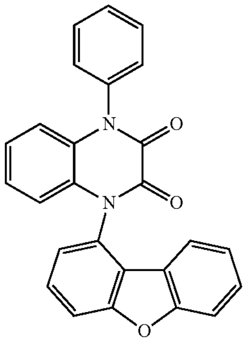
[Compound 180]
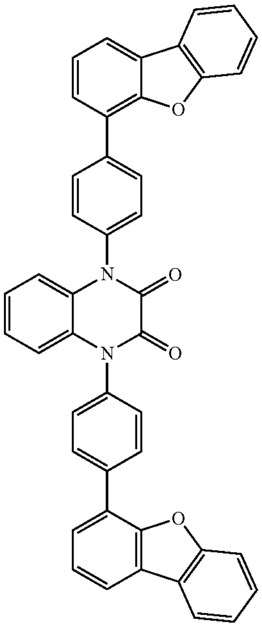
[Compound 181]
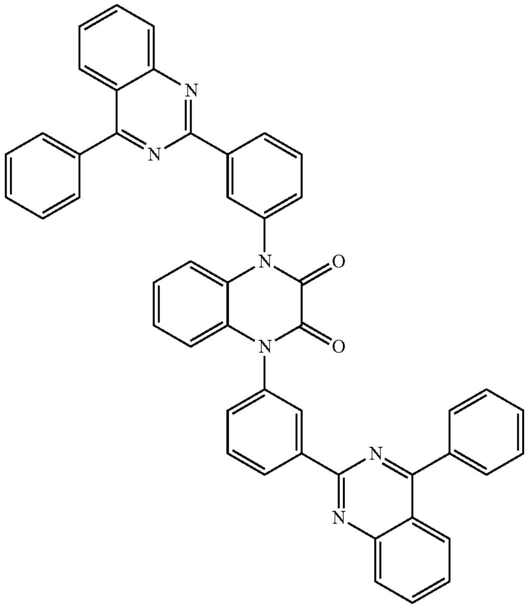
[Compound 182]
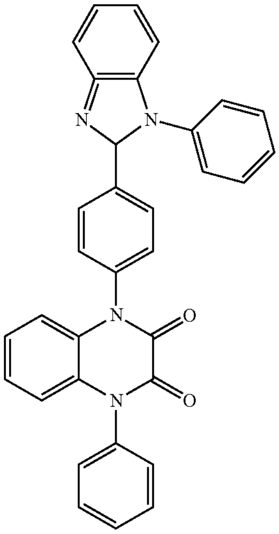

-continued
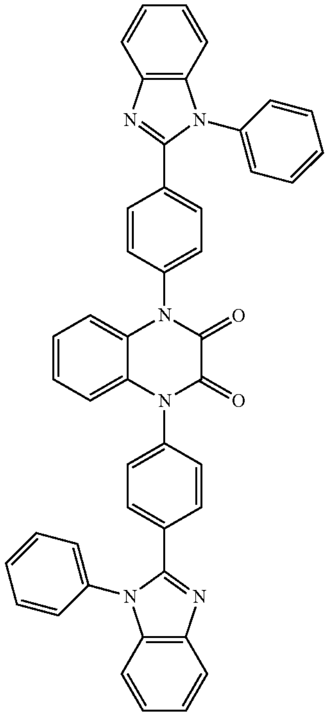
[Compound 183]
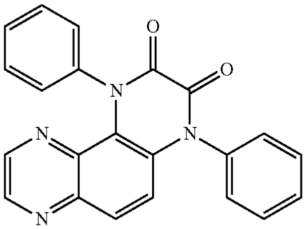
[Compound 184]
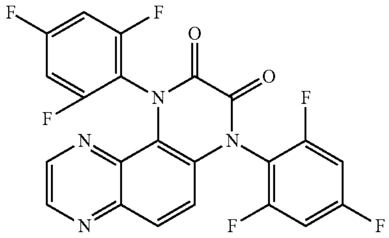
[Compound 185]
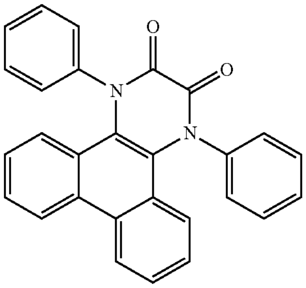
[Compound 186]
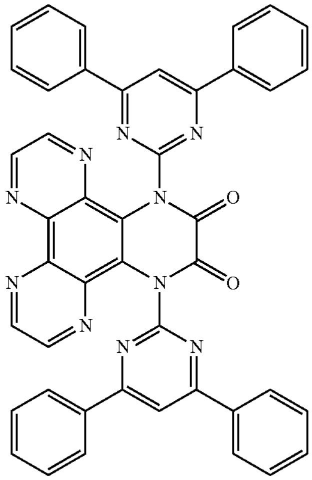
[Compound 187]
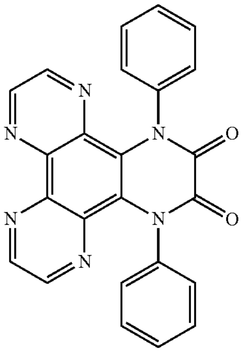
[Compound 188]

-continued
[Compound 189]
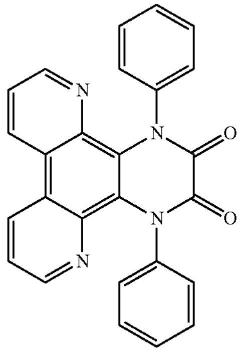
[Compound 190]
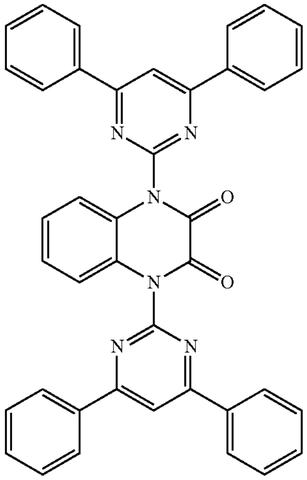
[Compound 191]
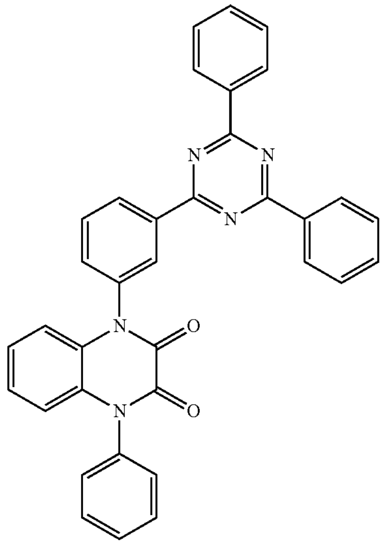
[Compound 192]
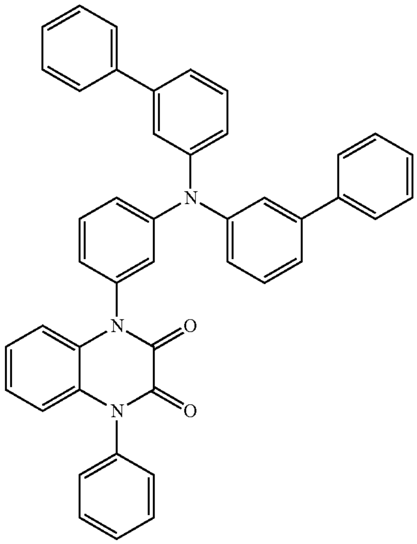
[Compound 193]
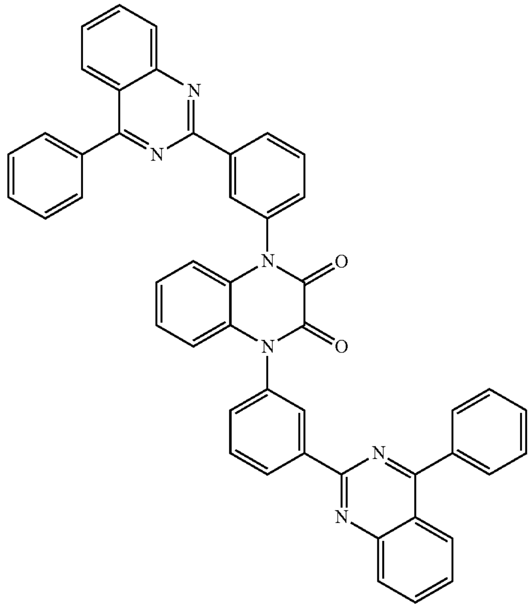
[Compound 194]
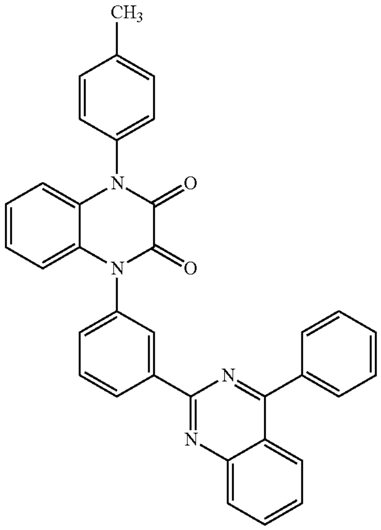

-continued
[Compound 195]
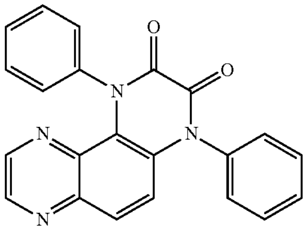
[Compound 196]
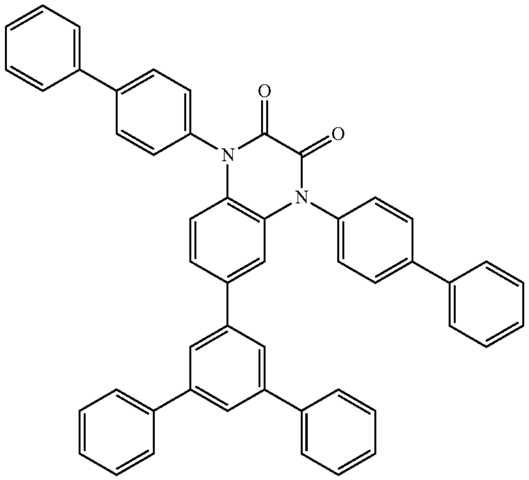
[Compound 197]
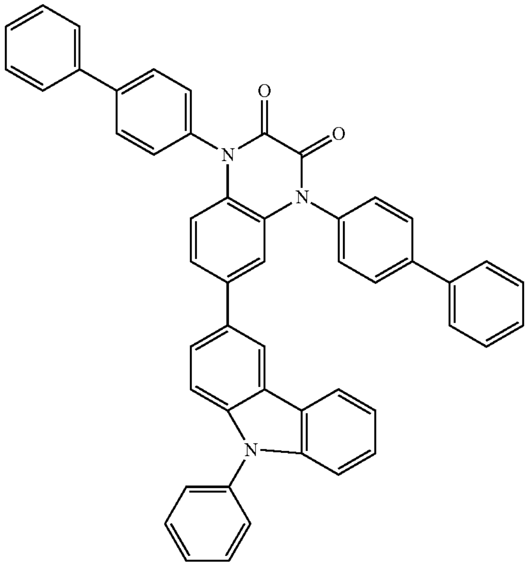
[Compound 198]
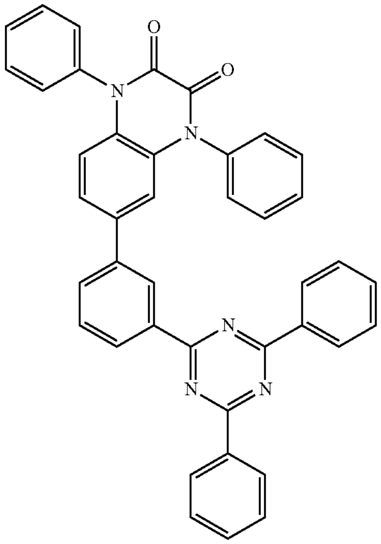
[Compound 199]
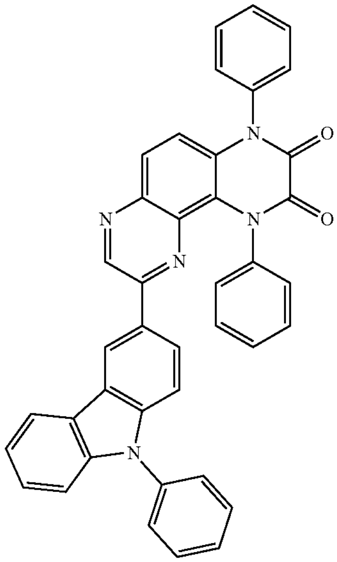
[Compound 200]
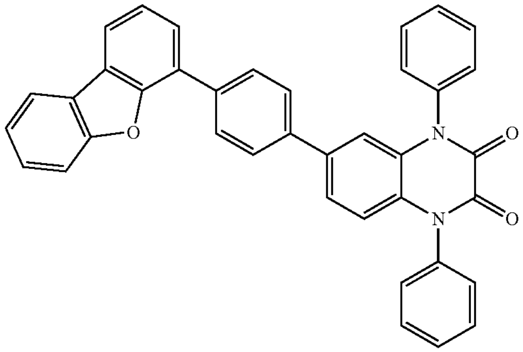

-continued
[Compound 201]
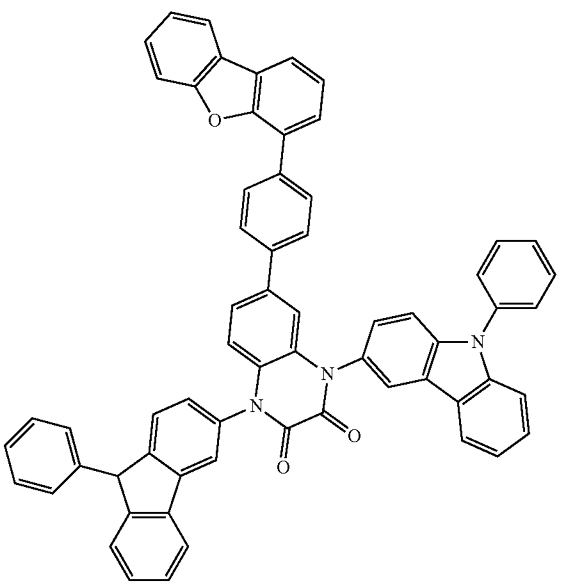
[Compound 202]
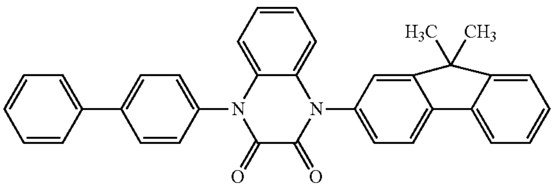
[Compound 203]
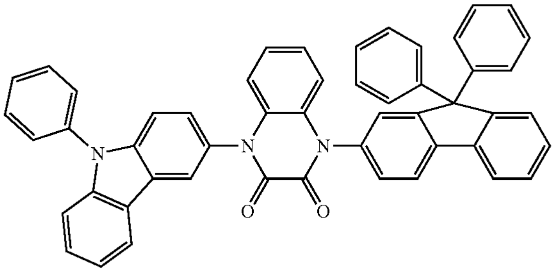
[Compound 204]
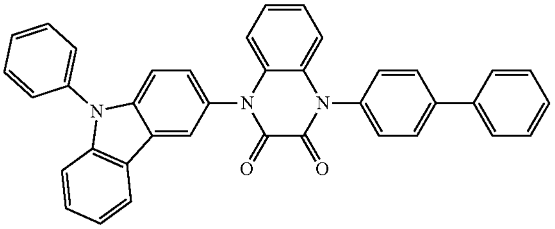
[Compound 205]
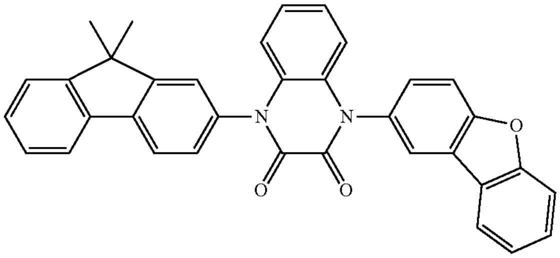
[Compound 206]
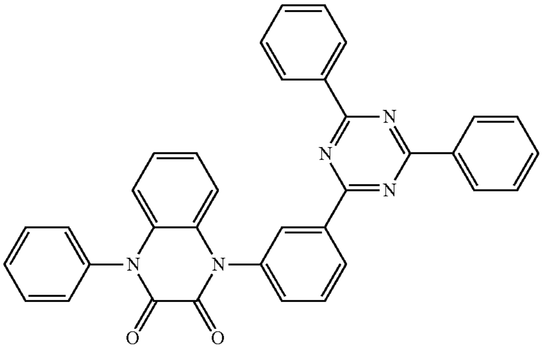
[Compound 207]
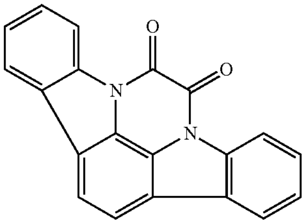
[Compound 208]
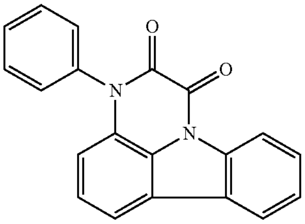

-continued
[Compound 209]
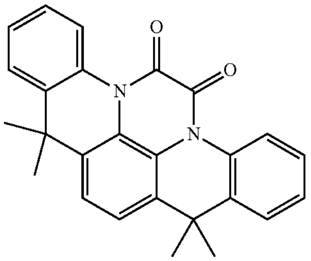
[Compound 210]
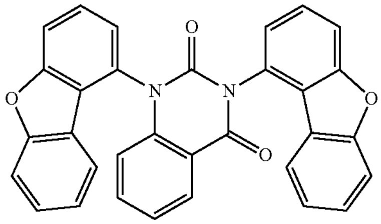
[Compound 211]
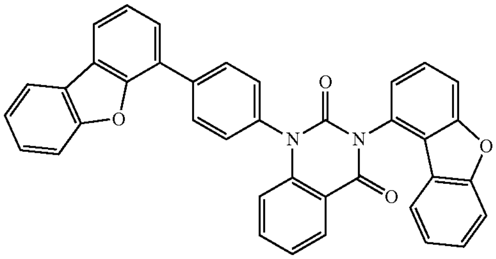
[Compound 212]
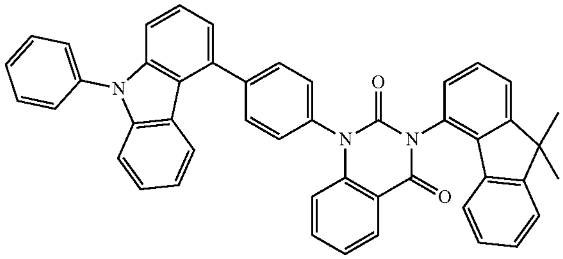
[Compound 213]
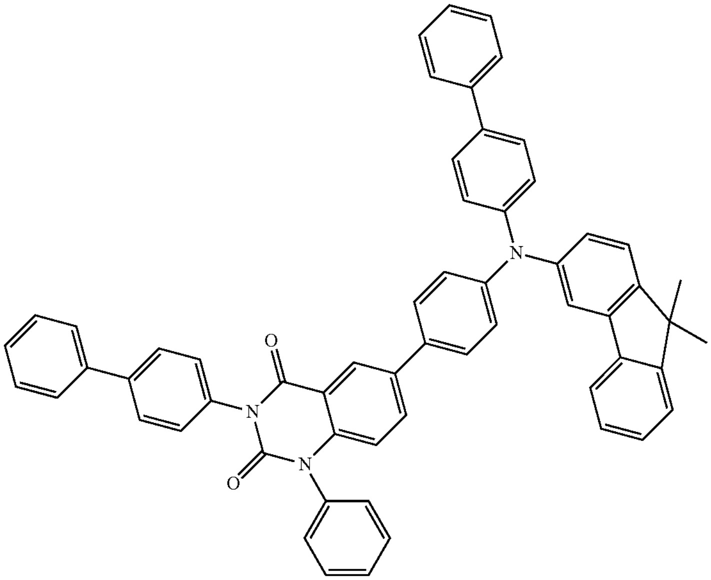
[Compound 214]
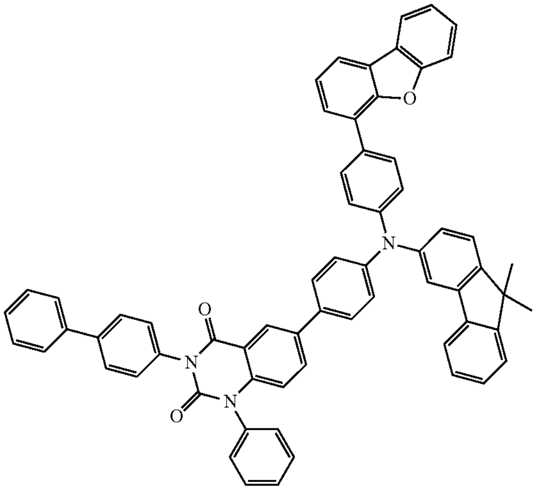
[Compound 215]
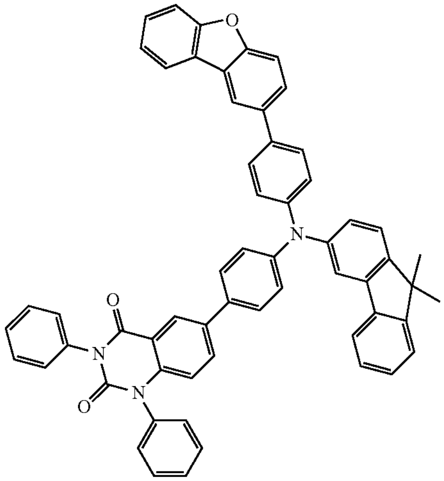

-continued
[Compound 216]
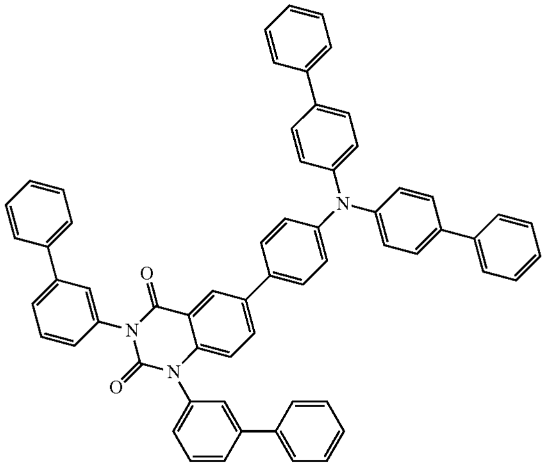
[Compound 217]
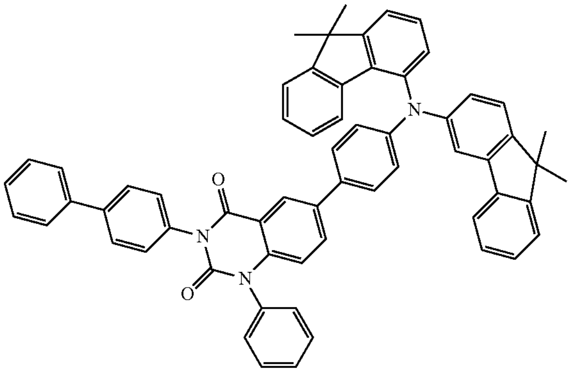
[Compound 218]
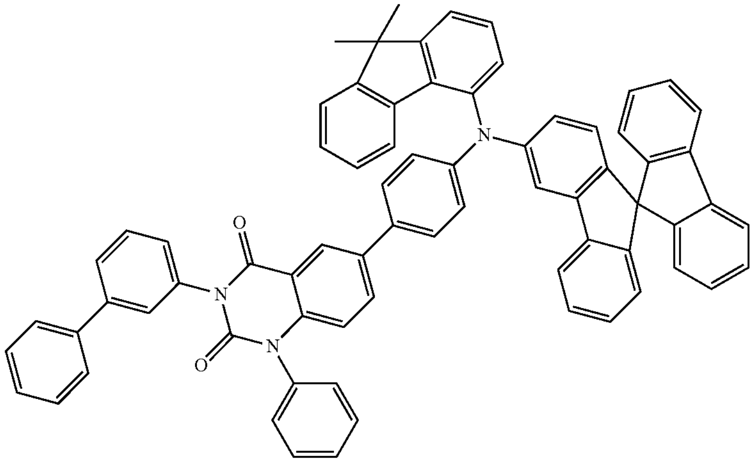
[Compound 219]
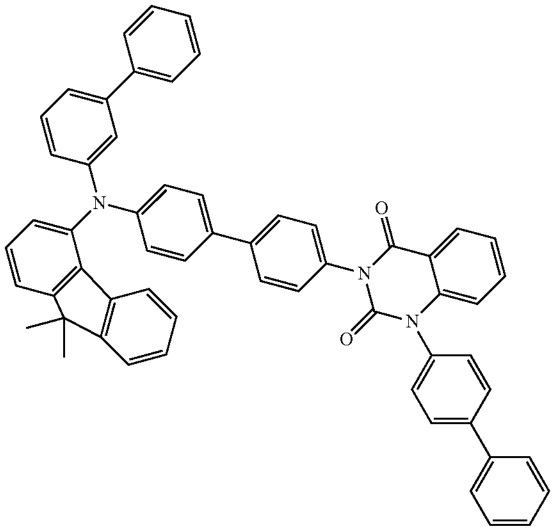
[Compound 220]
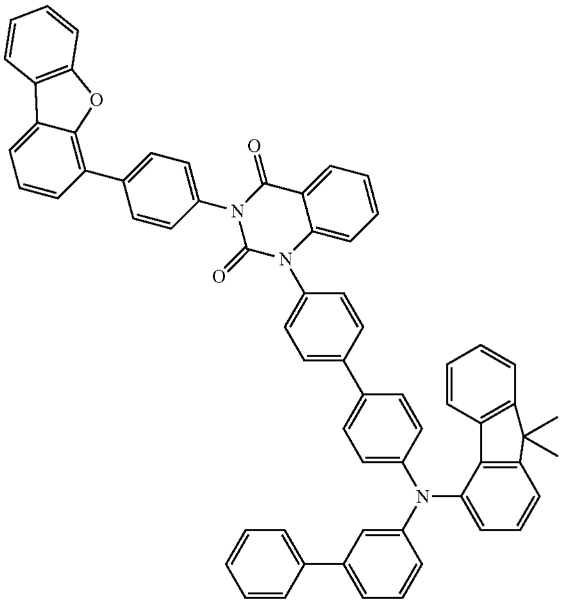

-continued
[Compound 221]
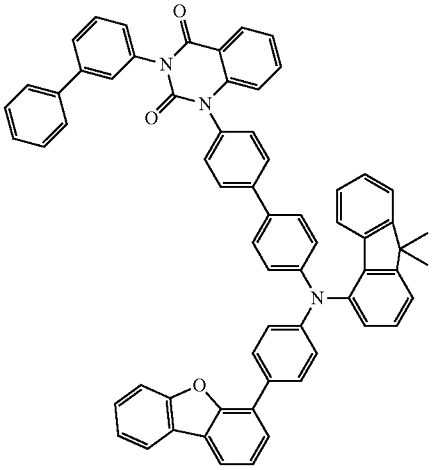
[Compound 222]
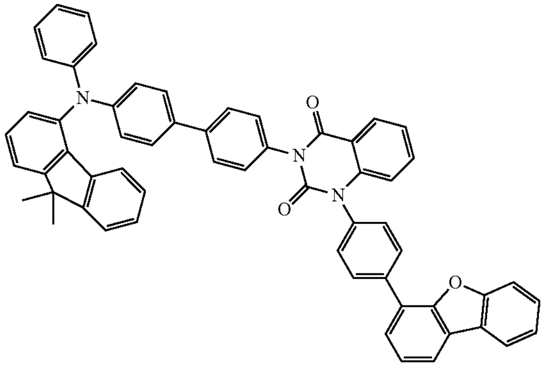
[Compound 223]
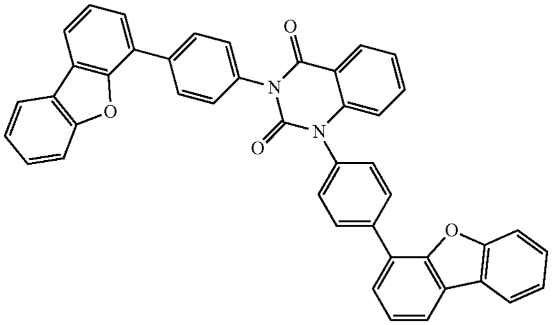
[Compound 224]
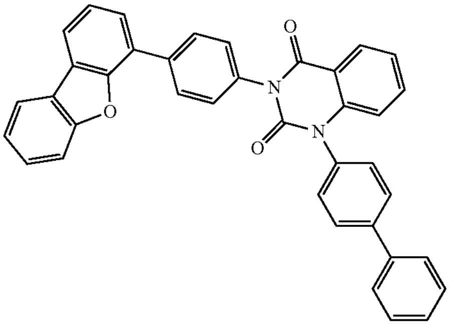
[Compound 225]
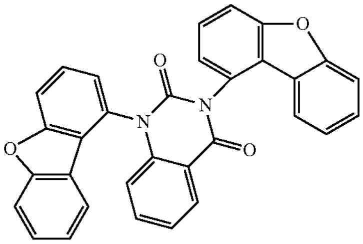
[Compound 226]
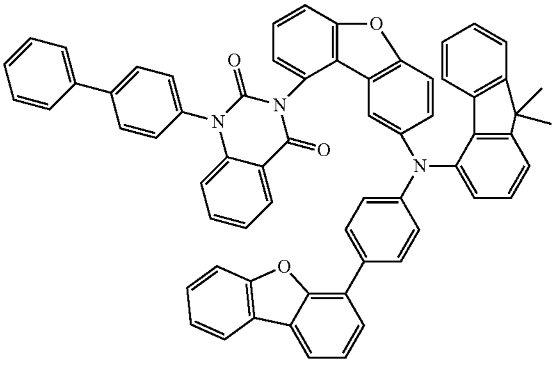

-continued
[Compound 227]
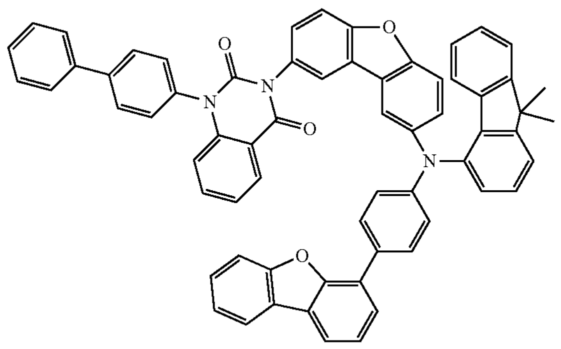
[Compound 228]
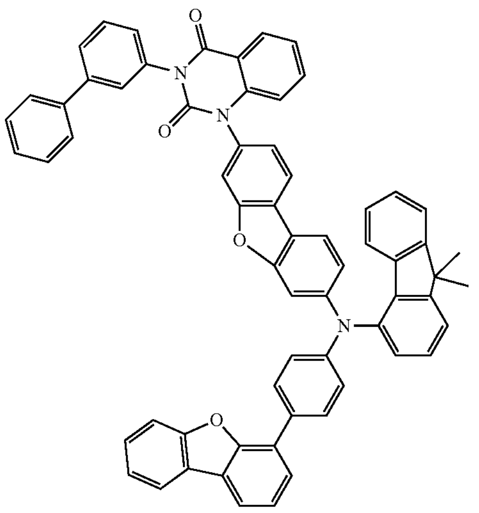
[Compound 229]
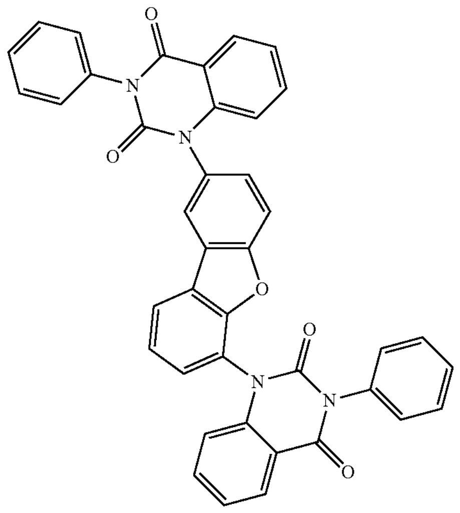
[Compound 230]
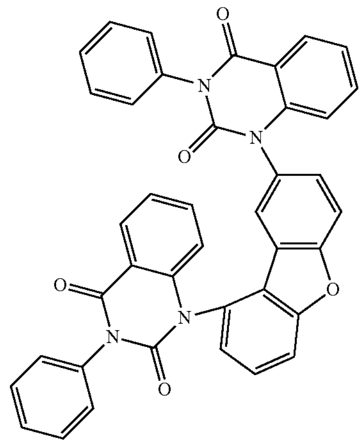
[Compound 231]
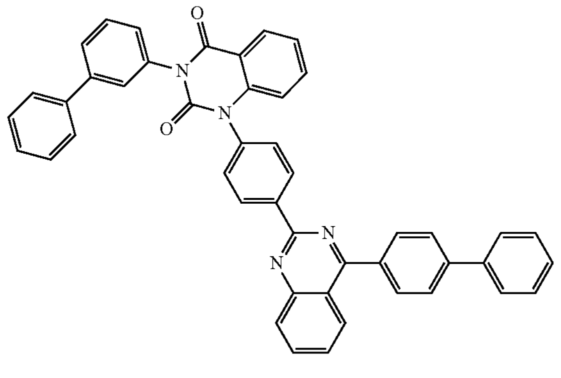
[Compound 232]
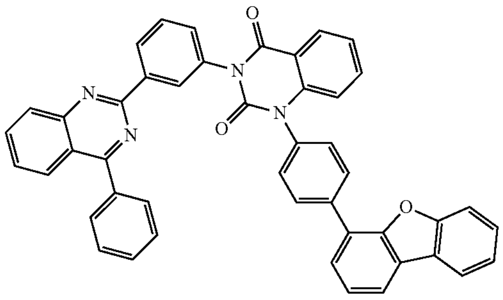

-continued

[Compound 233]

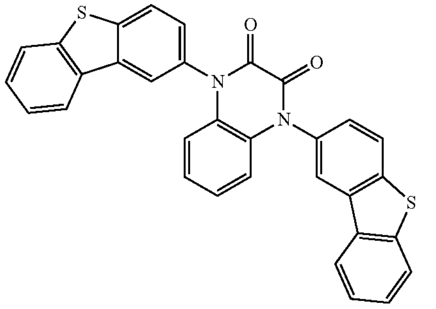

[Compound 234]

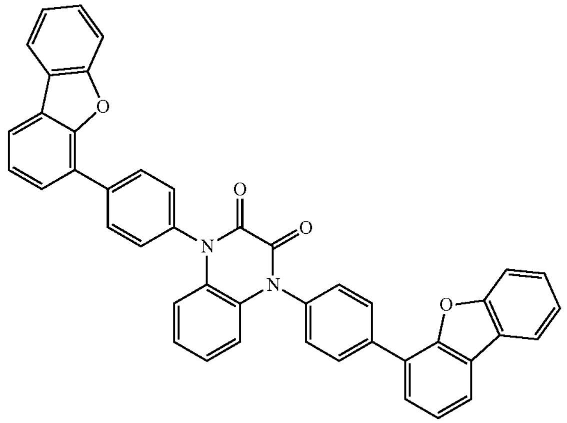

[Compound 235]

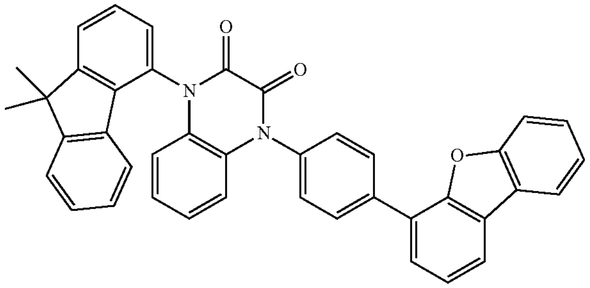

Particularly preferred individual compounds for inventive use in the electronic device are the compounds 1, 2, 6, 34, 55, 56, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 123, 124, 125, 141, 142, 143, 144, 145, 146, 147, 148, 149, 150, 151, 152, 153, 157, 162, 164, 170, 172, 178, 181, 184, 186, 187, 188, 199, 200, 201, 202, 203, 204, 205 and 206.

For the processing of the compounds of the invention or of the compounds to be used in accordance with the invention from a liquid phase, for example by spin-coating or by printing methods, formulations comprising the above-described compounds are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore further provides a formulation comprising at least one inventive compound of the formula (42), (47), (48), (49), (50), (51), (56) or (57) and at least one further compound. The further compound may, for example, be a solvent, especially one of the abovementioned solvents or a mixture of these solvents. The further compound may alternatively be a further organic or inorganic compound which is likewise used in the electronic device, for example an emitting compound, especially a phosphorescent compound.

The present invention further provides for the use of the inventive compounds of the formula (42), (47), (48), (49), (50), (51), (56) or (57) in an electronic device, especially in an organic electroluminescent device as described above.

The details with regard to the electronic device of the invention comprising at least one compound of the formula (1) are also correspondingly applicable to the specific compounds of the formula (1) described as compounds of the formula (42), (47), (48), (49), (50), (51), (56) or (57).

In a further embodiment of the invention, the organic electroluminescent device comprises the compound of formula (1) or the above-recited preferred embodiments in an optical outcoupling layer. An optical outcoupling layer is understood to mean a layer which is not between the anode and the cathode but is applied to an electrode outside the actual device, for example between an electrode and a substrate, in order to improve the optical outcoupling.

In a preferred embodiment of the invention, the compound of the invention is used as matrix material for a fluorescent or phosphorescent compound, especially for a phosphorescent compound, in an emitting layer. In this case, the organic electroluminescent device may contain one emitting layer, or it may contain a plurality of emitting layers, where at least one emitting layer contains at least one compound of formula (1) or a compound specified as preferred as matrix material.

When the compound of formula (1) or the above-recited preferred embodiments is used as matrix material for an emitting compound in an emitting layer, it is preferably used in combination with one or more phosphorescent materials (triplet emitters). Phosphorescence in the context of this invention is understood to mean luminescence from an excited state having spin multiplicity >1, especially from an excited triplet state. In the context of this application, all luminescent complexes with transition metals or lanthanides, especially all iridium, platinum and copper complexes, shall be regarded as phosphorescent compounds.

The mixture of the compound of formula (1) or the above-recited preferred embodiments and the emitting compound contains between 99% and 1% by volume, preferably between 98% and 10% by volume, more preferably between 97% and 60% by volume and especially between 95% and 80% by volume of the compound of formula (1) or the above-recited preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material. According to the choice of matrix material, a lower emitter concentration may also be preferable, as described, for example, in the unpublished application EP 11002816.4.

A further preferred embodiment of the present invention is the use of the compound of formula (1) or the above-recited preferred embodiments as matrix material for a phosphorescent emitter in combination with a further matrix material. A further preferred embodiment of the present invention is the use of the compound of formula (1) or according to the preferred embodiments as matrix material for a phosphorescent emitter in combination with a further matrix material. Particularly suitable matrix materials which can be used in combination with the compounds of formula (1) or according to the preferred embodiments are aromatic ketones, aromatic phosphine oxides or aromatic sulfoxides or sulfones, for example according to WO2004/013080, WO2004/093207, WO2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO2008/056746, indenocarbazole derivatives, for example according to WO2010/136109, WO2011/000455 or WO 2013/041176, azacarbazole derivatives, for example according to EP 1617710, EP 1617711, EP 1731584, JP 2005/347160, bipolar matrix materials, for example according to WO2007/137725, silanes, for example according to WO2005/111172, azaboroles or boronic esters, for example according to WO2006/117052, triazine derivatives, for example according to WO2010/015306, WO2007/063754 or WO2008/056746, zinc complexes, for example according to EP 652273 or WO2009/062578, diazasilole or tetraazasilole derivatives, for example according to WO 2010/054729, diazaphosphole derivatives, for example according to WO 2010/054730, bridged carbazole derivatives, for example according to US 2009/0136779, WO2010/050778, WO2011/042107, WO2011/088877 or WO2012/143080, triphenylene derivatives, for example according to WO 2012/048781, or lactams, for example according to WO2011/116865 or WO2011/137951. It is likewise possible for a further phosphorescent emitter which emits at a shorter wavelength than the actual emitter to be present as co-host in the mixture.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially,a metal having this atomic number. Preferred phosphorescent emitters used are compounds containing copper, molybdenum, tungsten, rhenium, ruthenium, osmium, rhodium, iridium, palladium, platinum, silver, gold or europium, especially compounds containing iridium, platinum or copper.

Examples of the above-described emitters can be found in applications WO 00/70655, WO01/41512, WO02/02714, WO02/15645, EP 1191613, EP 1191612, EP 1191614, WO05/033244, WO05/019373 and US 2005/0258742. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

In a further embodiment of the invention, the organic electroluminescent device of the invention does not contain any separate hole injection layer and/or hole transport layer and/or hole blacker layer and/or electron transport layer, meaning that the emitting layer directly adjoins the hole injection layer or the anode, and/or the emitting layer directly adjoins the electron transport layer or the electron injection layer or the cathode, as described, for example, in WO2005/053051. It is additionally possible to use a metal complex identical or similar to the metal complex in the emitting layer as hole transport or hole injection material directly adjoining the emitting layer, as described, for example, in WO2009/030981.

In a further preferred embodiment of the invention, the compound of formula (1) or the above-recited preferred embodiments is used as electron transport material in an electron transport or electron injection layer. In this case, the emitting layer may be fluorescent or phosphorescent. When the compound is used as electron transport material, it may be preferable for it to be doped, for example with alkali metal complexes, for example LiQ (lithium hydroxyquinolinate).

In yet a further preferred embodiment of the invention, the compound of formula (1) or the above-recited preferred embodiments is used in a hole blocker layer. A hole blocker layer is understood to be a layer which directly adjoins an emitting layer on the cathode side.

It is additionally possible to use the compound of formula (1) or the above-recited preferred embodiments both in a hole blocker layer or electron transport layer and as matrix in an emitting layer.

In yet a further embodiment of the invention, the compound of formula (1) or the above-recited preferred embodiments is used in a hole transport layer or in an electron blocker layer or exciton blocker layer.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution. These methods are especially also suitable for oligomers, dendrimers and polymers.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:

1 The inventive compounds used as matrix material for fluorescent or phosphorescent emitters lead to very high efficiencies and to long lifetimes. This is especially true when the compounds are used as matrix material for a red- or green-phosphorescing emitter.
2. The inventive compounds have high thermal stability,
3. The inventive compounds used in organic electroluminescent devices lead to high efficiencies and to steep current-voltage curves with low use voltages.
4. When used as electron transport material, the inventive compounds also lead to very good properties in relation to efficiency, lifetime and operating voltage of organic electroluminescent devices.

These abovementioned advantages are not accompanied by a deterioration in the further electronic properties.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere. The reactants can be sourced from ALDRICH or ABCR (palladium(II) acetate, tri-o-tolylphosphine, inorganic materials, solvents). The figures in the case of the reactants known from the literature are the CAS numbers.

Starting compounds used may, for example, be N,N'-diphenyl-1,2-benzenediamine (Organic Letters 2007, 9(7), 1339-1342) or N-phenyl-o-phenylenediamine (Indian Journal of Pharmaceutical Sciences 2003, 65(2), 135-138).

Example A 6-(4-bromophenyl)-1H-quinazoline-2,4-dione

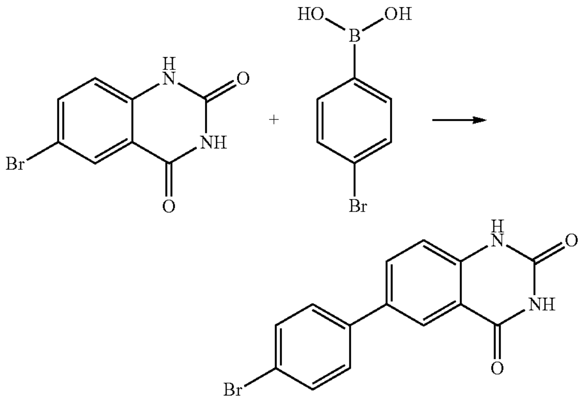

15.47 g (75 mmol) of 4-bromobenzeneboronic acid, 18 g (75 mmol) of 6-bromo-1H-quinazoline-2,4-dione (75 mmol) and 110 mL of a 2M $NaHCO_3$-containing aqueous solution (163 mmol) are suspended in 500 mL of dimethoxyethane. 3.0 g (3.45 mmol) of tetrakis(triphenylphosphine)palladium(0) are added to this suspension, and the reaction mixture is heated under reflux for 22 h. After cooling, the organic phase is removed, filtered through silica gel, washed four times with 400 mL of water and then concentrated to dryness. This is followed by recrystallization in toluene. The yield is 16.5 g (52 mmol), corresponding to 70% of theory.

The following compounds are prepared in an analogous manner:

| | Reactant 1 | Reactant 2 | Product | Yield [%] |
|---|---|---|---|---|
| a1 | 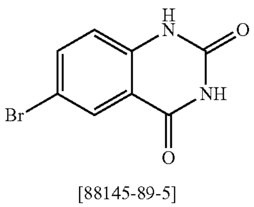 [SMILES: O=c1[nH]c(=O)c2cc(Br)ccc2[nH]1] [88145-89-5] | 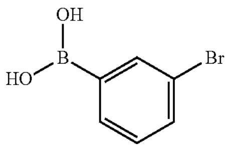 [89598-96-9] | 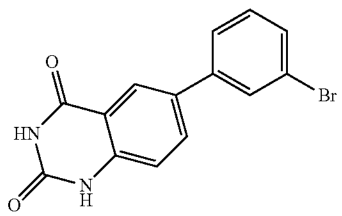 [SMILES: O=c1[nH]c(=O)c2cc(-c3cccc(Br)c3)ccc2[nH]1] | 58% |

-continued

| | Reactant 1 | Reactant 2 | Product | Yield [%] |
|---|---|---|---|---|
| a2 | 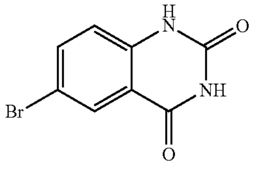 [88145-89-5] | 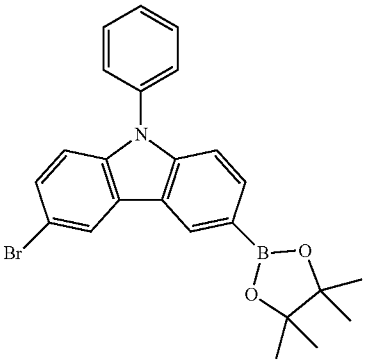 [1445991-41-2] | 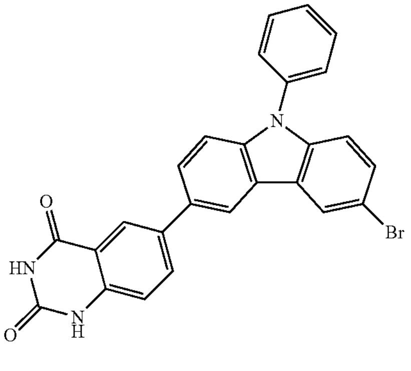 [SMILES: O=c1[nH]c(=O)c2cc(-c3ccc4c(c3)c3cc(Br)ccc3n4-c3ccccc3)ccc2[nH]1] | 49% |

Example B

6-phenyl-1H-quinazoline-2,4-dione

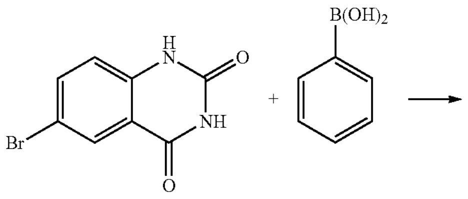

[99145-89-5]

-continued

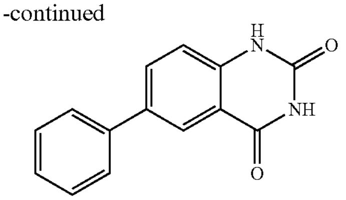

16.3 g (67.7 mmol) of 6-bromo-1H-quinazoline-2,4-dione, 7.3 g (80 mmol) of phenylboronic acid and 136 g (980 mmol) of tripotassium phosphate are suspended in 1000 mL of THF, 300 mL of water. Added to this suspension are 178 mg (0.67 mmol) of triphenylphosphine and then 152 mg (0.67 mmol) of palladium(II) acetate, and the reaction mixture is heated under reflux for 16 h. After cooling, the organic phase is removed, filtered through silica gel, washed three times with 200 mL of water and then concentrated to dryness. The residue is recrystallized from toluene/heptane. The yield is 13.4 g (56 mmol), corresponding to 85% of theory.

In an analogous manner, it is possible to obtain the following compounds:

| Example | Reactant 1 | Reactant 2 | Product | Yield [%] |
|---|---|---|---|---|
| b1 | 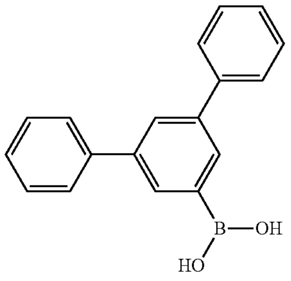 [128388-54-5] | 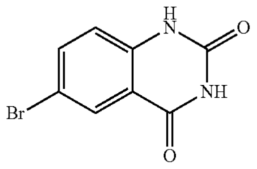 [88145-89-5] | 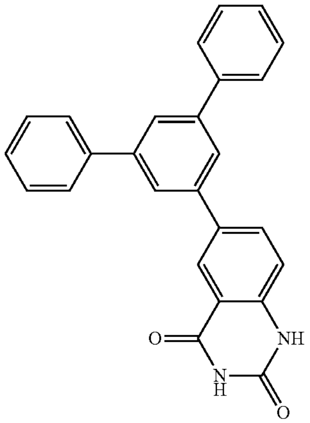 [SMILES: O=c1[nH]c(=O)c2cc(-c3cc(-c4ccccc4)cc(-c4ccccc4)c3)ccc2[nH]1] | 74 |

-continued
| Example | Reactant 1 | Reactant 2 | Product | Yield [%] |
|---|---|---|---|---|
| b2 | 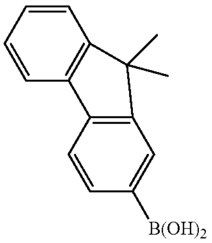 [333432-28-3] | 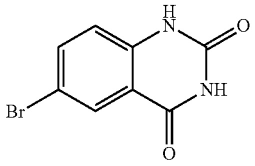 [88145-89-5] | 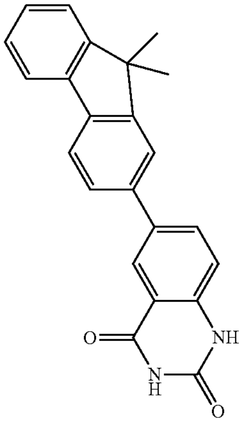 [SMILES: CC1(C)c2ccccc2-c2ccc(-c3ccc4[nH]c(=O)[nH]c(=O)c4c3)cc21] | 70 |
| b3 | 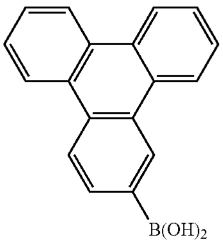 [654664-63-8] | 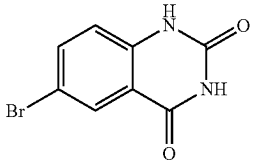 [88145-89-5] | 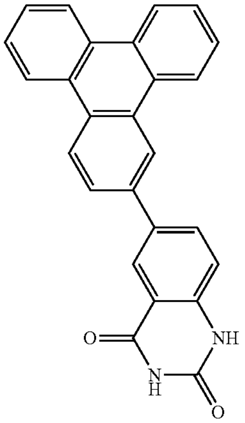 [SMILES: O=c1[nH]c(=O)c2cc(-c3ccc4c5ccccc5c5ccccc5c4c3)ccc2[nH]1] | 68 |
| b4 | 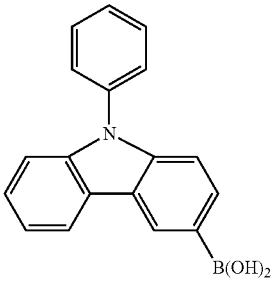 [854952-58-2] | 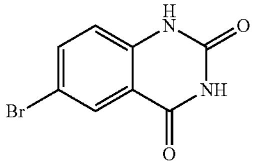 [88145-89-5] | 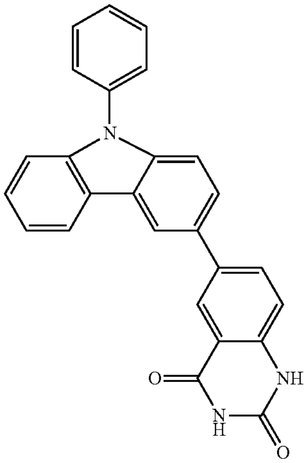 [SMILES: O=c1[nH]c(=O)c2cc(-c3ccc4c(c3)c3ccccc3n4-c3ccccc3)ccc2[nH]1] | 71 |
| b5 | 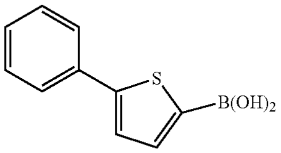 [306934-95-2] | 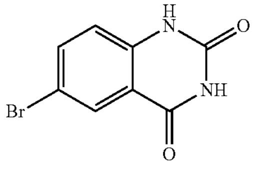 [88145-89-5] | 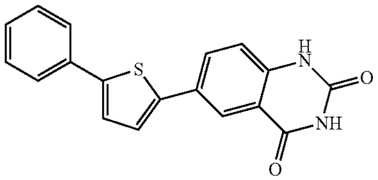 [SMILES: O=c1[nH]c(=O)c2cc(-c3ccc(-c4ccccc4)s3)ccc2[nH]1] | 64 |

-continued
| Example | Reactant 1 | Reactant 2 | Product | Yield [%] |
|---|---|---|---|---|
| b6 | 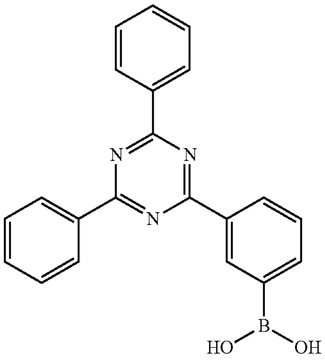 [1288508-31-7] | 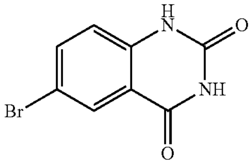 [88145-89-5] | 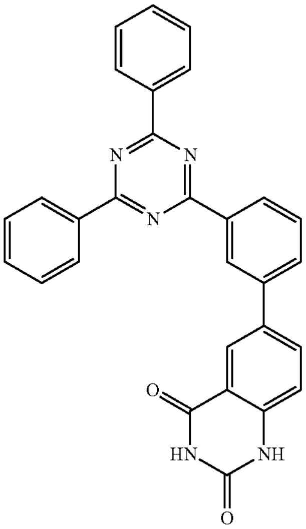 [SMILES: O=c1[nH]c(=O)c2cc(-c3cccc(-c4nc(-c5ccccc5)nc(-c5ccccc5)n4)c3)ccc2[nH]1] | 69 |
| b7 | 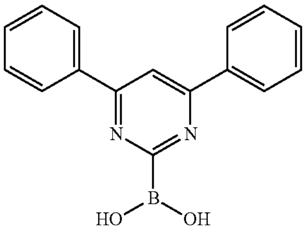 [1314221-56-1] | 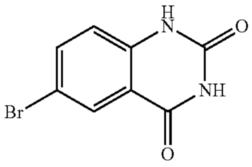 [88145-89-5] | 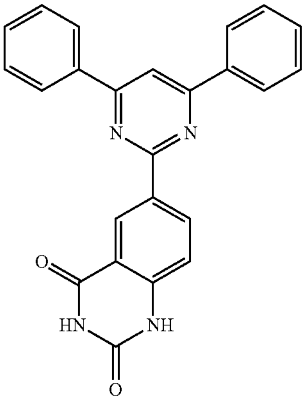 [SMILES: O=c1[nH]c(=O)c2cc(-c3nc(-c4ccccc4)cc(-c4ccccc4)n3)ccc2[nH]1] | 72 |
| b8 | 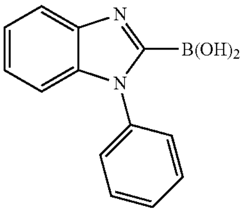 [1214723-25-7] | 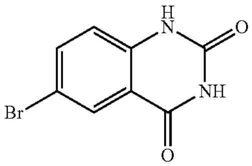 [88145-89-5] | 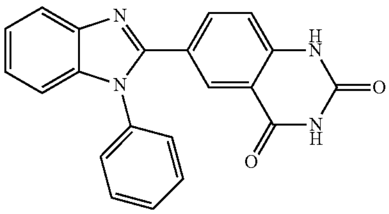 | 64 |

-continued
| Example | Reactant 1 | Reactant 2 | Product | Yield [%] |
|---|---|---|---|---|
| b9 | 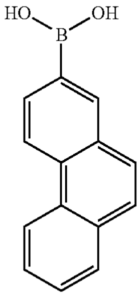 [1188094-10-1] | 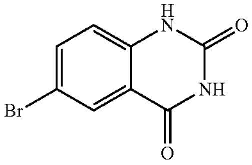 [88145-89-5] | 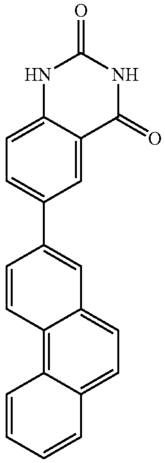 [SMILES: O=c1[nH]c(=O)c2cc(-c3ccc4c(ccc5ccccc54)c3)ccc2[nH]1] | 63 |
| b10 | 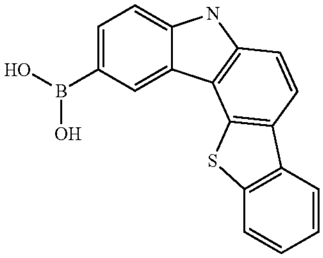 [1350842-21-5] | 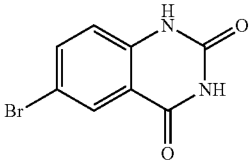 [88145-89-5] | 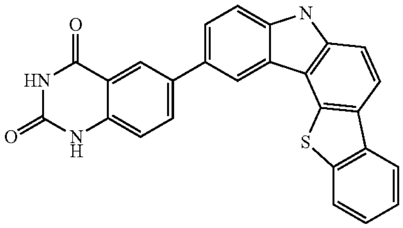 [SMILES: O=c1[nH]c(=O)c2cc(-c3ccc4[nH]c5ccc6c7ccccc7sc6c5c4c3)ccc2[nH]1] | 71 |
| b11 | 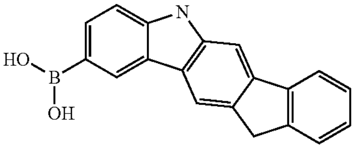 [1377576-52-7] | 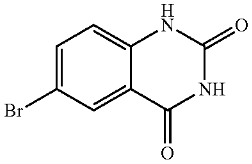 [88145-89-5] | 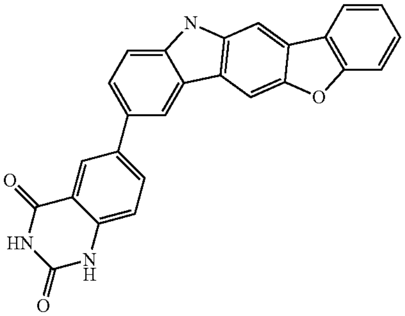 [SMILES: O=c1[nH]c(=O)c2cc(-c3ccc4[nH]c5cc6c(cc5c4c3)oc3ccccc36)ccc2[nH]1] | 69 |
| b12 | 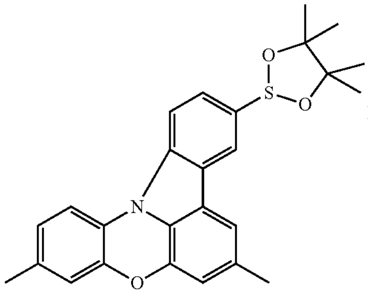 [1223056-04-6] | 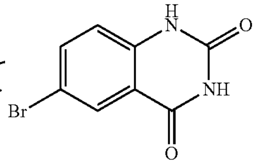 [88145-89-5] | 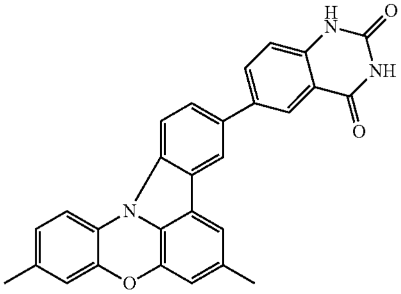 [SMILES: Cc1ccc2c(c1)Oc1cc(C)cc3c4cc(-c5ccc6[nH]c(=O)[nH]c(=O)c6c5)ccc4n-2c13] | 58 |

-continued
| Example | Reactant 1 | Reactant 2 | Product | Yield [%] |
| --- | --- | --- | --- | --- |
| b13 | 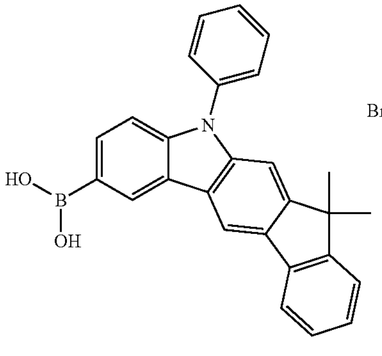 [1379585-25-7] | 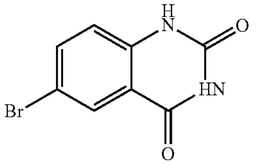 [88145-89-5] | 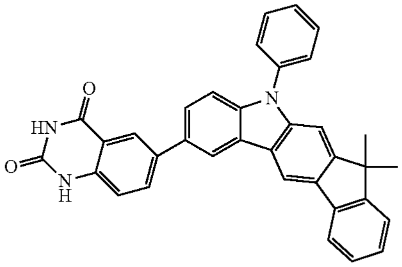 [SMILES: CC1(C)c2ccccc2-c2cc3c4cc(-c5ccc6[nH]c(=O)[nH]c(=O)c6c5)ccc4n(-c4ccccc4)c3cc21] | 72 |
| b14 | 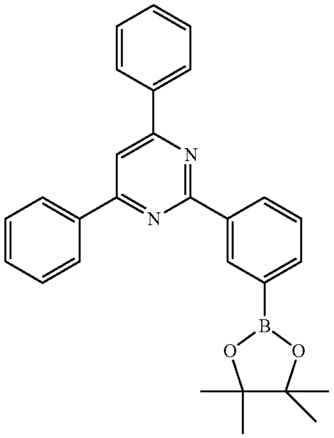 [1381862-91-4] | 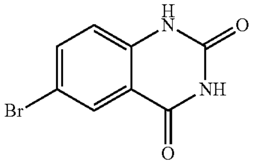 [88145-89-5] | 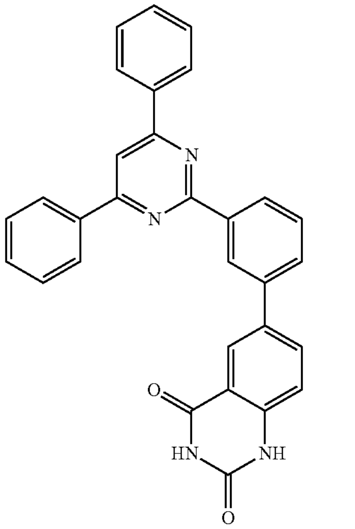 [SMILES: O=c1[nH]c(=O)c2cc(-c3cccc(-c4nc(-c5ccccc5)cc(-c5ccccc5)n4)c3)ccc2[nH]1] | 69 |
| b15 | 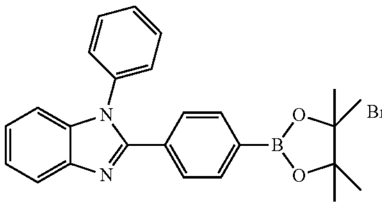 [1146340-38-6] | 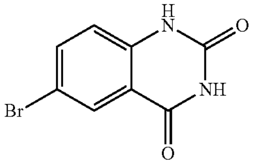 [88145-89-5] | 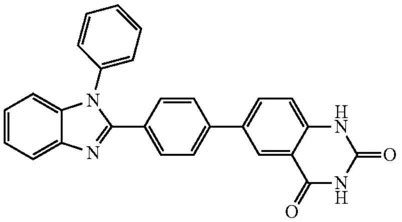 [SMILES: O=c1[nH]c(=O)c2cc(-c3ccc(-c4nc5ccccc5n4-c4ccccc4)cc3)ccc2[nH]1] | 65 |
| b16 | 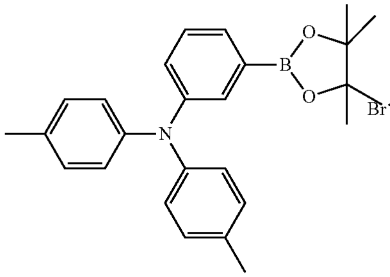 [1162753-18-5] | 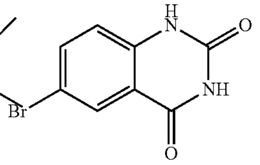 [88145-89-5] | 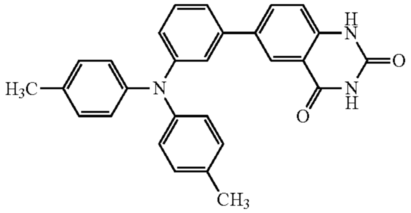 [SMILES: Cc1ccc(N(c2ccc(C)cc2)c2cccc(-c3ccc4[nH]c(=O)[nH]c(=O)c4c3)c2)cc1] | 67 |

-continued
| Example | Reactant 1 | Reactant 2 | Product | Yield [%] |
|---|---|---|---|---|
| b17 | 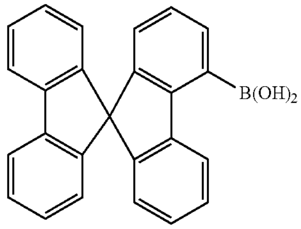 [1421789-05-0] | 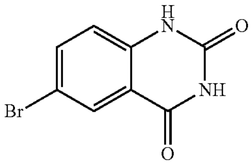 [88145-89-5] | 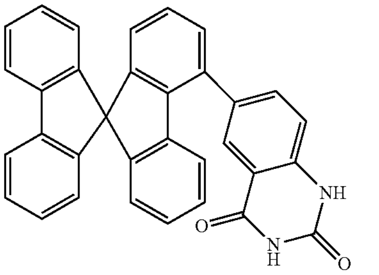 [SMILES: O=c1[nH]c(=O)c2cc(-c3cccc4c3-c3ccccc3C43c4ccccc4-c4ccccc43)ccc2[nH]1] | 58 |
| b18 | 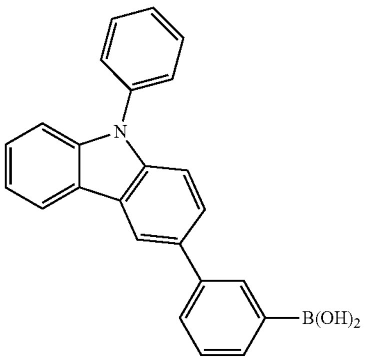 854952-60-6 | 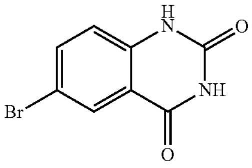 [88145-89-5] | 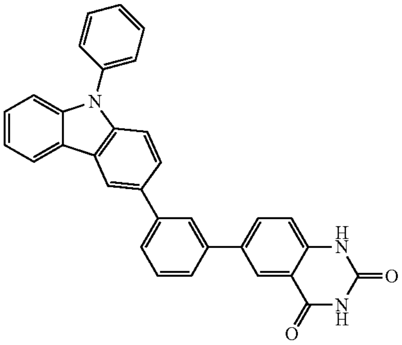 [SMILES: O=c1[nH]c(=O)c2cc(-c3cccc(-c4ccc5c(c4)c4ccccc4n5-c4ccccc4)c3)ccc2[nH]1] | 70 |
| b19 | 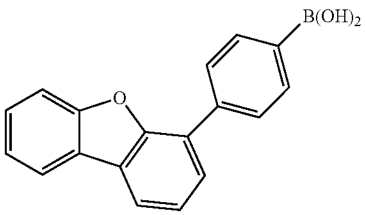 [796071-96-0] | 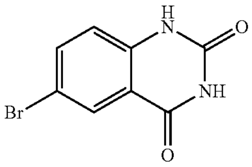 [88145-89-5] | 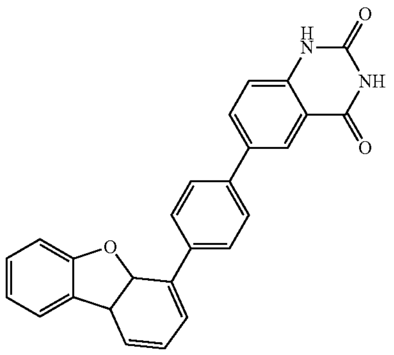 [SMILES: O=c1[nH]c(=O)c2cc(-c3ccc(C4=CC=CC5c6ccccc6OC45)cc3)ccc2[nH]1] | 72 |
| b20 | 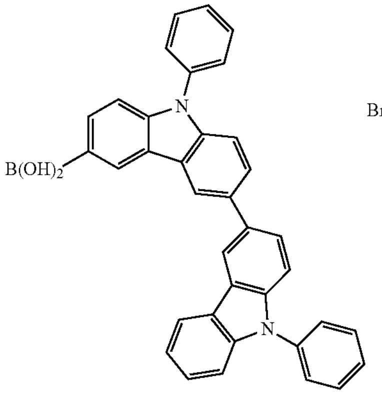 [918137-86-7] | 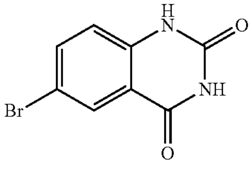 [88145-89-5] | 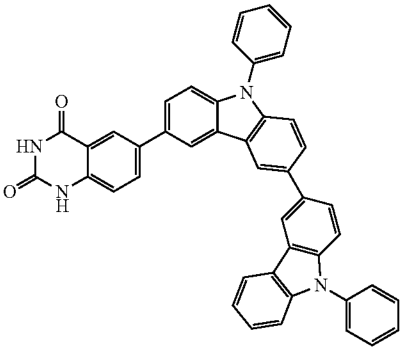 [SMILES: O=c1[nH]c(=O)c2cc(-c3ccc4c(c3)c3cc(-c5ccc6c(c5)c5ccccc5n6-c5ccccc5)ccc3n4-c3ccccc3)ccc2[nH]1] | 67 |

-continued
| Example | Reactant 1 | Reactant 2 | Product | Yield [%] |
|---|---|---|---|---|
| b21 | 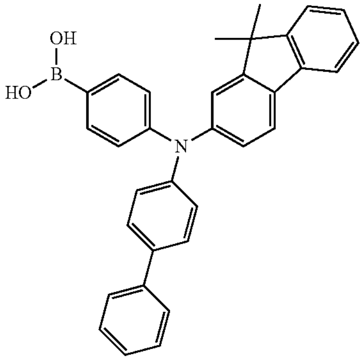 [1205177-27-2] | 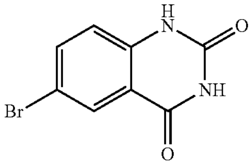 [88145-89-5] | 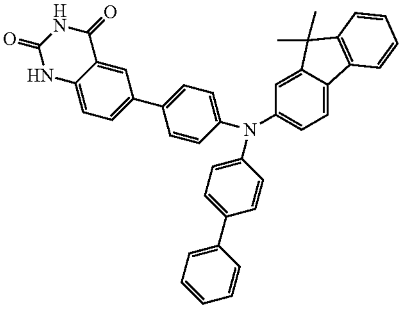 [SMILES: CC1(C)c2ccccc2-c2ccc(N(c3ccc(-c4ccccc4)cc3)c3ccc(-c4ccc5[nH]c(=O)[nH]c(=O)c5c4)cc3)cc21] | 68 |
| b22 | 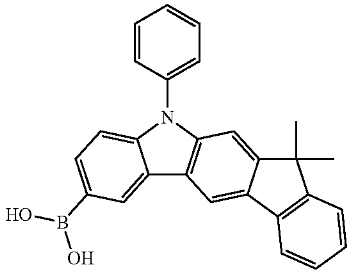 [1379585-25-7] | 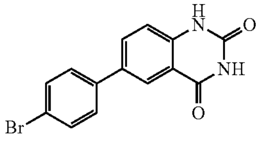 [SMILES: O=c1[nH]c(=O)c2cc(-c3ccc(Br)cc3)ccc2[nH]1] | 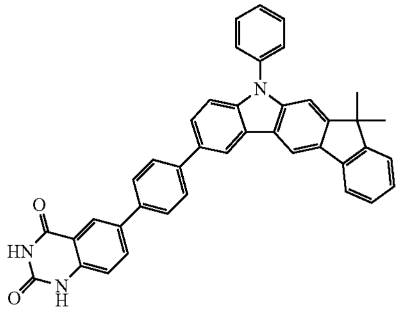 [SMILES: CC1(C)c2ccccc2-c2cc3c4cc(-c5ccc(-c6ccc7[nH]c(=O)[nH]c(=O)c7c6)cc5)ccc4n(-c4ccccc4)c3cc21] | 64 |
| b23 | 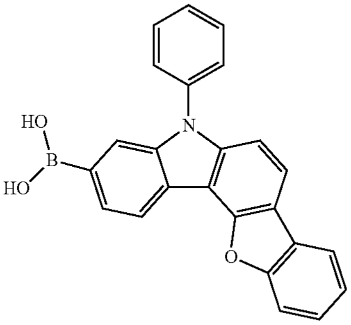 [1391729-62-6] | 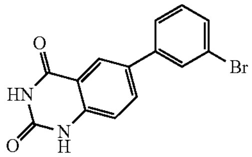 [SMILES: O=c1[nH]c(=O)c2cc(-c3cccc(Br)c3)ccc2[nH]1] | 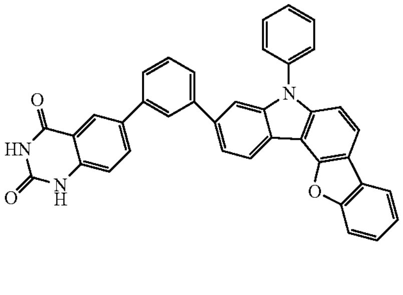 [SMILES: O=c1[nH]c(=O)c2cc(-c3cccc(-c4ccc5c6c7oc8ccccc8c7ccc6n(-c6ccccc6)c5c4)c3)ccc2[nH]1] | 70 |
| b24 | 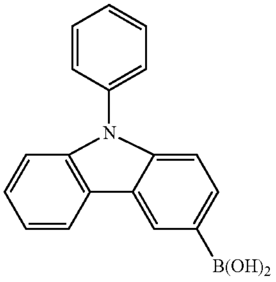 [854952-58-2] | 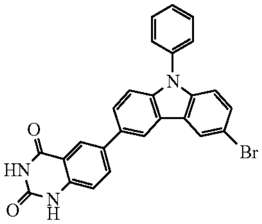 [SMILES: O=c1[nH]c(=O)c2cc(-c3ccc4c(c3)c3cc(Br)ccc3n4-c3ccccc3)ccc2[nH]1] | 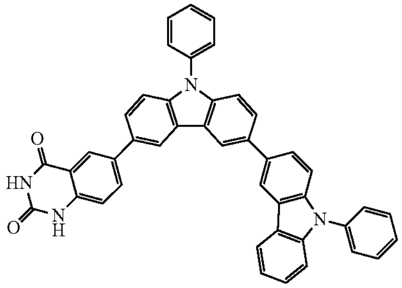 [SMILES: O=c1[nH]c(=O)c2cc(-c3ccc4c(c3)c3cc(-c5ccc6c(c5)c5ccccc5n6-c5ccccc5)ccc3n4-c3ccccc3)ccc2[nH]1] | 67 |

-continued

| Example | Reactant 1 | Reactant 2 | Product | Yield [%] |
|---|---|---|---|---|
| b25 | 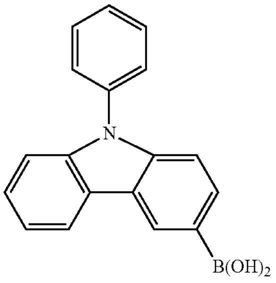 [854952-58-2] | 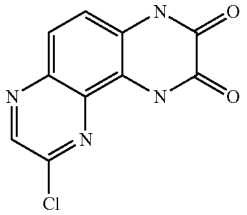 [1467073-28-4] | 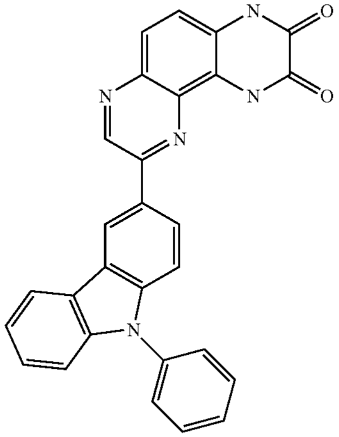 [SMILES: O=c1[nH]c2ccc3ncc(-c4ccc5c(c4)c4ccccc4n5-c4ccccc4)nc3c2[nH]c1=O] | 59 |
| b26 | 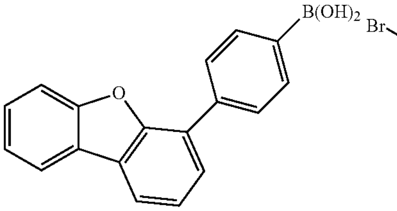 [796071-96-0] | 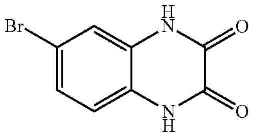 [1910-90-3] | 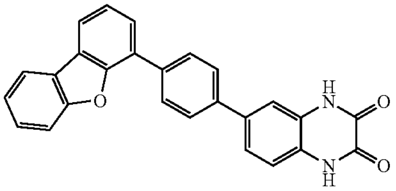 [SMILES: O=c1[nH]c2ccc(-c3ccc(-c4cccc5c4oc4ccccc45)cc3)cc2[nH]c1=O] | 63 |

Example C

6-(3-phenylcarbazol-9-yl)-1H-quinazoline-2,4-diones

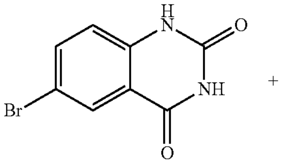

+

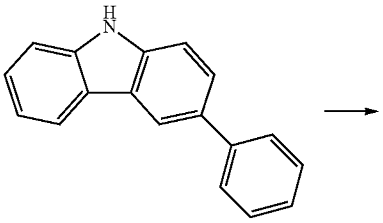

[103012-26-6]

-continued

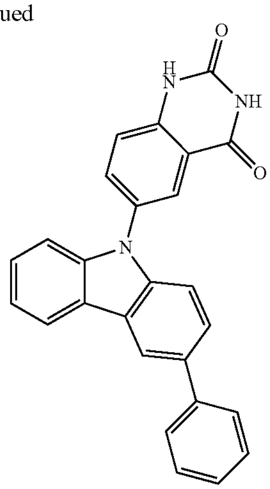

27.7 g (114 mmol) of 3-phenyl-9H-carbazole, 27.4 g (114 mmol) of 6-bromo-1H-quinazoline-2,4-dione and 30.5 g of NaOtBu are suspended in 1.5 L of p-xylene. To this suspension are added 0.5 g (2.11 mmol) of $Pd(OAc)_2$ and 1.6 mL of a 1M tri-tert-butylphosphine solution. The reaction mixture is heated under reflux for 16 h. After cooling, the organic phase is removed, washed three times with 200 mL of water and then concentrated to dryness. The residue is subjected to hot extraction with toluene and recrystallized from toluene. The yield is 39 g (97 mmol), corresponding to 87% of theory.

In an analogous manner, it is possible to obtain the following compounds:

| Example | Reacctant 1 | Reactant 2 | Product | Yield [%] |
|---|---|---|---|---|
| c1 | 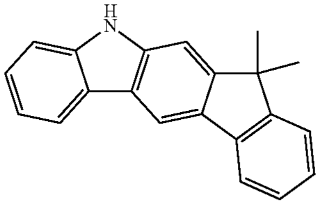 [1257220-47-5] | 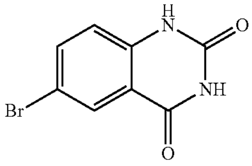 [88145-89-5] | 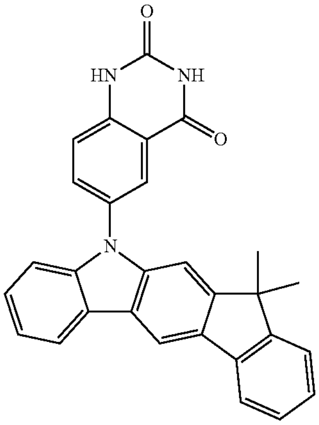 [SMILES: CC1(C)c2ccccc2-c2cc3c4ccccc4n(-c4ccc5[nH]c(=O)[nH]c(=O)c5c4)c3cc21] | 73 |
| c2 | 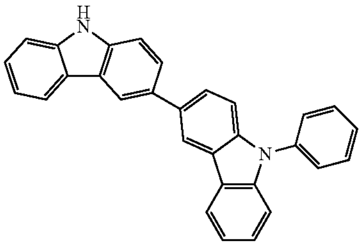 [1080735-14-9] | 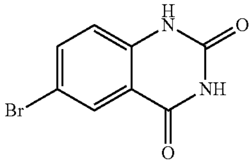 [88145-89-5] | 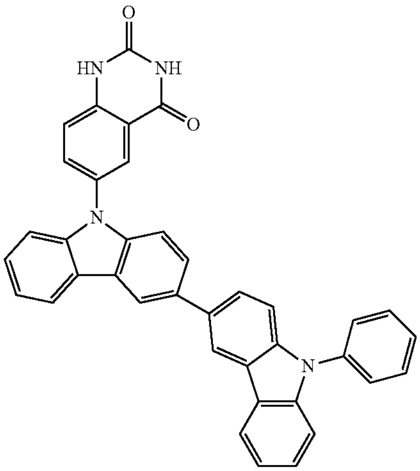 [SMILES: O=c1[nH]c(=O)c2cc(-n3c4ccccc4c4cc(-c5ccc6c(c5)c5ccccc5n6-c5ccccc5)ccc43)ccc2[nH]1] | 70 |
| c3 | 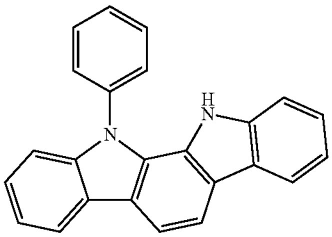 [1024598-06-8] | 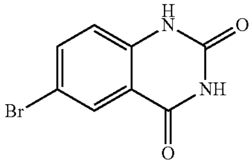 [88145-89-5] | 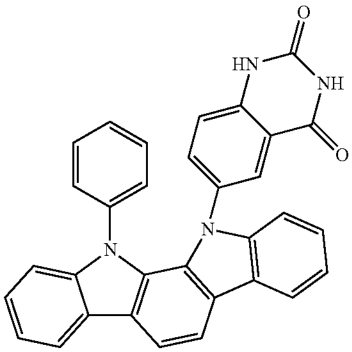 [SMILES: O=c1[nH]c(=O)c2cc(-n3c4ccccc4c4ccc5c6ccccc6n(-c6ccccc6)c5c43)ccc2[nH]1] | 69 |

-continued
| Example | Reacctant 1 | Reactant 2 | Product | Yield [%] |
|---|---|---|---|---|
| c4 | 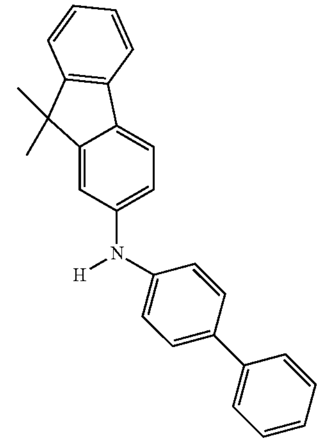 [1386375-27-4] | 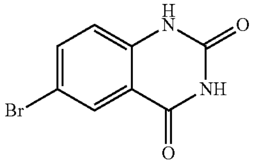 [88145-89-5] | 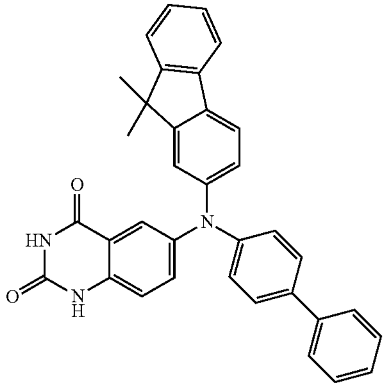 [SMILES: CC1(C)c2ccccc2-c2ccc(N(c3ccc(-c4ccccc4)cc3)c3ccc4[nH]c(=O)[nH]c(=O)c4c3)cc21] | 73 |
| c5 | 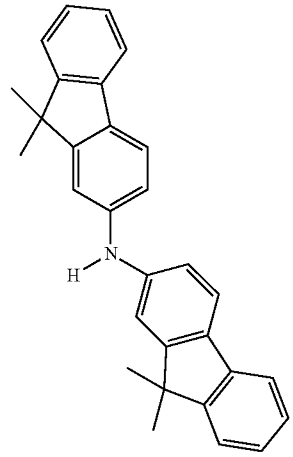 [1386375-16-1] | 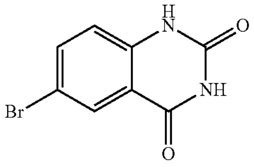 [88145-89-5] | 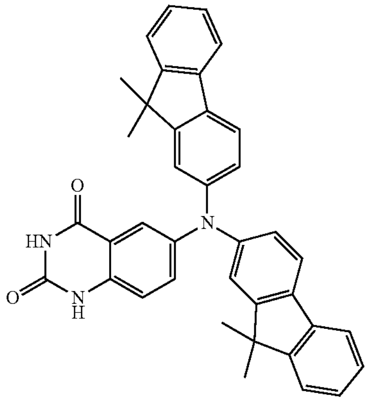 [SMILES: CC1(C)c2ccccc2-c2ccc(N(c3ccc4c(c3)C(C)(C)c3ccccc3-4)c3ccc4[nH]c(=O)[nH]c(=O)c4c3)cc21] | 71 |
Example D
1,3,6-triphenyl-1H-quinazoline-2,4-diones
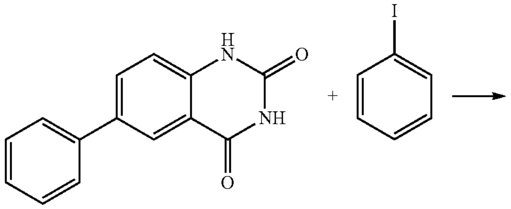
-continued
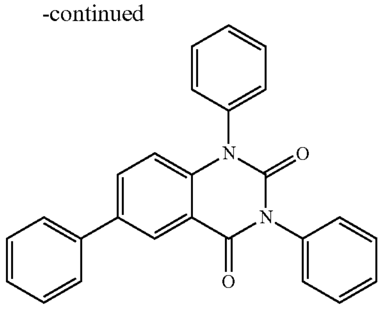
Compound 110
23 g (40 mmol) of 6-phenyl-1H-quinazoline-2,4-dione and 61.2 g (85 mmol) of 4-iodobenzene and 44.7 g (320 mmol) of potassium carbonate, 3 g (16 mmol) of copper(I)

iodide and 3.6 g (16 mmol) of 1,3-di(pyridin-2-yl)propane-1,3-dione are stirred in 100 mL of DMF at 150° C. for 30 h. The solution is diluted with water and extracted twice with ethyl acetate, and the combined organic phases are dried over $Na_2SO_4$ and concentrated by rotary evaporation. The residue is purified by chromatography (EtOAc/hexane: 2/3). The residue is recrystallized from toluene and finally sublimed under high vacuum ($p=5\times10^{-5}$ mbar). The purity is 99.9%. The yield is 24 g (62 mmol), 65% of theory.

In an analogous manner, it is possible to obtain the following compounds:

| Ex. | Reactant 1 | Reactant 2 | Product | Yield [%] |
|---|---|---|---|---|
| d1 | 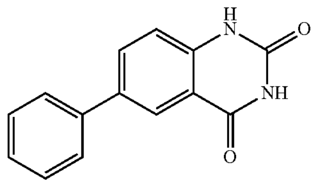 [SMILES: O=c1[nH]c(=O)c2cc(-c3ccccc3)ccc2[nH]1] | 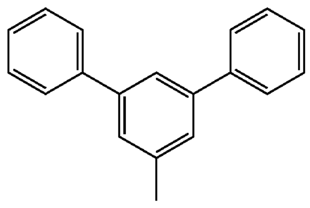 [87666-86-2] | 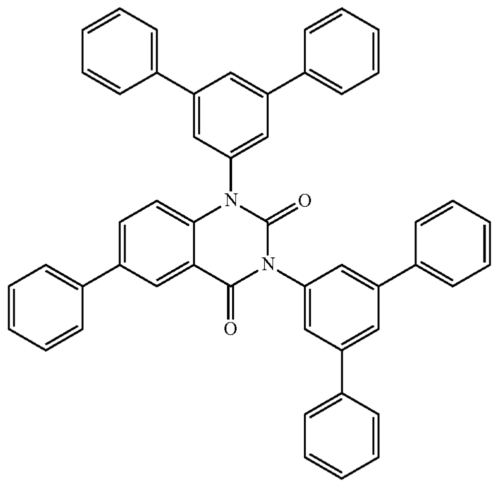 Compound 111 | 57 |
| d2 | 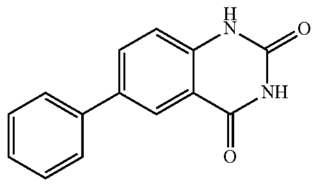 [SMILES: O=c1[nH]c(=O)c2cc(-c3ccccc3)ccc2[nH]1] | 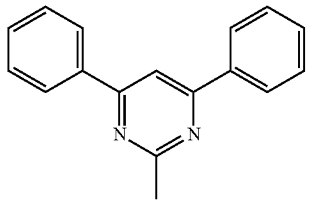 [374077-23-3] | 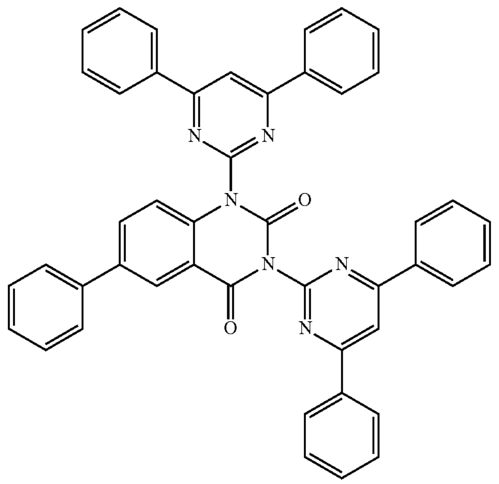 Compound 112 | 53 |

-continued
| Ex. | Reactant 1 | Reactant 2 | Product | Yield [%] |
|---|---|---|---|---|
| d3 | 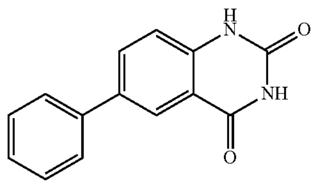 [SMILES: O=c1[nH]c(=O)c2cc(-c3ccccc3)ccc2[nH]1] | 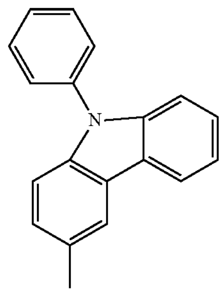 [502161-03-7] | 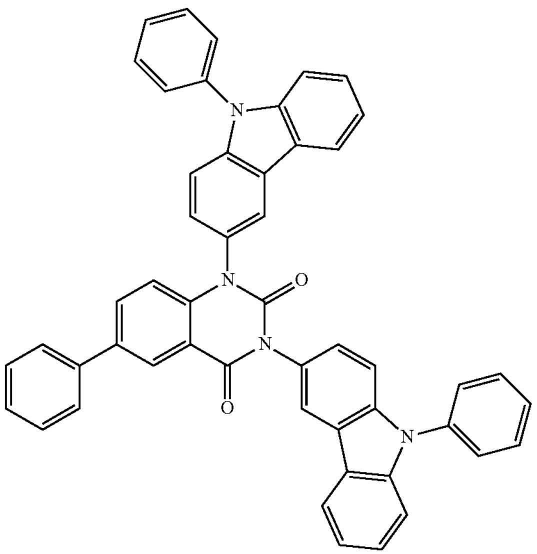 Compound 113 | 64 |

-continued
| Ex. | Reactant 1 | Reactant 2 | Product | Yield [%] |
| --- | --- | --- | --- | --- |
| d4 | 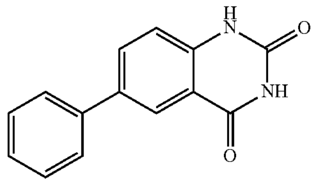 [SMILES: O=c1[nH]c(=O)c2cc(-c3ccccc3)ccc2[nH]1] | 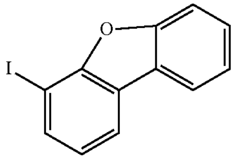 [65344-26-5] | 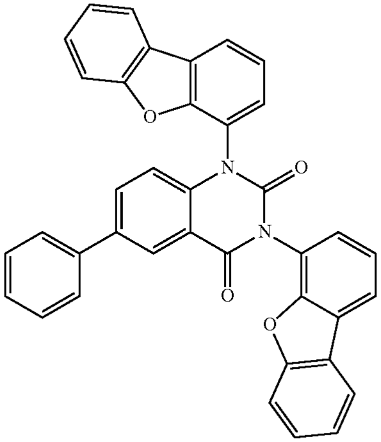 Compound 114 | 56 |

-continued
| Ex. | Reactant 1 | Reactant 2 | Product | Yield [%] |
|---|---|---|---|---|
| d5 | 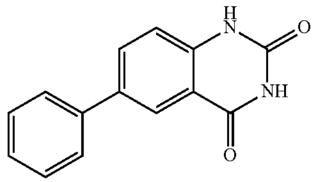 [SMILES: O=c1[nH]c(=O)c2cc(-c3ccccc3)ccc2[nH]1] | 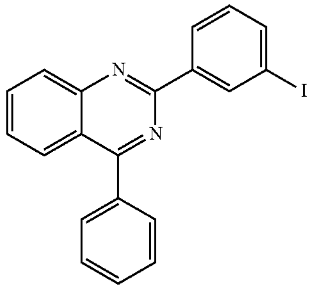 [1522379-08-3] | 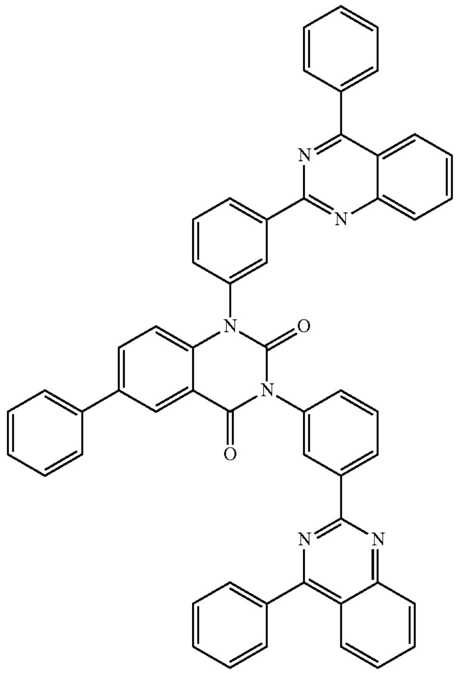 Compound 115 | 67 |

-continued
| Ex. | Reactant 1 | Reactant 2 | Product | Yield [%] |
|---|---|---|---|---|
| d6 | 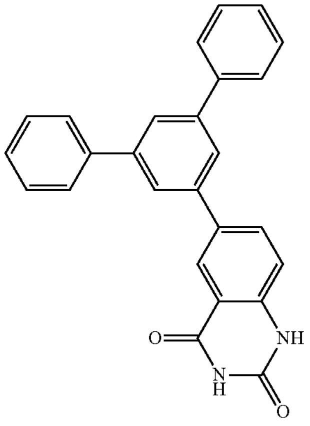 [SMILES: O=c1[nH]c(=O)c2cc(-c3cc(-c4ccccc4)cc(-c4ccccc4)c3)ccc2[nH]1] | 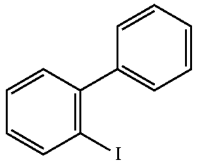 [2113-51-1] | 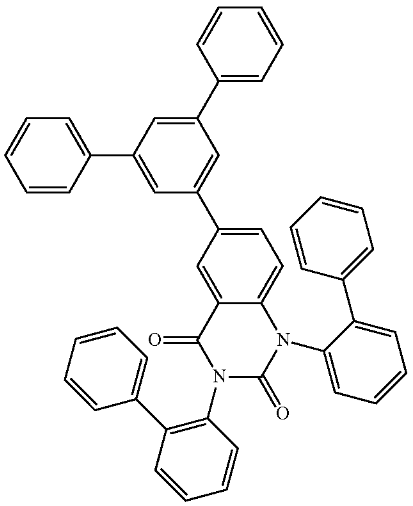 Compound 81 | 55 |

-continued
| Ex. | Reactant 1 | Reactant 2 | Product | Yield [%] |
|---|---|---|---|---|
| d7 | 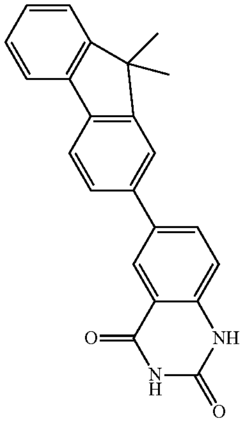 [SMILES: CC1(C)c2ccccc2-c2ccc(-c3ccc4[nH]c(=O)[nH]c(=O)c4c3)cc21] | 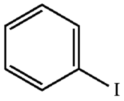 | 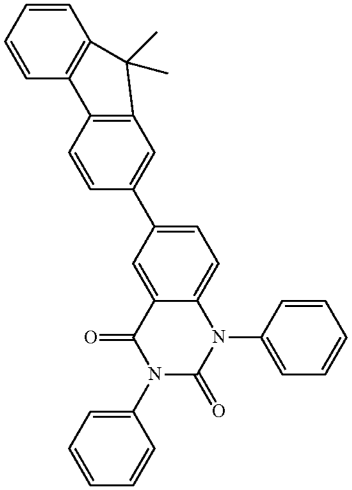 Compound 82 | 67 |

-continued
| Ex. | Reactant 1 | Reactant 2 | Product | Yield [%] |
|---|---|---|---|---|
| d8 | 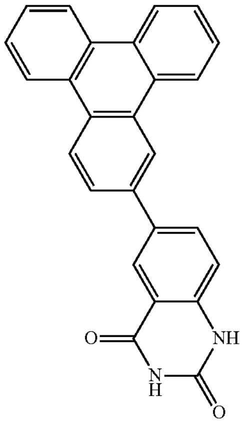 [SMILES: O=c1[nH]c(=O)c2cc(-c3ccc4c5ccccc5c5ccccc5c4c3)ccc2[nH]1] | 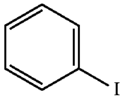 | 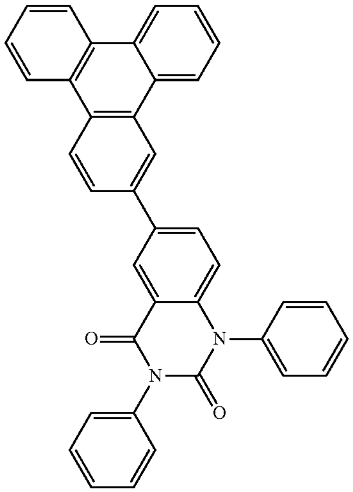 Compound 83 | 68 |

-continued
| Ex. | Reactant 1 | Reactant 2 | Product | Yield [%] |
|---|---|---|---|---|
| d9 | 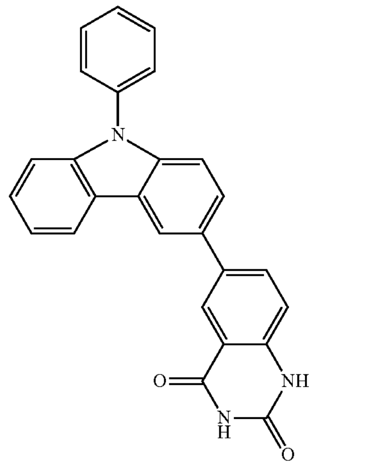 [SMILES: O=c1[nH]c(=O)c2cc(-c3ccc4c(c3)c3ccccc3n4-c3ccccc3)ccc2[nH]1] | 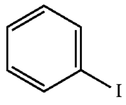 | 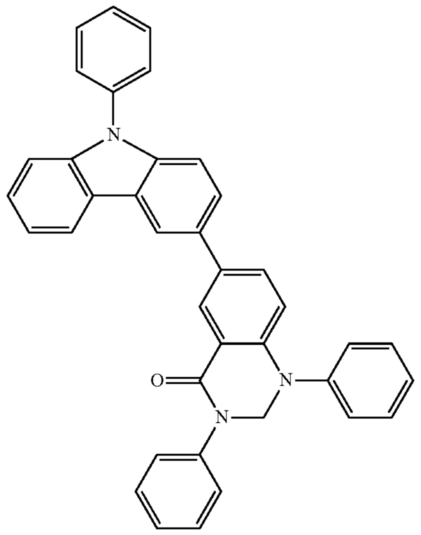 Compound 84 | 71 |
| d10 | 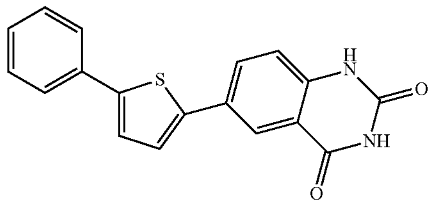 [SMILES: O=c1[nH]c(=O)c2cc(-c3ccc(-c4ccccc4)s3)ccc2[nH]1] | 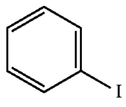 | 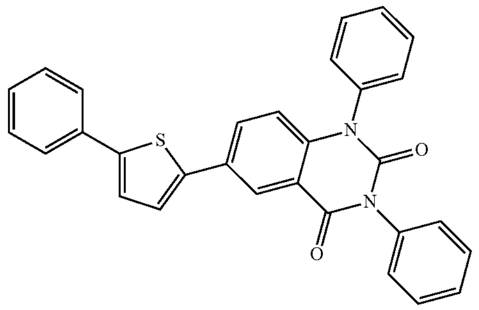 Compound 85 | 73 |

-continued
| Ex. | Reactant 1 | Reactant 2 | Product | Yield [%] |
|---|---|---|---|---|
| d11 | 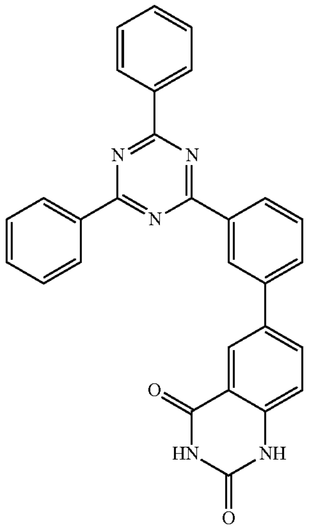 [SMILES: O=c1[nH]c(=O)c2cc(-c3cccc(-c4nc(-c5ccccc5)nc(-c5ccccc5)n4)c3)ccc2[nH]1] | 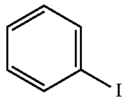 | 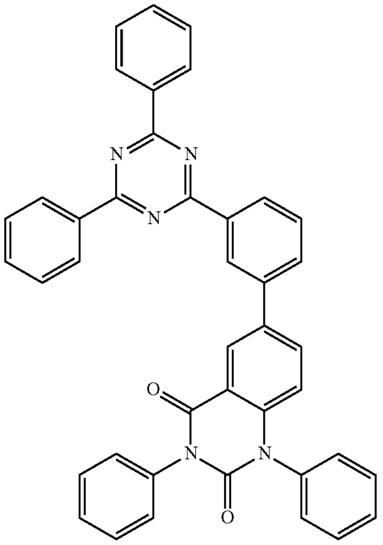 Compound 86 | 72 |
| d12 | 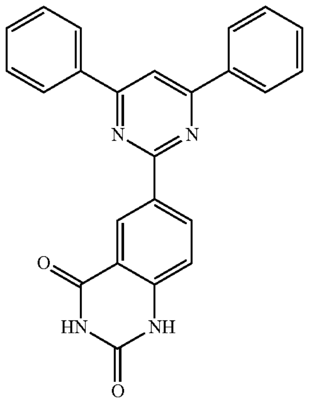 [SMILES: O=c1[nH]c(=O)c2cc(-c3nc(-c4ccccc4)cc(-c4ccccc4)n3)ccc2[nH]1] | 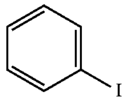 | 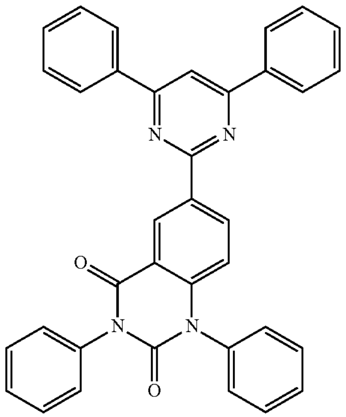 Compound 87 | 65 |

-continued
| Ex. | Reactant 1 | Reactant 2 | Product | Yield [%] |
|---|---|---|---|---|
| d13 | 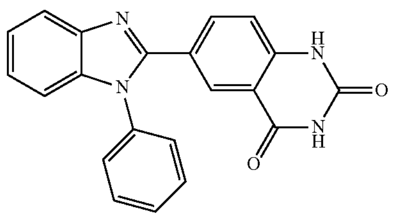 [SMILES: O=c1[nH]c(=O)c2cc(-c3nc4ccccc4n3-c3ccccc3)ccc2[nH]1] | 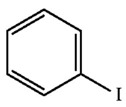 | 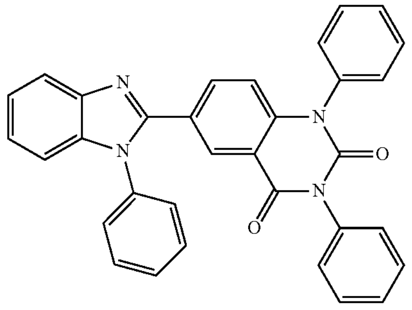 Compound 88 | 68 |
| d14 | 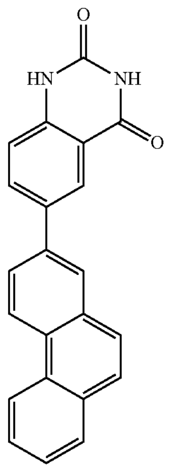 [SMILES: O=c1[nH]c(=O)c2cc(-c3ccc4c(ccc5ccccc54)c3)ccc2[nH]1] | 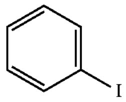 | 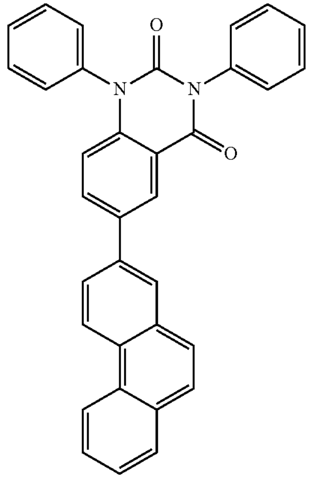 Compound 89 | 76 |

-continued
| Ex. | Reactant 1 | Reactant 2 | Product | Yield [%] |
|---|---|---|---|---|
| d15 | 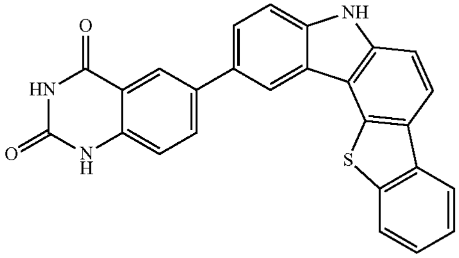 [SMILES: O=c1[nH]c(=O)c2cc(-c3ccc4[nH]c5ccc6c7ccccc7sc6c5c4c3)ccc2[nH]1] | 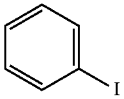 | 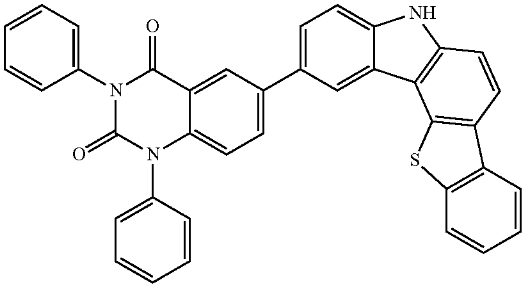<br>Compound 90 | 59 |
| d16 | 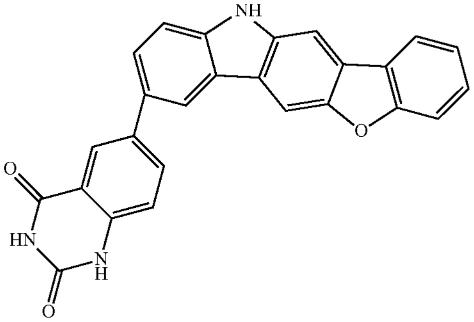 [SMILES: O=c1[nH]c(=O)c2cc(-c3ccc4[nH]c5cc6c(cc5c4c3)oc3ccccc36)ccc2[nH]1] | 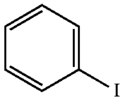 | 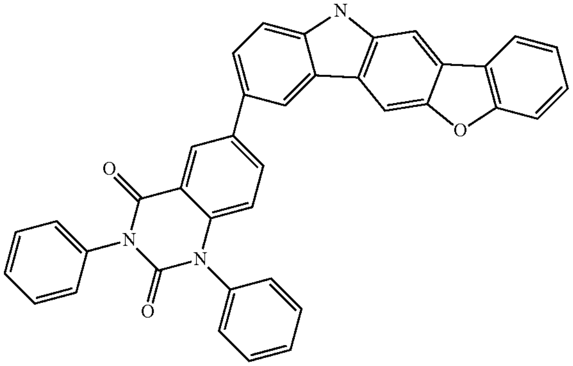<br>Compound 91 | 62 |

-continued
| Ex. | Reactant 1 | Reactant 2 | Product | Yield [%] |
|---|---|---|---|---|
| d17 | 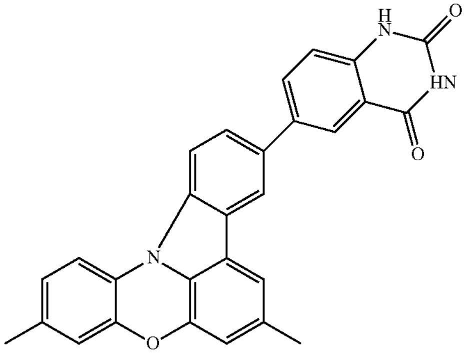 [SMILES: Cc1ccc2c(c1)Oc1cc(C)cc3c4cc(-c5ccc6[nH]c(=O)[nH]c(=O)c6c5)ccc4n-2c13] | 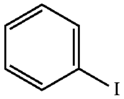 | 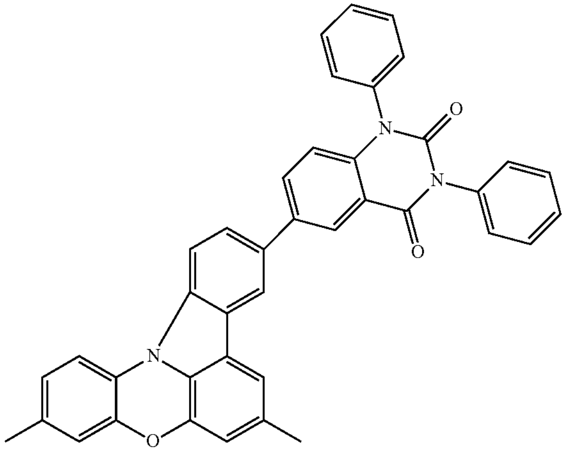 Compound 92 | 66 |
| d18 | 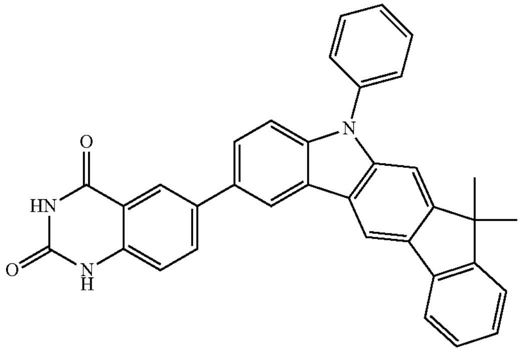 [SMILES: CC1(C)c2ccccc2-c2cc3c4cc(-c5ccc6[nH]c(=O)[nH]c(=O)c6c5)ccc4n(-c4ccccc4)c3cc21] | 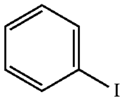 | 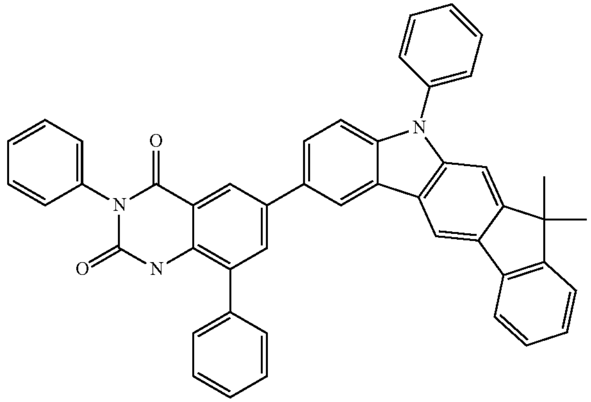 Compound 93 | 71 |

-continued
| Ex. | Reactant 1 | Reactant 2 | Product | Yield [%] |
|---|---|---|---|---|
| d19 | 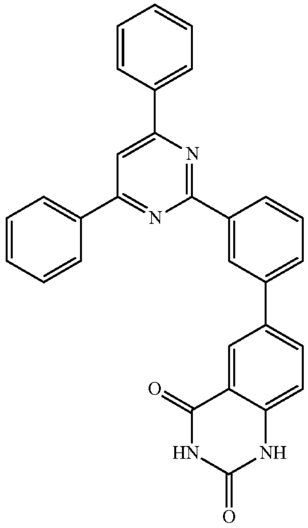 [SMILES: O=c1[nH]c(=O)c2cc(-c3cccc(-c4nc(-c5ccccc5)cc(-c5ccccc5)n4)c3)ccc2[nH]1] | 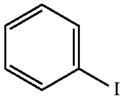 | 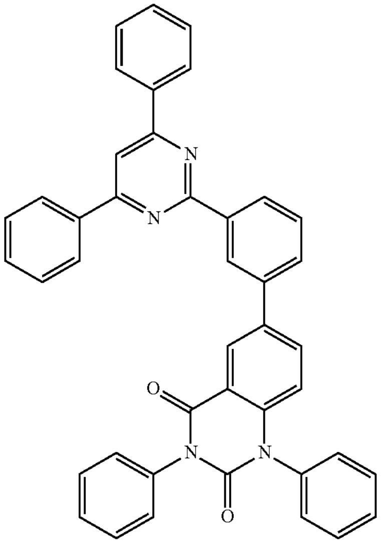 Compound 65 | 65 |
| d20 | 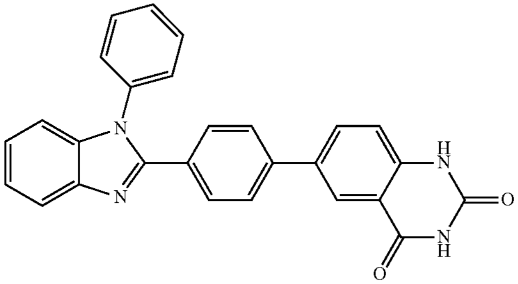 [SMILES: O=c1[nH]c(=O)c2cc(-c3ccc(-c4nc5ccccc5n4-c4ccccc4)cc3)ccc2[nH]1] | 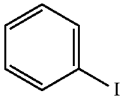 | 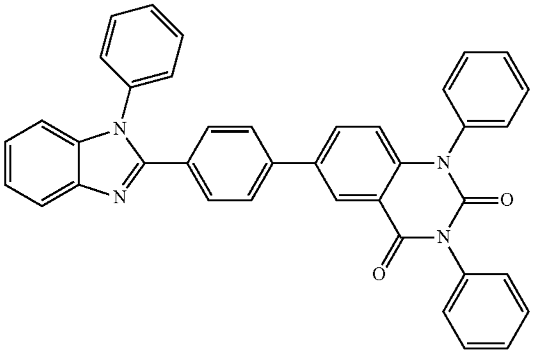 Compound 95 | 73 |

-continued
| Ex. | Reactant 1 | Reactant 2 | Product | Yield [%] |
|---|---|---|---|---|
| d21 | 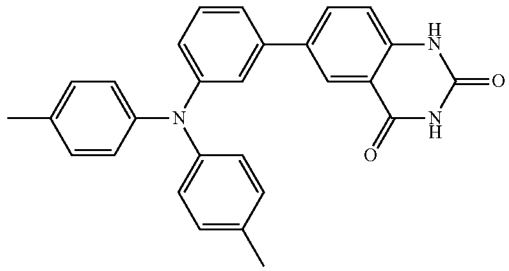 [SMILES: Cc1ccc(N(c2ccc(C)cc2)c2cccc(-c3ccc4[nH]c(=O)[nH]c(=O)c4c3)c2)cc1] | 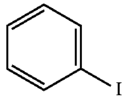 | 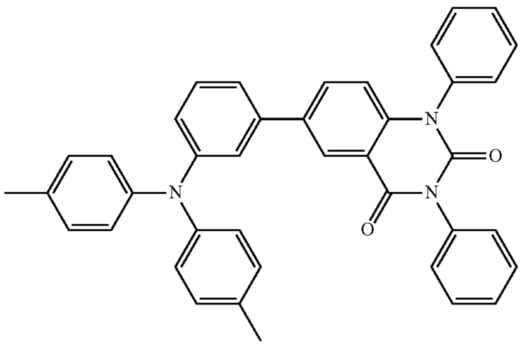 Compound 96 | 70 |
| d22 | 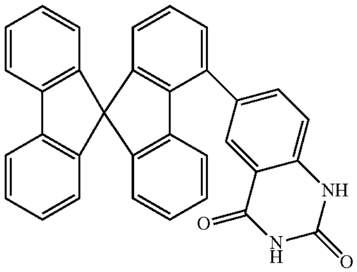 [SMILES: O=c1[nH]c(=O)c2cc(-c3cccc4c3-c3ccccc3C43c4ccccc4-c4ccccc43)ccc2[nH]1] | 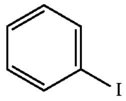 | 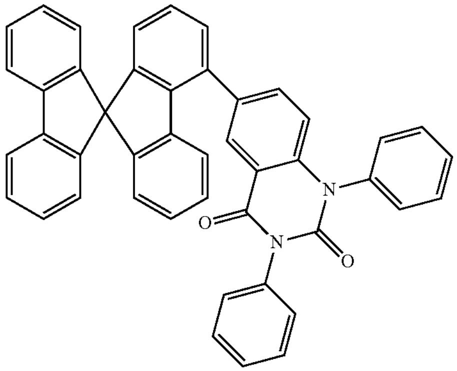 Compound 97 | 75 |

-continued
| Ex. | Reactant 1 | Reactant 2 | Product | Yield [%] |
|---|---|---|---|---|
| d23 | 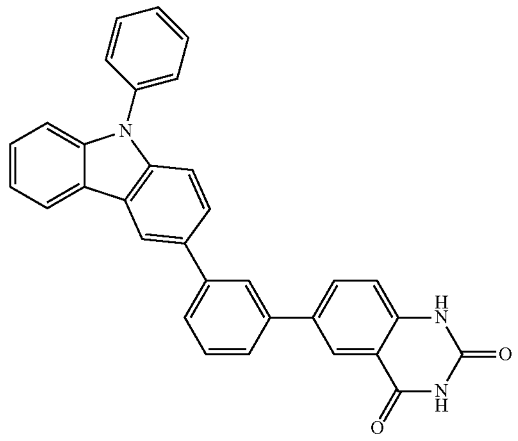 [SMILES: O=c1[nH]c(=O)c2cc(-c3cccc(-c4ccc5c(c4)c4ccccc4n5-c4ccccc4)c3)ccc2[nH]1] | 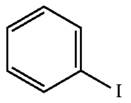 | 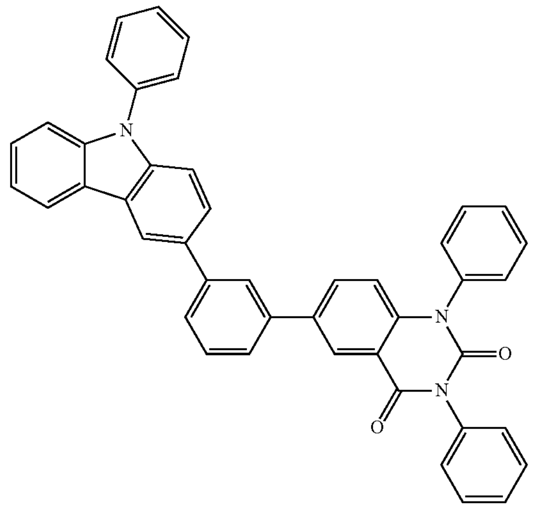 Compound 98 | 76 |
| d24 | 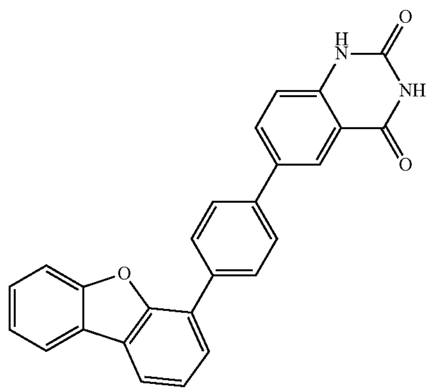 [SMILES: O=c1[nH]c(=O)c2cc(-c3ccc(-c4cccc5c4oc4ccccc45)cc3)ccc2[nH]1] | 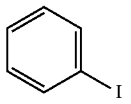 | 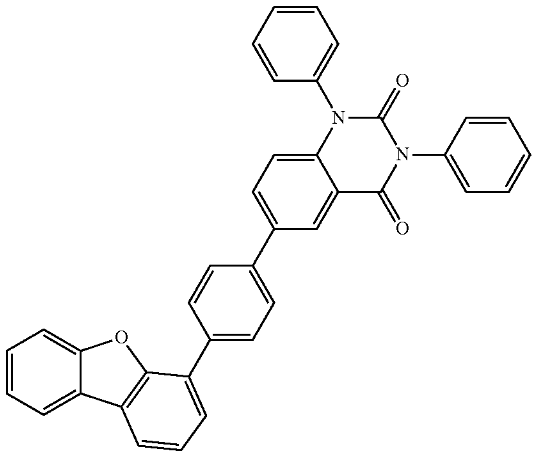 Compound 99 | 68 |

-continued
| Ex. | Reactant 1 | Reactant 2 | Product | Yield [%] |
|---|---|---|---|---|
| d25 | 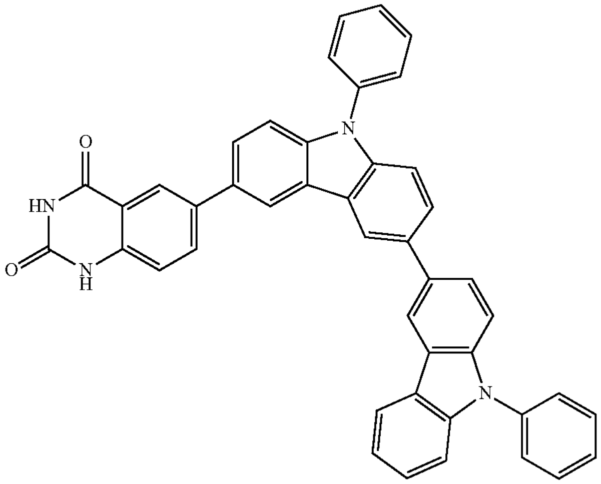 [SMILES: O=c1[nH]c(=O)c2cc(-c3ccc4c(c3)c3cc(-c5ccc6c(c5)c5ccccc5n6-c5ccccc5)ccc3n4-c3ccccc3)ccc2[nH]1] | 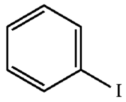 | 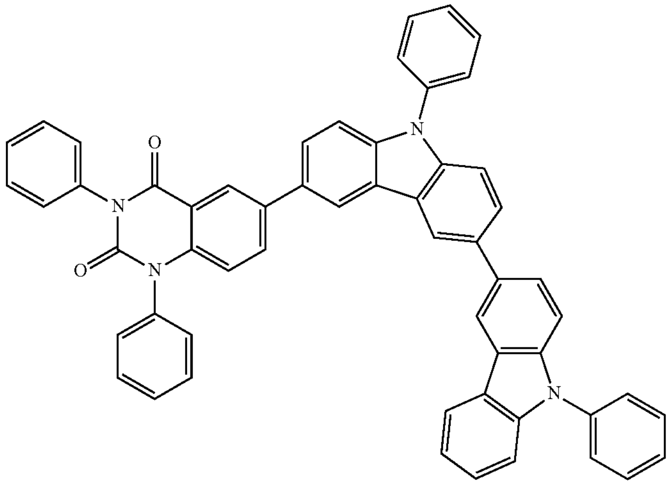<br>Compound 100 | 79 |

-continued
| Ex. | Reactant 1 | Reactant 2 | Product | Yield [%] |
|---|---|---|---|---|
| d26 | 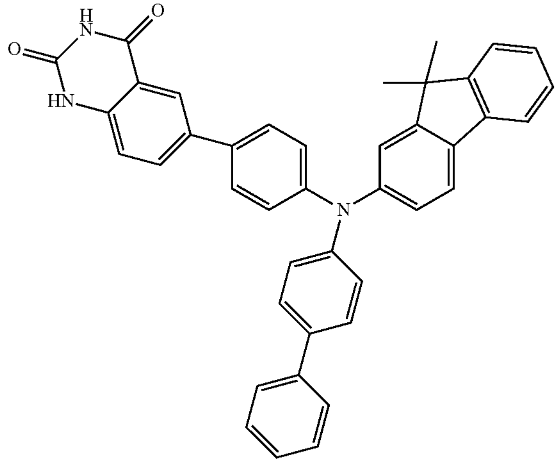 [SMILES: CC1(C)c2ccccc2-c2ccc(N(c3ccc(-c4ccccc4)cc3)c3ccc(-c4ccc5[nH]c(=O)[nH]c(=O)c5c4)cc3)cc21] | 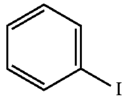 | 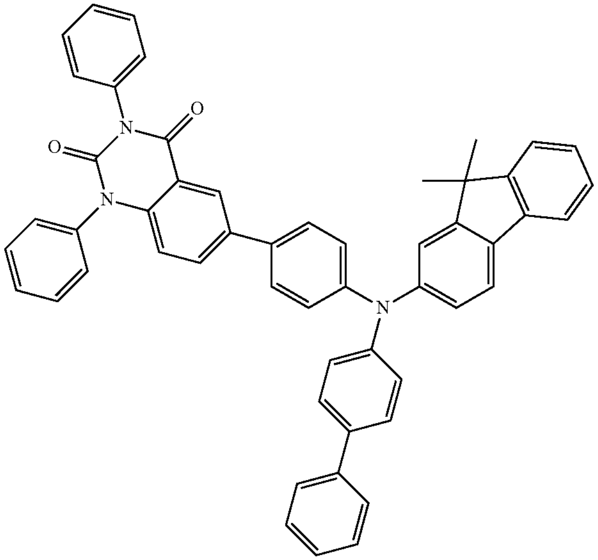 Compound 101 | 74 |

-continued
| Ex. | Reactant 1 | Reactant 2 | Product | Yield [%] |
|---|---|---|---|---|
| d27 | 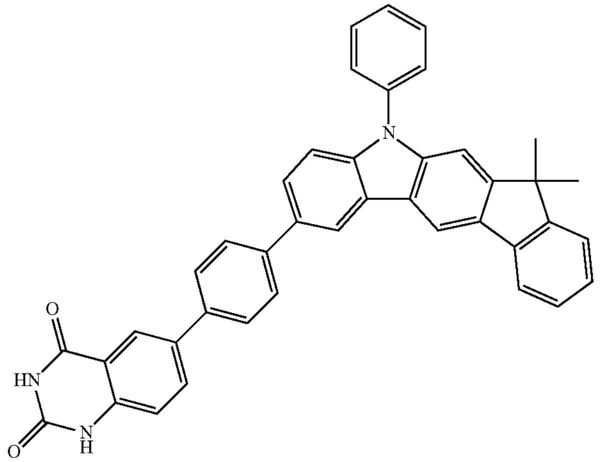 [SMILES: CC1(C)c2ccccc2-c2cc3c4cc(-c5ccc(-c6ccc7[nH]c(=O)[nH]c(=O)c7c6)cc5)ccc4n(-c4ccccc4)c3cc21] | 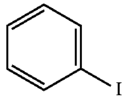 | 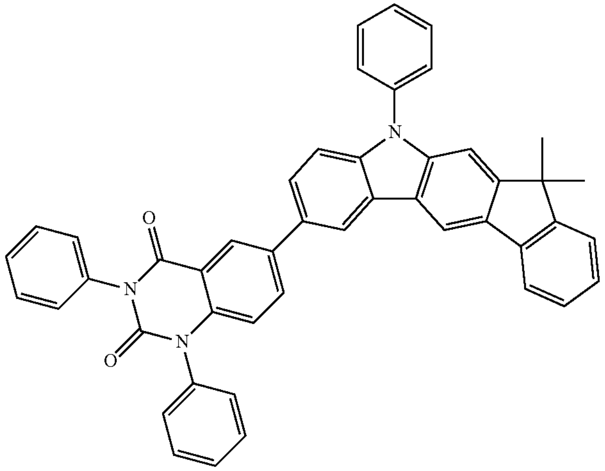 Compound 102 | 64 |
| d28 | 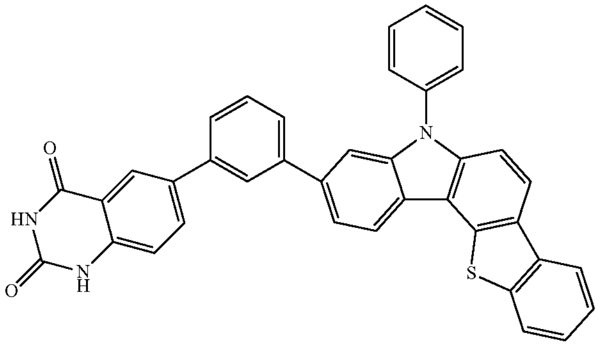 [SMILES: O=c1[nH]c(=O)c2cc(-c3cccc(-c4ccc5c6c7sc8ccccc8c7ccc6n(-c6ccccc6)c5c4)c3)ccc2[nH]1] | 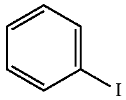 | 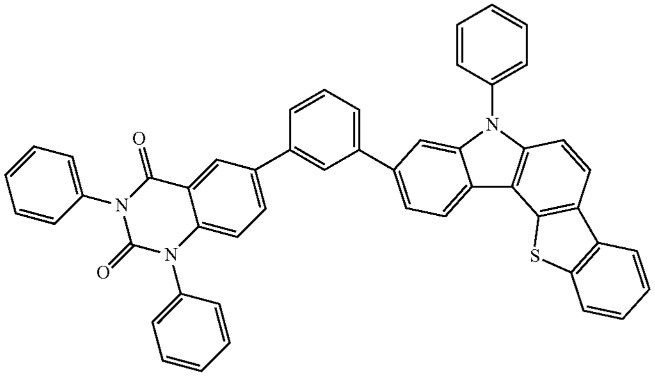 Compound 103 | 68 |

-continued
| Ex. | Reactant 1 | Reactant 2 | Product | Yield [%] |
|---|---|---|---|---|
| d30 | 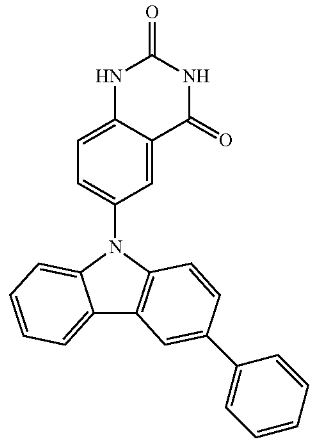 [SMILES: O=c1[nH]c(=O)c2cc(-n3c4ccccc4c4cc(-c5ccccc5)ccc43)ccc2[nH]1] | 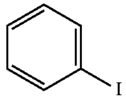 | 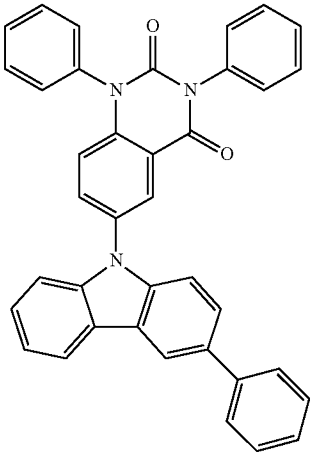 Compound 104 | 67 |
| d31 | 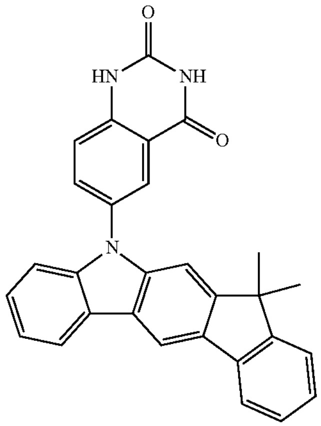 [SMILES: CC1(C)c2ccccc2-c2cc3c4ccccc4n(-c4ccc5[nH]c(=O)[nH]c(=O)c5c4)c3cc21] | 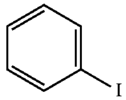 | 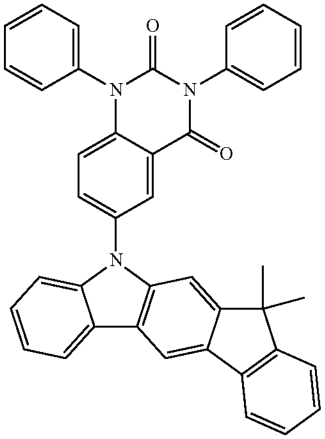 Compound 105 | 73 |

-continued
| Ex. | Reactant 1 | Reactant 2 | Product | Yield [%] |
|---|---|---|---|---|
| d32 | 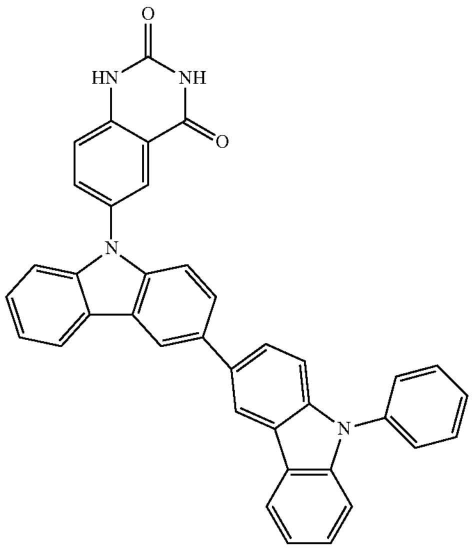 [SMILES: O=c1[nH]c(=O)c2cc(-n3c4ccccc4c4cc(-c5ccc6c(c5)c5ccccc5n6-c5ccccc5)ccc43)ccc2[nH]1] | 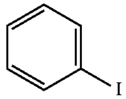 | 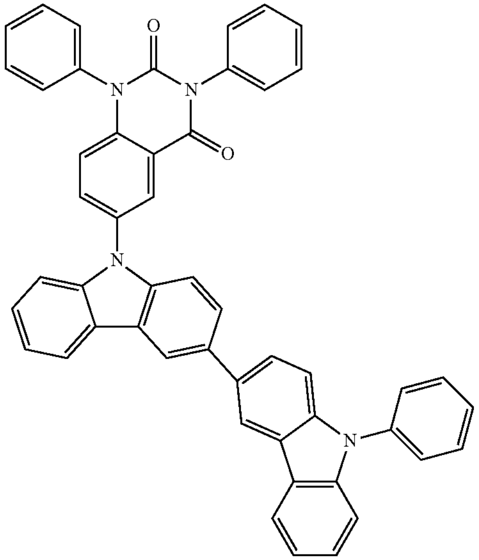 Compound 106 | 70 |
| d33 | 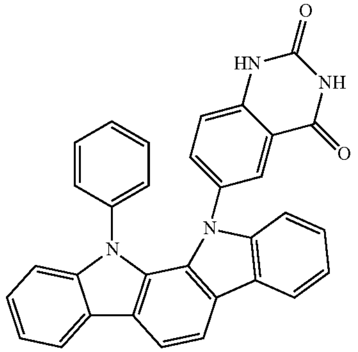 [SMILES: O=c1[nH]c(=O)c2cc(-n3c4ccccc4c4ccc5c6ccccc6n(-c6ccccc6)c5c43)ccc2[nH]1] | 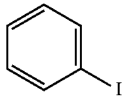 | 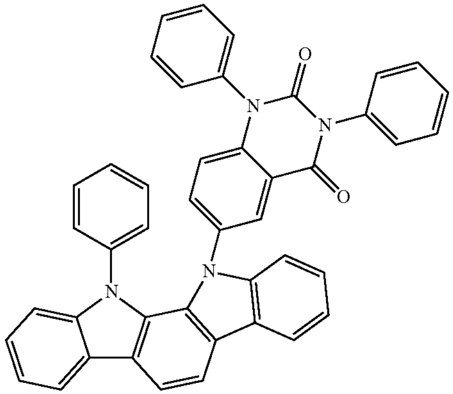 Compound 107 | 72 |

-continued
| Ex. | Reactant 1 | Reactant 2 | Product | Yield [%] |
| --- | --- | --- | --- | --- |
| d34 | 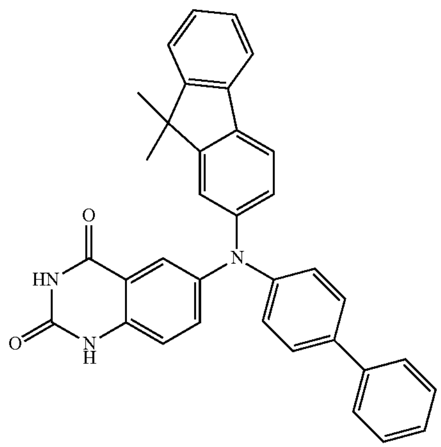 [SMILES: CC1(C)c2ccccc2-c2ccc(N(c3ccc(-c4ccccc4)cc3)c3ccc4[nH]c(=O)[nH]c(=O)c4c3)cc21] | 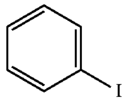 | 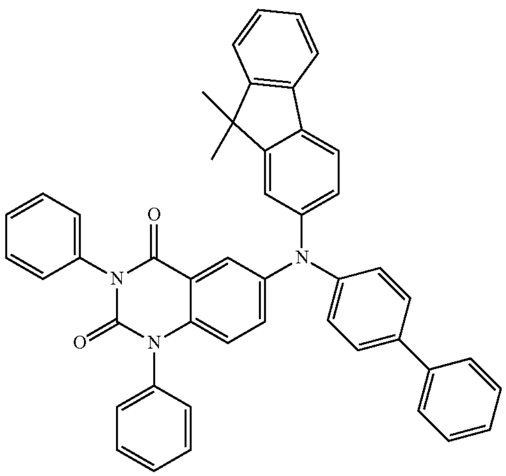 Compound 108 | 75 |
| d35 | 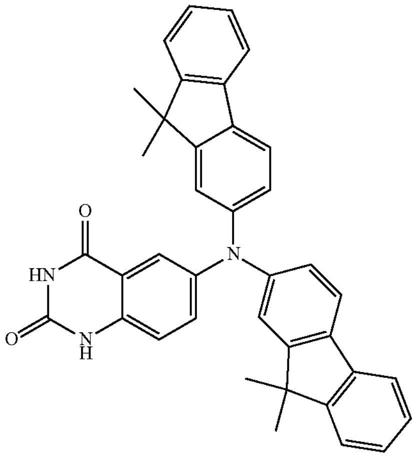 [SMILES: CC1(C)c2ccccc2-c2ccc(N(c3ccc4c(c3)C(C)(C)c3ccccc3-4)c3ccc4[nH]c(=O)[nH]c(=O)c4c3)cc21] | 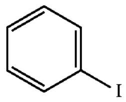 | 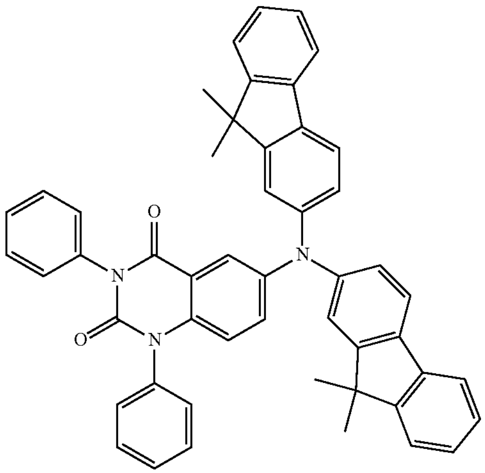 Compound 109 | 77 |

-continued
| Ex. | Reactant 1 | Reactant 2 | Product | Yield [%] |
| --- | --- | --- | --- | --- |
| d38 | 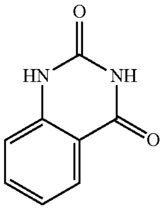 [86-96-4] | 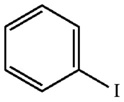 | 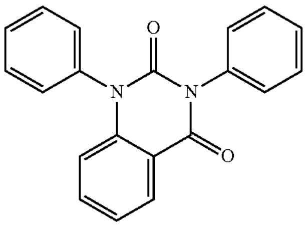 Compound 1 | 79 |
| d39 | 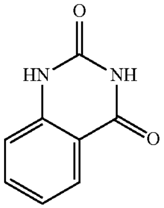 [86-96-4] | 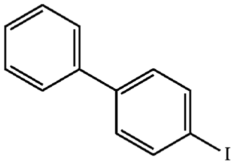 [1591-31-7] | 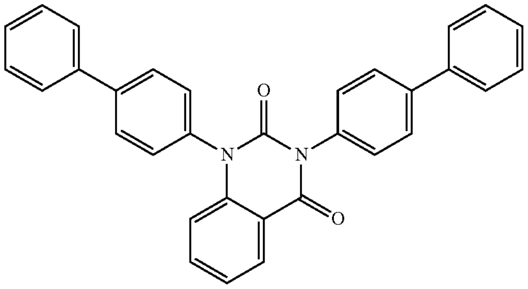 Compound 2 | 75 |

-continued
| Ex. | Reactant 1 | Reactant 2 | Product | Yield [%] |
|---|---|---|---|---|
| d40 | 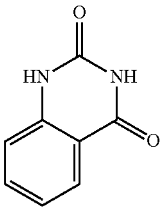 [86-96-4] | 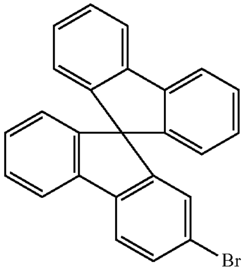 [171408-76-7] | 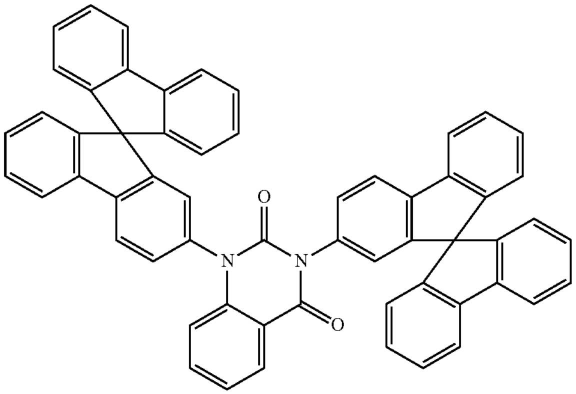 Compound 34 | 69 |
| d41 | 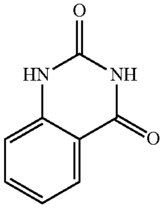 [86-96-4] | 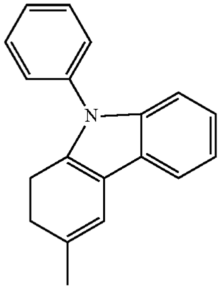 [502161-03-7] | 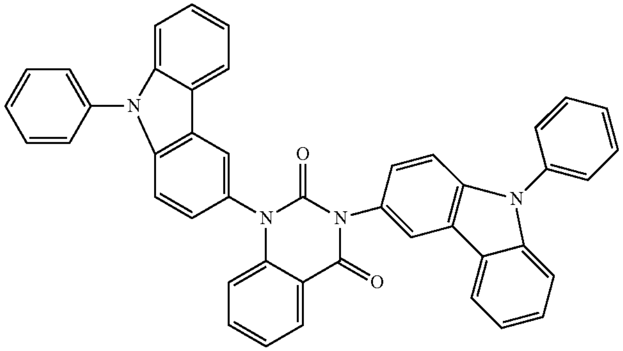 Compound 6 | 65 |

-continued
| Ex. | Reactant 1 | Reactant 2 | Product | Yield [%] |
|---|---|---|---|---|
| d42 | 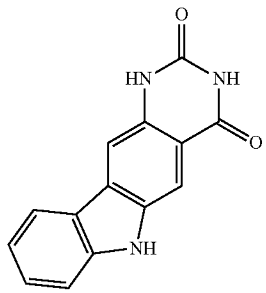 [97308-04-8] | 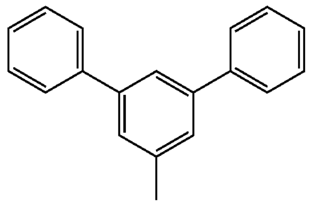 [87666-86-2] | 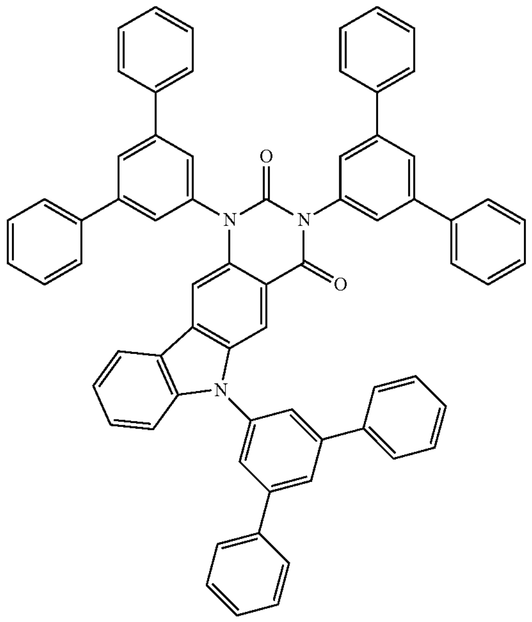 Compound 116 | 71 |

In an analogous manner, it is possible to use one equivalent of monosubstituted quinazoline-2,4-dione compounds to prepare the following:
| Ex. | Reactant 1 | Reactant 2 | Product | Yield [%] |
|---|---|---|---|---|
| d43 | 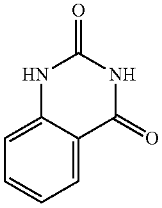 [86-96-4] | 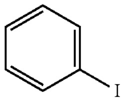 | 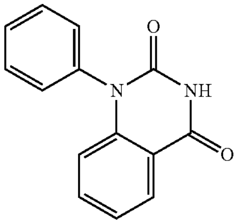 [SMILES: O=c1[nH]c(=O)n(-c2ccccc2)c2ccccc12] | 77 |
| d44 | 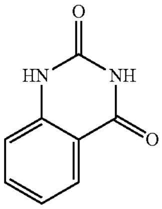 [86-96-4] | 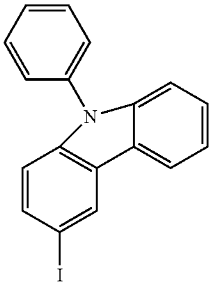 [502161-03-7] | 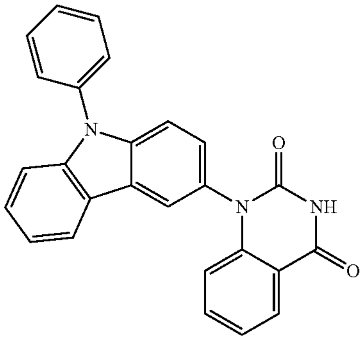 [SMILES: O=c1[nH]c(=O)n(-c2ccc3c(c2)c2ccccc2n3-c2ccccc2)c2ccccc12] | 75 |
| d45 | 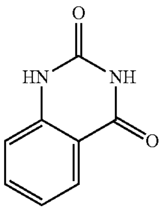 [86-96-4] | 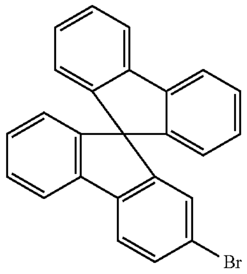 [171408-76-7] | 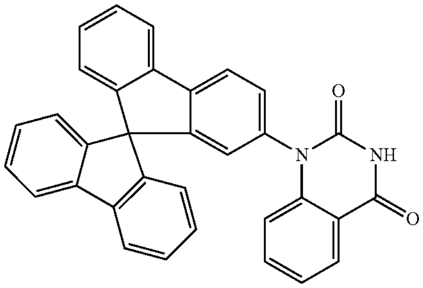 [SMILES: O=c1[nH]c(=O)n(-c2ccc3c(c2)C2(c4ccccc4-c4ccccc42)c2ccccc2-3)c2ccccc12] | 74 |
| d46 | 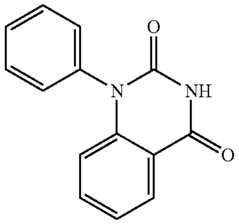 [SMILES: O=c1[nH]c(=O)n(-c2ccccc2)c2ccccc12] | 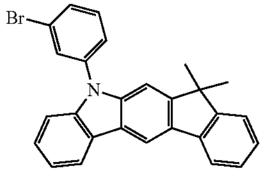 [1369587-63-2] | 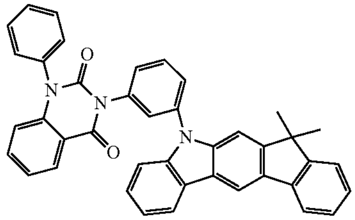 Compound 117 | 73 |

-continued

| Ex. | Reactant 1 | Reactant 2 | Product | Yield [%] |
|---|---|---|---|---|
| d47 | 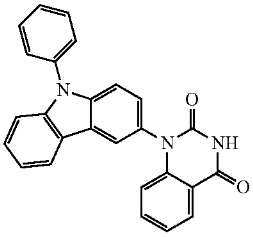 [SMILES: O=c1[nH]c(=O)n(-c2ccc3c(c2)c2ccccc2n3-c2ccccc2)c2ccccc12] | 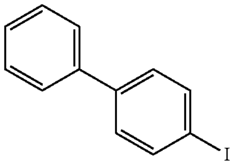 [1591-31-7] | 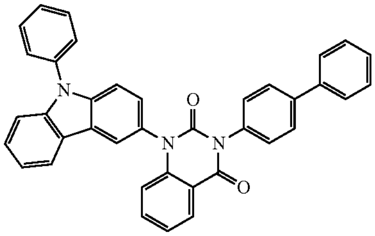 Compound 118 | 70 |
| d48 | 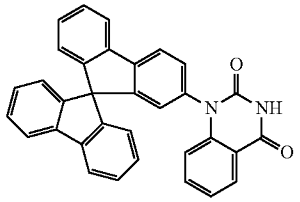 [SMILES: O=c1[nH]c(=O)n(-c2ccc3c(c2)C2(c4ccccc4-c4ccccc42)c2ccccc2-3)c2ccccc12] | 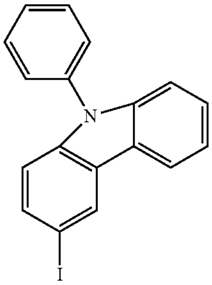 [502161-03-7] | 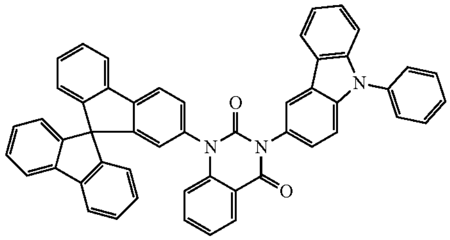 Compound 119 | 69 |

Example E

1,4-bis[1,1';3',1"]terphenyl-5'-yl-1,4-dihydroquinoxaline-2,3-dione

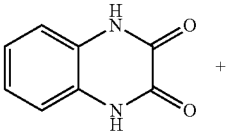

[15804-19-0]

+

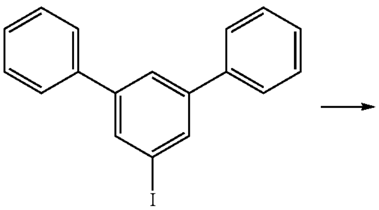

-continued

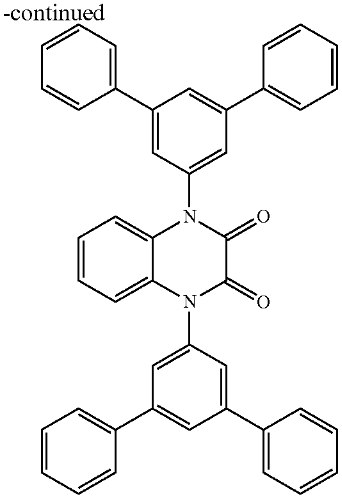

Compound 164

5.6 g (40 mmol) of 6-phenyl-1H-quinazoline-2,4-dione and 30 g (85 mmol) of 4-iodobenzene and 44.7 g (320 mmol) of potassium carbonate, 3 g (16 mmol) of copper(I) iodide and 3.6 g (16 mmol) of 1,3-di(pyridin-2-yl)propane-1,3-dione are stirred in 100 mL of DMF at 150° C. for 30 h. The solution is diluted with water and extracted twice with ethyl acetate, and the combined organic phases are dried over $Na_2SO_4$ and concentrated by rotary evaporation. The residue is recrystallized from toluene and finally sublimed under high vacuum ($p=5\times10^{-5}$ mbar). The purity is 99.9%. The yield is 14 g (23 mmol), 61% of theory.

In an analogous manner, it is possible to obtain the following compounds:

| Ex. | Reactant 1 | Reactant 2 | Product | Yield [%] |
| --- | --- | --- | --- | --- |
| e1 | 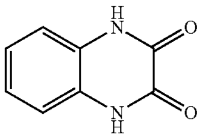 [15804-19-0] | 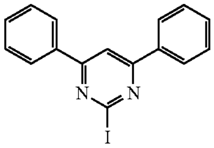 [374077-23-3] | 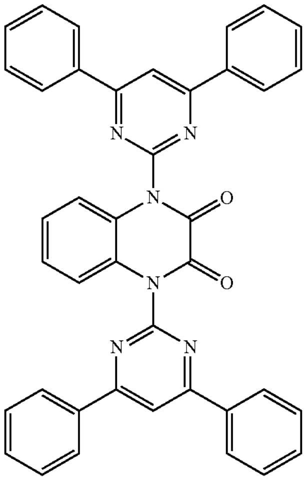 Compound 172 | 56 |
| e2 | 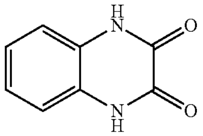 [15804-19-0] | 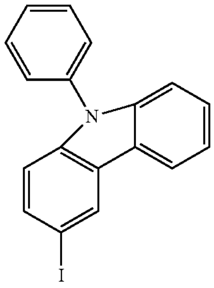 [502161-03-7] | 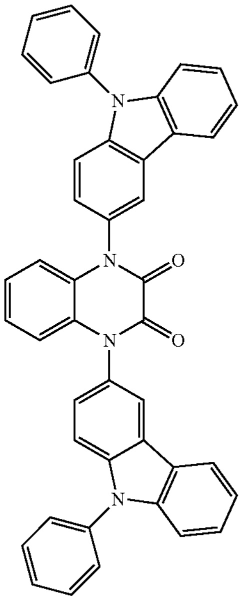 Compound 170 | 54 |
| e3 | 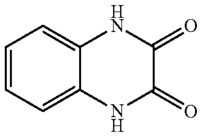 [15804-19-0] | 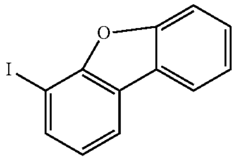 [65344-26-5] | 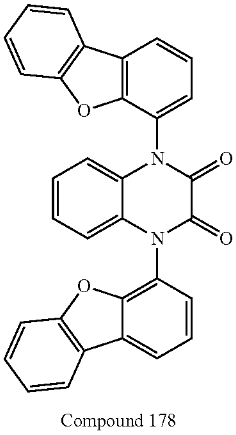 [SMILES: O=c1c(=O)n(-c2cccc3c2oc2ccccc23)c2ccccc2n1-c1cccc2c1oc1ccccc12] Compound 178 | 62 |

-continued
| Ex. | Reactant 1 | Reactant 2 | Product | Yield [%] |
|---|---|---|---|---|
| e4 | 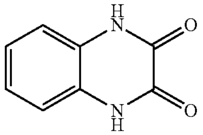 [15804-19-0] | 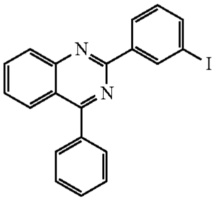 [1522379-08-3] | 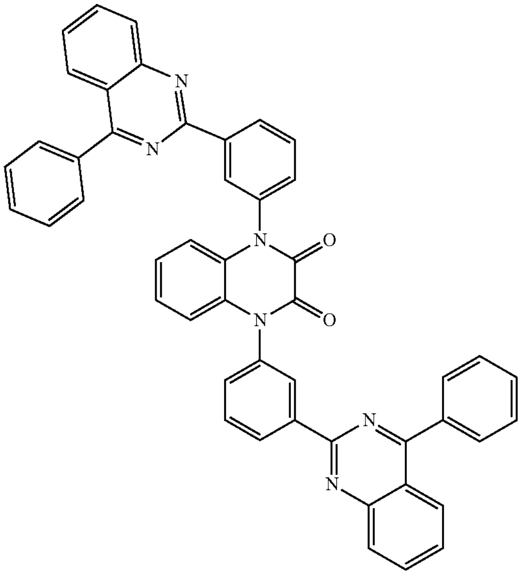 Compound 181 | 60 |
| e5 | 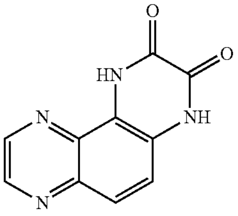 [71222-60-1] | 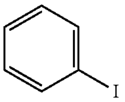 | 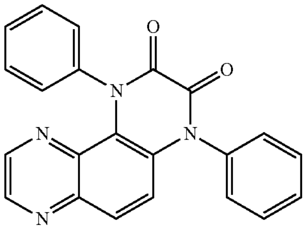 Compound 184 | 57 |
| e6 | 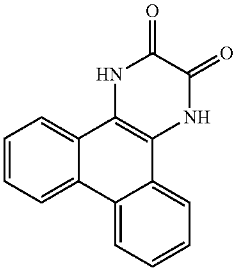 [1408317-52-1] | 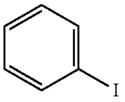 | 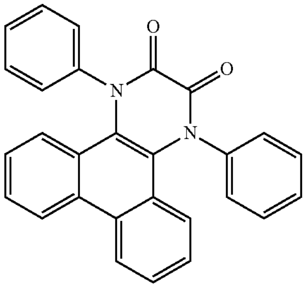 Compound 186 | 55 |

-continued
| Ex. | Reactant 1 | Reactant 2 | Product | Yield [%] |
|---|---|---|---|---|
| e7 | 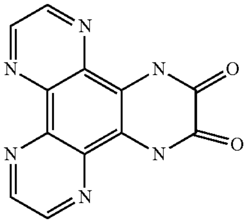 [1467073-25-1] | 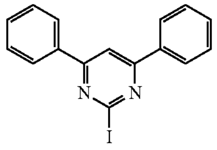 [374077-23-3] | 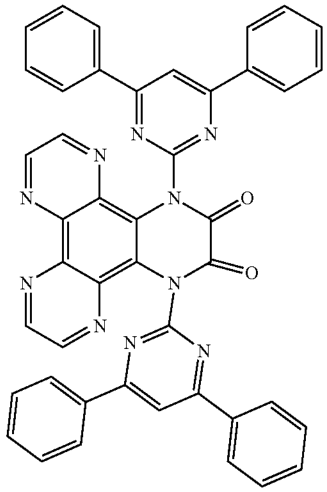 Compound 187 | 52 |
| e8 | 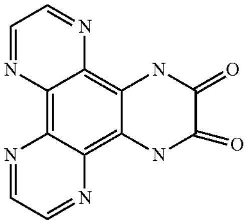 [1467073-25-1] | 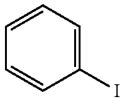 | 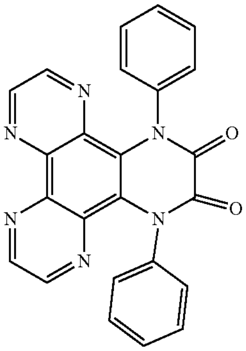 Compound 188 | 63 |
| e9 | 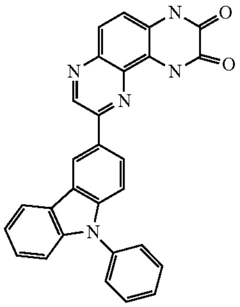 [SMILES: O=c1[nH]c2ccc3ncc(-c4ccc5c(c4)c4ccccc4n5-c4ccccc4)nc3c2[nH]c1=O] | 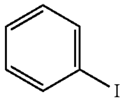 | 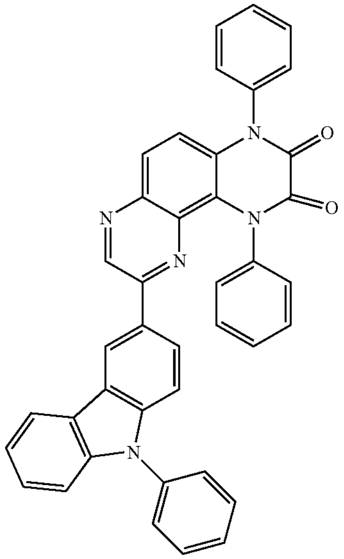 Compound 199 | 60 |

-continued
| Ex. | Reactant 1 | Reactant 2 | Product | Yield [%] |
|---|---|---|---|---|
| e10 | 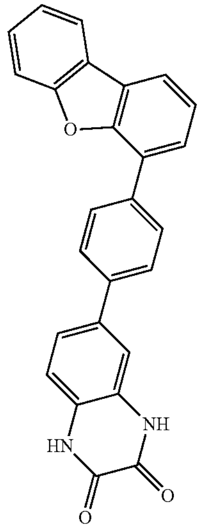 [SMILES: O=c1[nH]c2ccc(-c3ccc(-c4cccc5c4oc4ccccc45)cc3)cc2[nH]c1=O] | 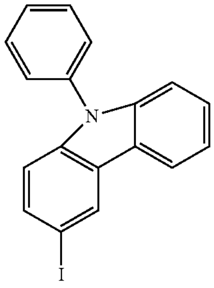 [502161-03-7] | 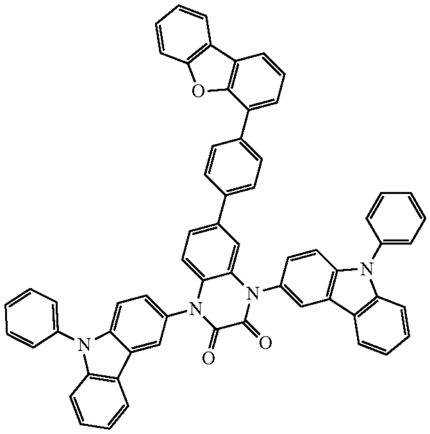 Compound 201 | 57 |
| e11 | 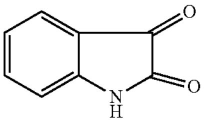 [91-56-5] | 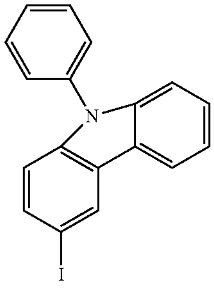 [502161-03-7] | 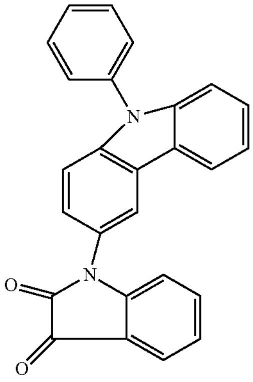 Compound 141 | 53 |
| e12 | 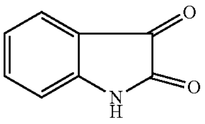 [91-56-5] | 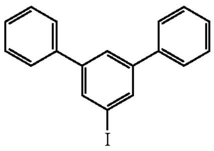 [87666-86-2] | 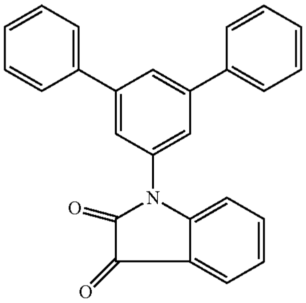 Compound 142 | 52 |

-continued

| Ex. | Reactant 1 | Reactant 2 | Product | Yield [%] |
|---|---|---|---|---|
| e13 | 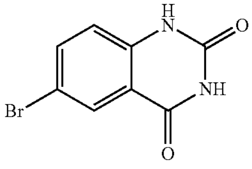 [88145-89-5] | 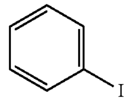 | 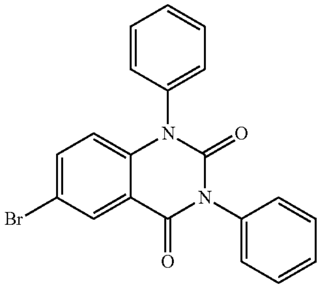 Compound 120 | 45 |

Example F

1,3-Diphenyl-6-phenylamino-1H-quinazoline-2,4-dione

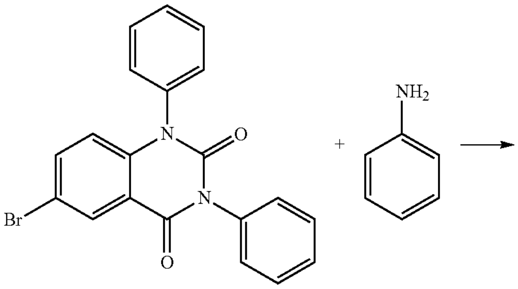

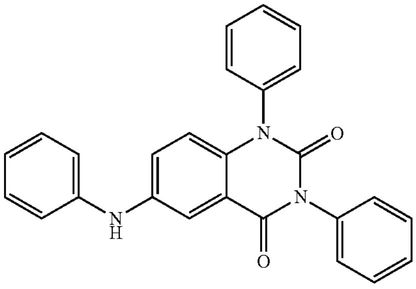

Compound 121

71.9 g (183 mmol) of 6-bromo-1,3-diphenyl-1H-quinazoline-2,4-dione, 20 mL of aniline (220 mmol), 1.5 g of DPPF (2.7 mmol), 0.5 g of palladium(II) acetate and 45 g of sodium tert-butoxide (486 mmol) are heated to boiling in 1.5 L of toluene under a protective atmosphere for 18 h. The mixture is subsequently partitioned between toluene and water, and the organic phase is washed three times with water and dried over $Na_2SO_4$ and concentrated by rotary evaporation. The remaining residue is recrystallized from heptane/ethyl acetate. The yield is 54 g (110 mmol, 57%).

Example G

1,3-Diphenyl-1,6-dihydropyrimido[5,4-b]carbazole-2,4-dione (a) and 2,4-diphenyl-4,7-dihydropyrimido [4,5-c]carbazole-1,3-dione (b)

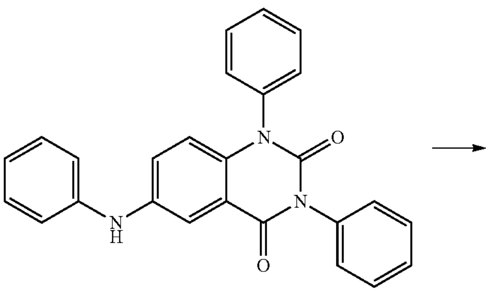

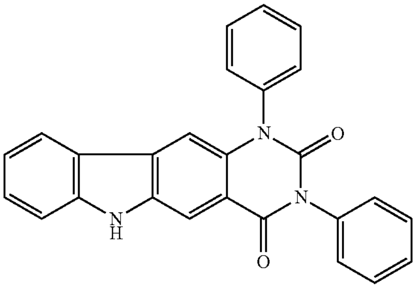

+ a

Compound 123

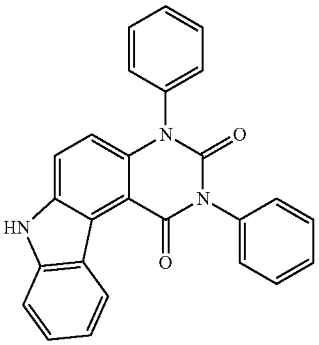 [SMILES: O=c1c2c3c(ccc2n(-c2ccccc2)c(=O)n1-c1ccccc1)[nH]c1ccccc13]

b

Compound 122

14 g (35 mmol) of 1,3-diphenyl-6-phenylamino-1H-quinazoline-2,4-dione, 0.4 g of palladium(II) acetate (1.78 mmol) and 0.5 g of potassium carbonate (3.62 mmol) are added to 35 mL of pivalic acid and the mixture is stirred at 120° C. for 9 h. After this time, 0.4 g of palladium(II) acetate (1.78 mmol) is added and stirring of the mixture is continued at 120° C. for 9 h. Then 200 mL of dichloromethane and 0.1 M $Na_2CO_3$ solution are added. The mixture is partitioned between water and dichloromethane, the aqueous phase is extracted three times with dichloromethane, and the combined organic phases are dried over $Na_2SO_4$ and concentrated by rotary evaporation. The residue is separated by chromatography. The yield is 3 g (9.9 mmol) of (a) and 9 g (29 mmol) of (b).

Analogously to example g, it is possible to obtain the following compounds:

| Ex. | Reactant 1 | Reactant 2 | Product | Yield [%] |
|---|---|---|---|---|
| g1 | 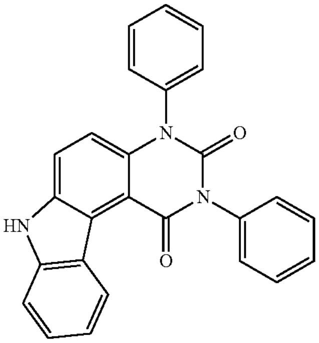 [SMILES: O=c1c2c3c(ccc2n(-c2ccccc2)c(=O)n1-c1ccccc1)[nH]c1ccccc13] | 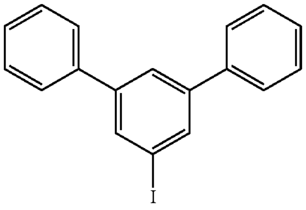 [87666-86-2] | 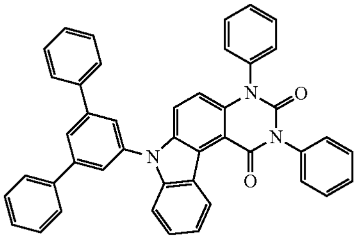 Compound 124 | 56 |
| g2 | 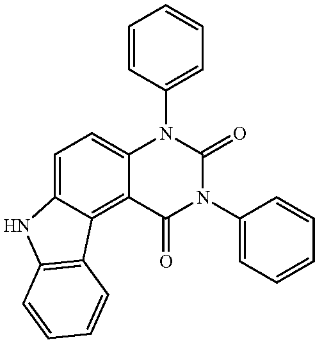 | 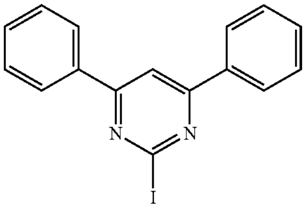 [374077-23-3] | 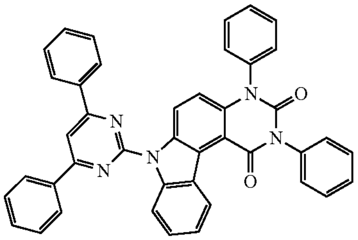 Compound 56 | 51 |
| g3 | 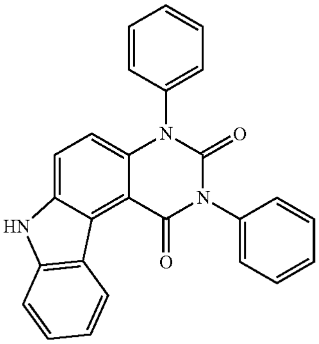 [SMILES: O=c1c2c3c(ccc2n(-c2ccccc2)c(=O)n1-c1ccccc1)[nH]c1ccccc13] | 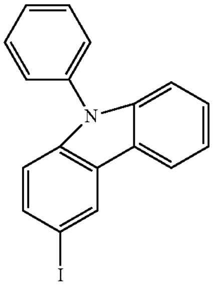 [502161-03-7] | 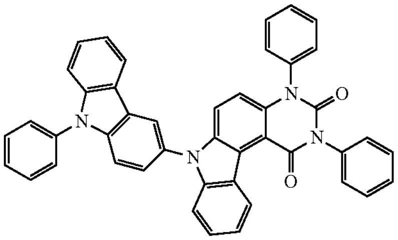 Compound 55 | 63 |
| g4 | 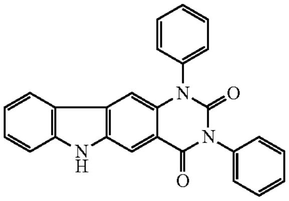 [SMILES: O=c1c2cc3[nH]c4ccccc4c3cc2n(-c2ccccc2)c(=O)n1-c1ccccc1] | 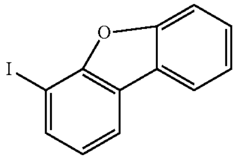 [65344-26-5] | 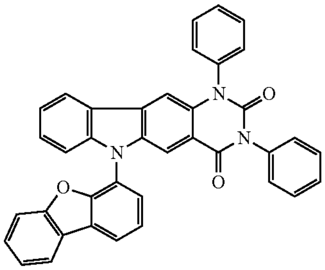 Compound 125 | 62 |

Example H

General synthesis of N,N'-diaryl-1 ,2-benzenediamine

To 660 mL of degassed toluene are added 1.06 g (4.75 mmol) of $Pd(OAc)_2$ and 14.46 mL (14.46 mmol) of tri-tert-butylphosphine (1M solution in toluene), and the mixture is stirred for 5 min. Then 240 mmol of the 1,2-dibromobenzene derivative, 505 mmol of the arylamine and 67.22 g (700 mmol) of sodium tert-butoxide are added to the solution, which is then degassed and stirred at 140° C. under a protective gas atmosphere for 10 h. After cooling, 600 mL of $NH_4Cl$ solution and 150 mL of ethyl acetate are added to the solution, and the phases are separated, washed with water, dried over $MgSO_4$ and concentrated. The solids are dissolved in toluene and the mixture is filtered through Celite. The crude product is stirred with hot heptane.

Example H1

Synthesis of N,N'-bis(biphenyl-4-yl)-1,2-benzenediamine

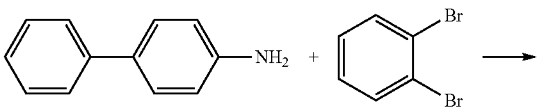

[92-67-1]

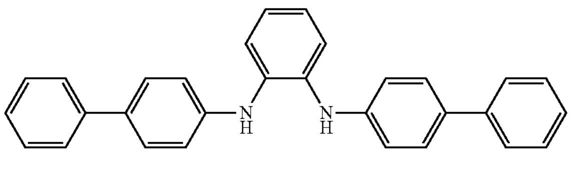

The synthesis is effected by the general method of example h from 56.6 g (240 mmol) of 1,2-dibromobenzene and 85.4 g (505 mmol) of 4-aminobiphenyl. The precipitated solids are recrystallized from toluene/acetonitrile (5:1) and the residue is washed with MeOH. This gives 78 g (189 mmol) of a crystalline solid. The overall yield is 80%.

In an analogous manner, it is possible to obtain the following compounds:

| Ex. | Reactant 1 | Reactant 2 | Product | Yield |
|---|---|---|---|---|
| h2 | 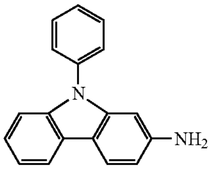 [1257982-95-8] | 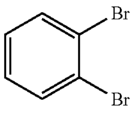 | 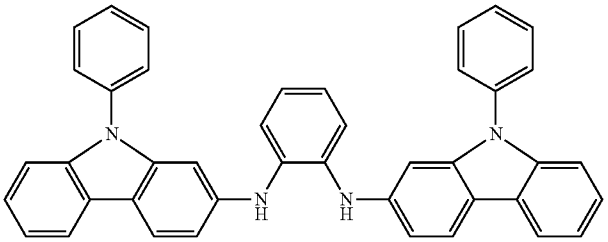 [SMILES: c1ccc(-n2c3ccccc3c3ccc(Nc4ccccc4Nc4ccc5c6ccccc6n(-c6ccccc6)c5c4)cc32)cc1] | 77% |
| h3 | 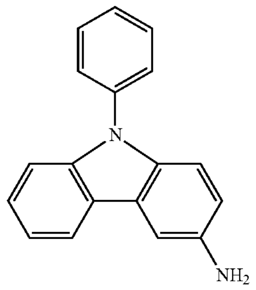 [1318253-36-9] | 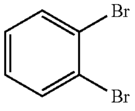 | 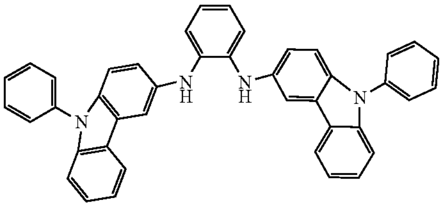 [SMILES: c1ccc(-n2c3ccccc3c3cc(Nc4ccccc4Nc4ccc5c(c4)c4ccccc4n5-c4ccccc4)ccc32)cc1] | 79% |

Example J

Synthesis of biphenyl-4-yl(2-bromophenyl)amine

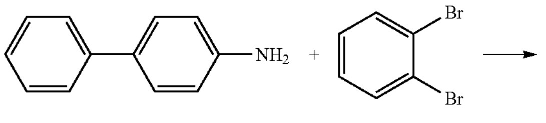

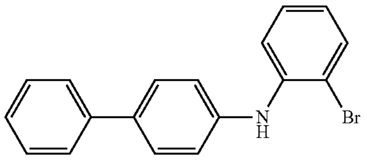

The synthesis is effected by the general method of example h from 118 g (700 mmol) of 1,2-dibromobenzene and 85.4 g (505 mmol) of 4-aminobiphenyl. The precipitated solids are recrystallized from toluene/acetonitrile (5:1) and the residue is washed with MeOH. This gives 82 g (255 mmol) of a crystalline solid. The overall yield is 71%.

In an analogous manner, it is possible to obtain the following compounds:

| Ex. | Reactant 1 | Reactant 2 | Product | Yield |
|---|---|---|---|---|
| j1 | 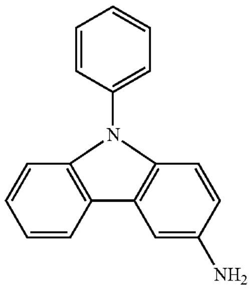 [1318253-36-9] | 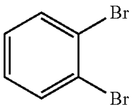 | 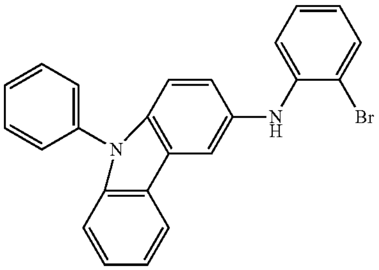 [SMILES: Brc1ccccc1Nc1ccc2c(c1)c1ccccc1n2-c1ccccc1] | 77% |
| j2 | 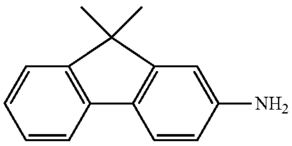 [108714-73-4] | 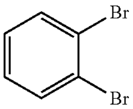 | 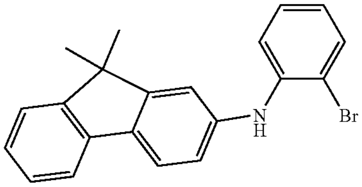 [SMILES: CC1(C)c2ccccc2-c2ccc(Nc3ccccc3Br)cc21] | 71% |

Example I

Synthesis of biphenyl-4-yl(2-bromophenyl)amine

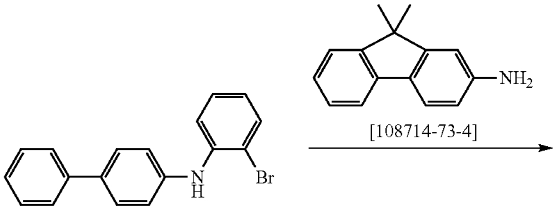

-continued

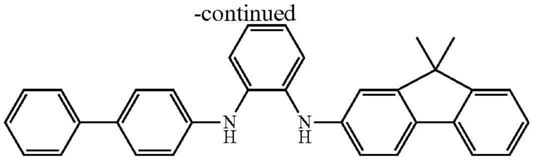

The synthesis is effected by the general method according to example h from 105.5 g (505 mmol) of biphenyl-4-yl(2-bromophenyl)amine and 163 g (505 mmol) of 9,9-dimethyl-9H-fluoren-2-ylamine. The precipitated solids are recrystallized from toluene/acetonitrile (5:1) and the residue is washed with MeOH. This gives 146 g (324 mmol) of a crystalline solid. The overall yield is 87%.

In an analoaous manner, it is possible to obtain the following compounds:

| Ex. | Reactant 1 | Reactant 2 | Product | Yield |
|---|---|---|---|---|
| i1 | 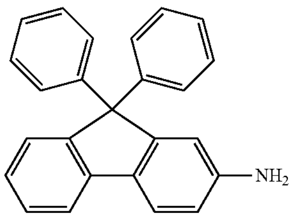 [1268519-74-9] | 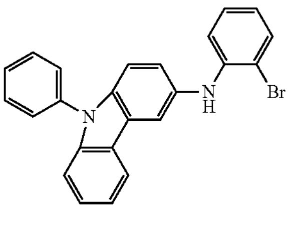 [SMILES: Brc1ccccc1Nc1ccc2c(c1)c1ccccc1n2-c1ccccc1] | 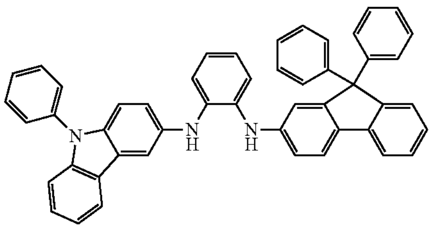 [SMILES: c1ccc(-n2c3ccccc3c3cc(Nc4ccccc4Nc4ccc5c(c4)C(c4ccccc4)(c4ccccc4)c4ccccc4-5)ccc32)cc1] | 76% |

-continued

| Ex. | Reactant 1 | Reactant 2 | Product | Yield |
|---|---|---|---|---|
| i2 | 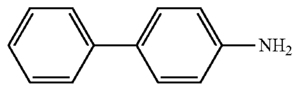 [92-67-1] | 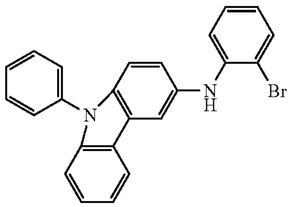 [SMILES: Brc1ccccc1Nc1ccc2c(c1)c1ccccc1n2-c1ccccc1] | 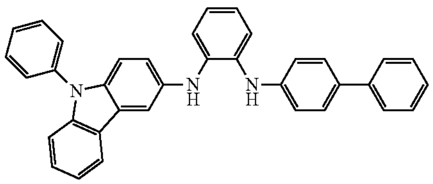 [SMILES: c1ccc(-c2ccc(Nc3ccccc3Nc3ccc4c(c3)c3ccccc3n4-c3ccccc3)cc2)cc1] | 79% |
| i3 | 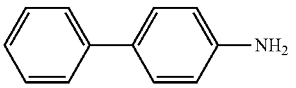 [92-67-1] | 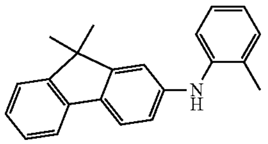 [SMILES: Cc1ccccc1Nc1ccc2c(c1)C(C)(C)c1ccccc1-2] | 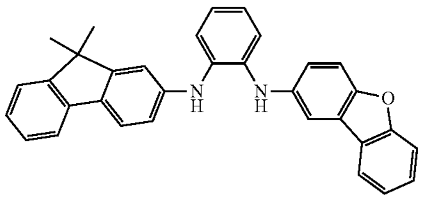 [SMILES: CC1(C)c2ccccc2-c2ccc(Nc3ccccc3Nc3ccc4oc5ccccc5c4c3)cc21] | 83% |

Example K

Synthesis of N-biphenyl-4-yl-N'-phenyl-1,2-benzenediamine

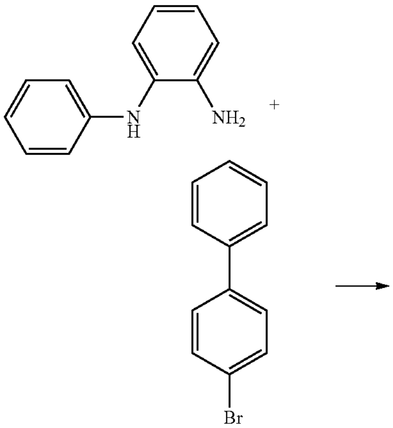

-continued

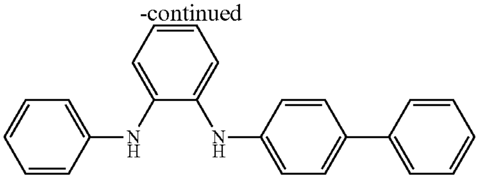

To 660 mL of degassed toluene are added 0.35 g (1.58 mmol) of $Pd(OAc)_2$ and 4.8 mL (4.86 mmol) of tri-tert-butylphosphine (1M solution in toluene), and the mixture is stirred for 5 min. Then 37.2 g (160 mmol) of 4-bromobiphenyl, 29.4 g (160 mmol) of N-phenyl-o-phenylenediamine and 22.4 g (233 mmol) of sodium Cert-butoxide are added to the solution, which is then degassed and stirred at 140° C. under a protective gas atmosphere for 10 h. After cooling, 200 mL of $NH_4Cl$ solution and 50 mL of ethyl acetate are added to the solution, and the phases are separated, washed with water, dried over $MgSO_4$ and concentrated. The solids are dissolved in toluene and the mixture is filtered through Celite. The crude product is stirred with hot heptane and washed with MeOH. This gives 47 g (140 mmol) of a crystalline solid. The overall yield is 80%.

In an analogous manner, it is possible to obtain the following compounds:

| Ex | Reactant 1 | Reactant 2 | Product | Yield |
|---|---|---|---|---|
| ka | 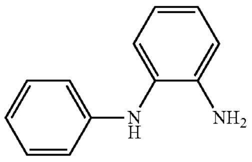 [SMILES: Nc1ccccc1Nc1ccccc1] | 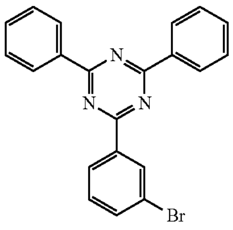 [864377-31-1] | 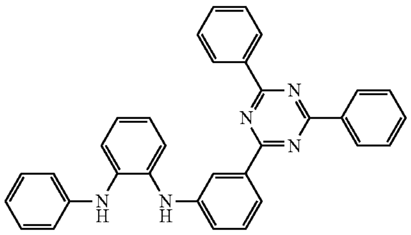 [SMILES: c1ccc(Nc2ccccc2Nc2cccc(-c3nc(-c4ccccc4)nc(-c4ccccc4)n3)c2)cc1] | 67% |

Example I 1-biphenyl-4-yl-4-{4-[(E)-((Z)-1-propenyl)-buta-1,3-dienyl]-phenyl}-1,4-dihydroquinoxaline-2,3-dione

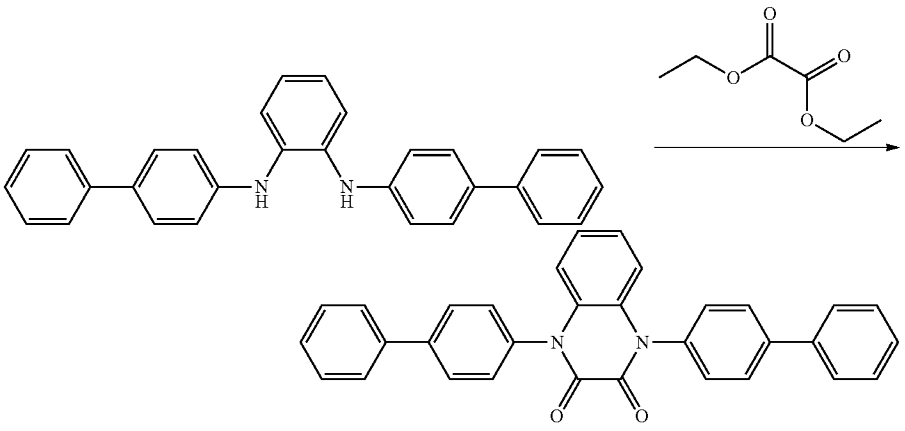

Compound 157

A mixture of 50 mL of diethyl alkoxylate and 78.2 g (190 mmol) of N,N'-bis(biphenyl-4-yl)benzene-1,2-diamine is heated to 160° C. under an argon atmosphere for 24 hours. In the course of this, the ethanol that forms is distilled off continuously. The reaction mixture is concentrated to dryness under reduced pressure and the remaining residue is recrystallized twice from ethanol. This gives 67 g (144 mmol) of a crystalline solid. The overall yield is 76%.

In an analogous manner, it is possible to obtain the following compounds:

| Ex. | Reactant 1 | Product | Yield |
|---|---|---|---|
| I1 | 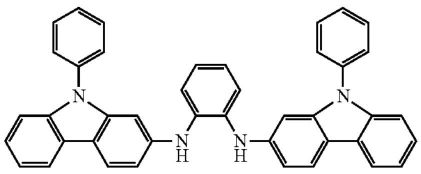 [SMILES: c1ccc(-n2c3ccccc3c3ccc(Nc4ccccc4Nc4ccc5c6ccccc6n(-c6ccccc6)c5c4)cc32)cc1] | 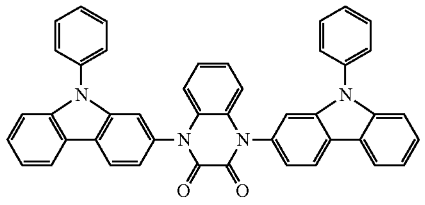 Compound 162 | 70% |
| I2 | 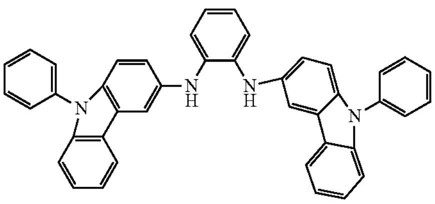 [SMILES: c1ccc(-n2c3ccccc3c3cc(Nc4ccccc4Nc4ccc5c(c4)c4ccccc4n5-c4ccccc4)ccc32)cc1] | 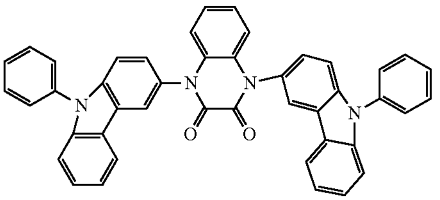 Compound 170 | 72% |
| I3 | 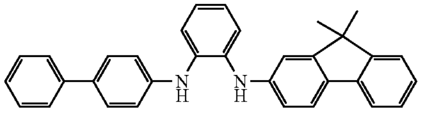 [SMILES: CC1(C)c2ccccc2-c2ccc(Nc3ccccc3Nc3ccc(-c4ccccc4)cc3)cc21] | 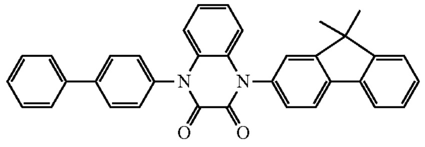 Compound 202 | 75% |

-continued
| Ex. | Reactant 1 | Product | Yield |
|---|---|---|---|
| I4 | 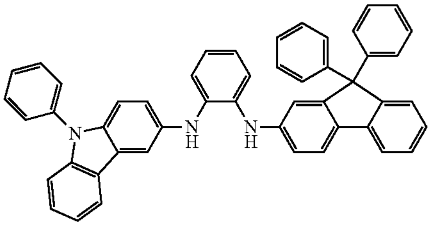 [SMILES: c1ccc(-n2c3ccccc3c3cc(Nc4ccccc4Nc4ccc5c(c4)C(c4ccccc4)(c4ccccc4)c4ccccc4-5)ccc32)cc1] | 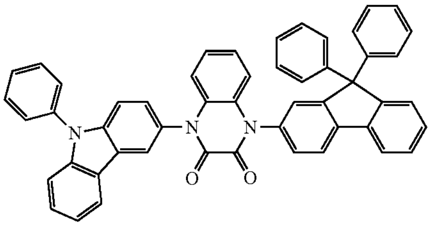 Compound 203 | 69% |
| I5 | 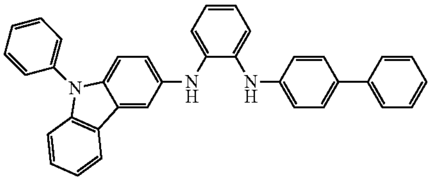 [SMILES: c1ccc(-c2ccc(Nc3ccccc3Nc3ccc4c(c3)c3ccccc3n4-c3ccccc3)cc2)cc1] | 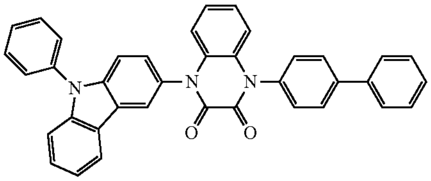 Compound 204 | 81% |
| I6 | 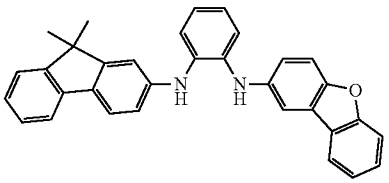 [SMILES: CC1(C)c2ccccc2-c2ccc(Nc3ccccc3Nc3ccc4oc5ccccc5c4c3)cc21] | 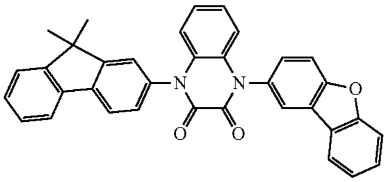 Compound 205 | 80% |
| I7 | 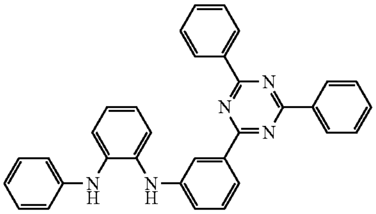 [SMILES: c1ccc(Nc2ccccc2Nc2cccc(-c3nc(-c4ccccc4)nc(-c4ccccc4)n3)c2)cc1] | 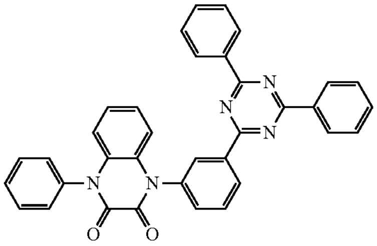 Compound 206 | 63% |
Example M
1-(9,9'-Spiro[9H-fluoren-2-yl])-1H-indole-2,3-diones
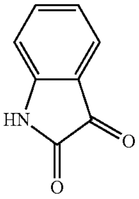
[91-56-5]
+
-continued
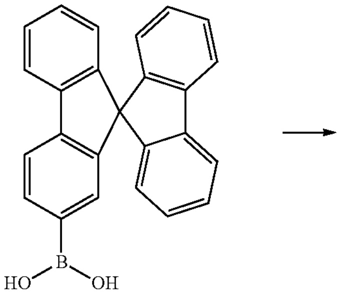
[236389-21-2]

-continued

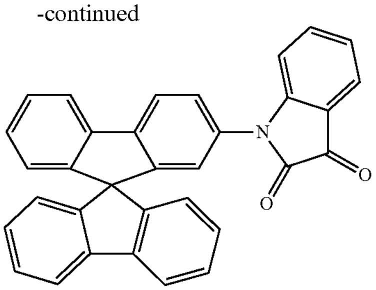

Compound 143

14.7 g (100 mmol) of spiro-9,9'-bifluoro-2-boronic acid, 12 g (34 mmol) of 1H-indole-2,3-dione, 64 g (52 mmol) of copper powder and 12 mL (88 mmol) of $NEt_3$ are suspended in 800 mL of $CH_2Cl_2$, a little 4 Å molecular sieve is added and the mixture is stirred vigorously at room temperature for 28 h, and the reaction mixture is heated under reflux for 16 h. Thereafter, the mixture is admixed with 40 mL of MeOH, the solids are filtered off and the mixture is concentrated. The residue is recrystallized from toluene and from dichloromethane and finally sublimed under high vacuum; purity is 99.9%. The yield is 12.1 g (26 mmol), corresponding to 79% of theory.

In an analogous manner, it is possible to obtain the following compounds:

| Ex. | Reactant 1 | Reactant 2 | Product | Yield |
|---|---|---|---|---|
| m1 | 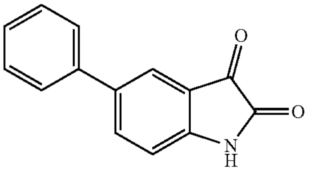 [109496-98-2] | 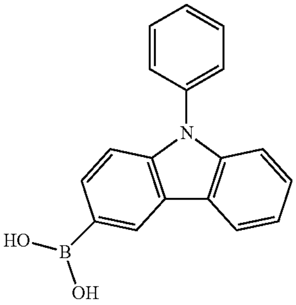 [854952-58-2] | 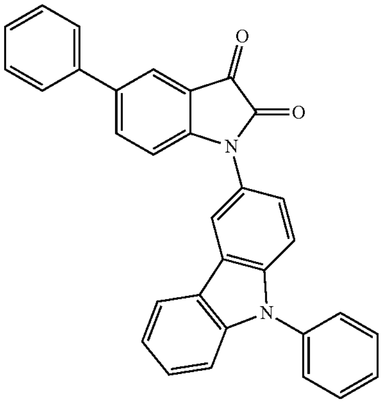 Compound 144 | 78% |
| m2 | 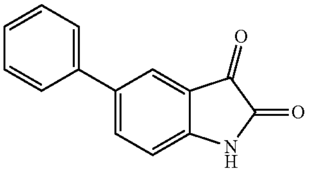 [109496-98-2] | 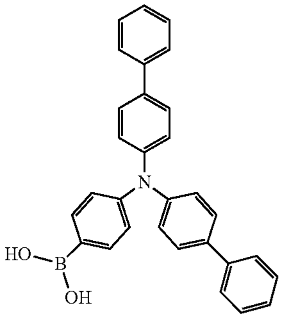 [943836-24-6] | 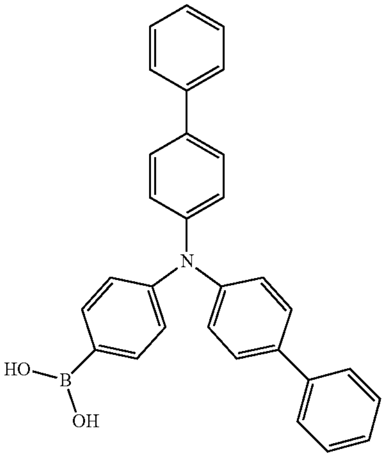 [943836-24-6] | 77% |

-continued
| Ex. | Reactant 1 | Reactant 2 | Product | Yield |
|---|---|---|---|---|
| m3 | 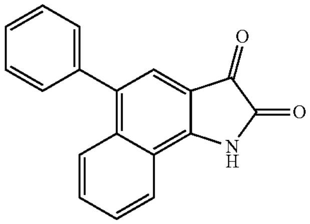 [109590-62-7] | 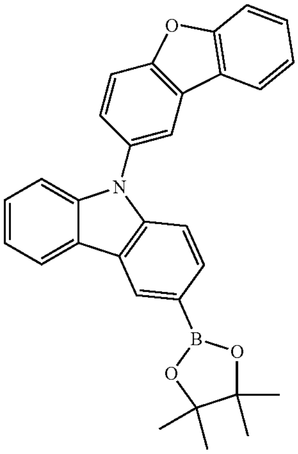 [1338488-91-7] | 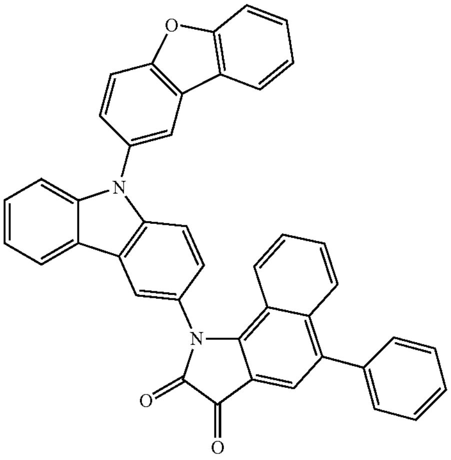 Compound 146 | 73% |
| m4 | 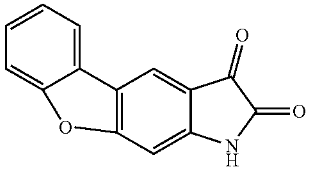 [6783-68-2] | 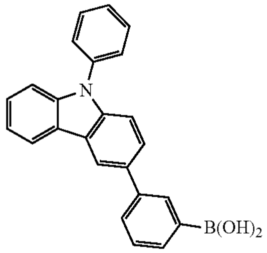 [854952-60-6] | 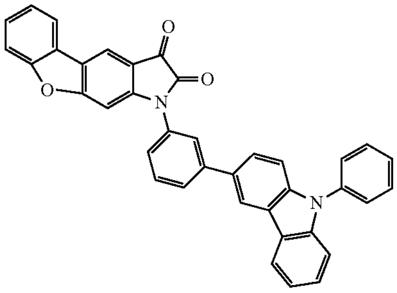 Compound 147 | 81% |
| m5 | 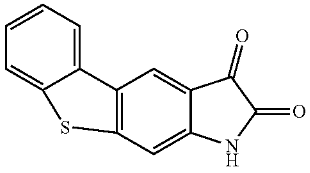 [2902082-22-5] | 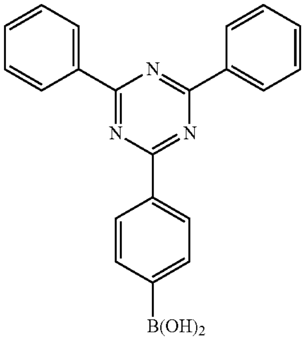 [1313018-07-3] | 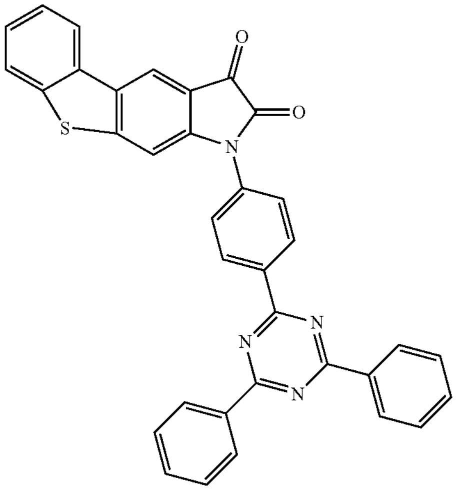 Compound 148 | 74% |

-continued

| Ex. | Reactant 1 | Reactant 2 | Product | Yield |
|---|---|---|---|---|
| m6 | 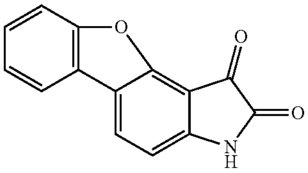 [6783-66-0] | 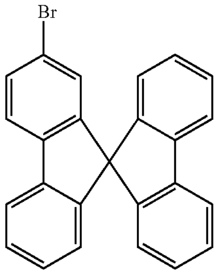 [171408-76-7] | 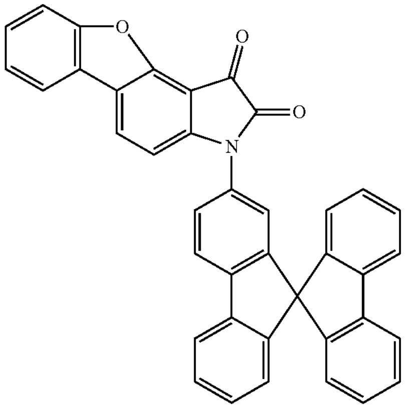 Compound 149 | 70% |

In an analogous manner, the compounds which follow can be obtained by the method according to example m from 250 mmol of arylboronic acid and 20 mmol of 1H-indole-2,3-dione. The precipitated solids are recrystallized from toluene/acetonitrile (5:1) and the residue is washed with MeOH. The residue is recrystallized from toluene and from dichloromethane and finally sublimed under high vacuum; purity is 99.9%.

| Ex. | Reactant 1 | Reactant 2 | Product | Yield |
|---|---|---|---|---|
| m7 | 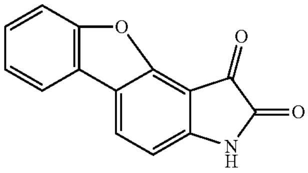 [6783-66-0] | 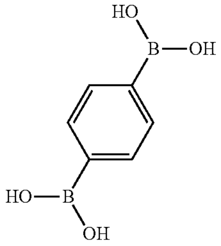 [4612-26-4] | 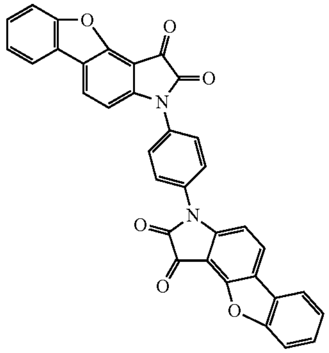 Compound 150 | 52% |
| m8 | 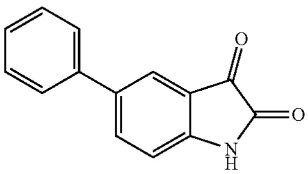 [109496-98-2] | 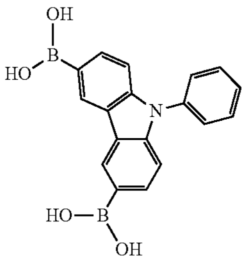 [1135916-40-3] | 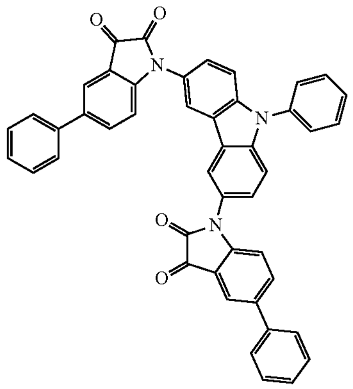 Compound 151 | 49% |

Example N 1-(9,9'-Spiro[9H-fluoren-2-yl])-1H-indole-2,3-diones

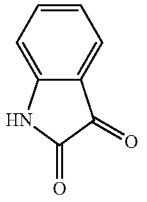

[91-56-5]

+

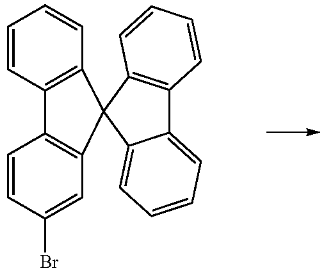

-continued

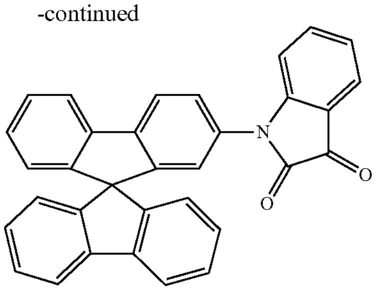

Compound 143

14.7 g (102.4 mmol) of 1H-indole-2,3-dione, 44 g (112 mmol) of spiro-9,9'-bifluoro-2-boronic acid and 2.3 (10.2 mmol) of 1,3-di[2-pyridyl]-1,3-propanedione, 28.3 g (204 mmol) of potassium carbonate and 1.9 g (10.2) of copper iodide in 1000 mL of DMF are stirred under reflux for 90 h. The solution is diluted with water and extracted twice with ethyl acetate, and the combined organic phases are dried over $Na_2SO_4$ and concentrated by rotary evaporation and purified by chromatography (EtOAc/hexane: 2/3). The residue is recrystallized from toluene and from dichloromethane and finally sublimed under high vacuum; purity is 99.9%. The yield is 36 g (79 mmol), corresponding to 80% of theory.

In an analogous manner, it is possible to obtain the following compounds:

| Ex. | Reactant 1 | Reactant 2 | Product | Yield |
|---|---|---|---|---|
| n1 | 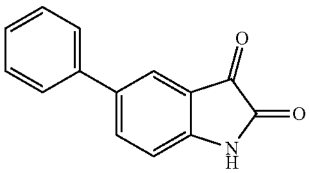 [109496-98-2] | 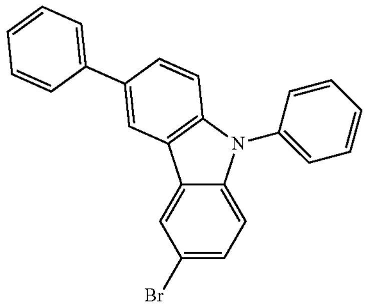 [1160294-85-8] | 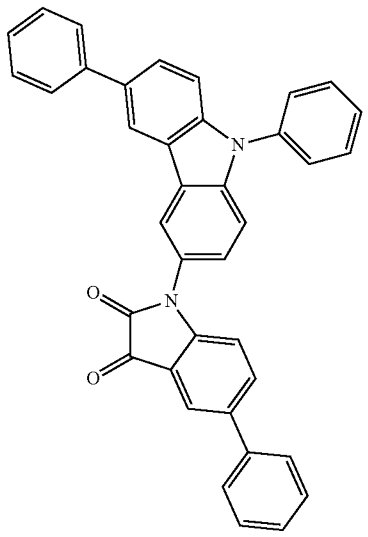 Compound 152 | 76% |

-continued

| Ex. | Reactant 1 | Reactant 2 | Product | Yield |
|---|---|---|---|---|
| n2 | 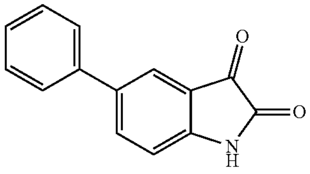 [109496-98-2] | 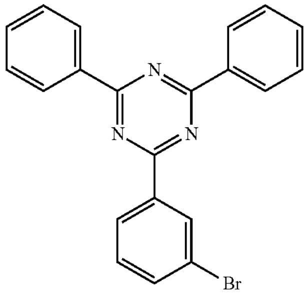 864377-31-1] | 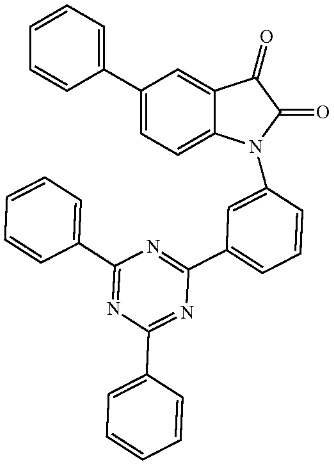 Compound 153 | 82% |

Example 1

Production of the OLEDs

In examples I1 to I11 which follow (see Tables 1.1 and 1.2), the data of various OLEDs are presented. Cleaned glass plaques (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 min, for improved processing, coated with 20 nm of PEDOT:PSS (poly(3,4-ethylenedioxythiophene) poly (styrenesulfonate), purchased as CLEVIOS™ P VP Al 4083 from Heraeus Precious Metals GmbH Deutschland, spun on from aqueous solution) and then baked at 180° C. for 10 min. These coated glass plaques form the substrates to which the OLEDs are applied.

The OLEDs basically have the following layer structure: substrate/hole transport layer (HTL)/interlayer (IL)/electron blocker layer (EBL) emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 1.1. The further materials required for production of the OLEDs and the abbreviations used are shown in Table 1.3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as d46:BIC1:TEG1 (50%:40%:10%) mean here that compound 117 is present in the layer in a proportion by volume of 50%, BIC1 in a proportion of 40% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in Im/W) and the external quantum efficiency (EQE, measured in percent) as a function of luminance, calculated from current-voltage-luminance characteristics (IUL characteristics) assuming Lambertian emission characteristics, and also the lifetime are determined. The electroluminescence spectra are determined at a luminance of 1000 $cd/m^2$, and the CIE 1931 x and y color coordinates are calculated therefrom. The parameter U1000 in Table 1.2 refers to the voltage which is required for a luminance of 1000 $cd/m^2$. CE1000 and PE1000 respectively refer to the current and power efficiencies which are achieved at 1000 $cd/m^2$. Finally, EQE1000 refers to the external quantum efficiency at an operating luminance of 1000 $cd/m^2$.

The data for the various OLEDs are collated in Table 1.2.

TABLE 1.1

Structure of the OLEDs

| Ex. | HTL thickness | IL thickness | EBL thickness | EML thickness | HBL thickness | ETL thickness | ETL thickness |
|---|---|---|---|---|---|---|---|
| I1 | SpA1 70 nm | HATCN 5 nm | SpMA1 90 nm | IC2:d1:TEG1 (60%:30%:10%) 30 nm | ST1 10 nm | ST1:LiQ (50%:50%) 30 nm | — |
| I2 | SpA1 70 nm | HATCN 5 nm | SpMA1 90 nm | IC2:d4:TEG1 (45%:45%:10%) 30 nm | ST1 10 nm | ST1:LiQ (50%:50%) 30 nm | — |
| I3 | SpA1 70 nm | HATCN 5 nm | SpMA1 90 nm | d11:TEG1 (85%:15%) 30 nm | — | ST1:LiQ (50%:50%) 40 nm | — |
| I4 | SpA1 70 nm | HATCN 5 nm | SpMA1 90 nm | g2:TEG1 (85%:15%) 30 nm | — | ST1:LiQ (50%:50%) 40 nm | — |

TABLE 1.1-continued

| Structure of the OLEDs | | | | | | | |
|---|---|---|---|---|---|---|---|
| Ex. | HTL thickness | IL thickness | EBL thickness | EML thickness | HBL thickness | ETL thickness | ETL thickness |
| I5 | SpA1 70 nm | HATCN 5 nm | SpMA1 90 nm | d46:TEG1 (85%:15%) 30 nm | ST1 10 nm | ST1:LiQ (50%:50%) 30 nm | — |
| I6 | SpA1 70 nm | HATCN 5 nm | SpMA1 90 nm | d46:BIC1:TEG1 (50%:40%:10%) 30 nm | ST1 10 nm | ST1:LiQ (50%:50%) 30 nm | — |
| I7 | SpA1 70 nm | HATCN 5 nm | SpMA1 90 nm | IC2:e2:TEG1 (55%:35%:10%) 30 nm | ST1 10 nm | ST1:LiQ (50%:50%) 30 nm | — |
| I8 | SpA1 70 nm | HATCN 5 nm | SpMA1 90 nm | IC1:TEG1 (85%:15%) 30 nm | — | I7 40 nm | LiQ 3 nm |
| I9 | SpA1 70 nm | HATCN 5 nm | SpMA1 90 nm | IC1:TEG1 (85%:15%) 30 nm | IC1 10 nm | n2 30 nm | LiQ 3 nm |
| I10 | SpA1 70 nm | HATCN 5 nm | SpMA1 90 nm | I7:BIC1:TEG1 (60%:30%:10%) 30 nm | ST1 10 nm | ST1:LiQ (50%:50%) 30 nm | — |
| I11 | SpA1 90 nm | HATCN 5 nm | SpMA1 130 nm | d46:TER1 (92%:8%) 40 nm | — | ST1:LiQ (50%:50%) 40 nm | — |

TABLE 1.2

| Data of the OLEDs | | | | | |
|---|---|---|---|---|---|
| Ex. | U1000 (V) | CE1000 (cd/A) | PE1000 (lm/W) | EQE 1000 | CIE x/y at 1000 cd/$m^2$ |
| I1 | 3.3 | 49 | 47 | 13.6% | 0.33/0.62 |
| I2 | 3.7 | 54 | 46 | 15.4% | 0.35/0.61 |
| I3 | 3.6 | 53 | 45 | 15.0% | 0.34/0.62 |
| I4 | 4.3 | 50 | 38 | 14.3% | 0.36/0.61 |
| I5 | 3.3 | 58 | 54 | 16.1% | 0.34/0.62 |
| I6 | 3.4 | 56 | 51 | 15.5% | 0.34/0.62 |
| I7 | 3.3 | 47 | 45 | 13.3% | 0.35/0.62 |
| I8 | 3.5 | 63 | 57 | 17.5% | 0.34/0.62 |
| I9 | 4.7 | 56 | 38 | 15.7% | 0.33/0.62 |
| I10 | 3.4 | 56 | 51 | 15.6% | 0.34/0.62 |
| I11 | 4.8 | 10.3 | 6.7 | 11.1% | 0.67/0.33 |

TABLE 1.3

Structural formulae of the materials for the OLEDs

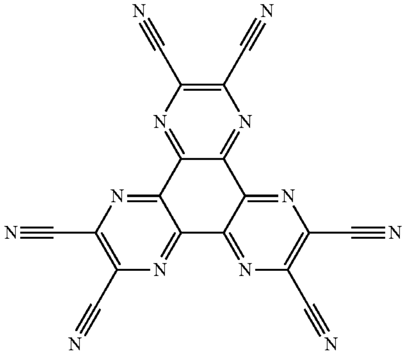

HATCN

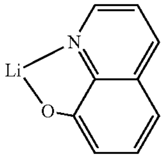

LiQ

TABLE 1.3-continued

Structural formulae of the materials for the OLEDs

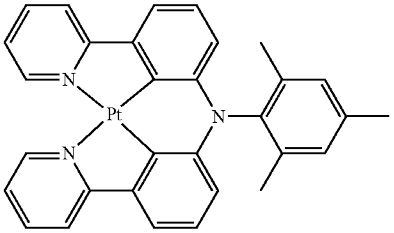

TER1

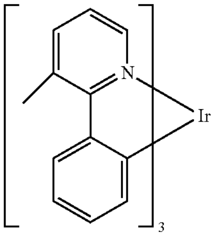

TEG1

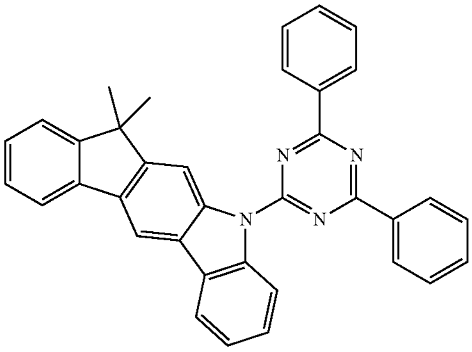

IC1

TABLE 1.3-continued
| Structural formulae of the materials for the OLEDs |
|---|
| 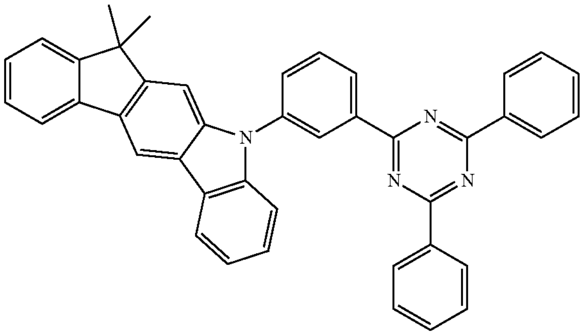 |
| IC2 |
| 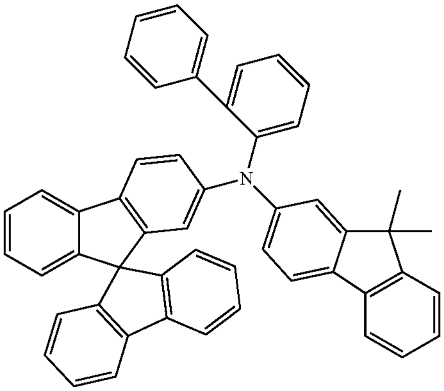 |
| SpMA1 |
| 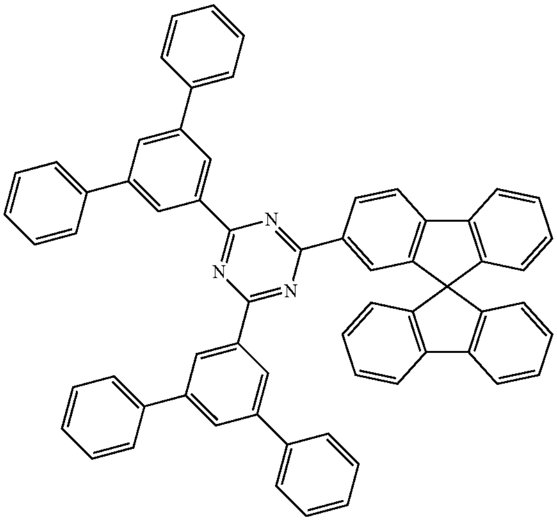 |
| ST1 |
TABLE 1.3-continued
| Structural formulae of the materials for the OLEDs |
|---|
| 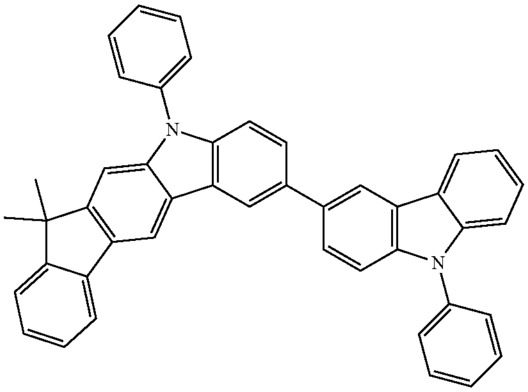 |
| BIC1 |
| 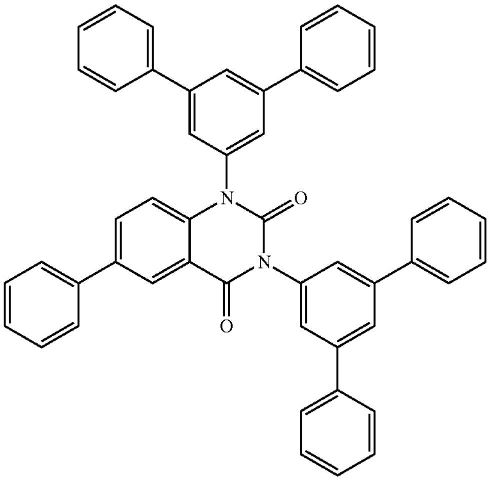 |
| d1 = compound 111 |
| 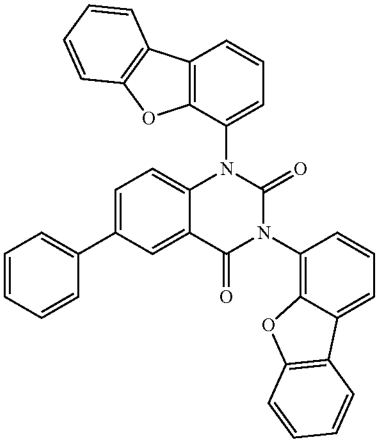 |
| d4 = compound 114 |

TABLE 1.3-continued

| Structural formulae of the materials for the OLEDs |
| --- |
| 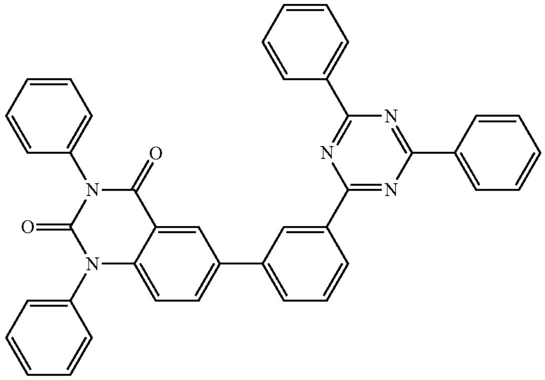 |
| d11 = compound 86 |
| 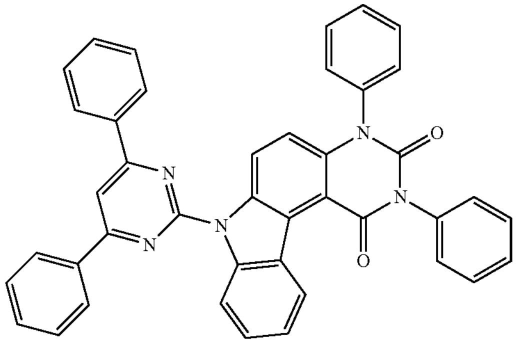 |
| g2 = compound 56 |
| 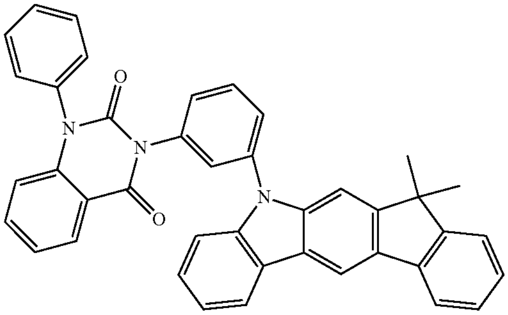 |
| d46 = compound 117 |
| 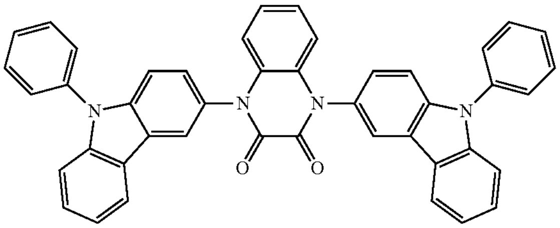 |
| e2 = compound 170 |

TABLE 1.3-continued

| Structural formulae of the materials for the OLEDs |
| --- |
| 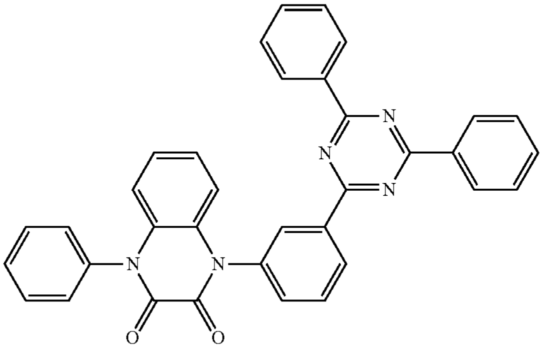 |
| I7 = compound 206 |
| 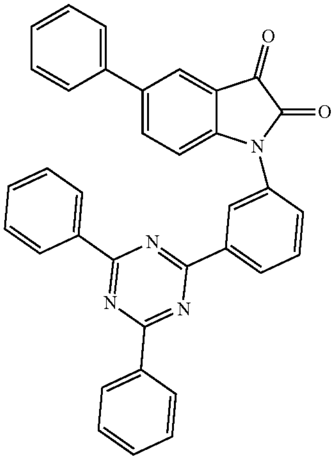 |
| n2 = compound 153 |

The invention claimed is:

1. An electronic device comprising at least one compound of the formula (1)

Formula (1)

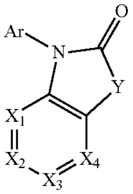

or at least two compounds of the formula (1) that are connected via at least one common aromatic or heteroaromatic ring system Ar or at least two compounds of the formula (1) that have a common structural unit

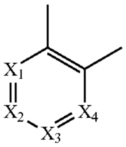

where the symbols used are as follows:

$X_1$, $X_2$, $X_3$, $X_4$ are each independently CR or N;

Y at each instance is

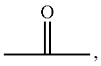, 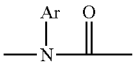 or 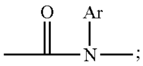;

Ar is the same or different at each instance and is an aromatic or heteroaromatic ring system which has 5-60 aromatic ring atoms and may be substituted by one or more $R^1$ radicals;

$Ar^1$ is the same or different at each instance and is an aromatic or heteroaromatic ring system which has 5-30 aromatic ring atoms and may be substituted by one or more $R^1$ radicals; at the same time, two $Ar^1$ radicals bonded to the same nitrogen atom or phosphorus atom may also be bridged to one another by a single bond or a bridge selected from $N(R^1)$, $C(R^1)_2$ and O;

R is the same or different at each instance and is selected from the group consisting of H, D, F, Cl, Br, I, CN, CHO, $NO_2$, $Si(R^2)_3$, $B(OR^2)_2$, $N(Ar^1)_2$, $N(R^1)_2$, $C(=O)Ar^1$, $C(=O)R^1$, $P(=O)(Ar^1)_2$, $S(=O)Ar^1$, $S(=O)(Ar^1)_2$, $CR^2=CR^2Ar^1$, $C\equiv CAr^1$, $OSO_2R^1$;

a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the hydrocarbyl groups mentioned may each be substituted by one or more $R^1$ radicals and where one or more nonadjacent $CH_2$ groups may be replaced by $R^1C=CR^1$, $-C\equiv C-$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$;

an aromatic or heteroaromatic ring system which has 5 to 60 aromatic ring atoms and may be substituted in each case by one or more $R^1$ radicals, an aryloxy or heteroaryloxy group which has 5 to 60 aromatic ring atoms and may be substituted by one or more $R^1$ radicals, an aralkyl or heteroaralkyl group which has 5 to 60 aromatic ring atoms and may be substituted by one or more $R^1$ radicals, or a combination of these systems, where two or more adjacent R substituents may form a monocyclic or polycyclic, aliphatic, aromatic or heteroaromatic ring system which may be substituted by one or more $R^1$ radicals or where the R substituent of X1 and/or the R substituent of X4 together with the adjacent N—Ar in each case may form a monocyclic or polycyclic, aliphatic, aromatic or heteroaromatic ring system which may be substituted by one or more $R^1$ radicals;

$R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, where two or more adjacent $R^1$ substituents together may form a mono- or polycyclic, aliphatic, aromatic or heteroaromatic ring system and $R^2$ is in each case independently selected from the group consisting of H, D or is an aliphatic, aromatic and/or heteroaromatic hydrocarbyl radical having 1 to 20 carbon atoms, where two or more $R^2$ radicals together may also form a ring system.

2. The electronic device as claimed in claim 1, wherein the device is an organic electroluminescent device, organic integrated circuit, organic field-effect transistor, organic thin-film transistor, organic light-emitting transistor, organic solar cell, organic dye-sensitized solar cell, solar cell comprising perovskite, organic optical detector, organic photoreceptor, organic field-quench device, light-emitting electrochemical cell, organic laser diode or organic plasmon-emitting device.

3. The electronic device as claimed in claim 1, wherein the compound of the formula (1) is used as matrix material for a fluorescent or phosphorescent emitter and/or in a hole blocker layer and/or in an electron transport layer and/or in an electron-blocking or exciton-blocking layer and/or in a hole transport layer.

4. The electronic device as claimed in claim 1, wherein Y in formula (1) is

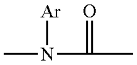

and Ar in each case independently has a definition given in claim 1.

5. The electronic device as claimed in claim 1, wherein Y in formula (1) is

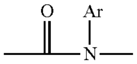

and Ar in each case independently has a definition given in claim 1.

6. The electronic device as claimed in claim 1, wherein Y in formula (1) is

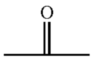.

7. The electronic device as claimed in claim 1, wherein at least one variable from the group of $X_1$, $X_2$, $X_3$ and $X_4$ is N and the rest of the variables are CR, and R in each case independently has one of the definitions given in claim 1.

8. The electronic device as claimed in claim 1, wherein the variables $X_1$, $X_2$, $X_3$ and $X_4$ are CR, and R in each case independently has one of the definitions given in claim 1.

9. A compound of the formula (52)

(52)

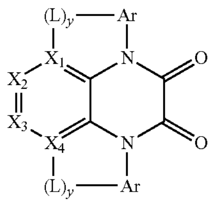

wherein y is in each case independently 0 or 1,

L is in each case independently —$C(R^1)_2$—, where $X_1$, $X_2$, $X_3$ and $X_4$ are each independently CR, where the R substituent of $X_1$and/or the R substituent of $X_4$ together with the adjacent N—Ar in each case form a monocyclic or polycyclic, aliphatic, aromatic or heteroaromatic ring system which may be substituted by one or more $R^1$ radicals, Ar is the same or different at each instance and is an aromatic or heteroaromatic ring system which has 5-60 aromatic ring atoms and may be substituted by one or more $R^1$ radicals;

R is the same or different at each instance and is selected from the group consisting of H, D, F, Cl, Br, I, CN, CHO, $NO_2$, $Si(R^2)_3$, $B(OR^2)_2$, $N(Ar^1)_2$, $N(R^1)_2$, $C(=O)Ar^1$, $C(=O)R^1$, $P(=O)(Ar^1)_2$, $S(=O)Ar^1$, $S(=O)(Ar^1)_2$, $CR^2=CR^2Ar^1$, $C\equiv CAr^1$, $OSO_2R^1$;

a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the hydrocarbyl groups mentioned may each be substituted by one or more $R^1$ radicals and where one or more nonadjacent $CH_2$ groups may be replaced by $R^1C=CR^1$, —C≡C—, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$;

an aromatic or heteroaromatic ring system which has 5 to 60 aromatic ring atoms and may be substituted in each case by one or more $R^1$ radicals, an aryloxy or heteroaryloxy group which has 5 to 60 aromatic ring atoms and may be substituted by one or more $R^1$ radicals, an aralkyl or heteroaralkyl group which has 5 to 60 aromatic ring atoms and may be substituted by one or more $R^1$ radicals, or a combination of these systems, where two or more adjacent R substituents may form a monocyclic or polycyclic, aliphatic, aromatic or heteroaromatic ring system which may be substituted by one or more $R^1$ radicals or where the R substituent of X1 and/or the R substituent of X4 together with the adjacent N—Ar in each case may form a monocyclic or polycyclic, aliphatic, aromatic or heteroaromatic ring system which may be substituted by one or more $R^1$ radicals;

$Ar^1$ is the same or different at each instance and is an aromatic or heteroaromatic ring system which has 5-30 aromatic ring atoms and may be substituted by one or more $R^1$ radicals; at the same time, two $Ar^1$ radicals bonded to the same nitrogen atom or phosphorus atom may also be bridged to one another by a single bond or a bridge selected from $N(R^1)$, $C(R^1)_2$ and O;

$R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, where two or more adjacent $R^1$ substituents together may form a mono- or polycyclic, aliphatic, aromatic or heteroaromatic ring system and $R^2$ is in each case independently selected from the group consisting of H, D or is an aliphatic, aromatic and/or heteroaromatic hydrocarbyl radical having 1 to 20 carbon atoms, where two or more $R^2$ radicals together may also form a ring system.

10. The compound according to clam 9, wherein the compound of formula (52) is a compound of the formula (53) to (55):

(53)

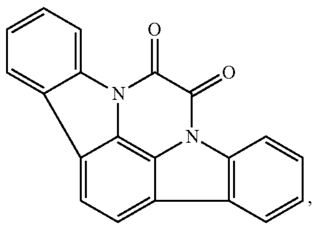

, (54)

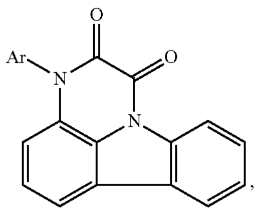

, (55)

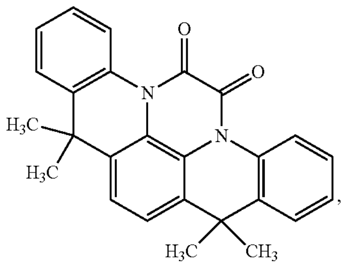

, which may be substituted by one or more $R^1$ radicals.

11. The compound according to clam 9, wherein the compound of formula (52) is a compound of the formula (42)

(42)

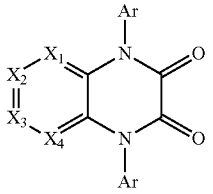

where $X_1$, $X_2$, $X_3$ and $X_4$ are each independently CR, where the R substituent of $X_1$ and/or the R substituent of $X_4$ together with the adjacent N—Ar in each case form a monocyclic or polycyclic, aliphatic, aromatic or heteroaromatic ring system which may be substituted by one or more $R^1$radicals, Ar is the same or different at each instance and is an aromatic or heteroaromatic ring system which has 5-60 aromatic ring atoms and may be substituted by one or more $R^1$radicals;

R is the same or different at each instance and is selected from the group consisting of H, D, F, Cl, Br, I, CN, CHO, $NO_2$, $Si(R^2)_3$, $B(OR^2)_2$, $N(Ar^1)_2$, $N(R^1)_2$, $C(=O)Ar^1$, $C(=O)R^1$, $P(=O)(Ar^1)_2$, $S(=O)Ar^1$, $S(=O)(Ar^1)_2$, $CR^2{=}CR^2Ar^1$, $C\equiv CAr^1$, $OSO_2R^1$;

a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the hydrocarbyl groups mentioned may each be substituted by one or more $R^1$radicals and where one or more nonadjacent $CH_2$ groups may be replaced by $R^1C{=}CR^1$, $-C\equiv C-$, $Si(R^1)_2$, $Ge(R^1)_2$, $Sn(R^1)_2$, C=O, C=S, C=Se, $C{=}NR^1$, $P(=O)(R^1)$, SO, $SO_2$, $NR^1$, O, S or $CONR^1$ and where one or more hydrogen atoms may be replaced by D, F, Cl, Br, I, CN or $NO_2$;

an aromatic or heteroaromatic ring system which has 5 to 60 aromatic ring atoms and may be substituted in each case by one or more $R^1$radicals, an aryloxy or heteroaryloxy group which has 5 to 60 aromatic ring atoms and may be substituted by one or more $R^1$radicals, an aralkyl or heteroaralkyl group which has 5 to 60 aromatic ring atoms and may be substituted by one or more $R^1$ radicals, or a combination of these systems, where two or more adjacent R substituents may form a monocyclic or polycyclic, aliphatic, aromatic or heteroaromatic ring system which may be substituted by one or more $R^1$ radicals or where the R substituent of X1 and/or the R substituent of X4 together with the adjacent N—Ar in each case may form a monocyclic or polycyclic, aliphatic, aromatic or heteroaromatic ring system which may be substituted by one or more $R^1$ radicals;

$Ar^1$ is the same or different at each instance and is an aromatic or heteroaromatic ring system which has 5-30 aromatic ring atoms and may be substituted by one or more $R^1$ radicals; at the same time, two $Ar^1$ radicals bonded to the same nitrogen atom or phosphorus atom may also be bridged to one another by a single bond or a bridge selected from $N(R^1)$, $C(R^1)_2$ and O;

$R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, where two or more adjacent $R^1$ substituents together may form a mono- or polycyclic, aliphatic, aromatic or heteroaromatic ring system and $R^2$ is in each case independently selected from the group consisting of H, D or is an aliphatic, aromatic and/or heteroaromatic hydrocarbyl radical having 1 to 20 carbon atoms, where two or more $R^2$ radicals together may also form a ring system.

12. A formulation comprising at least one compound as claimed in claim 11.

13. An electronic device comprising the compound as claimed in claim 11.

14. A compound of the formulae (47) to (51)

(47)

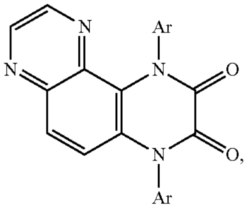

(48)

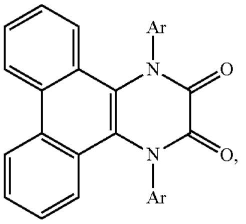

(49)

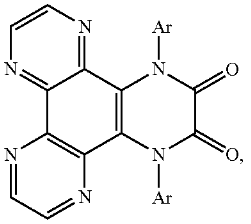

(50)

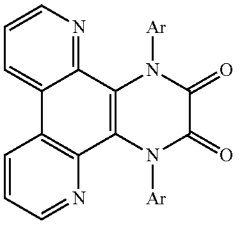

and (51)

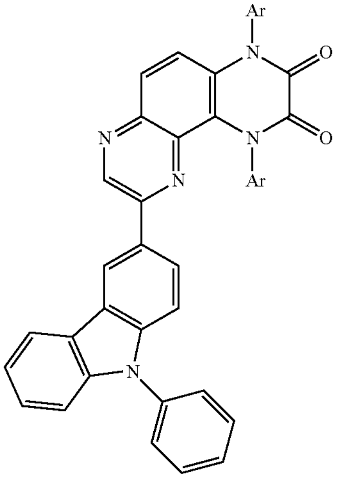

where

Ar is the same or different at each instance and is an aromatic or heteroaromatic ring system which has 5-60 aromatic ring atoms and may be substituted by one or more $R^1$ radicals;

$R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, where two or more adjacent $R^1$ substituents together may form a mono- or polycyclic, aliphatic, aromatic or heteroaromatic ring system.

15. A compound of the formula (56)

(56)

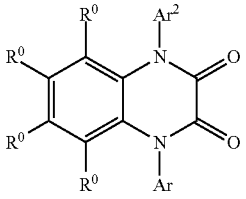

where

Ar is an aromatic or heteroaromatic ring system which has 5-60 aromatic ring atoms and may be substituted by one or more nonaromatic $R^1$ radicals, $Ar^2$ is an aromatic ring system which has 13 to 40 carbon atoms or a heteroaromatic ring system which has 4 to 40 carbon atoms and may be substituted by one or more nonaromatic $R^1$ radicals, $R^0$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, and $R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, where two or more adjacent $^1$ substituents together may form a mono- or polycyclic, aliphatic, aromatic or heteroaromatic ring system.

16. A compound of the formula (57)

(57)

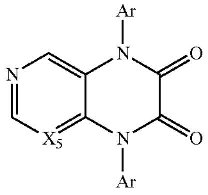

where $X_5$ is CR or N;

Ar is the same or different at each instance and is an aromatic or heteroaromatic ring system which has 5-60 aromatic ring atoms and may be substituted by one or more $R^1$ radicals;

R is the same or different at each instance and is selected from the group consisting of H, D, F, Cl, Br, I, CN, CHO, $NO_2$, $Si(R^2)_3$, $B(OR^2)_2$, $N(Ar^1)_2$, $N(R^1)_2$, $C(=O)Ar^1$, $C(=O)R^1$, $P(=O)(Ar^1)_2$, $S(=O)Ar^1$, $S(=O)(Ar^1)_2$, $CR^2=CR^2Ar^1$, $C\equiv CAr^1$, $OSO_2R^1$;

a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the hydrocarbyl groups mentioned may each be substituted by one or more $R^1$ radicals and where one or more nonadjacent $CH_2$ groups may be replaced by $R^1C=CR^1$, —C≡C—, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$;

an aromatic or heteroaromatic ring system which has 5 to 60 aromatic ring atoms and may be substituted in each case by one or more $R^1$ radicals, an aryloxy or heteroaryloxy group which has 5 to 60 aromatic ring atoms and may be substituted by one or more $R^1$ radicals, an aralkyl or heteroaralkyl group which has 5 to 60 aromatic ring atoms and may be substituted by one or more $R^1$ radicals, or a combination of these systems, where two or more adjacent R substituents may form a monocyclic or polycyclic, aliphatic, aromatic or heteroaromatic ring system which may be substituted by one or more $R^1$ radicals;

$Ar^1$ is the same or different at each instance and is an aromatic or heteroaromatic ring system which has 5-30 aromatic ring atoms and may be substituted by one or more $R^1$ radicals; at the same time, two $Ar^1$ radicals bonded to the same nitrogen atom or phosphorus atom may also be bridged to one another by a single bond or a bridge selected from $N(R^1)$, $C(R^1)_2$ and O;

$R^1$ is in each case independently selected from the group consisting of H, D, F, CN, a straight-chain or branched alkyl group having 1 to 20 carbon atoms, a straight-chain or branched alkenyl group having 2 to 20 carbon atoms, an aromatic or heteroaromatic ring system which has 5 to 30 aromatic ring atoms and in which one or more hydrogen atoms may be replaced by D, F, Cl, Br, I, CN or a straight-chain or branched alkyl group having 1 to 10 carbon atoms or a straight-chain or branched alkenyl group having 2 to 10 carbon atoms, where two or more adjacent $R^1$ substituents together may form a mono- or polycyclic, aliphatic, aromatic or heteroaromatic ring system and $R^2$ is in each case independently selected from the group consisting of H, D or is an aliphatic, aromatic and/or heteroaromatic hydrocarbyl radical having 1 to 20 carbon atoms, where two or more $R^2$ radicals together may also form a ring system.

* * * * *

UNITED STATES PATENT AND TRADEMARK OFFICE

CERTIFICATE OF CORRECTION

PATENT NO. : 10,249,831 B2
APPLICATION NO. : 15/549556
DATED : April 2, 2019
INVENTOR(S) : Philipp Stoessel et al.

It is certified that error appears in the above-identified patent and that said Letters Patent is hereby corrected as shown below:

In the Claims

In Column 268, Claim 10, Line number 10, please correct the phrase:
“The compound according to clam 9 wherein the....”

Should be:
“The compound according to claim 9 wherein the....”

In Column 268, Claim 11, Line number 47, please correct the phrase:
“The compound according to clam 9, where the....”

Should be:
“The compound according to claim 9, wherein the...”

In Column 271, Claim 15, Line number 50:
“where two or more adjacent $^1$ substituents together may....”

Should be:
“where two or more adjacent $\mathbf{R}^1$ substituents together may....”

Signed and Sealed this
Twenty-fifth Day of June, 2019

Andrei Iancu
*Director of the United States Patent and Trademark Office*